(12) United States Patent
Parsai et al.

(10) Patent No.: US 9,750,954 B2
(45) Date of Patent: *Sep. 5, 2017

(54) CONCURRENT DELIVERY OF INTERSTITIAL THERMOBRACHYTHERAPY (HYPERTHERMIA AND BRACHYTHERAPY) IN THE TREATMENT OF CANCER

(71) Applicant: The University of Toledo, Toledo, OH (US)

(72) Inventors: E. Ishmael Parsai, Toledo, OH (US); Diana Shvydka, Toledo, OH (US); Gregory Warrell, Toledo, OH (US)

(73) Assignee: The University of Toledo, Toledo, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/493,387

(22) Filed: Apr. 21, 2017

(65) Prior Publication Data

US 2017/0216623 A1    Aug. 3, 2017

Related U.S. Application Data

(63) Continuation-in-part of application No. 13/126,012, filed as application No. PCT/US2009/062430 on Oct. 28, 2009, now Pat. No. 9,682,246.

(60) Provisional application No. 61/109,105, filed on Oct. 28, 2008.

(51) Int. Cl.
*A61K 51/12* (2006.01)
*A61N 5/10* (2006.01)
*A61N 1/40* (2006.01)

(52) U.S. Cl.
CPC .......... *A61N 5/1027* (2013.01); *A61N 1/406* (2013.01); *A61N 2005/1024* (2013.01)

(58) Field of Classification Search
None
See application file for complete search history.

(56) References Cited

U.S. PATENT DOCUMENTS 6,497,647 B1 * 12/2002 Tucker .................. A61N 1/406
600/3

* cited by examiner

*Primary Examiner* — David J Blanchard
*Assistant Examiner* — Daniel F Coughlin
(74) *Attorney, Agent, or Firm* — MacMillan, Sobanski & Todd, LLC

(57) ABSTRACT

A system combines hyperthermia and radiation treatments in a single treatment modality by using a radioactive seed having magnetic, ferromagnetic, or ferrimagnetic properties.

26 Claims, 68 Drawing Sheets
(64 of 68 Drawing Sheet(s) Filed in Color)

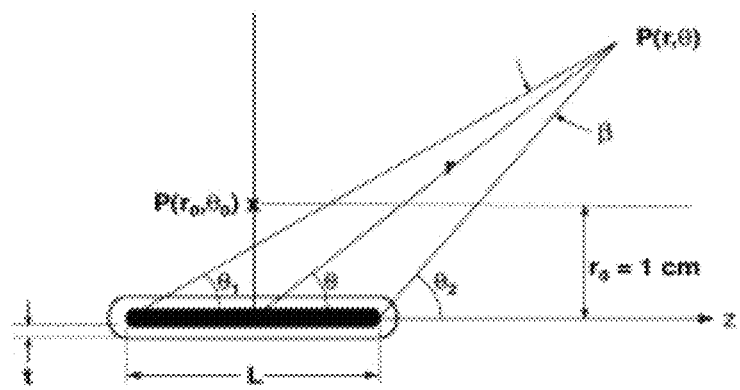
FIG. 1
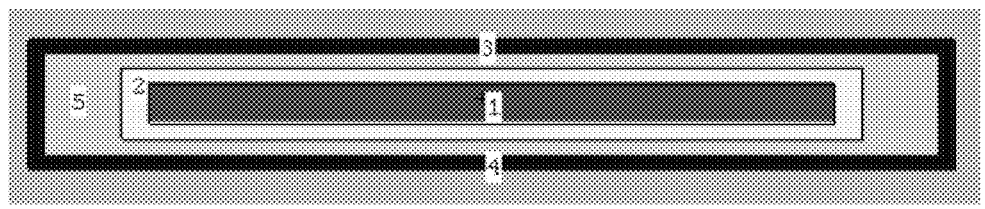
FIG. 2 - Prior Art
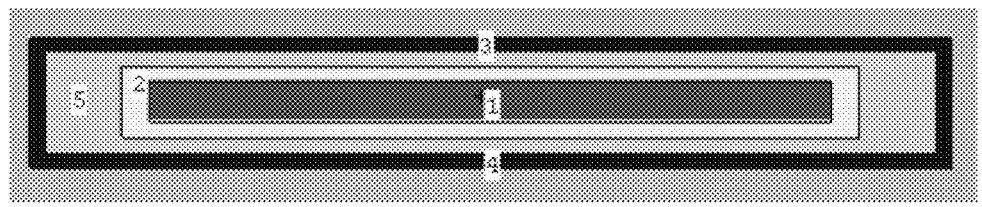
FIG. 3
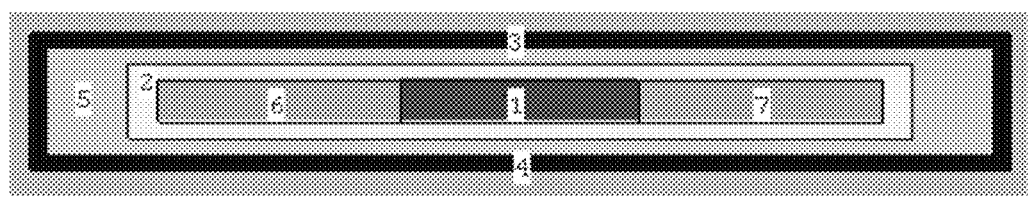
FIG. 4

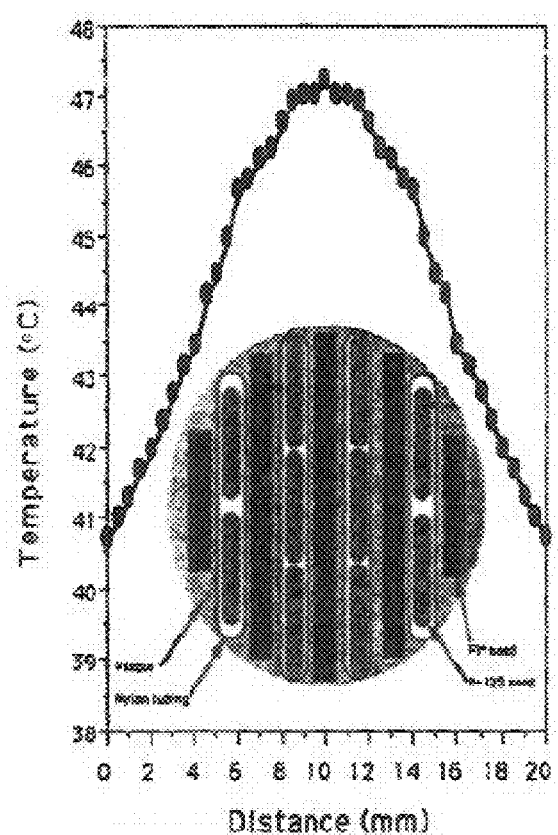
PRIOR ART FIG. 79
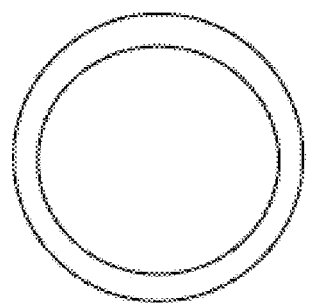
FIG. 80

CONCURRENT DELIVERY OF INTERSTITIAL THERMOBRACHYTHERAPY (HYPERTHERMIA AND BRACHYTHERAPY) IN THE TREATMENT OF CANCER

CROSS-REFERENCE TO RELATED APPLICATIONS

This is a continuation-in-part application of U.S. application Ser. No. 13/126,012, filed under 35 U.S.C. §371 on Apr. 26, 2011, now allowed; which is the national stage entry of international application PCT/US09/062430, filed under the authority of the Patent Cooperation Treaty on Oct. 28, 2009, published; which claims priority to U.S. Provisional Application No. 61/109,105, filed under 35 U.S.C. §111(b) on Oct. 28, 2008.

STATEMENT REGARDING SPONSORED RESEARCH

This invention was not made with government support. The government has no rights in this invention.

BACKGROUND OF THE INVENTION

There is no admission that the background art disclosed in this section legally constitutes prior art.

Brachytherapy, or radiotherapy, is a minimally invasive treatment where radioactive sources, often called seeds, are placed directly in and/or around the tumor site such that a prescribed radiation dose is delivered to the defined treatment area.

Hyperthermia, when used in addition to brachytherapy, can have a several-fold enhancement in the treatment of certain cancer types, especially if delivered concurrently with radiation therapy through interstitial ferromagnetic implants. One shortcoming, however, is that the resulting number of implants has to be dramatically increased to accommodate both types of seeds, resulting in more trauma to the patient.

There have been different methods used to deliver such treatments. In one method, brachytherapy and ferromagnetic hyperthermia implants are inserted separately, with the latter implants removed after the heat treatment is delivered.

Therefore, there is a need for an improved, more efficient and effective, and less traumatic to the patient, system for the delivery of interstitial concurrent thermobrachytherapy in the treatment of cancer.

SUMMARY OF THE INVENTION

In a broad aspect, there is provided a system for concurrent delivery of interstitial thermobrachytherapy (including both hyperthermia and brachytherapy) in the treatment of cancers.

In a first aspect, there is provided herein a therapeutic system which combines hyperthermia and radiation treatments in a single treatment modality that uses a radioactive interstitial thermobrachytherapeutic delivery system having magnetic properties.

In one aspect, there is provided herein a system for combining hyperthermia and radiation treatments in a single treatment modality. In some embodiments, the system is a therapeutic seed for combining hyperthermia and radiation treatments in a single treatment modality, comprising a radioactive material having magnetic properties.

In certain embodiments, the interstitial thermobrachytherapeutic delivery system includes one or more materials that possess ferromagnetic properties for hyperthermia delivery. In a particular embodiment, the radioactive material comprises one or more of I-125, Pd-103, or Cs-131 or other similar (in energy & half life) radionuclides.

In a particular aspect, the interstitial thermobrachytherapeutic delivery system comprises a seed-like system that has an inner section at least partially comprised of magnetic materials such as Ni—Cu, and an outer layer that can be at least partially composed of platinum or platinum-like materials. The seed can have a spherical, cylindrical, conical, frustoconical, ovoid, or bullet shape.

In another broad aspect, there is provided herein a method for the treatment of a patient in need thereof, the method comprising: determining one or more precise locations that need to be treated in the patient; and at least temporarily inserting one or more radioactive interstitial thermobrachytherapeutic delivery systems having magnetic properties into the patient. In certain embodiments, a hyperthermia segment of the treatment can be induced through the use of a strong magnetic field applied to the one or more seeds in the patient.

In a particular embodiment, the magnetic field strength can be on the order of about 2.5-10 kA/m, equivalent to about 30-120 gauss, and a frequency in the range of ~50-200 kHz is used. Further, in certain embodiments, the radiation dose can be delivered through brachytherapy as long as the seed is in location in the patient.

Also, in a particular embodiment, one or more thermometers can be at least temporarily introduced into the patient to record the temperature.

The method described herein provides a concurrent delivery of radiation dose and/or heat, and a substantially uniform distribution of temperature in a therapeutic regimen substantially suited for the patient.

In certain embodiments, the method is especially useful where the patient suffers from one or more types of cancers, such as, but not limited to: prostate, uterine, vaginal, uveal, and melanoma.

In another aspect, provided herein is a brachytherapy seed comprising a seed having within an interior space thereof a core comprising a ferromagnetic material, an electroplated conductive layer sheath on the surface of the core, and at least one layer comprising a radiation emission material that surrounds the core, where the radiation emission material comprises one or more of I-125, Pd-103, or Cs-131 radionuclides, and a metal shell surrounding the at least one layer comprising the radiation emission material.

In certain embodiments, the seed exhibits a Curie point in a therapeutic range of from about 49° C. to about 60° C. In certain embodiments, the electroplated conductive layer sheath comprises gold or copper. In certain embodiments, the electroplated conductive layer sheath has a thickness of about 15 microns. In certain embodiments, the ferromagnetic material comprises a ferrite. In certain embodiments, the ferromagnetic material comprises magnesium ferrite and copper. In certain embodiments, the ferromagnetic material comprises $Cu_{(0.5-x)}Mg_xZn_{0.5}Fe_2O_4$, wherein x ranges from 0 to 0.5. In particular embodiments, x is 0.25.

In certain embodiments, the ferromagnetic material comprises a manganese-zinc ferrite, such as $Mn_{(a)}Zn_{(1-a)}Fe_2O_4$, where a can be from 0 to 1. In particular embodiments, x is about 0.32.

In certain embodiments, the ferromagnetic material comprises NiCu. In certain embodiments, the ferromagnetic material comprises $Ni_{0.72}Cu_{0.28}$.

In certain embodiments, the electroplated conductive layer sheath is directly on the surface of the ferromagnetic material, and the at least one layer comprising a radiation emission material is directly on the electroplated conductive layer sheath. In certain embodiments, the shell comprises Ti.

In another aspect, provided herein is a system comprising one or more implantable medical seeds, each implantable medical seed of the one or more implantable medical seeds including a body having an interior space and having at least one outer surface; one or more ferromagnetic energy-emitting elements comprising a ferromagnetic material positioned within the interior space of each said implantable medical seed, the one or more ferromagnetic energy-emitting elements configured to at least intermittently deliver a therapeutic dose of heat to tissue proximate to the at least one outer surface of each said implantable medical seed; and one or more radiation-emitting elements positioned within the interior space of each of the implantable medical seeds, the one or more radiation-emitting elements forming at least one layer that completely surrounds the one or more ferromagnetic energy-emitting elements positioned within the interior space of each said implantable medical seed, the one or more radiation-emitting elements configured to deliver a therapeutic dose of radiation to tissue proximate to the at least one outer surface of each said implantable medical seed; where the system is adapted to include a controller configured to apply an electro-magnetic or magnetic field to the one or more implantable medical seeds.

In certain embodiments, the ferromagnetic energy-emitting element is covered with an electroplated conductive layer sheath. In particular embodiments, the electroplated conductive layer sheath comprises gold or copper. In particular embodiments, the electroplated conductive layer sheath has a thickness of about 15 microns. In certain embodiments, the ferromagnetic material comprises a ferrite. In certain embodiments, the ferromagnetic material comprises magnesium ferrite and copper. In certain embodiments, the ferromagnetic material comprises $Cu_{(0.5-x)}Mg_xZn_{0.5}Fe_2O_4$, wherein x ranges from 0 to 0.5. In particular embodiments, x is 0.25. In certain embodiments, the ferromagnetic material comprises NiCu. In certain embodiments, the ferromagnetic material comprises $Ni_{0.72}Cu_{0.28}$.

In another aspect, provided herein is a method of treating a subject in need thereof, the method comprising inserting at least one brachytherapy seed of claim 1 into the subject, and inducing a magnetic field applied to the brachytherapy seed to deliver a therapeutic dose of heat to tissue of the subject in proximity to the brachytherapy seed, wherein the brachytherapy seed also delivers a therapeutic dose of radiation to the tissue. In certain embodiments, the magnetic field strength can be on the order of about 2.5-10 kA/m, equivalent to about 30-120 gauss, and a frequency in the range of ~50-200 kHz is used.

Various objects and advantages of this invention will become apparent to those skilled in the art from the following detailed description of the preferred embodiment, when read in light of the accompanying drawings.

BRIEF DESCRIPTION OF THE FIGURES

The patent or application file contains at least one drawing executed in color. Copies of this patent or patent application publication with color drawing(s) will be provided by the Office upon request and payment of the necessary fee.

FIG. 1 shows the coordinate system used for AAPM TG-43 factors.

PRIOR ART FIG. 2 is a schematic diagram of Best Model 2301 $^{125}$I, where 1 is a Tungsten Radio-opaque Marker; 2 is a Carbon containing $^{125}$I; 3 is an Air compartment; 4 is an inner Titanium capsule; and, 5 is an outer Titanium capsule.

FIG. 3 is a schematic diagram of Thermobrachytherapy Seed#1, where 1 is a Ni—Cu Ferromagnetic Material; 2 is a Carbon containing $^{125}$I; 3 is an Air compartment; 4 is an inner Titanium capsule; and 5 is an outer Titanium capsule.

FIG. 4 is a schematic diagram of Thermobrachytherapy Seed#1, where 1 is a Tungsten Radioopaque Marker; 2 is a Carbon containing $^{125}$I; 3 is an Air compartment; 4 is an inner Titanium capsule; 5 is an outer Titanium capsule; 6 is a Left Ni—Cu Ferromagnetic Material; and 7 is a Right Ni—Cu Ferromagnetic Material.

PRIOR ART FIG. 79 illustrates a Prior Art seed where a middle of the seed has fairly larger temperature profile than the peripheral areas.

FIG. 80 is a schematic illustration of a radioactive interstitial thermobrachytherapeutic delivery system having magnetic properties.

PRIOR ART

In FIG. 88A, all plots of temperature rise and dose are normalized to 1 at the seed surface. FIG. 88B shows a comparison between normalized dose drop-off (black dashed line) and normalized drop-off of temperature rise (above normal body temperature) versus radial distance from the center of the TB seed (solid lines). All plots of temperature rise and dose in FIG. 88B are normalized to 1 at a radial distance of 1 cm. For comparison purposes, the normalized dose of a hypothetical point source with no attenuation or scatter is also plotted.

PRIOR ART

DETAILED DESCRIPTION

Figure 5:
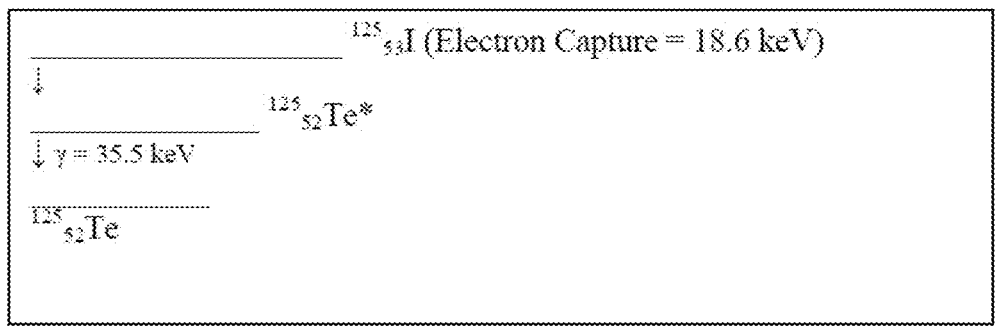
FIG. 5 is a diagram detailing the disintegration of $^{125}$I is shown in which shows the disintegration of 125 53I to 125 52Te releasing characteristic x-rays and γ-emission.

LDR brachytherapy is generally delivered to the prostate by means of numerous permanently-implanted cylindrical "seeds," each generally ~5 mm long and <1 mm in diameter. The seeds are implanted in an outpatient surgical procedure by means of hollow needles inserted with the guidance of images from a transrectal ultrasound probe, and contain a relatively short-lived radionuclide. This radionuclide is typically $^{125}$I or $^{103}$Pd, although $^{131}$Cs is used less frequently, and $^{198}$Au has formerly been used for this purpose. With the exception of $^{198}$Au, all these nuclides have similar average photon energies, albeit with substantially different half-lives. $^{125}$I, the most commonly-used nuclide in this application, has a half-life of 59.4 days, while $^{103}$Pd has a half-life of 17.0 days, and $^{131}$Cs has a half-life of 9.69 days. For more aggressive cancers, the nuclides with shorter half-lives may be used to deliver the dose more quickly, counteracting repopulation of tumor cells during therapy.

Hyperthermia is a means of providing adjuvant treatment to cancerous tissues, both by promoting cell death directly and by transiently sensitizing tissues to radiation. Depending on the type of hyperthermia being delivered, it typically involves raising the temperature of the target tissue to 40-48° C., for as short as 15 minutes for higher temperatures, and up to a few hours for lower temperatures. Provided hyperthermia is limited to target tissue, and the hyperthermia treatments are timed to take advantage of the radiosensitivity effect, it provides an ideal adjuvant therapy to radiation therapy.

Provided herein are thermo-brachytherapy (TB) seeds that can provide a simple means of adding hyperthermia to LDR prostate permanent implant brachytherapy. The TB seeds can provide an effective increase in dose delivered by LDR permanent implant brachytherapy, with minimal consequent increase in risk to organs at risk. The TB seeds can add an efficacious hyperthermia treatment to the already-established permanent prostate implant brachytherapy modality. By using many brachytherapy sources distributed within the tumor, each of which also generates heat as a thermoseed, a high interstitial hyperthermia source density may be obtained. This feature helps fulfill a criterion for successful implementation of thermoseed hyperthermia: that the source density be kept high in order to raise the entire volume of the tumor to a sufficient temperature.

In certain embodiments, the seed has an inner section at least partially comprising a magnetic material, and an outer layer that can be at least partially composed of platinum, titanium, or platinum-like, or titanium-like materials. In certain embodiments, the outer layer comprises palladium. In certain embodiments, the outer layer has a thickness from about 0.1 micron to about 20 microns. In certain embodiments, the seed has a spherical, cylindrical, conical, frustroconical, ovoid, or bullet shape or other suitable shape.

In certain embodiments, the magnetic material comprises Ni—Cu. In certain embodiments, the magnetic material comprises a Ni (70.4%)-Cu (29.6%) ferromagnetic alloy.

In another broad aspect, there is provided herein a method for the treatment of a patient in need thereof, comprising: determining one or more precise locations that need to be treated in the patient; and at least temporarily inserting one or more radioactive seeds into the patient.

In certain embodiments, a radiation dose is delivered through brachytherapy as long as the seed is in location in the patient and/or as long as the seed remains radioactive.

In certain embodiments, the method includes providing a concurrent delivery of radiation dose and/or heat, and a substantially uniform distribution of temperature in a therapeutic regimen substantially suited for the patient.

In another broad aspect, there is provided herein a method of treating a patient, comprising: positioning at least one seed within a patient; delivering a brachytherapeutic treatment from the seed to the patient; and simultaneously activating the seed, for at least a period of time, to deliver a thermotherapeutic treatment to the patient by exposing the seed to a magnetic field.

In certain embodiments, the thermotherapeutic treatment is intermittently delivered over a set period of time.

In another broad aspect, there is provided herein a method of treating a patient, comprising: positioning a seed capable of delivering a dose of radiation within the patient; and at least intermittently exposing the seed to a magnetic field sufficient to deliver heat to the patient in an area surrounding the seed.

In certain embodiments, the method includes exposing the seed to one or more oscillating magnetic fields that range between a maximum flux density between about 30 gauss and about 120 gauss. In certain embodiments, the seed is exposed to more than one oscillating magnetic field in more than one treatment period of time.

In certain embodiments, the magnetic field oscillates within the range of from about 50 kHz to about 200 kHz.

In certain embodiments, the seed exhibits a Curie point in a therapeutic range between about 41.5° C. and about 100° C.

In a particular aspect, the system described herein includes the use of a dual-seed system, that is, a radioactive seed having magnetic properties. In one embodiment, the dual-seed system can contain a radioactive material suitable for permanent seed such as I-125, Pd-103, or Cs-131 or other similar (in energy and half life) radionuclides. In one embodiment the dual-seed system can include one or more materials that possess ferromagnetic properties for hyperthermia delivery.

In certain embodiments, the seed includes a decay product comprised of an isotope layer. In certain embodiments, the isotope comprises one or more of I-125, Pd-103, or Cs-131 or other similar (in energy & half life) radionuclides.

One advantage of the dual-seed system is that two modalities of treatment can be combined in one delivery vehicle. The dual-seed system provides a more efficient method since two modalities can be designed to work in synergy with one another.

Another advantage of the dual-seed system is that there can now be a method for concurrent delivery of radiation dose and/or heat, a substantially uniform distribution of temperature, and substantially optimal design particularly suited for each individual patient.

In an additional aspect, there is provided herein a method for the treatment of cancers, such as, but not limited to: prostate cancer, vaginal cancer, choroidal melanoma, uveal melanoma, and other cancers.

The dual-seed delivery system also provides the clinician with an advanced technology in order to provide heat distribution and a monitoring system using the dual-system seeds.

In another aspect, there is provided herein a treatment planning method that can be used to determine the precise location and the number of dual-seed systems that need to be inserted in the target volume.

In certain embodiments, a hyperthermia segment of the treatment can be induced through the use of a strong magnetic field in the order of about 5000 A/m. In certain embodiments, useful ranges of 50-100 gauss can be used.

In use, one or more thermometers (placed in multiple locations) can be introduced to record the temperatures in the patient. In one embodiment, radiation dose is delivered through brachytherapy as long as the dual-seed systems are in place. It is to be understood that the uniformity and effectiveness of heat and dose distribution can depend, in part, on the treatment prescribed for the patient in need thereof.

Also, in certain embodiments, the dual-seed system can be used for permanent implantation in a patient in need thereof. In such embodiments, the radiation dose can be delivered continuously, while the hyperthermia can be delivered at determined segments, including times and dosages.

In other embodiments, provided is a seed designed for concurrent delivery of hyperthermia and brachytherapy to solid tumors. The seed combines a sealed radioactive source with a ceramic ferrite (i.e., a ceramic compound composed of a mixed oxide of iron and one or more other metals) core serving as a self-regulating hyperthermia source when placed in an alternating electromagnetic field. This is in contrast to clinically available technology where hyperthermic is delivered by microwave and ultrasound applicators, resulting in limited penetration and the inherent need for invasive thermometry.

The use of permanent combinational seed implants has several advantages over the existing approach of delivering the two modalities through separate implants, especially since multiple thermal treatments are typically required. A typical prostate implant procedure requires placing 80 to 110 seeds through 15-25 needles. The combination of I-125 and the ceramic ferrite materials in a single seed reduces trauma to the tissues compared to the circumstance where additional seeds are separately placed for magnetic heating. The spacing of seeds for radioactive implant is generally about 1 cm apart. With the Curie point of the thermo-brachytherapy seed selected by adjusting the percentage of the diluents in the alloy, optimized seed spacing which provides ideal isodose coverage provides ideal isothermal coverage through optimization of coil current and magnetic field frequency. This obviates the need for invasive thermometry and spares the patient additional trauma due to invasive thermometry. Additional advantages may be realized for patients who fail radiation and become resistant to hormonal manipulations, and systemic cytotoxic chemotherapy. Response rates to chemotherapy are known to be very poor in prostate cancer. Hyperthermia has been shown to enhance the effects of at least some cytotoxic drugs, including the common agents Cisplatin, Adriamycin, Melphalan, Cyclophosphamide, and Vincristine. Mechanisms of action are believed to include increased rates of alkylation, inhibition of repair of single strand DNA breaks, and enhanced drug uptake. Since the seeds remain in the patient permanently, and maintain their heat producing characteristics, they are readily available for fractionated heat treatments during cytotoxic chemotherapy.

If separately implanted thermal seeds have the same size as the radioactive seeds, they are indistinguishable in post-implant CT verification. Current techniques in post implant CT dosimetry require identification of the exact locations of implanted seeds through CT imaging to verify adequate radiation dose distribution within the tumor volume. Making thermal seeds significantly larger (at least to the size noticeable compared to radioactive seeds under CT image) is not feasible, as it would result in extended trauma to the patient due to increased prostate perforation and other complications. Additionally, it would require utilization of a separate set of needles, as well as increase procedure time, entailing prolongation of patient anesthesia.

In some embodiments, the seed is a modified version of a standard LDR permanent implant seed, with a ferromagnetic or ferrimagnetic core within the sealed capsule containing the radioactive material. A seed can include a ferromagnetic or ferrimagnetic core having an electroplated conductive metal layer sheath (e.g., a thin layer of gold or copper having a thickness of about 15 microns) on the surface thereof, surrounded by at least one layer comprising a radiation emission material (such as I-125, Pd-103, or Cs-131 radionuclides), all encased in a metal shell, such as a Ti shell. An external oscillating magnetic field produces heat within the seed primarily due to generation of eddy currents, thus providing interstitial radiation and hyperthermia from the same implant. Temperature regulation can be achieved by strategically selecting the Curie temperature of the ferromagnetic or ferrimagnetic material such that the magnitude of the eddy currents in the seed abruptly decreases at the temperature setpoint, decreasing the thermal power production of the seed.

Ferromagnetic materials are those which exhibit parallel alignment of moments resulting in large net magnetization even in the absence of a magnetic field. Ferromagnetic materials are characterized by spontaneous magnetization and the existence of a magnetic ordering temperature. The Curie temperature ($T_C$) is the temperature at which thermal energy overcomes the electronic exchange forces in ferromagnets and produces a randomizing effect. Below the Curie temperature, the ferromagnet is ordered, and above it, the ferromagnet is disordered. The elements Fe, Ni, and Co, and many alloys thereof, are ferromagnetic materials. Non-limiting examples of ferromagnetic materials are iron oxides, Cu—Mg—Zn alloys, Ni—Cu—Zn alloys, NiCu, NiCr, NiSi, PdNi, PdCo, and FePt.

Ferrimagnetic materials are those in which the magnetic moments of two sublattices are not equal and result in a net magnetic moment. Ferrimagnetic materials therefore exhibit the hallmarks of ferromagnetic behavior (namely, spontaneous magnetization, Curie temperatures, hysteresis, and remanence). However, ferro- and ferrimagnetic materials have different magnetic ordering. A non-limiting example ferrimagnetic material is magnetite. For clarity, the terms "ferromagnetic material" and "ferrite" as used herein may refer to either ferromagnetic materials or ferrimagnetic materials, unless otherwise specified.

In some embodiments, the ferromagnetic material is a Cu—Mg—Zn ferrite. High density, high permeability Cu—Mg—Zn ferrites can be prepared using oxalate precursors, with various $Mg^{2+}$ contents represented as $Cu_{(0.5-x)}Mg_xZn_{0.5}Fe_2O_4$, where x ranges from 0 to 0.5. In certain non-liming examples, x is selected from 0, 0.20, 0.25, or 0.40. These ferrites generally have superior magnetic properties, a single spinel phase, and a cubic lattice. The magnetic properties of this ferrite system are correlated with high density and grain structure. The Mg—Cu—Zn ferrites have magnetic properties similar to those of Ni—Cu—Zn ferrites, and are more economical.

Figure 95:
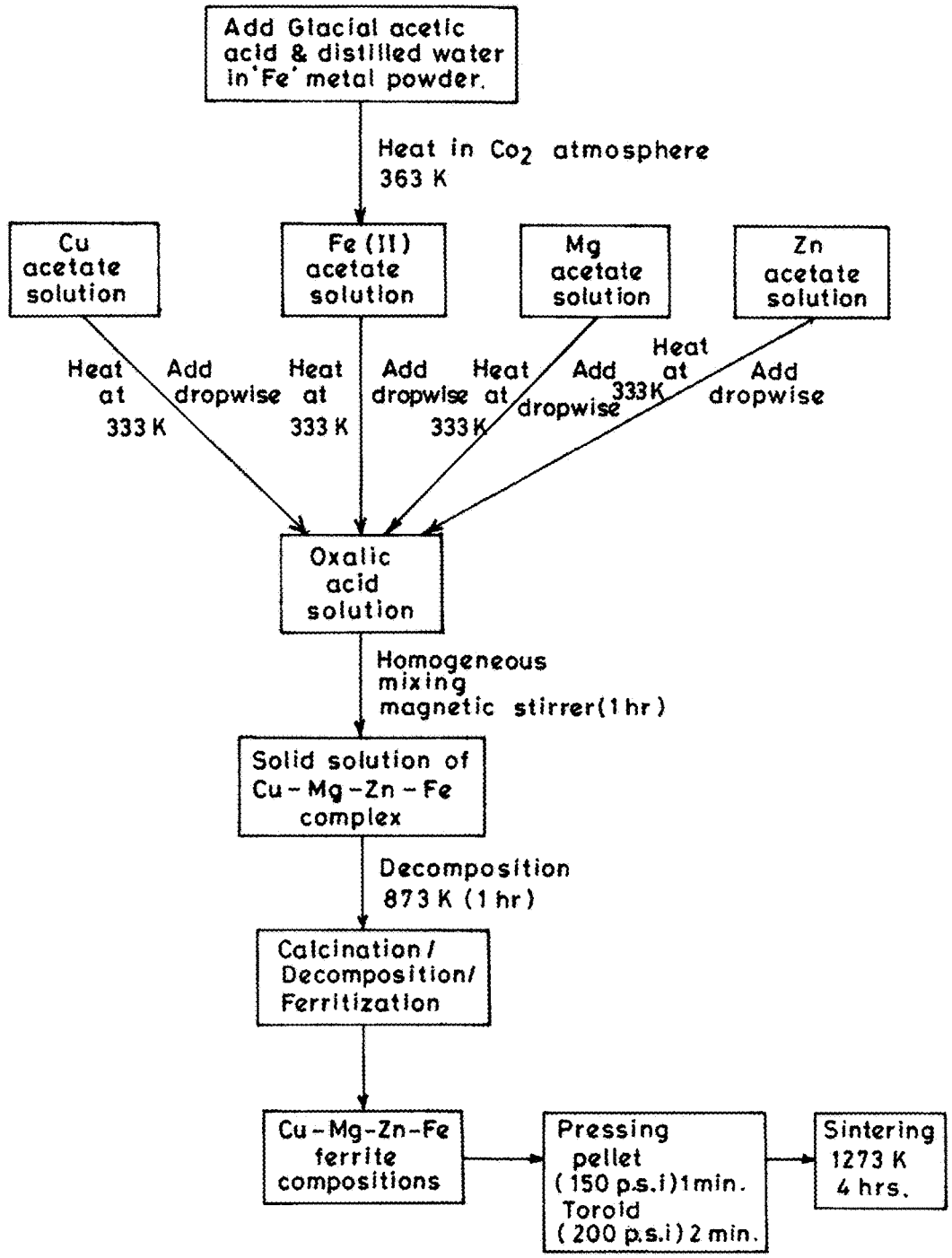
FIG. 95 shows a flow chart showing a non-limiting example route of synthesis for a Cu—Mg—Zn ferrite system.

In some embodiments, the ferromagnetic core of a seed comprises $Cu_{(0.5-x)}Mg_xZn_{0.5}Fe_2O_4$, where x ranges from 0 to 0.5. Methods of synthesizing such $Cu_{(0.5-x)}Mg_xZn_{0.5}Fe_2O_4$ ferrites are known. In one non-limiting example of producing a ferromagnetic material, Fe(II) acetate is prepared by adding glacial acetic acid (slight excess) to the required quantity of AR grade Fe metal powder. To avoid oxidation of Fe(II) to Fe(III), the reaction is carrier out in a $CO_2$ atmosphere instead of an $N_2$ atmosphere. To maintain the desired stoichiometry, the required quantities of copper acetate, zinc acetate, and magnesium acetate are dissolved in doubly distilled water, warmed at 333 K. The prepared Fe(II) acetate solution and Cu-, Mg-, and Zn-acetate solutions (total metal ion concentration=0.45 M) are drop-wise added to 0.60 M oxalic acid solution to precipitate the required oxalate complex. The oxalic acid is continuously stirred during addition of acetate solutions for 1 h for homogenous mixing until its completion. The solution with yellow crystalline precipitate is stirred for 1 h at its boiling point, digested for 10 min, and allowed to cool to room temperature. The supernatant liquid/solution is filtered off. The precipitate is washed with doubly distilled water and dried in an oven at 373 K. Oxalate complexes having the general composition $Cu_{(0.5-x)}Mg_xZn_{0.5}Fe_2(C_2O_4)_3 \cdot nH_2O$ are thus synthesized, yielding the desired ferrite compositions on subsequent decomposition. The formation of ferrite (i.e., ferritization) and decomposition processes occur simultaneously in the temperature range of 482-643 K as nascent MOs (where M=$Mg^{2+}$, $Ni^{2+}$, $Zn^{2+}$, $Mn^{2+}$, or $Co^{2+}$) are highly reactive and therefore ferritization occurs at such a low temperature in the range of 599-643 K. The ferritization temperature generally varies with increasing $Mg^{2+}$ content. However, complete decomposition of oxalate complexes to the desired ferrite composition can be ensured by calcining the oxalate complex at 873 K. Microparticles can be obtained from this process with a relatively narrow particle size distribution. The average particle size generally increases with an increase in processing temperature and $Mg^{2+}$ content. This synthetic method is depicted in the flow chart in PRIOR ART FIG. 95. The resulting particles can be utilized as ferromagnetic core materials in the seeds described herein.

In order for an interstitial hyperthermia treatment to be successful, the target should contain closely-spaced sources that generate enough power to raise the tissue to a sufficiently high temperature, despite the significant effects of heat loss due to blood perfusion. A ferrite and conductive outer layer generates high power with a rapid Curie transition. The sheath can be either a metallic tube or a coating on the core.

The high blood perfusion rate (BPR) within the prostate facilitates the use of the ferrite and conductive outer layer configuration for the seed cores. The Examples herein describe the results of computational analyses of the thermal properties of the ferrite-based TB seed in modeled patient-specific anatomy, as well as studies of the interseed and scatter (ISA) effect. Experimental and computational studies have been conducted to optimize the configuration of the TB (as well as hyperthermia-only) seeds and to quantitatively assess their ability to heat and irradiate defined, patient-specific targets. Experiments were performed with seed-sized ferromagnetic samples in tissue-mimicking phantoms heated by an industrial induction iv heater. The magnetic and thermal properties of the seeds were studied computationally in the finite element analysis (FEA) solver COMSOL Multiphysics, modeling realistic patient-specific seed distributions derived from previous LDR permanent prostate implants. Various modifications of the seeds' design were evaluated. The calculated temperature distributions were analyzed by generating temperature-volume histograms, which were used to quantify coverage and temperature homogeneity for a range of blood perfusion rates, as well as for a range of seed Curie temperatures and thermal power production rates. The impact of the interseed attenuation and scatter (ISA) effect on radiation dose distributions of this seed was also quantified by Monte Carlo studies in the software package MCNP5.

Experimental and computational analyses agree that the seeds may heat a defined target with safe and attainable seed spacing and magnetic field parameters. These studies show the use of a ferrite-based ferromagnetic core within the seeds delivers hyperthermia of acceptable quality even for the high rate of blood perfusion in prostate tissue. The loss of radiation coverage due to the ISA effect of distributions of TB and HT-only seeds may be rectified by slightly increasing the prescribed dose in standard dose superposition-based treatment planning software. A systematic approach of combining LDR prostate brachytherapy with hyperthermia is thus described.

Interstitial magnetic hyperthermia thermoseeds typically are made not to exceed a particular temperature by means of strategic selection of the Curie point, that is, the temperature at which they lose their ferromagnetic (or ferrimagnetic) properties, becoming paramagnetic. As this change greatly decreases the magnetization of the seed and therefore the magnitude of the eddy currents, it also greatly decreases the power production, permitting temperature self-regulation. In some embodiments, the ferromagnetic material-containing seeds described herein exhibit a Curie point in a therapeutic range of from about 49° C. to about 55° C.

In sum, provided is a dual-modality thermo-brachytherapy (TB) seed as a simple and effective combination of hyperthermia and radiation therapy. Heat is generated from a ferromagnetic or ferrimagnetic core within the seed, which produces Joule heating by eddy currents. A strategically-selected Curie temperature provides thermal self-regulation. In order to obtain a uniform and sufficiently high temperature distribution, additional hyperthermia-only (HT-only) seeds can be used in vacant spots within the needles used to implant the TB seeds; this permits a high seed density without the use of additional needles.

EXAMPLES

The present invention is further defined in the following Examples, in which all parts and percentages are by weight and degrees are Celsius, unless otherwise stated. It should be understood that these Examples, while indicating preferred embodiments of the invention, are given by way of illustration only.

Example I

Materials & Methods:
American Association of Physicists in Medicine Task Group-43 (AAPM TG-43). The AAPM TG-43 Report published in March 2004 is a revised AAPM protocol for brachytherapy dose calculations. The revised model is different from the original model in the following ways:

Air Kerma Strength (SK):
The new model has a revised definition of air-kerma strength. The original AAPM definition of the air kerma strength did not account for a low-energy cutoff (S).

The lower energy parameter is needed to discriminate against low energy photons, mostly characteristic x-rays from exterior capsules, that increase the air kerma rate (Ks(d)) without contributing significantly to doses at distances greater than 0.1 cm in tissue. The cut-off is usually 5 keV for low-energy brachytherapy source. This correction was necessary to ensure that the dose rate being recorded was accurately representative of the energy contribution from the radioactive sources.

Apparent Activity ($A_{app}$):
The new model eliminated apparent activity for specification of the strength of a source. Apparent activity is the activity from an unfiltered point source that has the same air-kerma strength as an encapsulated source. It was found that using $A_{app}$ for reporting source strength specification suffers from problems. In order to specify source strength, vendors had used $A_{app}$. Vendors convert air kerma strength to $A_{app}$ by dividing it by an assumed exposure rate constant r6 (x). The vendor supplied $A_{app}$ is multiplied by the assumed r6 (x) to get Absorbed Dose. r6 (x) has no meaningful physical role in the dosimetry of output calibrated source. Thus, quantities such as this might mislead the user if they use the wrong r6 (x). Therefore, Aapp is no longer used for specifying source strength. Air Kerma Strength has taken its place and is used for all aspects of dose calculations.

Anisotropy Constant ($\Phi$an) Versus One-Dimensional Anisotropy Function ($\Phi_{an}$ (r))

The earlier anisotropy constant was eliminated in favor of distance dependent one-dimensional anisotropy function. $\Phi_{an}$ (r) is the ratio of the solid angle-weighted dose rate, averaged over the entire 47C steradian space, to the dose rate at the same distance 'r' on the transverse plane.

$$\Phi_{an}(r) = \frac{\int_0^\pi \dot{D}(r, \theta)\sin(\theta)d\theta}{2\dot{D}(r, \theta)} \quad (1)$$

The change from $^{(D}$an to $\Phi_{an}$ (r) was suggested to compensate for inadequacies in the treatment planning system. It is important to use the $\Phi_{an}$ (r) to minimize dose-calculation errors at small distances, for example, r<1 cm.

Recommendations on Extrapolating Data to Varied Distances:
The revised TG43 Report listed that care must be taken in evaluating dose rates at distances falling outside the range of tabulated data (especially at r<0.5 cm). At shorter radii, points at small polar angles near 0° and 180° are located inside the source capsule. The outcome from this is that the anisotropy function cannot be defined over the full interval from 0° to 90°. The TG-43 formalism breaks down at r<L/2. It has been recommended that it is essential when working with small distances to use the same geometry function and length of the source for evaluating absorbed dose as when used in the Monte Carlo data. Often the anisotropy function and radial function will exhibit nonphysical properties due to breaking down of the line source very near the source.

Correction in Minor Inconsistencies in the Original Protocol:

There are now consistent guidelines for use of point- and line-source geometries as applicable. Also, the report recommends a unified approach to compare reference dose distributions derived from different investigators to develop a single evaluated consensus data.

FIG. 1 shows the coordinate system used for AAPM TG-43 factors.

P (r0, 00)=>Reference Point of interest at r0=1 cm 00=90°
P (r, 0)=>Point of interest
L=>Length of the source
0=>Angle from the center of the source to the point of interest
$\theta_1$ & $\theta_2$=>Angles from the end of the source to the point of interest
β=>Angle formed at the Point of Interest by the tips of the source
r=>radii from center of the source to the Point of Interest
t=>Thickness of the Titanium capsule.

The AAPM TG-43 Report is a task group report recommending the various factors required in commissioning a clinical seed. There are several factors that have been recommended that ensure the dose function and anisotropy factors for seeds used in clinical trials.

Air-Kerma Strength (SK):

Air Kerma Strength is the air kerma rate (Ks(d)) due to photons greater than the cut-off energy (S) at distance (d), multiplied by the square of this distance ($d^2$)

$$SK = Ks(d)d2 \tag{2}$$

An important designation to be noted is that the term "d" is the distance from the source center to the point where the dose rate is being measured. This distance is required to be on the transverse plane of the source.

Dose—rate (D):

Dose rate, per se, is not a highlighted parameter in the TG 43 factors. However, it is used in the calculation of the dose rate constant Dose rate, like air kerma strength, is measured at reference positions (0=90°, r=1 cm) on the transverse plane. These measurements are taken in the medium designated by the phantom (water or solid water).

$$\dot{D} = \frac{D}{time} \tag{3}$$

Dose-Rate Constant (Λ):

Dose rate constant in water is the ratio of dose-rate at the reference position, [P(r0, 00)] and the air kerma strength [SK].

$$\Lambda = \frac{\dot{D}(r_0, \theta_0)}{S_K} \tag{4}$$

Dose-rate constant depends on both the radionuclide being used and the source model being considered. It is also affected by the internal design of the source.

Geometry Function (G(r, θ)):

The purpose of the geometry function is for improving accuracy for dose rates when discrete points are used for interpolating the data.

This is done using the inverse square law correction that takes into account an approximate model of the distribution of radioactivity within the source.

$$G_P(r, \theta) = r^{-2} \rightarrow \text{for point source approximation} \tag{5}$$

$$G_L(r, \theta) = \frac{\beta}{Lr\sin\theta} \text{ if } \theta \neq 0° \rightarrow \text{for line source approximation} \tag{6}$$

$$\text{or, } = (r^2 - L^2/4)^{-1} \text{ if } \theta = 0° \rightarrow \text{for line source approximation} \tag{7}$$

Units of $G_P$ or $G_L$ are $cm^{-2}$

Radial Dose Function g(r):

The need for the radial dose function is to account for dose fall-off on the transverse-plane due to photon scatter and attenuation. This does not include the dose fall-off that has already been included by the geometry function.

$$gx(r) = \frac{\dot{D}(r, \theta_0) * Gx(r_0, \theta_0)}{\dot{D}(r_0, \theta_0) * Gx(r, \theta_0)} \tag{8}$$

The subscript X refers to either point-source (P) or line-source (L). Most commercial treatment planning systems use a fifth order polynomial fit to the collected g (r) data.

2D Anisotropy Function F (r, θ):

2D anisotropy function is important to understand the variation in dose as the polar angle changes to the transverse plane.

$$F(r, \theta) = \frac{\dot{D}(r, \theta) * Gx(r, \theta_0)}{\dot{D}(r, \theta_0) * Gx(r, \theta)} \tag{9}$$

The value of F (r, 0) usually decreases as a) r decreases, b) as θ approaches 0° C. or 180° C.) as encapsulation thickness increases and/or d) as photon energy decreases.

Correction Factor and Wide Angle Free-Air Chamber (WAFAC) Anomaly

National Institute of Standards and Technology (NIST) located a shift in well chamber coefficients for certain batch of seeds. Further investigations led to more seeds having a downward in the air kerma strengths of several sources. NIST completed a number of measurements comparing the results in WAFAC and in the re-entrant chamber. The results indicate a combined ratio for the sources of 0.897±0.028. The conclusion is that the WAFAC air-kerma strengths measured in 1999 were too large by 2% to 7%, and required dose rate constant measurements normalized to NIST 1999 SK calibrations to be revised accordingly.

General Monte Carlo N-Particle Transport Code (MCNP) Version 5 (MCNP5)

In the MCNP5 code there are options for the operator to select from a choice of tallies that pertain to the particular problem that is being dealt with. They are normalized to be per starting particle except for a few special cases with criticality sources. It is important to note that tallies can be made for any cells and surfaces and do not require special geometry to be created. Any quantity in the form below can be tallied.

$$C = \int \Phi(E) f(E) d(E) \quad (10)$$

Where, $\Phi(E)$ is the energy dependent fluence, f(E) is any product or summation of quantities in the cross sectional libraries or a response function provided by the user. The basic MCNP tallies depends on the final answer that individual is interested in.

The Table below lists some of the tallies and their uses.

TABLE 1

Tallies used in MCNP5 designate depend on the point of interest for the user.

| Tally#1 | Tally#2 | Tally#3 | Description |
| --- | --- | --- | --- |
| F1:N or | F1:P or | F1:E | Surface current |
| F2:N or | F2:P or | F2:E | Surface flux |
| F4:N or | F4:P or | F4:E | Track length estimate of cell flux |
| F5a:N or | F5a:P or | | Flux at a point or ring detector |
| F6:N or | F6:P or | F1:N, P | Track length estimate of energy deposition |
| F7:N | | | Track length estimate of fission energy deposition |
| F68:N or | F8:P or | F8:E or F8:P, E | Pulse height tally |

For the purpose of this research paper, the F6 tally type is used. This tally directly calculates the dose at a given point per photon by determining the average energy deposition over a tally cell in the unit Mev/g.

$$H_t = \frac{\rho_a}{m} \int de \int dt \int dV \int d\Omega \sigma_t(E) H(E) \psi(r\hat{\Omega}, E, t) \quad (11)$$

Where, $H_t$=total energy deposition in a cell (MeV/g); $\rho_a$=atom density (atom/barn-cm); m=cell mass (g); r, n,E, t=particle position vector (cm), direction vector, energy (MeV), and time (sh, sh=$10^{-9}$ S); $\sigma_t$=microscopic total cross-section (barns); H(E)=heating number (MeV/collision).

Monte Carlo results are obtained by sampling possible random walks and assigning a value for each walk. Random walks produce a range of score depending on the tally selected and the variance reduction chosen. There is also an important distinction between the precision and accuracy chosen in Monte Carlo calculations. Precision is the uncertainty in mean caused by statistical uncertainty. Accuracy is a measure of how close the expected value of the mean is to the true value being estimated. Uncertainties in Monte Carlo calculations refer only to the precision of the result and not to the accuracy. In order to get good statistical results, it is imperative to use a significant number of histories. Increasing the number of interactions, improves the statistical score. However, in doing so, the time required for computations also increases and increases the duration of the computations.

An introduction of the procedure involved in the development of the MCNP output data follows. An input file needs to be created in order to produce the output file with the dose values. There are 5 different steps that need to be created:

1—Cell Cards

This card creates the cells based on different surfaces. The cell card allows the orientation of different surfaces to one another and allows in the formation of the overall geometry. This is also the card where the density of the atom/compound/mixture of the surface is designated.

2—Surface Cards

The surface card creates surfaces and promotes the dimensions of the different materials being used in the creation of the cells. Dimensions of the detector are also added here.

3—Material Cards

This is where the different materials are designated and the atomic number and atomic masses recorded. A negative sign before an atomic fraction suggests fraction designation by weight and a positive sign indicates fraction by atomic number.

4—Data Cards

Data card is where the source is specified, including the radius and length of the source, the axis it is placed on and the probability of the detection. Energy along with the probability from the radioactive source is also designated here.

5—Tally Cards

The tally card follows the data card and it accounts for the Multiplier (FM6) in this project. Also the number of histories or the number of particles to be started is recorded in this section. MCNP5 is a versatile program that is easy to use. It includes a powerful general source, geometry tally plotters, variance reduction techniques, a flexible tally structure and an extensive collection of cross-section data. It is an important code that creates a particle and tracks it's interaction through different materials, through cells composed of varied surfaces, as it ventures it ways through the geometry under question. It should also be noted that the MCNP5 code can be used for various reasons and uses. The code in this project is used to detect dose rate at selected distances and angles from the source.

The Three Modeled Seeds: A) Best Model 2301 $^{125}$I Seed:

This seed has an inner radio-opaque Tungsten marker, followed by a Carbon containing $^{125}$I. The outer layer consists of an inner and outer Titanium capsule.

FIG. 2 is a schematic diagram of Best Model 2301 $^{125}$I, where 1 is a Tungsten Radio-opaque Marker; 2 is a Carbon containing $^{125}$I; 3 is an Air compartment; 4 in an inner Titanium capsule; and, 5—is an outer Titanium capsule.

Dimensions for the seed are as follows:

Tungsten marker (cell 1): length—3.7 mm, diameter—0.25 mm

Carbon containing $^{125}$I (cell 2)—length—4 mm, diameter—0.45 mm, thickness—0.1 mm (0.15 mm at edges)

Air compartment (cell 3)—length—4.84 mm, diameter—0.64 mm, thickness—0.095 mm (0.42 mm at edges)

Inner Titanium Capsule (cell 4)—length—4.92 mm, diameter—0.72 mm, thickness—0.04 mm Outer Titanium Capsule (cell 5)—length—5.0 mm, diameter—0.8 mm, thickness—0.04 mm After the overall values were compared and were within an acceptable (5-6%), two models of thermobrachytherapy seeds were created. It is also important to note that the vendor's Best Model seed has a slight curvature to the I-125 compartment at the ends. However, the dimensions for the curvature are unavailable in any literature and therefore, the curvature was not incorporated into the calculated modeled seeds. This will cause very slight deviation in the results from the calculated values at the ends of the seed.

Thermobrachytherapy Seed#1

Thermobrachytherapy Seed#1 is similar in geometry to the Best Model 2301 seed with the radiographic marker replaced by a ferromagnetic material. The ferromagnetic material is 70.4% Nickel and 29.6% Copper. The dimensions stay the same.

FIG. 3 is a schematic diagram of Thermobrachytherapy Seed#1, where 1 is a Ni—Cu Ferromagnetic Material; 2 is a Carbon containing $^{125}$I; 3 is an Air compartment; 4 is an inner Titanium capsule; and 5 is an outer Titanium capsule.

Dimensions for the seed are as follows:

Ferromagnetic marker (cell 1): length—3.7 mm, diameter—0.25 mm

Carbon containing $^{125}$I—length (cell 2)—4 mm, diameter—0.45 mm, thickness—0.1 mm (0.15 mm at edges)

Air compartment (cell 3)—length—4.84 mm, diameter—0.64 mm, thickness—0.095 mm (0.42 mm at edges)

Inner Titanium Capsule (cell 4)—length—4.92 mm, diameter—0.72 mm, thickness—0.04 mm Outer Titanium Capsule (cell 5)—length—5.0 mm, diameter—0.8 mm, thickness—0.04 mm Thermobrachytherapy Seed#2

Thermobrachytherapy Seed#2 has both a ferromagnetic component and radio-opaque Tungsten marker in the seed. The ferromagnetic seed is similar to thermobrachytherapy seed#2 with 70.4% Nickel and 29.6% Copper.

The outer compartments are the same as previous two seeds. However, the inner radio-opaque marker is smaller in size covering the middle of the seed and two ferromagnetic components are added to the two ends of the seed. The dimension of the ferromagnetic-radio-opaque-ferromagnetic component stays the same as the original radio-opaque (Best Model 2301 $^{125}$I) or the ferromagnetic component (thermobrachytherapy seed#1).

FIG. 4 is a schematic diagram of Thermobrachytherapy Seed#1, where 1 is a Tungsten Radioopaque Marker; 2 is a Carbon containing $^{125}$I; 3 is an Air compartment; 4 is an inner Titanium capsule; 5 is an outer Titanium capsule; 6 is a Left Ni—Cu Ferromagnetic Material; and 7 is a Right Ni—Cu Ferromagnetic Material.

Dimensions for the seed are as follows:

Tungsten marker (cell 1): length—1.23 mm, diameter—0.25 mm

Left Ferromagnetic marker (cell 6): length—1.23 mm, diameter—0.25 mm

Right Ferromagnetic marker (cell 7): length—1.23 mm, diameter—0.25 mm

Carbon containing $^{125}$I—length (cell 2)—4 mm, diameter—0.45 mm, thickness—0.1 mm (0.15 mm at edges)

Air compartment (cell 3)—length—4.84 mm, diameter—0.64 mm, thickness—0.095 mm (0.42 mm at edges)

Inner Titanium Capsule (cell 4)—length—4.92 mm, diameter—0.72 mm, thickness—0.04 mm Outer Titanium Capsule (cell 5)—length—5.0 mm, diameter—0.8 mm, thickness—0.04 mm Radioactive Material:

$^{125}$I is used as the radioactive material. It is useful because of its short half life with a T½ of 59.4 days[32]. As a result it is convenient for storage. Furthermore, its low 28 keV energy allows for less shielding. A diagram detailing the disintegration of $^{125}$I is shown in FIG. 5 which shows the disintegration of 125 53I to 125 52Te releasing characteristic x-rays and γ-emission.

$^{125}$I Decays via electron capture (100% of the time) to first excited state of $^{125}$Te. This in turn de-excites spontaneously to the ground state with the emission of a 35.5-keV γ-emission accounting for 7% of the released x-rays, the production of characteristic x-rays, in the range of 27-35 keV, account for the other 93% produced to electron capture and internal conversion. On an average, 1.4 photons are emitted per disintegration of $^{125}$I.

The low energy electrons (maximum energy of 35 keV) emitted can be filtered by iodine and by the thin encapsulation materials. The nuclear data for $^{125}$I brachytherapy sources are listed in Table 2.

TABLE 2[11]

| Nuclear Data for $^{125}$I for brachytherapy dosimetry | |
|---|---|
| Photon energy (keV) | Photons per disintegration |
| 27.202 | 0.406 |
| 27.472 | 0.757 |
| 30.98 | 0.202 |
| 31.71 | 0.0439 |
| 35.492 | 0.0668 |

The Gamma Constant $(T_{5kev})$ = 0.0355 μGym$^2$h$^{-1}$Bq$^{-1}$

It should be noted that, as stated in AAPM TG-43 report[11], the tungsten k-shell binding energy exceeds the maximum energy emitted during $^{125}$I decay and therefore, no characteristic k-shell x-rays are produced and L-shell x-rays are absorbed in the encapsulation.

Ferromagnetic Material

The ferromagnetic material is an alloy of 70.4% Nickel and 29.6% Copper. This alloy has a curie temperature of 48.2° C. Nickel has an atomic number of 28, atomic mass of 59 amu while Copper's atomic number 29 and atomic mass 64 amu. Together, the density of the material is 8.92 g/cm$^3$.

The density of the material is higher than the bone. Therefore, it is deciphered that the Ni—Cu alloy will show under kilo-voltage beams as an identifier and could possibly replace the radio-opaque marker.

Methods:

Hyperthermia and Brachytherapy have a synergy effect; this property was introduced to be combined together to kill cancer cells.

General Monte Carlo N-Particle Transport Code version 5 (MCNP5) was undertaken as a useful resource to create and simulate the seed. This program allows the creation and tracking of particle(s) from their initiation to their transportation through materials.

An in-depth study of the MCNP5 code was performed. This took the form of understanding the various commands associated with creating the files, comprehending the cell, surface and data commands and becoming aware of the various atomic mixtures and material commands. Understanding the input and output files was also extensively studied. This started by creating one generic cell with one compartment, followed by a seed with several sub-compartments (or cells). After perfecting this method, method for two and then multiple seeds, at a required distance from one another, was learned. It was also ensured that the system, as created, did produce particle or particles. It was also imperative to confirm that the particles were being created in the source and not from any other compartments. Detectors were also created and methods to form multiple detectors were learned through the Transfer (TRCL) command at the required coordinates, distances and angles. This proved to be vital during the course of simulating dose rates from the modeled seeds.

The Best Model 2301 $^{125}$I Seed was modeled. After modeling the seed, the TG-43 factors were measured for the seed in the simulated program. The values were compared to Book values. This was done to ensure that the modeling of the seed was done accurately. When the values were within an acceptable range of 5-6% for both solid and liquid water, two thermobrachytherapy seeds were modeled and TG-43 factors were calculated for the models to study the closeness of the newly developed seed to the Best Model seed already in clinical practice. The values for the two thermobrachytherapy seeds were calculated in both liquid water and liquid water phantoms.

Calculating Geometry Function for the Anisotropy Function at Different Angles θ:

Cosine Law:

$$a^2 = b^2 + c^2 - 2bc\cos(\alpha) \quad (12)$$

where, $b$ = Radial Distance
$\alpha = \theta$

Sine Law:

$$\frac{\sin\alpha}{a} = \frac{\sin\beta}{b} = \frac{\sin\gamma}{c} \quad (13)$$

$a$ => get from cosine law $c$ => length of half of the source ($L/2$)

Figure 6:
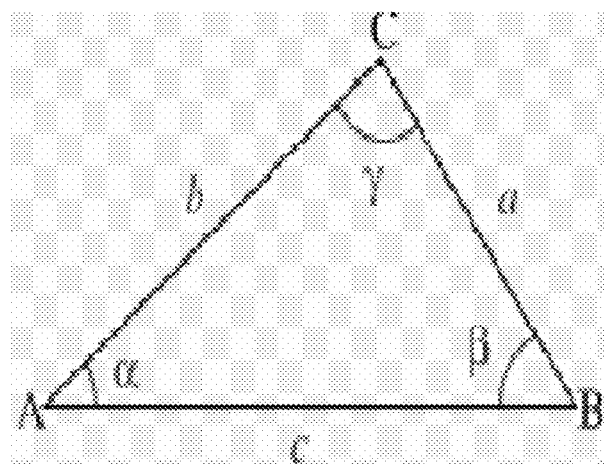
FIG. 6 is a schematic illustration showing the β covers two triangles and has to be repeated for the second triangle.

This will give angle γ for one triangle. The β covers two triangles and has to be repeated for the second triangle, as shown in FIG. 6.

Figure 7:
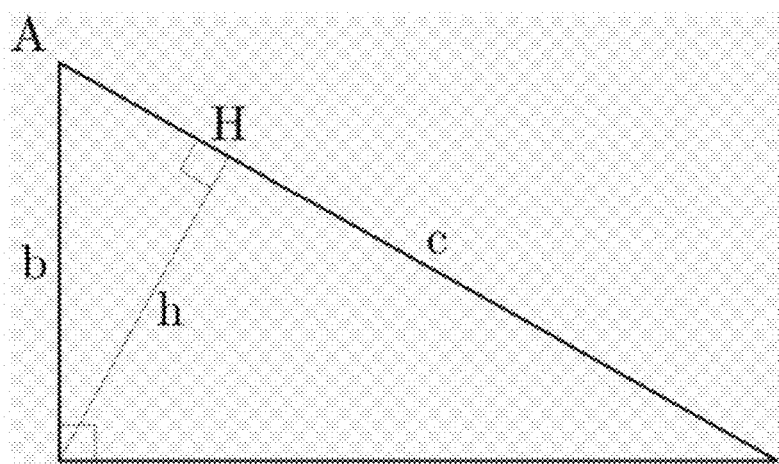
FIG. 7 is a schematic illustration used to calculate the coordinates of the detectors.

Calculating Coordinates for the placements of detectors at varied angles:

$$x \text{ coordinate} = r*\sin\theta \quad (14)$$

$$z \text{ coordinate} = r*\cos\theta \quad (15)$$

where, r=radial distance (or h from FIG. 7 used to calculate the coordinates of the detectors).

θ=angle (taken from center of the source) at which the detectors are placed

Error Calculations:

The T-43 discusses three sources of error: a) uncertainty due to uncertainty of the cross-sections; b) Uncertainty from the seed geometric model; and, c) Statistical uncertainty due to the Monte Carlo technique. However, in the present example, the statistical uncertainty is the uncertainty that is taken into account for all measurements. Two different error calculations are done Calculating Error Percentage:

Error percentage is taken between two values to find out how one deviates from the other.

$$\text{Error Percentage} == \frac{(Calculauted \text{ Value} - \text{Book Value})}{\text{Book Value}} \quad (16)$$

Calculating Standard Deviation:

Standard Deviation is required to add the error bars on the data points and to provide the error range for the values.

$$\left(\frac{\sigma_Z}{Z}\right)^2 = \left(\frac{\sigma_X}{X}\right)^2 + \left(\frac{\sigma_Y}{Y}\right)^2 \quad (17)$$

where,

X=>value in the numerator

σX=>standard deviation for X

Y=>value in the denominator

σY=>standard deviation for Y

Z=>Final answer from X/Y

σZ=>standard deviation for Z

Results

The three sets of seeds (Best Model 2301 $^{125}$I seed, Thermobrachytherapy seed#1, Thermobrachytherapy seed#2) were modeled on MCNP5. TG-43 factors were calculated in both liquid and solid water and recorded for the three sets and exported to Excel for further computations.

1) Best Model 2301 $^{125}$I Seed in liquid water.

i) Dose Rate (D):

Dose Rate was calculated for seed at 1 cm on the transverse plane (θ=90°) of the source (from the center of the source) in water. Therefore, for this measurement the phantom was taken to be liquid water since it is the liquid water measurement.

Table 3 shows the Dose Rate for Best Model 2301 $^{125}$I Seed in liquid water calculated using Monte Carlo. The dose rate recorded is 0.237±4.84*10$^{-3}$ cGy*sec$^{-1}$*Ci$^{-1}$

TABLE 3

Dose Rate for Best Model 2301 $^{125}$I Seed in liquid water calculated using Monte Carlo

| Calculated Dose Rate (cGy * sec$^{-1}$ * Ci$^{-1}$) | Book Value (Meigooni et al) | Error |
|---|---|---|
| 0.236993 | N/A | N/A | ii) Air Kerma Strength (SK):

Air Kerma Strength was calculated for the seed again at 1 cm on the transverse plane of the source (from the center of the source) but it was measured in air. Therefore, the material inside the phantom was taken as air.

Also, the 0.897 WAFAC correction factor (as discussed in the Materials & Methods section) is used for SK. Table 4 shows the Air Kerma Strength for Best Model 2301 $^{125}$I Seed in Air calculated using Monte Carlo. The Air Kerma Strength recorded is 0.224±4.98*10$^{-3}$ cGy*cm$^2$sec$^{-1}$*Ci$^{-1}$

TABLE 4

Air Kerma Strength for Best Model 2301 $^{125}$I Seed in Air calculated using Monte Carlo

| Calculated Air Kerma Strength (cGy * cm$^2$sec$^{-1}$ * Ci$^{-1}$) | Book Value (Meigooni et al) | Error |
|---|---|---|
| 0.224332 | N/A | N/A | iii) Dose Rate Constant (Λ):

Dose rate constant is calculated using equation #4. In order to calculate it, the ratio of the dose rate and air kerma strength is taken. Table 5 shows the Monte Carlo calculated Dose Rate Constant for Best Model 2301 $^{125}$I Seed in liquid water. The error is calculated by using equation #. Therefore, the error between the measured value and the book value is 4.6%. The measured value of Dose Rate Constant is 1.056±0.0055 cGy*h$^{-1}$*U$^{-1}$

TABLE 5

Monte Carlo calculated Dose Rate Constant for
Best Model 2301 $^{125}$I Seed in liquid water

| Calculated Dose Rate (Gy * h$^{-1}$ * U$^{-1}$) | Book Value (Meigooni et al) (Gy * h$^{-1}$ * U$^{-1}$) | Error |
|---|---|---|
| 1.05644 | 1.01 | 0.04598 | iv) Radial Function:

Calculation of the radial function is a two-fold process.

a) Geometry Function

Using equations #6 & #7 the geometry function was calculated for each distance along the transverse plane from the center of the seed at varied distances.

Table 6 shows the Geometry Function calculated for the seeds where the Geometry Function is independent of the components of the seed. It depends on the geometry/dimensions of the source component of the seed.

TABLE 6

Geometry Function calculated for the seeds (Please note that Geometry Function is independent of the components of the seed. It depends on the geometry/dimensions of the source component of the seed.)

| Transverse distance (r) cm | Geometry Function G(r, θ) cm$^{-2}$ |
|---|---|
| 0.1 | 55.34268 |
| 0.15 | 30.90395 |
| 0.2 | 19.63125 |
| 0.25 | 13.48885 |
| 0.3 | 9.801083 |
| 0.4 | 5.795581 |
| 0.5 | 3.8041 |
| 0.6 | 2.680029 |
| 0.7 | 1.988054 |
| 0.75 | 1.736857 |
| 0.8 | 1.531238 |
| 0.9 | 1.214714 |
| 1 | 0.986798 |
| 1.5 | 0.441485 |
| 2 | 0.249099 |
| 2.5 | 0.159493 |
| 3 | 0.110808 |
| 3.5 | 0.081516 |
| 4 | 0.062384 |
| 4.5 | 0.049248 |
| 5 | 0.039961 |
| 5.5 | 0.032996 |
| 6 | 0.027775 |
| 6.5 | 0.023625 |
| 7 | 0.020441 |
| 7.5 | 0.017799 |
| 8 | 0.015596 |
| 8.5 | 0.013857 |
| 9 | 0.012312 |
| 9.5 | 0.011113 |
| 10 | 0.010034 | b) Radial Dose Function Using the Geometry Function

Radial Dose Function was calculated using equation #8 incorporating the geometry function calculated in part a) above. Table 7 shows the Radial Dose Function calculated at the transverse plane for the Best Model 2301 $^{125}$I Seed in liquid water using Monte Carlo.

TABLE 7

Radial Dose Function calculated at the transverse plane for the Best Model 2301 $^{125}$I Seed in liquid water using Monte Carlo

| Transverse distance (r) cm | Radial Dose Function g(r) | Book Value | Error |
|---|---|---|---|
| 0.1 | 0.945629 | 1.033 | −0.08458 |
| 0.15 | 0.972143 | 1.029 | −0.05525 |
| 0.2 | 1.004325 | 1.028 | −0.02303 |
| 0.25 | 0.978685 | 1.027 | −0.04704 |
| 0.3 | 0.999578 | 1.027 | −0.0267 |
| 0.4 | 0.99135 | 1.027 | −0.03471 |
| 0.5 | 1.02054 | 1.028 | −0.00726 |
| 0.6 | 0.963113 | 1.034 | −0.06856 |
| 0.7 | 0.931244 | 1.036 | −0.10112 |
| 0.75 | 0.959788 | 1.03 | −0.06817 |
| 0.8 | 0.935891 | 1.024 | −0.08604 |
| 0.9 | 1.038878 | 1.013 | 0.025546 |
| 1 | 1.000001 | 1 | 5.07E−07 |
| 1.5 | 0.926622 | 0.938 | −0.01213 |
| 2 | 0.847695 | 0.866 | −0.02114 |
| 2.5 | 0.762436 | 0.79 | −0.03489 |
| 3 | 0.688111 | 0.707 | −0.02672 |
| 3.5 | 0.607313 | 0.635 | −0.0436 |
| 4 | 0.536531 | 0.555 | −0.03328 |
| 4.5 | 0.482933 | 0.488 | −0.01038 |
| 5 | 0.407078 | 0.427 | −0.04666 |
| 5.5 | 0.360958 | 0.372 | −0.02968 |
| 6 | 0.299346 | 0.32 | −0.06454 |
| 6.5 | 0.268061 | 0.285 | −0.05944 |
| 7 | 0.239495 | 0.248 | −0.0343 |
| 7.5 | 0.203286 | 0.215 | −0.05448 |
| 8 | 0.181816 | 0.187 | −0.02772 |
| 8.5 | 0.154299 | 0.16 | −0.03563 |
| 9 | 0.132667 | 0.142 | −0.06573 |
| 9.5 | 0.10157 | 0.123 | −0.17422 |
| 10 | 0.099486 | 0.103 | −0.03412 |

Figure 8:
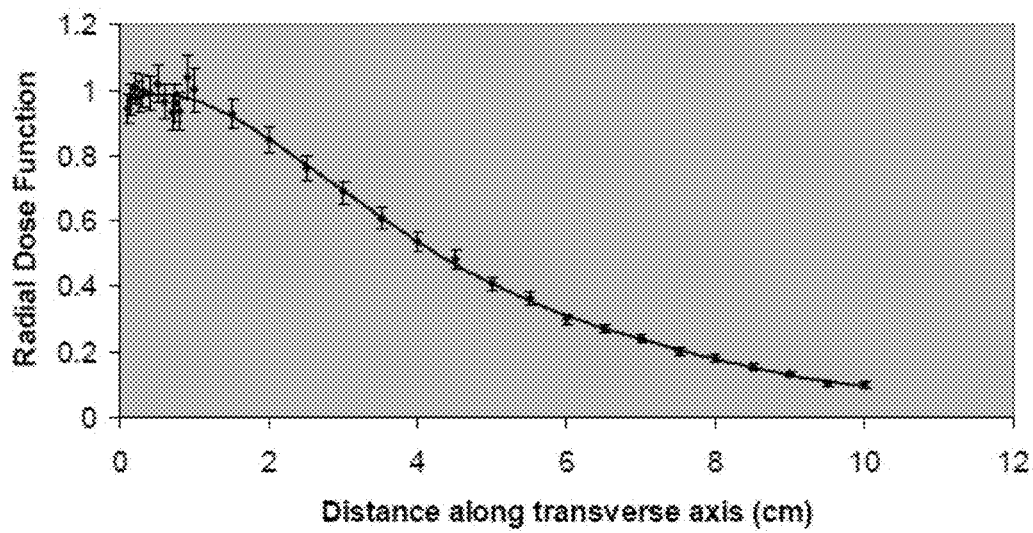
FIG. 8 is a graph for radial dose function versus distance on the transverse plane fits, in which illustrates Radial Dose Function calculated in Liquid Water for the Best Model 2301 $^{125}$I Seed.

The graph for radial dose function versus distance on the transverse plane fits as show in FIG. 8 which illustrates Radial Dose Function calculated in Liquid Water for the Best Model 2301 125$_I$ Seed. The curve is fitted to 5th order polynomial Function.

iv) Anisotropy Function:

Calculation of the radial function is a three-fold process.

a) Calculating Geometry Function

Equations #12 & #13 is used to calculate (f for the various angles which in turn is used to calculate the Geometry Function at various angles.

Table 8a shows the Geometry Function calculated for the various angles for the Best Model 2301 $^{125}$I Seed at 1, 2, 3 and 4 cm where the Geometry Function is independent of the components of the seed.

TABLE 8a

Geometry Function calculated for the various angles for the Best Model 2301 $^{125}$I Seed at 1, 2, 3 and 4 cm (Please note that Geometry Function is independent of the components of the seed)

| Angle | GF at 1 cm | GF at 2 cm | GF at 3 cm | GF at 4 cm |
|---|---|---|---|---|
| 0 | 1.0416667 | 0.25252525 | 0.111607 | 0.06265 |
| 5 | 1.041096617 | 0.250143349 | 0.111730696 | 0.062535837 |
| 10 | 1.040481322 | 0.253225575 | 0.11115182 | 0.062679598 |
| 15 | 1.037567568 | 0.251812259 | 0.111729408 | 0.062742519 |
| 20 | 1.035774854 | 0.251927997 | 0.111826267 | 0.062822551 |
| 25 | 1.031323877 | 0.251643026 | 0.111382979 | 0.062652926 |
| 30 | 1.0391475 | 0.2521525 | 0.111389167 | 0.06282 |
| 35 | 1.022223432 | 0.251565767 | 0.111469222 | 0.062511433 |
| 40 | 1.017690513 | 0.251030327 | 0.11149365 | 0.062757582 |
| 45 | 1.012568953 | 0.250828324 | 0.111273574 | 0.06262995 |
| 50 | 1.008045039 | 0.250587467 | 0.111055809 | 0.062646867 |
| 55 | 1.003534799 | 0.250084707 | 0.111148759 | 0.062454594 |
| 60 | 0.999445727 | 0.249861432 | 0.11116147 | 0.062465358 |

TABLE 8a-continued

Geometry Function calculated for the various angles for the Best Model 2301 $^{125}$I Seed at 1, 2, 3 and 4 cm (Please note that Geometry Function is independent of the components of the seed)

| Angle | GF at 1 cm | GF at 2 cm | GF at 3 cm | GF at 4 cm |
|---|---|---|---|---|
| 65 | 0.995767108 | 0.249904801 | 0.111068801 | 0.0624762 |
| 70 | 0.992700798 | 0.249451463 | 0.111073582 | 0.062536902 |
| 75 | 0.989917184 | 0.249285714 | 0.111546325 | 0.06243433 |
| 80 | 0.988538071 | 0.249127538 | 0.110870981 | 0.06244797 |
| 85 | 0.98813253 | 0.249223143 | 0.110960509 | 0.062415286 |
| 90 | 0.99072375 | 0.24909875 | 0.1108075 | 0.06238375 |

Table 8b shows the Geometry Function calculated for the various angles for the Best Model 2301 $^{125}$I Seed at 5, 6 and 7 cm where the Geometry Function is independent of the components of the seed.

TABLE 8b

Geometry Function calculated for the various angles for the Best Model 2301 $^{125}$I Seed at 5, 6 and 7 cm (Please note that Geometry Function is independent of the components of the seed)

| Angle | GF at 5 cm | GF at 6 cm | GF at 7 cm |
|---|---|---|---|
| 0 | 0.0401 | 0.02781 | 0.020425 |
| 5 | 0.040022936 | 0.027599149 | 0.020726163 |

TABLE 8b-continued

Geometry Function calculated for the various angles for the Best Model 2301 $^{125}$I Seed at 5, 6 and 7 cm (Please note that Geometry Function is independent of the components of the seed)

| Angle | GF at 5 cm | GF at 6 cm | GF at 7 cm |
|---|---|---|---|
| 10 | 0.041117816 | 0.027579023 | 0.02041564 |
| 15 | 0.040087838 | 0.027791988 | 0.020452978 |
| 20 | 0.04030848 | 0.027637671 | 0.020591583 |
| 25 | 0.040221631 | 0.027673857 | 0.020479146 |
| 30 | 0.0399605 | 0.02792 | 0.020441429 |
| 35 | 0.039976916 | 0.027867305 | 0.020411896 |
| 40 | 0.04002916 | 0.027816874 | 0.020450733 |
| 45 | 0.04010785 | 0.027766973 | 0.020362447 |
| 50 | 0.039980091 | 0.027811412 | 0.020421251 |
| 55 | 0.039949634 | 0.027698413 | 0.020393337 |
| 60 | 0.039997979 | 0.027790368 | 0.020437974 |
| 65 | 0.039965508 | 0.0277672 | 0.020429872 |
| 70 | 0.039912234 | 0.027845745 | 0.020353913 |
| 75 | 0.040012164 | 0.02777368 | 0.02038672 |
| 80 | 0.039948985 | 0.027754653 | 0.020436367 |
| 85 | 0.039945783 | 0.027813128 | 0.020398379 |
| 90 | 0.0399605 | 0.027774583 | 0.020441429 | b) Calculating Coordinates for Detectors

Equations #14 & #15 are used to calculate the x and z coordinates in order to place detectors for measuring the dose rates at various angles. Table 9 shows the Coordinates for detectors as calculated for the listed angles.

TABLE 9

Coordinates for detectors as calculated for the listed angles

| Angle | Axis | 1 cm | 2 cm | 3 cm | 4 cm | 5 cm | 6 cm | 7 cm |
|---|---|---|---|---|---|---|---|---|
| 0 | x | 0 | 0 | 0 | 0 | 0 | 0 | 0 |
| 0 | z | 1 | 2 | 3 | 4 | 5 | 6 | 7 |
| 5 | x | 0.087 | 0.174 | 0.261 | 0.348 | 0.435 | 0.522 | 0.609 |
| 5 | z | 0.996 | 1.992 | 2.988 | 3.948 | 4.98 | 5.976 | 6.972 |
| 10 | x | 0.1736 | 0.348 | 0.5208 | 0.6944 | 0.868 | 1.044 | 1.218 |
| 10 | z | 0.985 | 1.97 | 2.955 | 3.94 | 4.925 | 5.91 | 6.895 |
| 15 | x | 0.259 | 0.518 | 0.777 | 1.036 | 1.295 | 1.554 | 1.813 |
| 15 | z | 0.966 | 1.932 | 2.898 | 3.864 | 4.83 | 5.796 | 6.762 |
| 20 | x | 0.342 | 0.684 | 1.026 | 1.368 | 1.71 | 2.052 | 2.394 |
| 20 | z | 0.94 | 1.88 | 2.82 | 3.76 | 4.7 | 5.64 | 6.58 |
| 25 | x | 0.4226 | 0.8452 | 1.2678 | 1.6904 | 2.113 | 2.5356 | 2.9582 |
| 25 | z | 0.906 | 1.812 | 2.718 | 3.624 | 4.53 | 5.436 | 6.342 |
| 30 | x | 0.5 | 1 | 1.5 | 2 | 2.5 | 3 | 3.5 |
| 30 | z | 0.866 | 1.732 | 2.598 | 3.464 | 4.33 | 5.196 | 6.062 |
| 35 | x | 0.574 | 1.148 | 1.722 | 2.296 | 2.87 | 3.444 | 4.018 |
| 35 | z | 0.819 | 1.638 | 2.4597 | 3.276 | 4.095 | 4.914 | 5.733 |
| 40 | x | 0.643 | 1.286 | 1.929 | 2.572 | 3.215 | 3.858 | 4.501 |
| 40 | z | 0.766 | 1.532 | 2.298 | 3.064 | 3.83 | 4.596 | 5.362 |
| 45 | x | 0.707 | 1.414 | 2.121 | 2.828 | 3.535 | 4.242 | 4.949 |
| 45 | z | 0.707 | 1.414 | 2.121 | 2.828 | 3.535 | 4.242 | 4.949 |
| 50 | x | 0.766 | 1.532 | 2.298 | 3.064 | 3.83 | 4.596 | 5.362 |
| 50 | z | 0.643 | 1.286 | 1.929 | 2.572 | 3.215 | 3.858 | 4.501 |
| 55 | x | 0.819 | 1.638 | 2.4597 | 3.276 | 4.095 | 4.914 | 5.733 |
| 55 | z | 0.574 | 1.148 | 1.722 | 2.296 | 2.87 | 3.444 | 4.018 |
| 60 | x | 0.866 | 1.732 | 2.598 | 3.464 | 4.33 | 5.196 | 6.962 |
| 60 | z | 0.5 | 1 | 1.5 | 2 | 2.5 | 3 | 3.5 |
| 65 | x | 0.906 | 1.812 | 2.718 | 3.624 | 4.53 | 5.436 | 6.342 |
| 65 | z | 0.4226 | 0.8452 | 1.2678 | 1.6904 | 2.113 | 2.5356 | 2.9582 |
| 70 | x | 0.94 | 1.88 | 2.82 | 3.76 | 4.7 | 5.64 | 6.58 |
| 70 | z | 0.342 | 0.684 | 1.026 | 1.368 | 1.71 | 2.052 | 2.394 |
| 75 | x | 0.966 | 1.932 | 2.898 | 3.864 | 4.83 | 5.796 | 6.762 |
| 75 | z | 0.259 | 0.518 | 0.777 | 1.036 | 1.295 | 1.554 | 1.813 |
| 80 | x | 0.985 | 1.97 | 2.955 | 3.94 | 4.925 | 5.91 | 6.895 |
| 80 | z | 0.174 | 0.348 | 0.5208 | 0.6944 | 0.868 | 1.044 | 1.218 |
| 85 | x | 0.996 | 1.992 | 2.988 | 3.948 | 4.98 | 5.976 | 6.972 |
| 85 | z | 0.087 | 0.174 | 0.261 | 0.348 | 0.435 | 0.522 | 0.609 |
| 90 | x | 1 | 2 | 3 | 4 | 5 | 6 | 7 |
| 90 | z | 0 | 0 | 0 | 0 | 0 | 0 | 0 | c) Calculating Anisotropy Function Using the Data Accumulated in Tables 7 and 8

The Anisotropy Function was calculated using all the factors listed in equation #9. Tables 8a and 8b were used to calculate the Geometry Function at various angles. Table 9 was used to find the coordinates needed to place the detectors at the various angles and radial distances. Table 10a shows the Monte Carlo calculated Anisotropy Function of the Best Model 2301 $125_I$ Seed in liquid water for Radial Distances of 1 cm and 2 cm. A comparison between book values is also calculated.

TABLE 10a

Monte Carlo calculated Anisotropy Function of the Best Model 2301 $^{125}$I Seed in liquid water for Radial Distances of 1 cm and 2 cm. A comparison between book values is also calculated.

| Angle | AF at 1 cm | Book Value | Error | AF at 2 cm | Book Value | Error |
|---|---|---|---|---|---|---|
| 0 | 1.016857 | 0.867 | 0.172846 | 0.986817 | 0.854 | 0.155523 |
| 5 | 0.857865 | 0.724 | 0.184896 | 0.810992 | 0.72 | 0.126377 |
| 10 | 0.677306 | 0.653 | 0.037222 | 0.724824 | 0.671 | 0.080214 |
| 15 | 0.725931 | 0.721 | 0.006839 | 0.718106 | 0.734 | −0.021655 |
| 20 | 0.7474 | 0.785 | −0.047899 | 0.819861 | 0.794 | 0.03257 |
| 25 | 0.803672 | 0.85 | −0.054504 | 0.853352 | 0.847 | 0.007499 |
| 30 | 0.821182 | 0.9 | −0.087576 | 0.858304 | 0.89 | −0.035614 |
| 35 | 0.890772 | 0.946 | −0.05838 | 0.821552 | 0.926 | −0.112794 |
| 40 | 0.906355 | 0.982 | −0.077032 | 0.940464 | 0.954 | −0.014189 |
| 45 | 0.953106 | 1.001 | −0.047847 | 0.883125 | 0.978 | −0.09701 |
| 50 | 0.959333 | 1.014 | −0.053593 | 0.903854 | 0.992 | −0.088857 |
| 55 | 0.978387 | 1.024 | −0.044544 | 0.944112 | 1.003 | −0.058712 |
| 60 | 0.98857 | 1.03 | −0.040223 | 0.963059 | 1.01 | −0.046476 |
| 65 | 0.988487 | 1.033 | −0.043091 | 0.971319 | 1.019 | −0.046792 |
| 70 | 0.986962 | 1.036 | −0.047334 | 0.984718 | 1.026 | −0.040236 |
| 75 | 1.031196 | 1.039 | −0.007511 | 1.000409 | 1.029 | −0.027786 |
| 80 | 1.009489 | 1.1 | −0.082283 | 1.019994 | 1.03 | −0.009715 |
| 85 | 0.998686 | 1 | −0.001314 | 0.976201 | 1.022 | −0.044813 |
| 90 | 0.996037 | 1 | −0.003963 | 1 | 1 | 0 |

Figure 9:
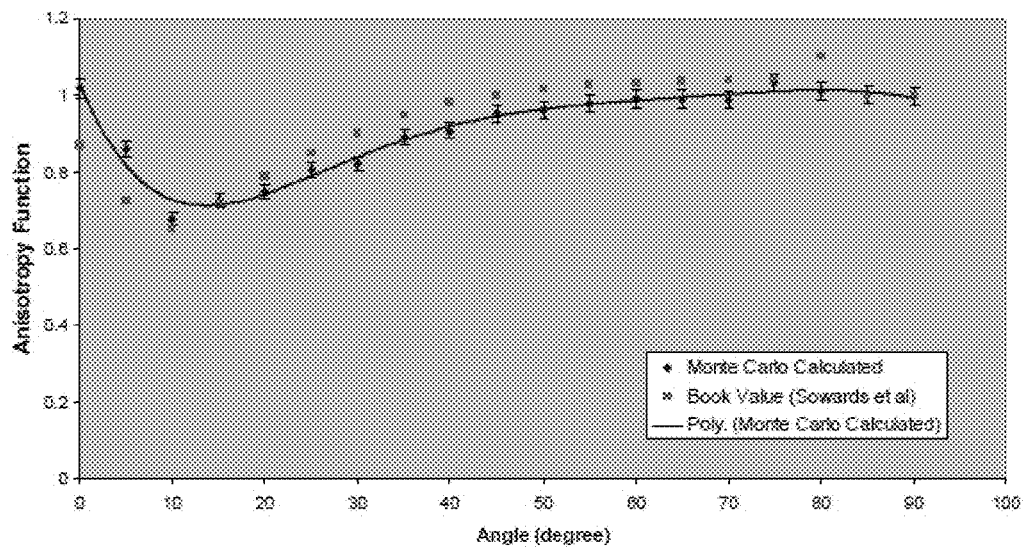
FIG. 9 shows the Comparison between the calculated and book value data Anisotropy Function for Best Model 2301 $^{125}$I in liquid water at 1 cm radii.

FIG. 9 shows the Comparison between the calculated and book value data Anisotropy Function for Best Model 2301 $^{125}$I in liquid water at 1 cm radii. The plot is fitted with a 6th order polynomial function.

Figure 10:
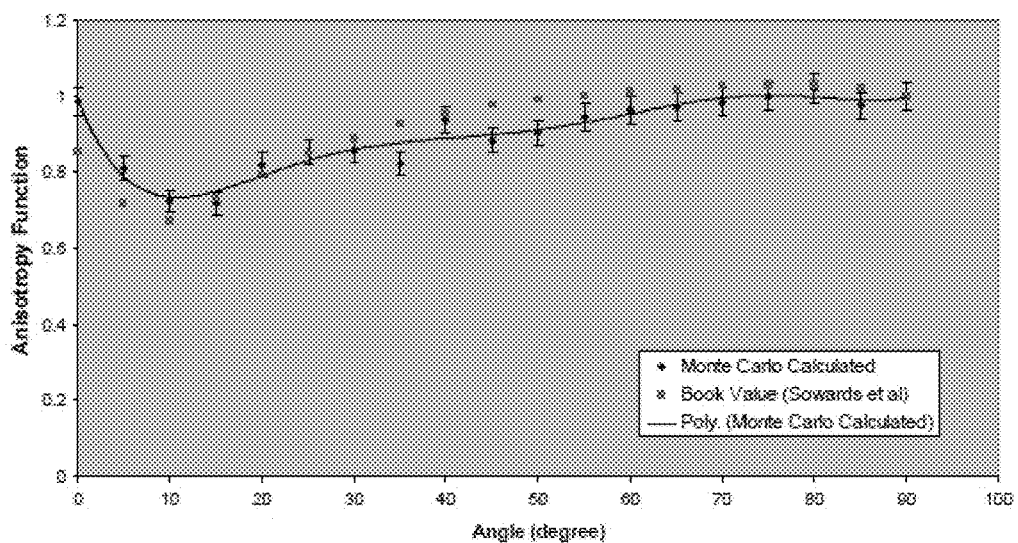
FIG. 10 shows the Comparison between the calculated and book value data Anisotropy Function for Best Model 2301 $^{125}$I in liquid water at 2 cm radii.

FIG. 10 shows the Comparison between the calculated and book value data Anisotropy Function for Best Model 2301 $^{125}$I in liquid water at 2 cm radii. The plot is fitted with a 6th order polynomial function Table 10b shows the Monte Carlo calculated Anisotropy Function of the Best Model 2301 $125_I$ Seed in liquid water for Radial Distances of 3 cm and 4 cm. A comparison between book values is also calculated.

TABLE 10b

Monte Carlo calculated Anisotropy Function of the Best Model 2301 $^{125}$I Seed in liquid water for Radial Distances of 3 cm and 4 cm. A comparison between book values is also calculated.

| Angle | AF at 3 cm | Book Value | Error | AF at 4 cm | Book Value | Error |
|---|---|---|---|---|---|---|
| 0 | 1.081703 | 0.922 | 0.173213 | 1.067157 | 0.902 | 0.183101 |
| 5 | 0.827588 | 0.726 | 0.139928 | 0.856189 | 0.728 | 0.176084 |
| 10 | 0.750467 | 0.699 | 0.07363 | 0.849553 | 0.727 | 0.168574 |
| 15 | 0.833466 | 0.756 | 0.102468 | 0.762809 | 0.779 | −0.020784 |
| 20 | 0.808948 | 0.809 | −6.37E−05 | 0.843573 | 0.814 | 0.03633 |
| 25 | 0.872956 | 0.852 | 0.024597 | 0.917008 | 0.863 | 0.062582 |
| 30 | 0.930988 | 0.885 | 0.051963 | 0.921985 | 0.892 | 0.033615 |
| 35 | 0.953275 | 0.919 | 0.037296 | 0.927006 | 0.918 | 0.009811 |
| 40 | 0.987268 | 0.947 | 0.042521 | 0.928846 | 0.939 | −0.010813 |
| 45 | 0.95516 | 0.968 | −0.013264 | 0.992994 | 0.976 | 0.017412 |
| 50 | 0.973073 | 0.985 | −0.012109 | 0.968645 | 0.991 | −0.022558 |
| 55 | 1.008446 | 0.997 | 0.011481 | 1.028106 | 1.004 | 0.92401 |

TABLE 10b-continued

Monte Carlo calculated Anisotropy Function of the Best Model 2301 $^{125}$I Seed in liquid water for Radial Distances of 3 cm and 4 cm. A comparison between book values is also calculated.

| Angle | AF at 3 cm | Book Value | Error | AF at 4 cm | Book Value | Error |
|---|---|---|---|---|---|---|
| 60 | 0.988973 | 1.009 | −0.019849 | 1.000959 | 1.007 | −0.005999 |
| 65 | 1.000178 | 1.012 | −0.011682 | 1.017048 | 1.009 | 0.007976 |
| 70 | 1.030136 | 1.016 | 0.013913 | 1.020551 | 1.023 | −0.002394 |
| 75 | 1.018382 | 1.018 | 0.000375 | 1.009032 | 1.017 | −0.007835 |
| 80 | 0.960588 | 1.019 | −0.057323 | 0.975997 | 1.017 | −0.040317 |
| 85 | 0.996809 | 1.019 | −0.021778 | 0.998651 | 1.018 | −0.019007 |
| 90 | 1 | 1 | 0 | 0.999983 | 1 | −1.73E−05 |

Figure 11:
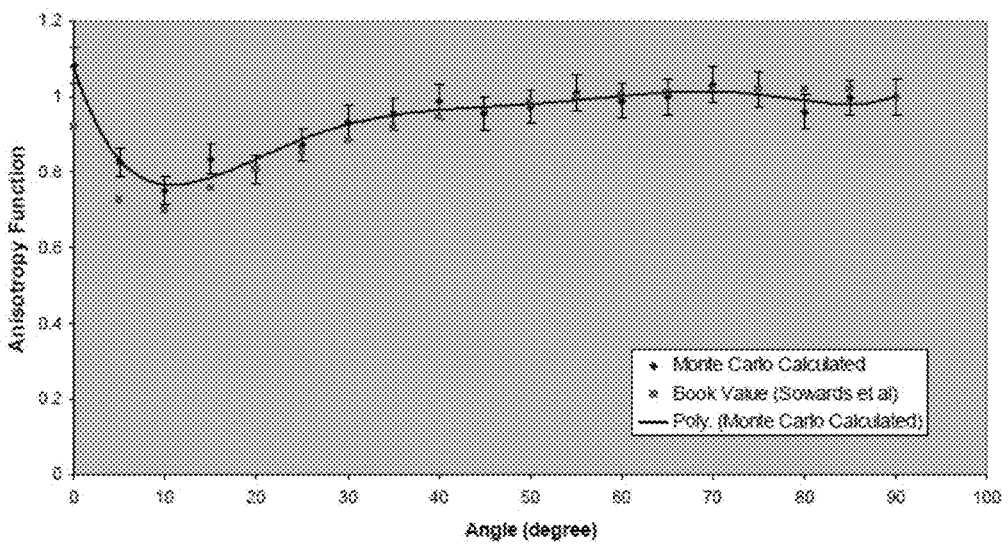
FIG. 11 shows the Comparison between the calculated and book value data Anisotropy Function for Best Model 2301 $^{125}$I in liquid water at 3 cm radii.

FIG. 11 shows the Comparison between the calculated and book value data Anisotropy Function for Best Model 2301 $^{125}$I in liquid water at 3 cm radii. The plot is fitted with a 6th order polynomial function.

Figure 12:
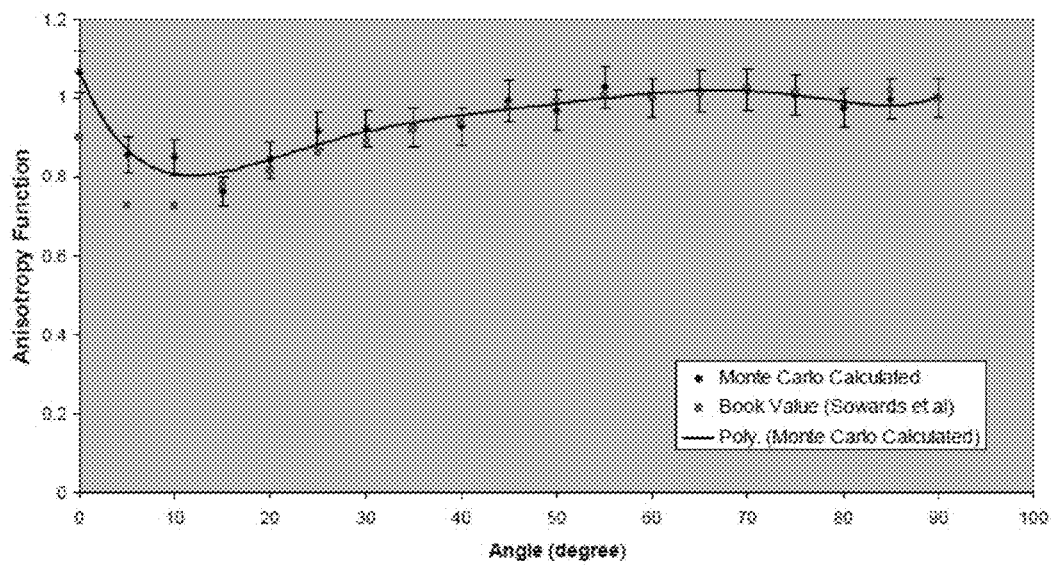
FIG. 12 shows the Comparison between the calculated and book value data Anisotropy Function for Best Model 2301 $^{125}$I in liquid water at 4 cm radii.

FIG. 12 shows the Comparison between the calculated and book value data Anisotropy Function for Best Model 2301 $^{125}$I in liquid water at 4 cm radii. The plot is fitted with a 6th order polynomial function.

Table 10c shows the Monte Carlo calculated Anisotropy Function of the Best Model 2301 $125_I$ Seed in liquid water for Radial Distances of 5 cm and 6 cm. A comparison between book values is also calculated.

Figure 13:
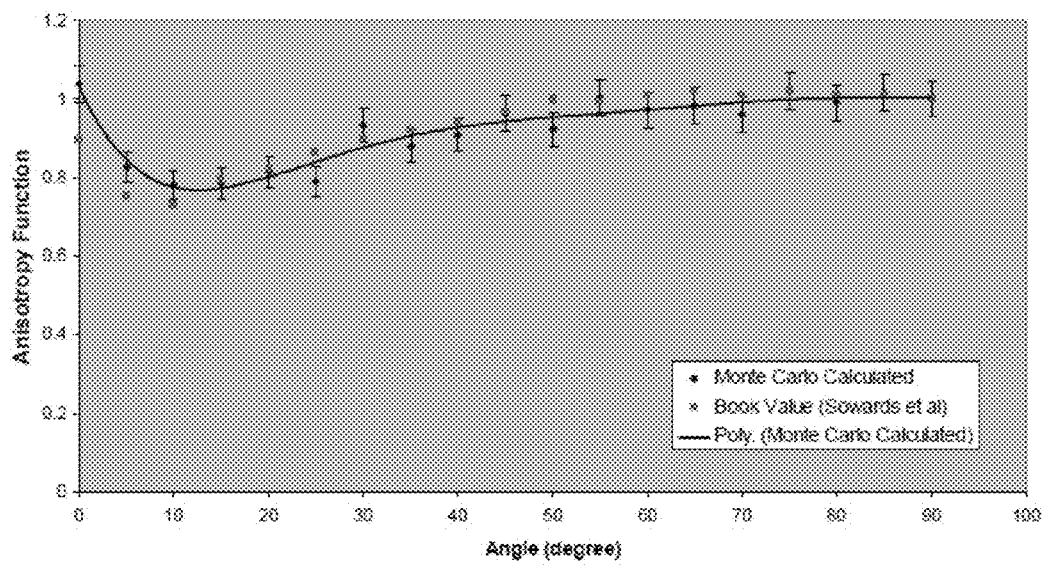
FIG. 13 shows the Comparison between the calculated and book value data Anisotropy Function for Best Model 2301 $^{125}$I in liquid water at 5 cm radii.
Figure 14:
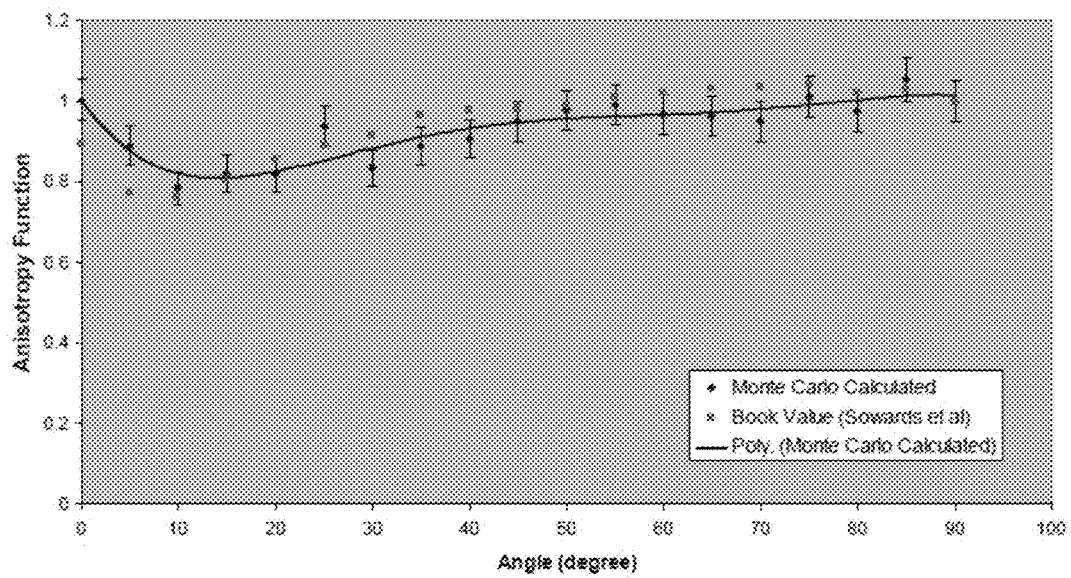
FIG. 14 shows the Comparison between the calculated and book value data Anisotropy Function for Best Model 2301 $^{125}$I in liquid water at 6 cm radii.

FIG. 13 shows the Comparison between the calculated and book value data Anisotropy Function for Best Model 2301 $^{125}$I in liquid water at 5 cm radii. The plot is fitted with a 6th order polynomial function FIG. 14 shows the Comparison between the calculated and book value data Anisotropy Function for Best Model 2301 $^{125}$I in liquid water at 6 cm radii. The plot is fitted with a 6th order polynomial function.

Table 10d shows the Monte Carlo calculated Anisotropy Function of the Best Model 2301 $^{125}$I Seed in liquid water for Radial Distance of 7 cm. A comparison between book values is also calculated.

TABLE 10c

Monte Carlo calculated Anisotropy Function of the Best Model 2301 $^{125}$I Seed in liquid water for Radial Distances of 5 cm and 6 cm. A comparison between book values is also calculated.

| Angle | AF at 5 cm | Book Value | Error | AF at 6 cm | Book Value | Error |
|---|---|---|---|---|---|---|
| 0 | 1.037909 | 0.894 | 0.160972 | 1.002815 | 0.893 | 0.122973 |
| 5 | 0.826259 | 0.753 | 0.097289 | 0.888127 | 0.771 | 0.151915 |
| 10 | 0.781112 | 0.732 | 0.067093 | 0.782999 | 0.764 | 0.024867 |
| 15 | 0.785625 | 0.795 | −0.011792 | 0.819448 | 0.805 | 0.017947 |
| 20 | 0.814253 | 0.825 | −0.013026 | 0.817894 | 0.852 | −0.040031 |
| 25 | 0.790151 | 0.865 | −0.08653 | 0.936581 | 0.89 | 0.052338 |
| 30 | 0.93407 | 0.899 | 0.03901 | 0.833299 | 0.915 | −0.089291 |
| 35 | 0.880933 | 0.92 | −0.042464 | 0.886202 | 0.964 | −0.080703 |
| 40 | 0.909002 | 0.943 | −0.036053 | 0.904777 | 0.976 | −0.072974 |
| 45 | 0.965222 | 0.968 | −0.00287 | 0.948816 | 0.979 | −0.030831 |
| 50 | 0.921762 | 0.997 | −0.075464 | 0.976859 | 0.989 | −0.012276 |
| 55 | 1.00322 | 0.993 | 0.010292 | 0.98898 | 1.011 | −0.02178 |
| 60 | 0.972524 | 1.01 | −0.037105 | 0.967874 | 1.019 | −0.050173 |
| 65 | 0.982562 | 1.024 | −0.040466 | 0.960829 | 1.034 | −0.070765 |
| 70 | 0.959269 | 1.011 | −0.051168 | 0.948077 | 1.035 | −0.083983 |
| 75 | 1.020911 | 1.02 | 0.000894 | 1.01108 | 1.043 | −0.030604 |
| 80 | 0.991336 | 1.01 | −0.018479 | 0.972717 | 1.02 | −0.046356 |
| 85 | 1.015815 | 1.011 | 0.004762 | 1.053106 | 1.031 | 0.021441 |
| 90 | 1 | 1 | 0 | 1 | 1 | 0 |

Figure 15:
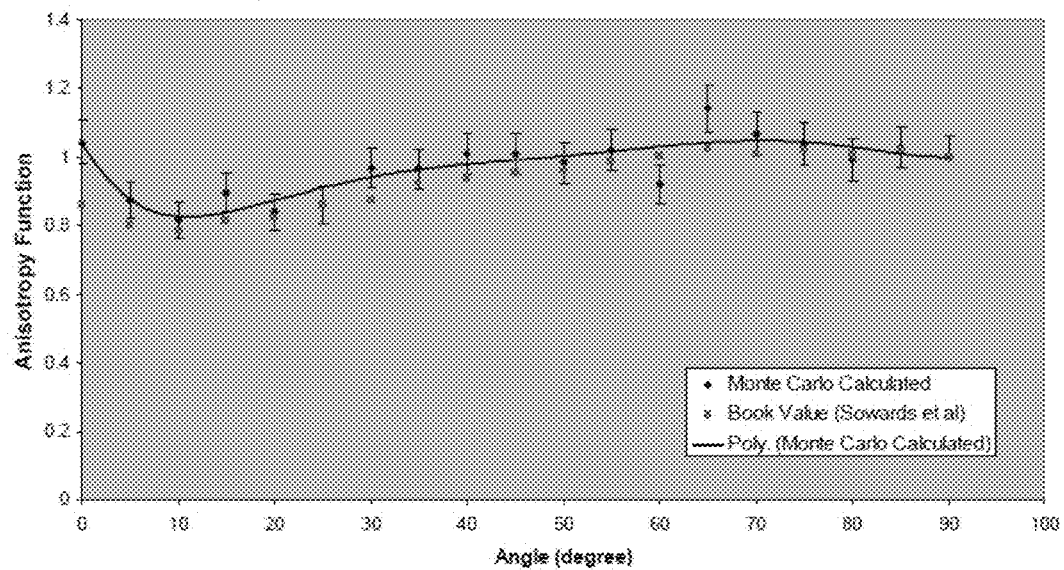
FIG. 15: The Comparison between the calculated and book value data Anisotropy Function for Best Model 2301 $^{125}$I in liquid water at 7 cm radii.

FIG. 15: The Comparison between the calculated and book value data Anisotropy Function for Best Model 2301 $^{125}$I in liquid water at 7 cm radii. The plot is fitted with a 6th order polynomial function.

Average Anisotropy Function:

The average anisotropy constant is taken by taking an average of the calculated anisotropy functions for all the angles.

Table 11a shows the Average Anisotropy Constant calculated for radial distances of 1 cm and 2 cm in liquid water.

TABLE 11a

Average Anisotropy Constant calculated for radial distances of 1 cm and 2 cm in liquid water

|  | 1 cm | Book value | Error | 2 cm | Book value | Error |
|---|---|---|---|---|---|---|
| Avg. Anisotropy Constant $\Phi_{an}$ (r) | 0.913 | 0.986 | −0.0745 | 0.904 | 0.976 | −0.0735 |

Table 11b shows the Average Anisotropy Constant calculated for radial distances of 3 cm and 4 cm in liquid water.

TABLE 11b

Average Anisotropy Constant calculated for radial distances of 3 cm and 4 cm in liquid water

|  | 3 cm | Book value | Error | 4 cm | Book value | Error |
|---|---|---|---|---|---|---|
| Avg. Anisotropy Constant $\Phi_{an}$ (r) | 0.946 | 0.968 | −0.0224 | 0.952 | 0.971 | −0.0197 |

Table 11c shows the Average Anisotropy Constant calculated for radial distances of 5 cm and 6 cm in liquid water.

TABLE 11c

Average Anisotropy Constant calculated for radial distances of 5 cm and 6 cm in liquid water

|  | 5 cm | Book value | Error | 6 cm | Book value | Error |
|---|---|---|---|---|---|---|
| Avg. Anisotropy Constant $\Phi_{an}$ (r) | 0.926 | 0.969 | −0.0445 | 0.932 | 0.991 | −0.0599 |

Table 11d shows the Average Anisotropy Constant calculated for radial distances of 7 cm in liquid water.

TABLE 11d

Average Anisotropy Constant calculated for radial distance of 7 cm in liquid water

|  | 7 cm | Book value | Error |
|---|---|---|---|
| Avg. Anisotropy Constant $\Phi_{an}$ (r) | 0.972 | 0.969 | 0.003 |

Source Anisotropy Constant:

The Source Anisotropy Constant is taken by averaging all the average Anisotropy Constants. Table 12 shows the Source Anisotropy Constant for Best Model 2301 $^{125}$I Seed in liquid water. The Source Anisotropy Constant is 0.935 and deviates from the book value by 4.6%

TABLE 12

Source Anisotropy Constant for Best Model 2301 $^{125}$I Seed in liquid water.

|  | Calculated value | Book value | Error |
|---|---|---|---|
| Source Anisotropy Constant $\overline{\Phi_{an}}$ (r) | 0.935 | 0.98 | −0.0459 |

1) Best Model 2301 $^{125}$I Seed in Solid Water i) Dose Rate (D):

Dose Rate was calculated for seed at 1 cm on the transverse plane (θ=90°) of the source (from the center of the source) in solid water. Therefore, for this measurement the phantom was taken to be Solid Water since it is the Solid Water measurement. Table 13 shows the Dose Rate for Best Model 2301 $^{125}$I Seed in solid water calculated using Monte Carlo. The dose rate recorded is 0.231±4.78*10$^{-3}$ cGy*sec$^{-1}$*Ci$^{-1}$.

TABLE 13

Dose Rate for Best Model 2301 $^{125}$I Seed in Solid Water calculated using Monte Carlo

| Calculated Dose Rate (cGy * sec$^{-1}$ * Ci$^{-1}$) | Book Value (Meigooni et al) | Error |
|---|---|---|
| 0.230994 | N/A | N/A | ii) Air Kerma Strength (SK):

Air Kerma Strength was calculated for the seed again at 1 cm on the transverse plane of the source (from the center of the source) but now it was in air. Therefore, the material inside the phantom was taken as air. Also, the 0.897 WAFAC correction factor (as discussed in the Materials & Methods section) is used for SK. Table 14 shows the Air Kerma Strength for Best Model 2301 $^{125}$I Seed in Air calculated using Monte Carlo. The Air Kerma Strength recorded is 0.224±4.98*10$^{-3}$ cGy*cm$^2$sec$^{-1}$*Ci$^{-1}$.

TABLE 14

Air Kerma Strength for Best Model 2301 $^{125}$I Seed in Air calculated using Monte Carlo

| Calculated Air Kerma Strength (cGy * cm$^2$sec$^{-1}$ * Ci$^{-1}$) | Book Value (Meigooni et al) | Error |
|---|---|---|
| 0.224332 | N/A | N/A | iii) Dose Rate Constant (Λ):

Dose rate constant is calculated using equation #4. In order to calculate it, the ratio of the dose rate and air kerma strength is taken. Table 15 shows the Monte Carlo calculated Dose Rate Constant for Best Model 2301 $^{125}$I Seed in solid water. The error between the measured value and the book value is 5.1%. The measured value of Dose Rate Constant is 1.03±0.031 cGy*h$^{-1}$*U$^{-1}$.

TABLE 15

Monte Carlo calculated Dose Rate Constant for Best Model 2301 $^{125}$I Seed in Solid Water

| Calculated Dose Rate Constant (cGy * h$^{-1}$ * U$^{-1}$) | Book Value (Meigooni et al) (cGy * h$^{-1}$ * U$^{-1}$) | Error |
|---|---|---|
| 1.02969 | 0.98 | 0.05071 | iv) Correction/Multiplicative Factor:

Meigooni et al calculated that a conversion factor of 1.05 was needed to convert the dose rate constant in solid water to liquid water.

The calculated Correction/Multiplicative factor obtained is 1.026 v) Radial Dose Function:

Calculation of the radial function is a two-fold process.

a) Geometry Function

The Geometry function is independent of the material content of the phantom and therefore, the geometry factor from Table 6 is applicable here.

b) Radial Dose Function Using the Geometry Function

The Radial Function was calculated using equation#8 incorporating the geometry function calculated in part a) above. Table 16* shows the Radial Dose Function calculated at the transverse plane for the Best Model 2301 $^{125}$I Seed in solid water using Monte Carlo. *Note that the empty cells refer to unavailable book values (and hence no error to calculate).

TABLE 16*

Radial Dose Function calculated at the transverse plane for the Best Model 2301 $^{125}$I Seed in Solid Water using Monte Carlo.

| Transverse distance (r) cm | Radial Dose Function g (r) | Book Value | Error |
|---|---|---|---|
| 0.1 | 0.974085 | | |
| 0.15 | 0.987273 | | |
| 0.2 | 1.024577 | | |
| 0.25 | 0.997152 | | |
| 0.3 | 1.010615 | | |
| 0.4 | 1.002436 | | |
| 0.5 | 0.996278 | | |
| 0.6 | 0.960112 | 1.044 | −0.08035 |
| 0.7 | 0.907923 | | |
| 0.75 | 0.946739 | | |
| 0.8 | 0.955411 | | |
| 0.9 | 0.966749 | | |
| 1 | 1.000001 | 1 | 5.07E−07 |
| 1.5 | 0.904062 | 0.926 | −0.02369 |
| 2 | 0.812967 | 0.842 | −0.03448 |
| 2.5 | 0.728075 | 0.752 | −0.03182 |
| 3 | 0.650595 | 0.666 | −0.02313 |
| 3.5 | 0.563531 | 0.581 | −0.03007 |
| 4 | 0.512549 | 0.509 | 0.006973 |
| 4.5 | 0.43286 | 0.443 | −0.02289 |
| 5 | 0.381773 | 0.386 | −0.01095 |
| 5.5 | 0.317848 | 0.336 | −0.05402 |
| 6 | 0.275389 | 0.286 | −0.0371 |
| 6.5 | 0.230972 | 0.245 | −0.05726 |
| 7 | 0.204101 | 0.207 | −0.014 |
| 7.5 | 0.176629 | 0.178 | −0.0077 |
| 8 | 0.157109 | 0.159 | −0.0119 |
| 8.5 | 0.124603 | 0.14 | −0.10998 |
| 9 | 0.109814 | 0.116 | −0.05333 |
| 9.5 | 0.093497 | 0.097 | −0.03611 |
| 10 | 0.079492 | 0.08 | −0.00635 |

Figure 16:
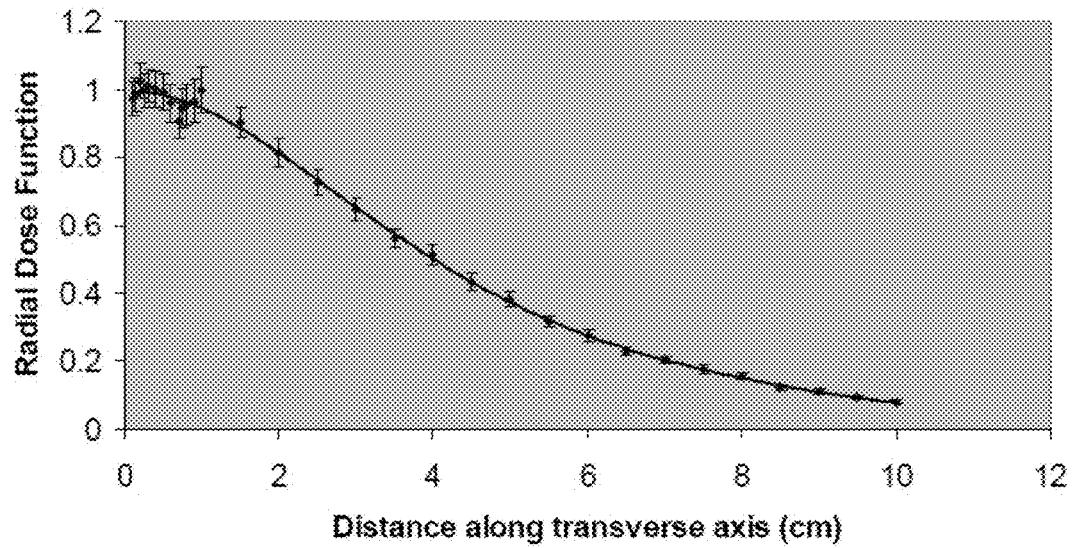
FIG. 16 is a graph for radial dose function versus distance on the transverse plane fits, which illustrates the Radial Dose Function calculated in solid water for the Best Model 2301 $^{125}$I Seed.

The graph for radial dose function versus distance on the transverse plane fits as shown in FIG. 16 which illustrates the Radial Dose Function calculated in solid water for the Best Model 2301 125$_I$ Seed. The curve is fitted to 5th order polynomial function.

iv) Anisotropy Function:

Calculation of the Anisotropy function is a three-fold process.

a) Calculating Geometry Function

The Geometry function is independent of the material content of the phantom and therefore, the geometry function from Tables 8a and 8b is applicable here.

b) Calculating Coordinates for Detectors

The coordinates are independent of the material content of the phantom and therefore, the coordinates from Table 9 are applicable here.

c) Calculating Anisotropy Function Using the Data Accumulated in Tables 8a, 8b and 9

The Anisotropy Function was calculated using all the factors listed in equation #9. Tables 8a and 8b were used to calculate the Geometry Function at various angles. Table 9 was used to find the coordinates needed to place the detectors at the various angles (and radial distances). Table 17a shows the Monte Carlo calculated Anisotropy Function of the Best Model 2301 125$_I$ Seed in solid water for Radial Distances of 1 cm, 2 cm, 3 cm and 4 cm. A comparison between book values is also calculated. *Note that there are no any book values (and hence no error to calculate) **Empty cells refer to no book values (and hence no error to calculate).

TABLE 17a

Monte Carlo calculated Anisotropy Function of the Best Model 2301 $^{125}$I Seed in Solid Water for Radial Distances of 1 cm, 2 cm, 3 cm and 4 cm. A comparison between book values is also calculated.

| Angle | AF at 1 cm* | AF at 2 cm | Book Value** | Error | AF at 3 cm* | AF at 4 cm* |
|---|---|---|---|---|---|---|
| 0 | 1.026252 | 1.002986 | 0.837 | 0.198311 | 1.045494 | 0.996217 |
| 5 | 0.866304 | 0.829332 | | | 0.767353 | 0.804645 |
| 10 | 0.672536 | 0.677051 | 0.659 | 0.027391 | 0.706056 | 0.786272 |
| 15 | 0.739002 | 0.689879 | | | 0.742168 | 0.766287 |
| 20 | 0.75897 | 0.779294 | 0.782 | −0.003461 | 0.769965 | 0.821381 |
| 25 | 0.793086 | 0.81592 | | | 0.864285 | 0.865759 |
| 30 | 0.822657 | 0.83656 | 0.882 | −0.05152 | 0.835925 | 0.928838 |
| 35 | 0.897361 | 0.803188 | | | 0.876294 | 0.940615 |
| 40 | 0.906809 | 0.876187 | 0.946 | −0.073798 | 0.919709 | 0.956302 |
| 45 | 0.957336 | 0.901717 | | | 0.893813 | 0.963304 |
| 50 | 0.971523 | 0.924023 | 0.985 | −0.061905 | 0.89036 | 0.909226 |
| 55 | 0.989839 | 0.948227 | | | 0.916484 | 1.009165 |
| 60 | 0.987353 | 0.928041 | 1.007 | −0.078411 | 0.900548 | 0.967434 |
| 65 | 0.99135 | 0.912797 | | | 0.880534 | 0.964955 |
| 70 | 0.998792 | 0.952063 | 1.02 | −0.066605 | 0.97229 | 1.007641 |
| 75 | 1.038309 | 0.987641 | | | 0.944857 | 0.970099 |
| 80 | 1.032288 | 1.004358 | 1.027 | −0.022046 | 0.899939 | 0.956987 |
| 85 | 0.986828 | 0.984115 | | | 0.95404 | 0.990027 |
| 90 | 0.996037 | 1 | 1 | 0 | 1 | 1 |

The comparison of the graph for Anisotropy Function versus Angle was fitted to a 6th order polynomial. The Anisotropy Function at 1 cm, 2 cm, 3 cm and 4 cm (calculated and measured) for Best Model 2301 $^{125}$I are plotted in the FIGS. 17-20.

Figure 17:
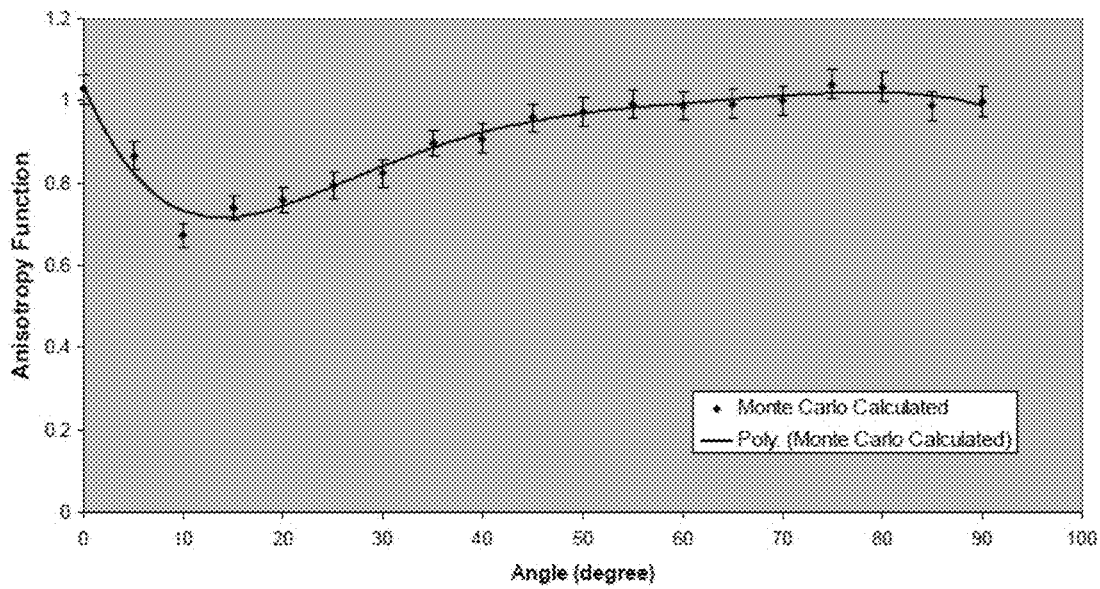
FIG. 17 illustrates anisotropy Function of Monte Carlo calculated value for Best Model 2301 $^{125}$I in solid water at 1 cm radii. The plot is fitted with a 6th order polynomial function.

FIG. 17 illustrates Anisotropy Function of Monte Carlo calculated value for Best Model 2301 $^{125}$I in solid water at 1 cm radii. The plot is fitted with a 6th order polynomial function.

Figure 18:
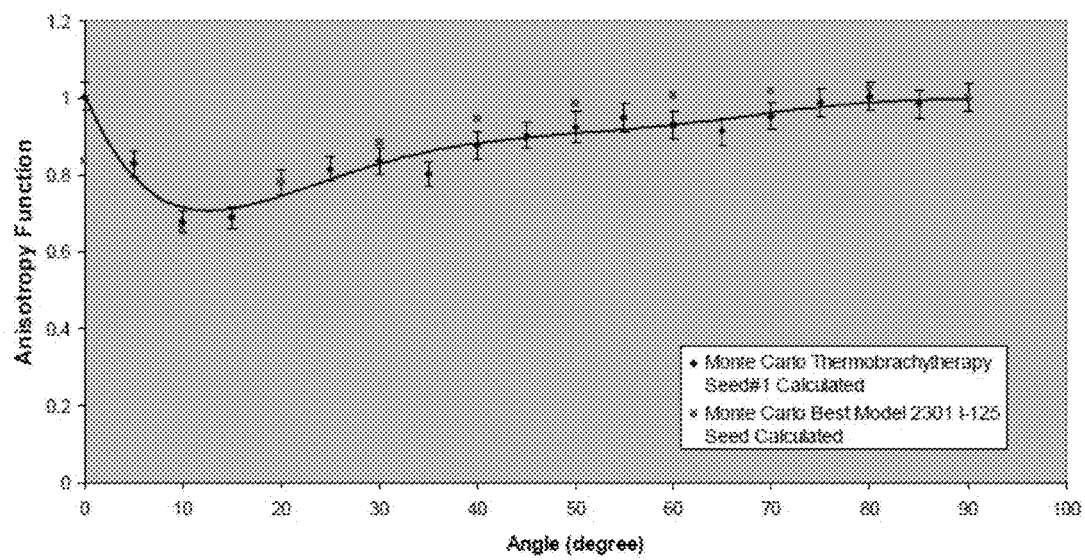
FIG. 18 illustrates the Comparison between the calculated and book value data Anisotropy Function for Best Model 2301 $^{125}$I in solid water at 2 cm radii.

FIG. 18 illustrates the Comparison between the calculated and book value data Anisotropy Function for Best Model 2301 $^{125}$I in solid water at 2 cm radii. The plot is fitted with a 6th order polynomial function.

Figure 19:
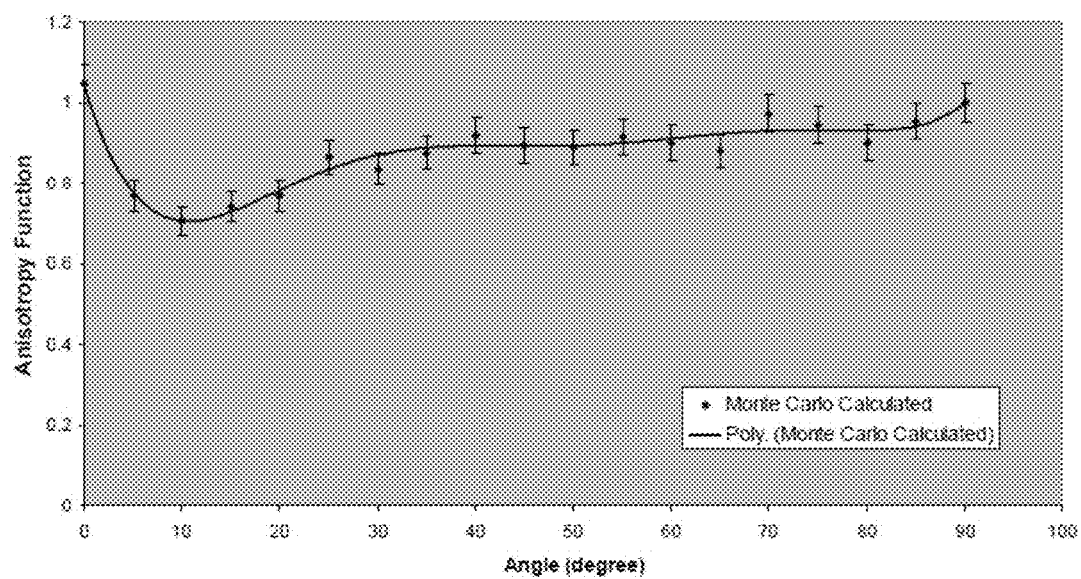
FIG. 19 illustrates Anisotropy Function of Monte Carlo calculated value for Best Model 2301 $^{125}$I in solid water at 3 cm radii.

FIG. 19 illustrates Anisotropy Function of Monte Carlo calculated value for Best Model 2301 $^{125}$I in solid water at 3 cm radii. The plot is fitted with a 6th order polynomial function.

Figure 20:
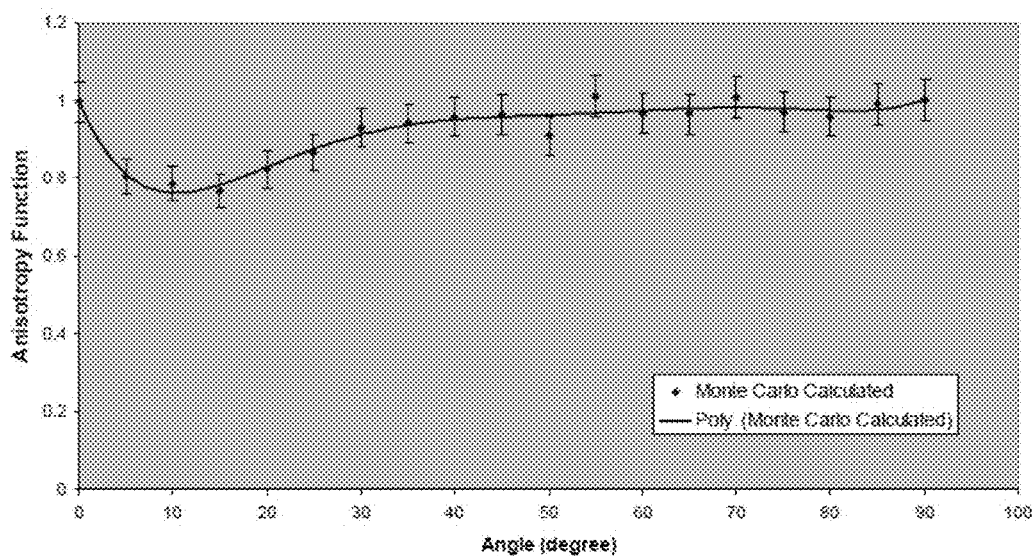
FIG. 20 illustrates Anisotropy Function of Monte Carlo calculated value for Best Model 2301 $^{125}$I in solid water at 4 cm radii.

FIG. 20 illustrates Anisotropy Function of Monte Carlo calculated value for Best Model 2301 $^{125}$I in solid water at 4 cm radii. The plot is fitted with a 6th order polynomial function.

Table 17b shows the Monte Carlo calculated Anisotropy Function of the Best Model 2301 125$_I$ Seed in solid water for Radial Distances of 5 cm, 6 cm and 7 cm. A comparison between book values is also calculated. *Note that there are no any book values (and hence no error to calculate). **Empty cells refer to no book values (and hence no error to calculate).

TABLE 17b

Monte Carlo calculated Anisotropy Function of the Best Model 2301 $^{125}$I Seed in Solid Water for Radial Distances of 5 cm, 6 cm and 7 cm. A comparison between book values is also calculated.

| Angle | AF at 5 cm | Book Value** | Error | AF at 6 cm* | AF at 7 cm | Book Value | Error |
|---|---|---|---|---|---|---|---|
| 0 | 1.06538 | 0.886 | 0.20246 | 0.961176 | 1.106333 | 0.888 | 0.24587 |
| 5 | 0.863781 | | | 0.869443 | 0.855329 | | |
| 10 | 0.788669 | 0.719 | 0.096898 | 0.754599 | 0.96212 | 0.751 | 0.281119 |
| 15 | 0.773249 | | | 0.77439 | 0.860677 | | |
| 20 | 0.817595 | 0.801 | 0.020717 | 0.754773 | 0.907204 | 0.82 | 0.106346 |
| 25 | 0.879567 | | | 0.868662 | 0.933333 | | |
| 30 | 0.840307 | 0.873 | −0.037449 | 0.82609 | 0.944759 | 0.905 | 0.043933 |
| 35 | 0.911502 | | | 0.864491 | 0.904032 | | |
| 40 | 0.949538 | 0.938 | 0.012301 | 0.85658 | 1.018978 | 0.952 | 0.070355 |
| 45 | 0.936324 | | | 0.878697 | 1.095808 | | |
| 50 | 0.99784 | 0.962 | 0.037255 | 0.853307 | 1.006513 | 0.972 | 0.035507 |
| 55 | 1.018567 | | | 0.938518 | 1.133607 | | |
| 60 | 0.948673 | 0.99 | −0.041745 | 0.912431 | 1.091072 | 1.004 | 0.086725 |
| 65 | 1.02104 | | | 1.005409 | 1.189276 | | |
| 70 | 1.024804 | 1.001 | 0.02378 | 0.962483 | 0.984267 | 0.999 | −0.014748 |
| 75 | 1.013883 | | | 0.972179 | 1.061721 | | |
| 80 | 1.06825 | 1.011 | 0.056627 | 1.025741 | 1.096051 | 1.015 | 0.079853 |
| 85 | 1.000983 | | | 0.987695 | 1.141173 | | |
| 90 | 1 | 1 | 0 | 1 | 0.999979 | 1 | −2.1E−05 |

Figure 21A:
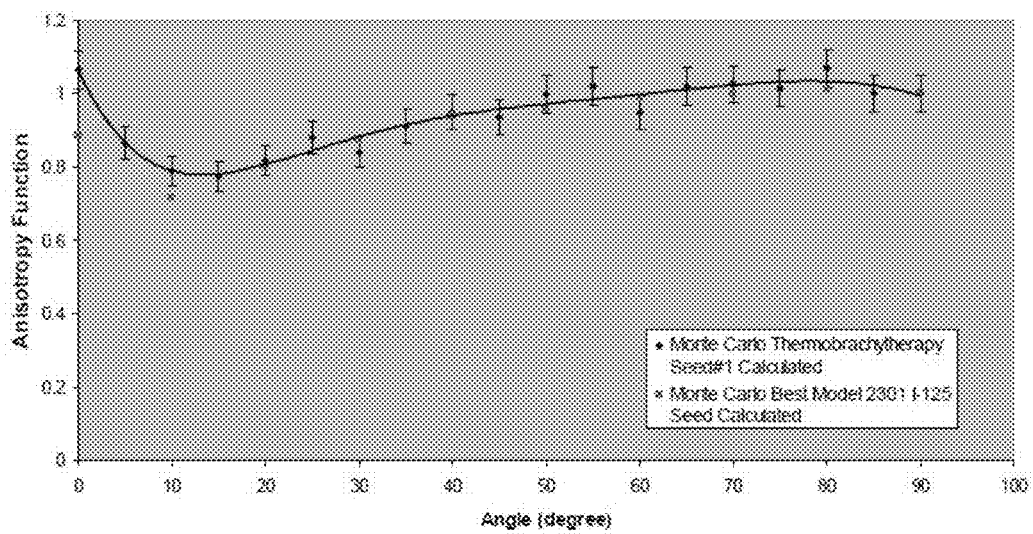
FIG. 21A illustrates the Comparison between the calculated and book value data Anisotropy Function for Best Model 2301 $^{125}$I in solid water at 5 cm radii.

FIG. 21A illustrates the Comparison between the calculated and book value data Anisotropy Function for Best Model 2301 $^{125}$I in solid water at 5 cm radii. The plot is fitted with a 6th order polynomial function.

Figure 21B:
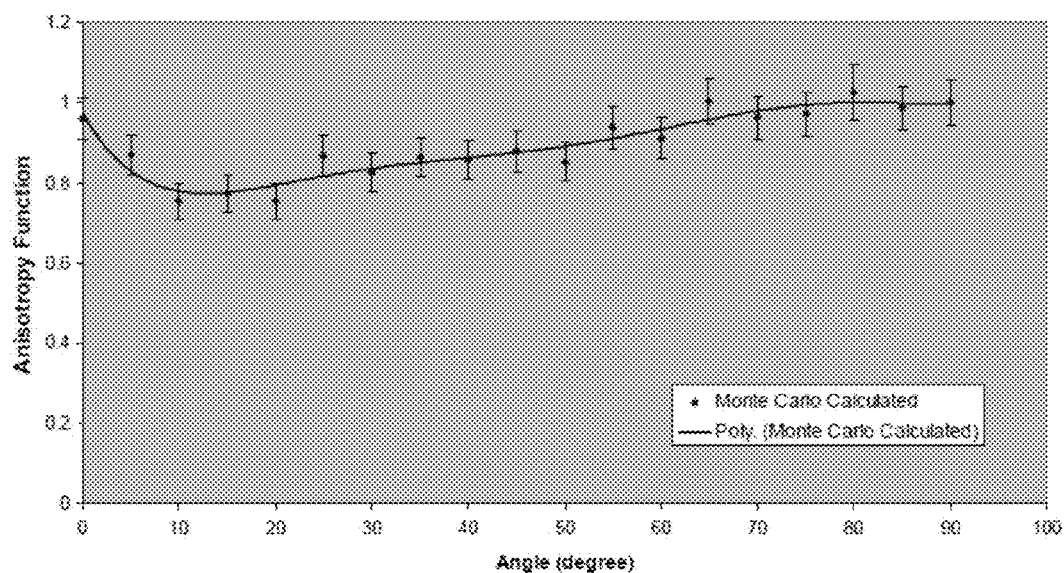
FIG. 21B illustrates Anisotropy Function of Monte Carlo calculated value for Best Model 2301 $^{125}$I in solid water at 6 cm radii.

FIG. 21B illustrates Anisotropy Function of Monte Carlo calculated value for Best Model 2301 $^{125}$I in solid water at 6 cm radii. The plot is fitted with a 6th order polynomial function.

Figure 22:
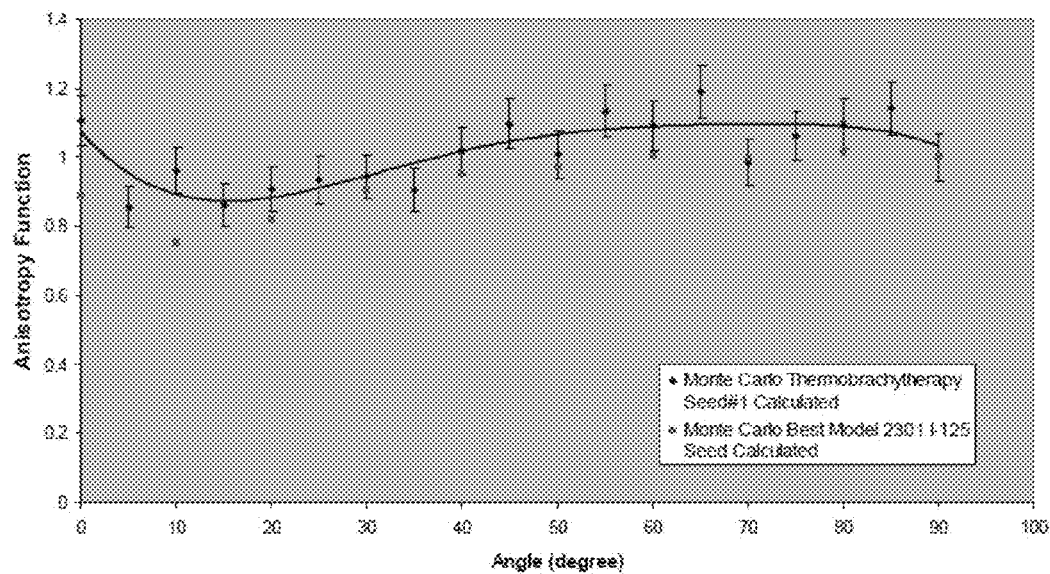
FIG. 22 illustrates Anisotropy Function of Monte Carlo calculated value for Best Model 2301 $^{125}$I in solid water at 7 cm radii.

FIG. 22 illustrates Anisotropy Function of Monte Carlo calculated value for Best Model 2301 $^{125}$I in solid water at 7 cm radii. The plot is fitted with a 6th order polynomial function.

Average Anisotropy Function:

The average anisotropy function is taken by taking an average of the calculated anisotropy functions for all the angles. Table 18a illustrates the Average Anisotropy Function calculated for radial distances of 1 cm, 2 cm, 3 cm, 4 cm in solid water.

TABLE 18a

Average Anisotropy Function calculated for radial distances of 1 cm, 2 cm, 3 cm, 4 cm in Solid Water

| | 1 cm | 2 cm | Book value | Error | 3 cm | 4 cm |
|---|---|---|---|---|---|---|
| Avg. Anisotropy Constant $\Phi_{an}(r)$ | 0.917 | 0.898 | 0.975 | −0.0789 | 0.883 | 0.926 |

Table 18b illustrates the Average Anisotropy Function calculated for radial distances of 5 cm and 6 cm in solid water.

TABLE 18b

Average Anisotropy Function calculated for radial distances of 5 cm and 6 cm in Solid Water

| | 5 cm | Book value | Error | 6 cm |
|---|---|---|---|---|
| Avg. Anisotropy Constant $\Phi_{an}(r)$ | 0.950 | 0.965 | −0.015 | 0.898 |

Table 18c illustrates the Average Anisotropy Function calculated for radial distance of 7 cm in solid water.

TABLE 18c

Average Anisotropy Function calculated for radial distance of 7 cm in Solid Water

| | 7 cm | Book Value | Error |
|---|---|---|---|
| Avg. Anisotropy | 1.01 | 0.977 | 0.0355 |

TABLE 18c-continued

Average Anisotropy Function calculated for radial distance of 7 cm in Solid Water

|  | 7 cm | Book Value | Error |
|---|---|---|---|
| Constant $\Phi_{an}(r)$ | | | |

Source Anisotropy Constant:

The Source Anisotropy Constant is taken by averaging all the average Anisotropy Constants.

Table 19 illustrates the Source Anisotropy Constant for Best Model 2301 $^{125}$I Seed in solid water. The Source Anisotropy Constant is 0.926 and deviates from the book value by 4.5%

TABLE 19

Source Anisotropy Constant for Best Model 2301 $^{125}$I Seed in Solid Water.

|  | Calculated value | Book value | Error |
|---|---|---|---|
| Source Anisotropy Constant $\overline{\Phi}_{an}(r)$ | 0.926 | 0.97 | −0.0453 |

1) Thermobrachytherapy Seed#1 in Liquid Water
i) Dose Rate (D):

Dose Rate was calculated for seed at 1 cm on the transverse plane (θ=90°) of the source (from the center of the source) in water. Therefore, for this measurement the phantom was taken to be liquid water since it is the liquid water measurement.

Table 20 illustrates the Dose Rate for Thermobrachytherapy Seed#1 in liquid water calculated using Monte Carlo. The error is calculated by using equation #16. Therefore, the error between the calculated thermobrachytherapy seed#1 value and the calculated Best Model 2301 $^{125}$I seed is 6.1%. The measured value of Dose Rate is 0.25±4.98*10$^{-3}$ cGy*sec$^{-1}$*Ci$^{-1}$.

TABLE 20

Dose Rate for Thermobrachytherapy Seed#1 in liquid water calculated using Monte Carlo

| Calculated Dose Rate (cGy * sec$^{-1}$ * Ci$^{-1}$) | Calculated Best Model 2301 $^{125}$I Seed (cGy * sec$^{-1}$ * Ci$^{-1}$) | Error | Book Value (Meigooni et al) | Error |
|---|---|---|---|---|
| 0.251432 | 0.236993 | 0.06093 | N/A | N/A | ii) Air Kerma Strength (SK):

Air Kerma Strength was calculated for the seed again at 1 cm on the transverse plane of the source (from the center of the source) but now it was in air. Therefore, the material inside the phantom was taken as air. Also, the 0.897 WAFAC correction factor (as discussed in the Materials & Methods section) is used for SK. Table 21 illustrates the Air Kerma Strength for Thermobrachytherapy Seed#1 in Air calculated using Monte Carlo. The error is calculated by using equation #16. Therefore, the error between the calculated thermobrachytherapy value and the calculated Best Model 2301 $^{125}$I seed is 6.0%. The measured value of Air Kerma Strength is 0.238±5.14*10$^{-3}$ cGy*cm$^2$sec$^{-1}$*Ci$^{-1}$.

TABLE 21

Air Kerma Strength for Thermobrachytherapy Seed#1 in Air calculated using Monte Carlo

| Calculated Air Kerma Strength (cGy * cm$^2$ sec$^{-1}$ * Ci$^{-1}$) | Calculated Best Model 2301 $^{125}$I Seed (cGy * cm$^2$ sec$^{-1}$ * Ci$^{-1}$) | Error | Book Value (Meigooni et al) | Error |
|---|---|---|---|---|
| 0.237773 | 0 224332 | 0.0599 | N/A | N/A | iii) Dose Rate Constant (Λ):

Dose rate constant is calculated using equation #4. In order to calculate it, the ratio of the dose rate and air kerma strength is taken. Table 22 illustrates the Monte Carlo calculated Dose Rate Constant for Thermobrachytherapy Seed#1 in liquid water. The error is calculated by using equation #16. Therefore, the error between the calculated thermobrachytherapy value and the calculated Best Model 2301 $^{125}$I seed is 0.091%. Also, the error between the calculated thermobrachytherapy value and the Book Value for Best Model 2301 $^{125}$I seed is 4.69%. The measured value of Dose Rate Constant is 1.057±0.031 cGy*h$^{-1}$U$^{-1}$

TABLE 22

Monte Carlo calculated Dose Rate Constant for Thermobrachytherapy Seed#1 in liquid water

| Calculated Dose Rate Constant (cGy * h$^{-1}$U$^{-1}$) | Best Model 2301 $^{125}$I Seed Dose Rate Constant (cGy * h$^{-1}$U$^{-1}$) | Error | Book Value (Meigooni et al) (cGy * h$^{-1}$U$^{-1}$) | Error |
|---|---|---|---|---|
| 1.0574 | 1.05644 | 0.00091 | 1.01 | 0.04693 | iv) Radial Dose Function:

Calculation of the radial dose function is a two-fold process.

a) Geometry Function

The Geometry function is independent of the material content of the phantom. And also, the geometry (and dimension) of the source cell remains the same. Therefore, the geometry factor from Table 6 is applicable here.

b) Radial Dose Function Using the Geometry Function

Radial Dose Function was calculated using equation#8 incorporating the geometry function calculated in part a) above. Table 23 illustrates the Radial Dose Function calculated at the transverse plane for the Thermobrachytherapy Seed#1 in liquid water using Monte Carlo.

TABLE 23

Radial Dose Function calculated at the transverse plane for the Thermobrachytherapy Seed#1 in liquid water using Monte Carlo

| Transverse distance (r) cm | Radial Dose Function g (r) | Best Model 2301 $^{125}$I Seed | Error | Book Value (Meigooni et al) | Error |
|---|---|---|---|---|---|
| 0.1 | 0.934737 | 0.9456286 | −0.01152 | 1.033 | −0.09512 |
| 0.15 | 0.963187 | 0.972143 | −0.00921 | 1.029 | −0.06396 |
| 0.2 | 0.996078 | 1.0043252 | −0.00821 | 1.028 | −0.03105 |
| 0.25 | 0.973889 | 0.9786852 | −0.0049 | 1.027 | −0.05171 |
| 0.3 | 0.986499 | 0.9995776 | −0.01308 | 1.027 | −0.03944 |
| 0.4 | 0.978327 | 0.9913498 | −0.01314 | 1.027 | −0.04739 |
| 0.5 | 1.012846 | 1.0205403 | −0.00754 | 1.028 | −0.01474 |
| 0.6 | 0.953455 | 0.9631128 | −0.01003 | 1.034 | −0.0779 |
| 0.7 | 0.922393 | 0.9312438 | −0.0095 | 1.036 | −0.10966 |
| 0.75 | 0.95948 | 0.9597881 | −0.00032 | 1.03 | −0.06847 |

TABLE 23-continued

Radial Dose Function calculated at the transverse plane for the Thermobrachytherapy Seed#1 in liquid water using Monte Carlo

| Transverse distance (r) cm | Radial Dose Function g (r) | Best Model 2301 $^{125}$I Seed | Error | Book Value (Meigooni et al) | Error |
|---|---|---|---|---|---|
| 0.8 | 0.931838 | 0.9358905 | −0.00433 | 1.024 | −0.09 |
| 0.9 | 1.019078 | 1.0388782 | −0.01906 | 1.013 | 0.006 |
| 1 | 1.000001 | 1.0000005 | 2.22E−16 | 1 | 5.07E−07 |
| 1.5 | 0.923599 | 0.9266222 | −0.00326 | 0.938 | −0.01535 |
| 2 | 0.842546 | 0.8476955 | −0.00607 | 0.866 | −0.02708 |
| 2.5 | 0.757101 | 0.7624361 | −0.007 | 0.79 | −0.04164 |
| 3 | 0.682296 | 0.6881108 | −0.00845 | 0.707 | −0.03494 |
| 3.5 | 0.60327 | 0.6073126 | −0.00666 | 0.635 | −0.04997 |
| 4 | 0.532988 | 0.5365308 | −0.0066 | 0.555 | −0.03966 |
| 4.5 | 0.478261 | 0.4829325 | −0.00967 | 0.488 | −0.01996 |
| 5 | 0.405112 | 0.4070779 | −0.00483 | 0.427 | −0.05126 |
| 5.5 | 0.359484 | 0.3609578 | −0.00408 | 0.372 | −0.03365 |
| 6 | 0.299933 | 0.2993458 | 0.001961 | 0.32 | −0.06271 |
| 6.5 | 0.268552 | 0.2680607 | 0.001832 | 0.285 | −0.05771 |
| 7 | 0.240006 | 0.2394946 | 0.002136 | 0.248 | −0.03223 |
| 7.5 | 0.202435 | 0.2032859 | −0.00418 | 0.215 | −0.05844 |
| 8 | 0.179735 | 0.1818156 | −0.01144 | 0.187 | −0.03885 |
| 8.5 | 0.152857 | 0.1542993 | −0.00935 | 0.16 | −0.04464 |
| 9 | 0.133356 | 0.1326667 | 0.005198 | 0.142 | −0.06087 |
| 9.5 | 0.102986 | 0.1015704 | 0.013935 | 0.123 | −0.16272 |
| 10 | 0.101814 | 0.0994859 | 0.0234 | 0.103 | −0.01152 |

Figure 23:
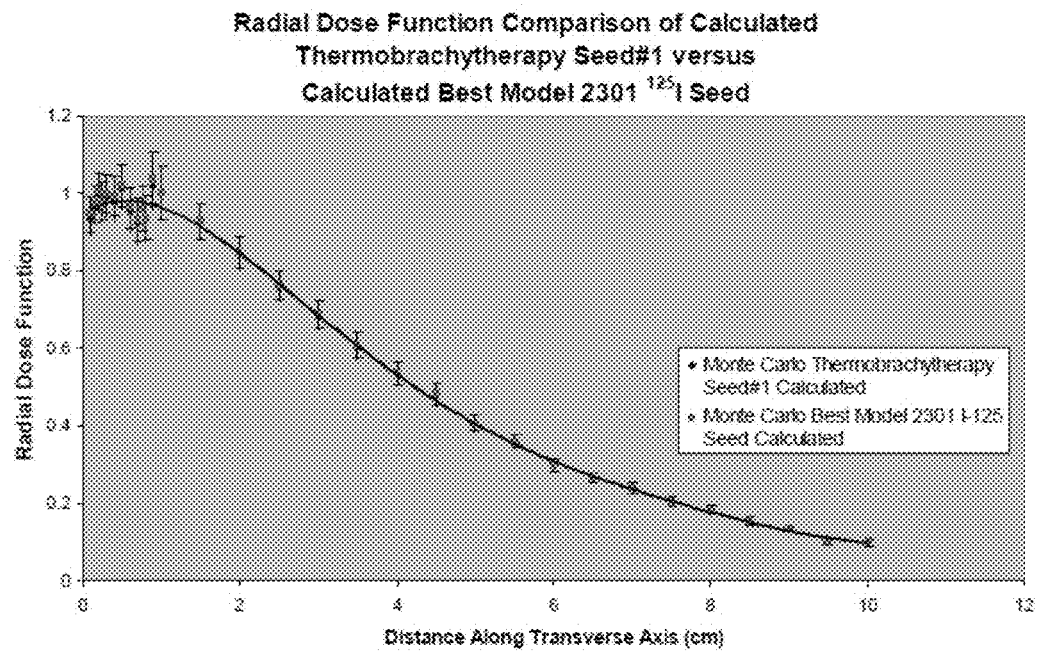
FIG. 23 illustrates the Radial Dose Function of Monte Carlo calculated value for Thermobrachytherapy Seed#1 and the Monte Carlo calculated value for the Best Model 2301 $^{125}$I in liquid water.

FIG. 23 illustrates the Radial Dose Function of Monte Carlo calculated value for Thermobrachytherapy Seed#1 and the Monte Carlo calculated value for the Best Model 2301 $^{125}$I in liquid water. The plot is fitted with a 5th order polynomial function.

Figure 24:
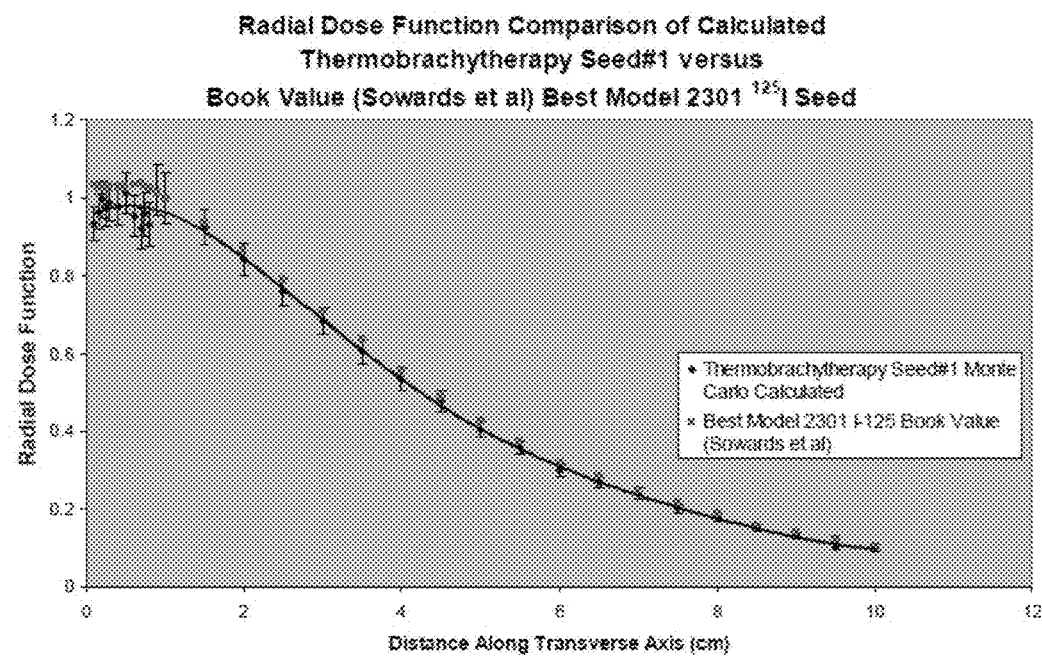
FIG. 24 illustrates the Radial Dose Function of Monte Carlo calculated value for Thermobrachytherapy Seed#1 and the Book Value for the Best Model 2301 $^{125}$I in liquid water.

FIG. 24 illustrates the Radial Dose Function of Monte Carlo calculated value for Thermobrachytherapy Seed#1 and the Book Value for the Best Model 2301 $^{125}$I in liquid water. The plot is fitted with a 5th order polynomial function.

iv) Anisotropy Function:

Calculation of the radial function is a three-fold process.

a) Calculating Geometry Function

The Geometry function is independent of the material content of the phantom and therefore, the geometry function from Tables 8a & 8b is applicable here.

b) Calculating Coordinates for Detectors

The coordinates are independent of the material content of the phantom and therefore, the coordinates from Table 9 are applicable here.

c) Calculating Anisotropy Function Using the Data Accumulated in Tables 8a, 8b & 9

The Anisotropy Function was calculated using all the factors listed in equation #9. Table 8a & 8b was used to calculate the Geometry Function at various angles. Table 9 was used to find the coordinates needed to place the detectors at the various angles (and radial distances). Table 24a illustrates the Monte Carlo calculated Anisotropy Function of the Thermobrachytherapy Seed#1 in liquid water for Radial Distances of 1 cm. A comparison between calculated and book values of the Best Model 2301 $^{125}$I Seed is also calculated.

TABLE 24a

Monte Carlo calculated Anisotropy Function of the Thermobrachytherapy Seed#1 in liquid water for Radial Distances of 1 cm. A comparison between calculated and book values of the Best Model 2301 $^{125}$I Seed is also calculated.

| Angle | AF at 1 cm | Best Model 2301 $^{125}$I Seed | Error | Book Value (Meigooni et al) | Error |
|---|---|---|---|---|---|
| 0 | 0.987793 | 1.016857 | −0.02942 | 0.867 | 0.139323 |
| 5 | 0.834117 | 0.857865 | −0.02847 | 0.724 | 0.152096 |
| 10 | 0.660437 | 0.677306 | −0.02554 | 0.653 | 0.011389 |
| 15 | 0.710819 | 0.725931 | −0.02126 | 0.721 | −0.01412 |
| 20 | 0.730699 | 0.7474 | −0.02286 | 0.785 | −0.06917 |
| 25 | 0.785677 | 0.803672 | −0.0229 | 0.85 | −0.07567 |
| 30 | 0.80466 | 0.821182 | −0.02053 | 0.9 | −0.10593 |
| 35 | 0.87556 | 0.890772 | −0.01737 | 0.946 | −0.07446 |
| 40 | 0.89236 | 0.906355 | −0.01568 | 0.982 | −0.09128 |
| 45 | 0.9378 | 0.953106 | −0.01632 | 1.001 | −0.06314 |
| 50 | 0.953471 | 0.959333 | −0.00615 | 1.014 | −0.05969 |
| 55 | 0.976016 | 0.978387 | −0.00243 | 1.024 | −0.04686 |
| 60 | 0.979357 | 0.98857 | −0.00941 | 1.03 | −0.04917 |
| 65 | 0.988796 | 0.988487 | 0.000312 | 1.033 | −0.04279 |
| 70 | 0.989097 | 0.986962 | 0.002158 | 1.036 | −0.04527 |
| 75 | 1.030016 | 1.031196 | −0.00115 | 1.039 | −0.00865 |
| 80 | 1.00686 | 1.009489 | −0.00261 | 1.1 | −0.08467 |
| 85 | 1.000187 | 0.998686 | 0.001501 | 1 | 0.000187 |
| 90 | 0.996037 | 0.996037 | 1.11E−16 | 1 | −0.00396 |

Figure 25:
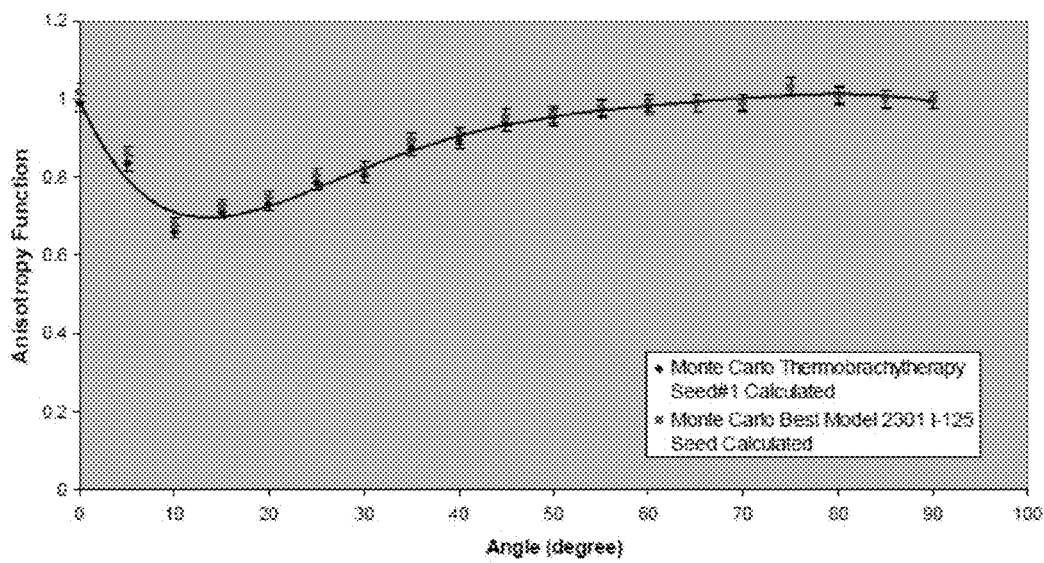
FIG. 25 illustrates the Anisotropy Function of Monte Carlo calculated value for Thermobrachytherapy Seed#1 and the Monte Carlo calculated value for the Best Model 2301 $^{125}$I in liquid water at 1 cm radii.

FIG. 25 illustrates the Anisotropy Function of Monte Carlo calculated value for Thermobrachytherapy Seed#1 and the Monte Carlo calculated value for the Best Model 2301 $^{125}$I in liquid water at 1 cm radii. The plot is fitted with a 6th order polynomial function.

Figure 26:
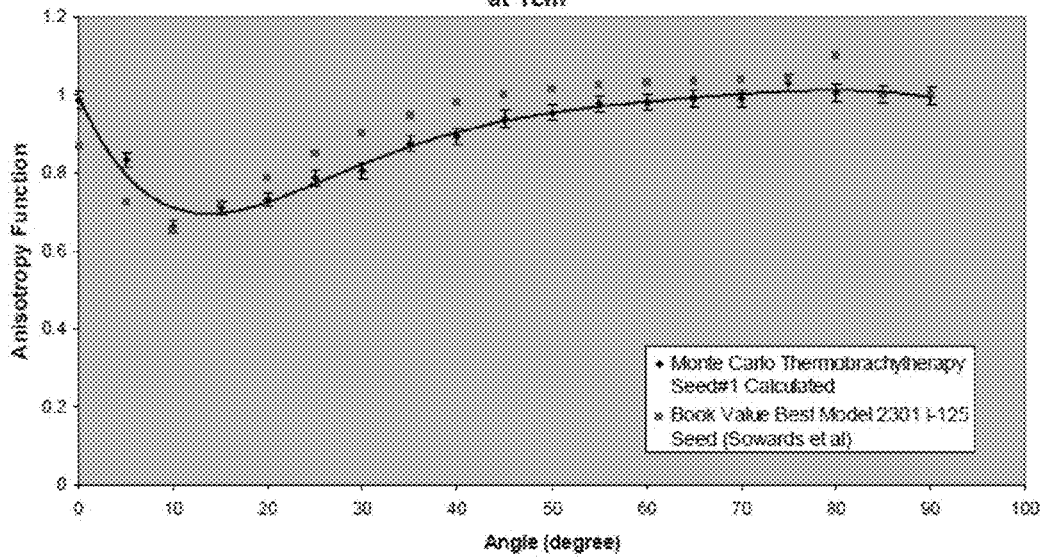
FIG. 26 illustrates the Anisotropy Function of Monte Carlo calculated value for Thermobrachytherapy Seed#1 and the Book Value for the Best Model 2301 $^{125}$I in liquid water at 1 cm radii.

FIG. 26 illustrates the Anisotropy Function of Monte Carlo calculated value for Thermobrachytherapy Seed#1 and the Book Value for the Best Model 2301 $^{125}$I in liquid water at 1 cm radii. The plot is fitted with a 6th order polynomial function.

Table 24b illustrates the Monte Carlo calculated Anisotropy Function of the Thermobrachytherapy Seed#1 in liquid water for Radial Distances of 2 cm. A comparison between calculated and book values of the Best Model 2301 $^{125}$I Seed is also calculated.

TABLE 24b

Monte Carlo calculated Anisotropy Function of the Thermobrachytherapy Seed#1 in liquid water for Radial Distances of 2 cm. A comparison between calculated and book values of the Best Model 2301 $^{125}$I Seed is also calculated.

| Angle | AF at 2 cm | Best Model 2301 $^{125}$I Seed | Error | Book Value (Meigooni et al) | Error |
|---|---|---|---|---|---|
| 0 | 0.965729 | 0.986817 | −0.02184 | 0.854 | 0.130831 |
| 5 | 0.791594 | 0.810992 | −0.0245 | 0.72 | 0.099436 |
| 10 | 0.701235 | 0.724824 | −0.03364 | 0.671 | 0.04506 |
| 15 | 0.697762 | 0.718106 | −0.02916 | 0.734 | −0.04937 |
| 20 | 0.796005 | 0.819861 | −0.02997 | 0.794 | 0.002526 |
| 25 | 0.826486 | 0.853352 | −0.03251 | 0.847 | −0.02422 |
| 30 | 0.848773 | 0.858304 | −0.01123 | 0.89 | −0.04632 |
| 35 | 0.809979 | 0.821552 | −0.01429 | 0.926 | −0.12529 |
| 40 | 0.917837 | 0.940464 | −0.02465 | 0.954 | −0.03791 |
| 45 | 0.867312 | 0.883125 | −0.01823 | 0.978 | −0.11318 |
| 50 | 0.893594 | 0.903854 | −0.01148 | 0.992 | −0.0992 |
| 55 | 0.931811 | 0.944112 | −0.0132 | 1.003 | −0.07098 |
| 60 | 0.94777 | 0.963059 | −0.01613 | 1.01 | −0.06161 |
| 65 | 0.953051 | 0.971319 | −0.01917 | 1.019 | −0.06472 |
| 70 | 0.985862 | 0.984718 | 0.001161 | 1.026 | −0.03912 |
| 75 | 0.989964 | 1.000409 | −0.01055 | 1.029 | −0.03794 |
| 80 | 1.014289 | 1.019994 | −0.00562 | 1.03 | −0.01525 |
| 85 | 0.971096 | 0.976201 | −0.00526 | 1.022 | −0.04981 |
| 90 | 1 | 1 | 0 | 1 | 0 |

Figure 27:
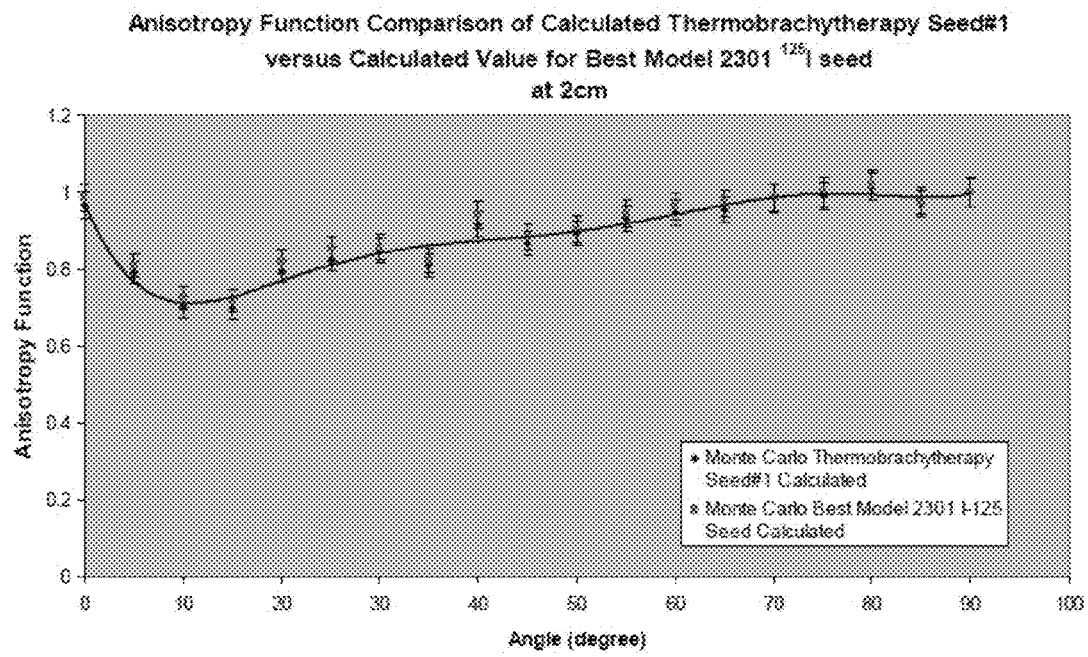
FIG. 27 illustrates the Anisotropy Function of Monte Carlo calculated value for Thermobrachytherapy Seed#1 and the Monte Carlo calculated value for the Best Model 2301 $^{125}$I in liquid water at 2 cm radii.

FIG. 27 illustrates the Anisotropy Function of Monte Carlo calculated value for Thermobrachytherapy Seed#1 and the Monte Carlo calculated value for the Best Model 2301 $^{125}$I in liquid water at 2 cm radii. The plot is fitted with a 6th order polynomial function.

Figure 28:
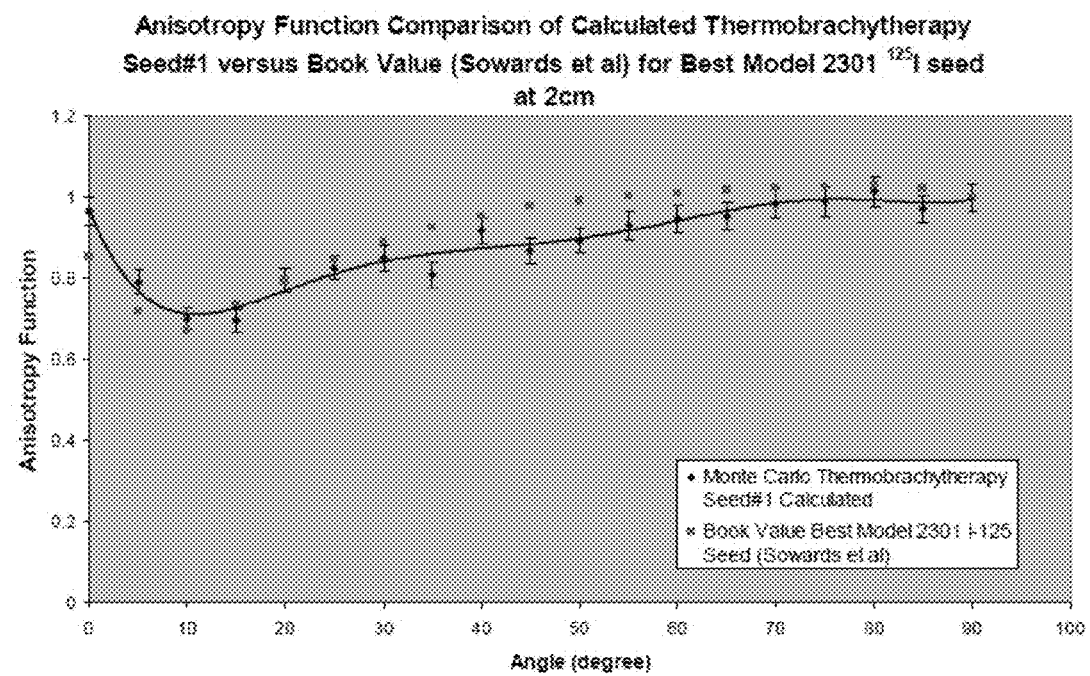
FIG. 28 illustrates the Anisotropy Function of Monte Carlo calculated value for Thermobrachytherapy Seed#1 and the Book Value for the Best Model 2301 $^{125}$I in liquid water at 2 cm radii.

FIG. 28 illustrates the Anisotropy Function of Monte Carlo calculated value for Thermobrachytherapy Seed#1 and the Book Value for the Best Model 2301 $^{125}$I in liquid water at 2 cm radii. The plot is fitted with a 6th order polynomial function.

Table 24c illustrates the Monte Carlo calculated Anisotropy Function of the Thermobrachytherapy Seed#1 in liquid water for Radial Distances of 3 cm. A comparison between calculated and book values of the Best Model 2301 $^{125}$I Seed is also calculated.

TABLE 24c

Monte Carlo calculated Anisotropy Function of the Thermobrachytherapy Seed#1 in liquid water for Radial Distances of 3 cm. A comparison between calculated and book values of the Best Model 2301 $^{125}$I Seed is also calculated.

| Angle | AF at 3 cm | Best Model 2301 $^{125}$I Seed | Error | Book Value (Meigooni et al) | Error |
|---|---|---|---|---|---|
| 0 | 1.046749 | 1.081703 | −0.03339 | 0.922 | 0.135303 |
| 5 | 0.834596 | 0.827586 | 0.008398 | 0.726 | 0.149581 |
| 10 | 0.736561 | 0.750467 | −0.01888 | 0.699 | 0.053736 |
| 15 | 0.812837 | 0.833466 | −0.02538 | 0.756 | 0.075182 |
| 20 | 0.793065 | 0.808948 | −0.02003 | 0.809 | −0.0197 |
| 25 | 0.844568 | 0.872956 | −0.03361 | 0.852 | −0.00872 |
| 30 | 0.920348 | 0.930988 | −0.01156 | 0.885 | 0.039941 |
| 35 | 0.935357 | 0.953275 | −0.01916 | 0.919 | 0.017799 |
| 40 | 0.990214 | 0.987268 | 0.002976 | 0.947 | 0.045633 |
| 45 | 0.949857 | 0.95516 | −0.00558 | 0.968 | −0.01874 |
| 50 | 0.969268 | 0.973073 | −0.00393 | 0.985 | −0.01597 |
| 55 | 0.98734 | 1.008446 | −0.02138 | 0.997 | −0.00969 |
| 60 | 0.985163 | 0.988973 | −0.00387 | 1.009 | −0.02362 |
| 65 | 1.001282 | 1.000178 | 0.001103 | 1.012 | −0.01059 |
| 70 | 1.022119 | 1.030136 | −0.00784 | 1.016 | 0.006022 |
| 75 | 1.010293 | 1.018382 | −0.00801 | 1.018 | −0.00757 |
| 80 | 0.959631 | 0.960588 | −0.001 | 1.019 | −0.05826 |
| 85 | 0.994327 | 0.996809 | −0.0025 | 1.019 | −0.02421 |
| 90 | 1 | 1 | 0 | 1 | 0 |

Figure 29:
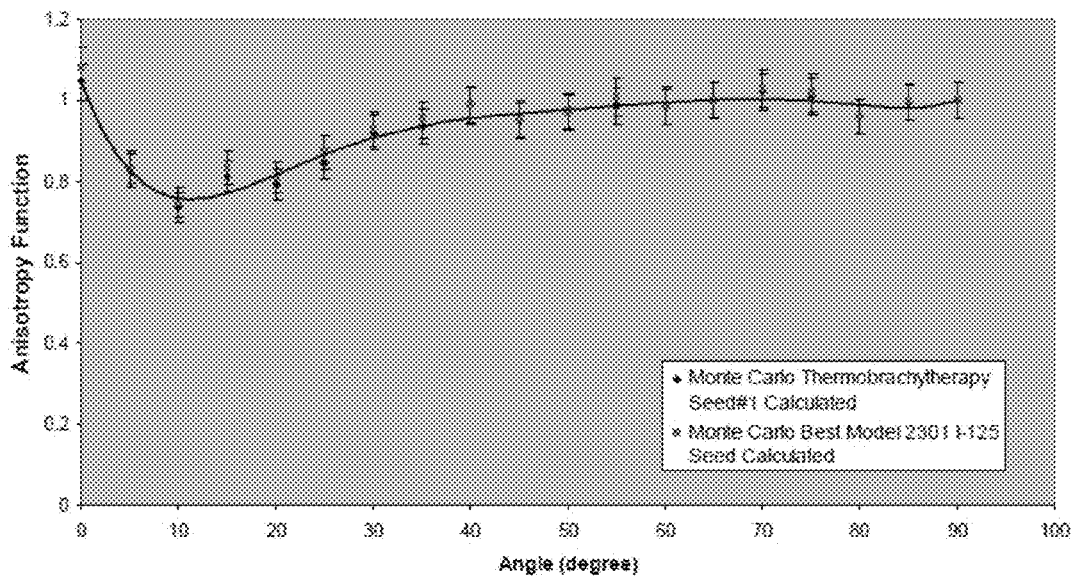
FIG. 29 illustrates the Anisotropy Function of Monte Carlo calculated value for Thermobrachytherapy Seed#1 and the Book Value for the Best Model 2301 $^{125}$I in liquid water at 3 cm radii.

FIG. 29 illustrates the Anisotropy Function of Monte Carlo calculated value for Thermobrachytherapy Seed#1 and the Book Value for the Best Model 2301 $^{125}$I in liquid water at 3 cm radii. The plot is fitted with a 6th order polynomial function.

Figure 30:
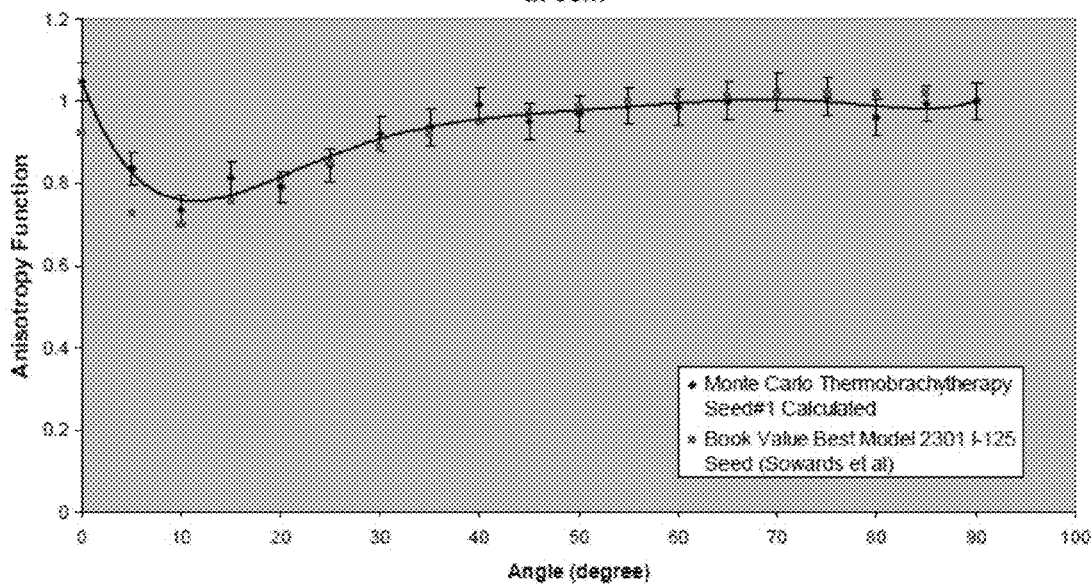
FIG. 30 illustrates the Anisotropy Function of Monte Carlo calculated value for Thermobrachytherapy Seed#1 and the Book Value for the Best Model 2301 $^{125}$I in liquid water at 3 cm radii.

FIG. 30 illustrates the Anisotropy Function of Monte Carlo calculated value for Thermobrachytherapy Seed#1 and the Book Value for the Best Model 2301 $^{125}$I in liquid water at 3 cm radii. The plot is fitted with a 6th order polynomial function.

Table 24d illustrates the Monte Carlo calculated Anisotropy Function of the Thermobrachytherapy Seed#1 in liquid water for Radial Distances of 4 cm. A comparison between calculated and book values of the Best Model 2301 $^{125}$I Seed is also calculated.

TABLE 24d

Monte Carlo calculated Anisotropy Function of the Thermobrachytherapy Seed#1 in liquid water for Radial Distances of 4 cm. A comparison between calculated and book values of the Best Model 2301 $^{125}$I Seed is also calculated.

| Angle | AF at 4 cm | Best Model 2301 $^{125}$I Seed | Error | Book Value (Meigooni et al) | Error |
|---|---|---|---|---|---|
| 0 | 1.044159 | 1.067157 | −0.02202 | 0.902 | 0.157605 |
| 5 | 0.843972 | 0.856189 | −0.01448 | 0.728 | 0.159303 |
| 10 | 0.846344 | 0.849553 | −0.00379 | 0.727 | 0.16416 |
| 15 | 0.752004 | 0.762809 | −0.01437 | 0.779 | −0.03465 |
| 20 | 0.835638 | 0.843573 | −0.0095 | 0.814 | 0.026583 |
| 25 | 0.909071 | 0.917008 | −0.00873 | 0.863 | 0.053385 |
| 30 | 0.908464 | 0.921985 | −0.01488 | 0.892 | 0.018457 |
| 35 | 0.916856 | 0.927006 | −0.01107 | 0.918 | −0.00125 |
| 40 | 0.918556 | 0.928846 | −0.0112 | 0.939 | −0.02177 |
| 45 | 0.983039 | 0.992994 | −0.01013 | 0.976 | 0.007213 |
| 50 | 0.968012 | 0.968645 | −0.00065 | 0.991 | −0.0232 |
| 55 | 1.009604 | 1.028106 | −0.01833 | 1.004 | 0.005582 |
| 60 | 0.993738 | 1.000959 | −0.00727 | 1.007 | −0.01317 |
| 65 | 1.023079 | 1.017048 | 0.005895 | 1.009 | 0.013953 |
| 70 | 1.032431 | 1.020551 | 0.011507 | 1.023 | 0.009219 |
| 75 | 1.024549 | 1.009032 | 0.015145 | 1.017 | 0.007423 |
| 80 | 0.986329 | 0.975997 | 0.010475 | 1.017 | −0.03016 |
| 85 | 1.013189 | 0.998651 | 0.014348 | 1.018 | −0.00473 |
| 90 | 1 | 0.999983 | 1.73E−05 | 1 | 0 |

Figure 31:
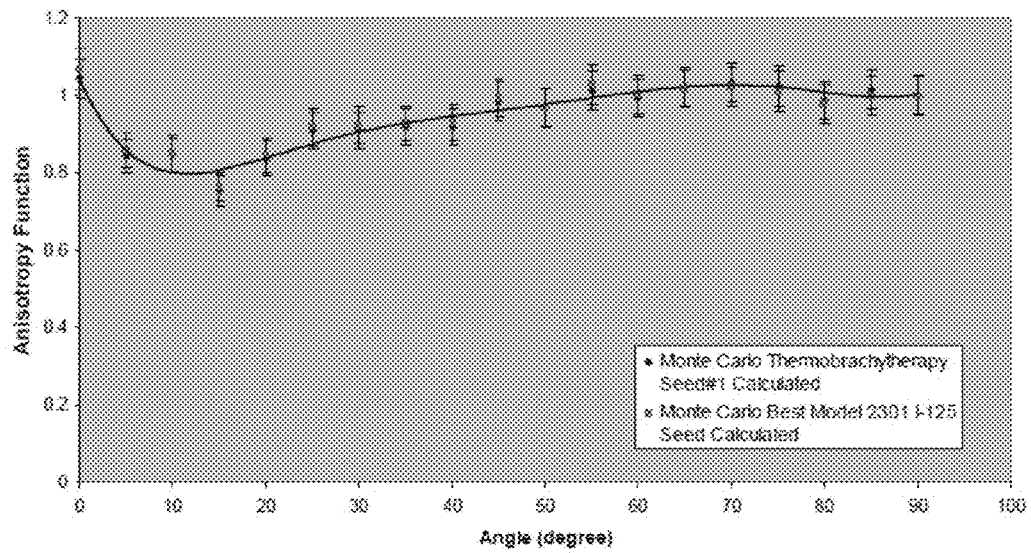
FIG. 31 illustrates the Anisotropy Function of Monte Carlo calculated value for Thermobrachytherapy Seed#1 and the Book Value for the Best Model 2301 $^{125}$I in liquid water at 4 cm radii.

FIG. 31 illustrates the Anisotropy Function of Monte Carlo calculated value for Thermobrachytherapy Seed#1 and the Book Value for the Best Model 2301 $^{125}$I in liquid water at 4 cm radii. The plot is fitted with a 6th order polynomial function.

Figure 32:
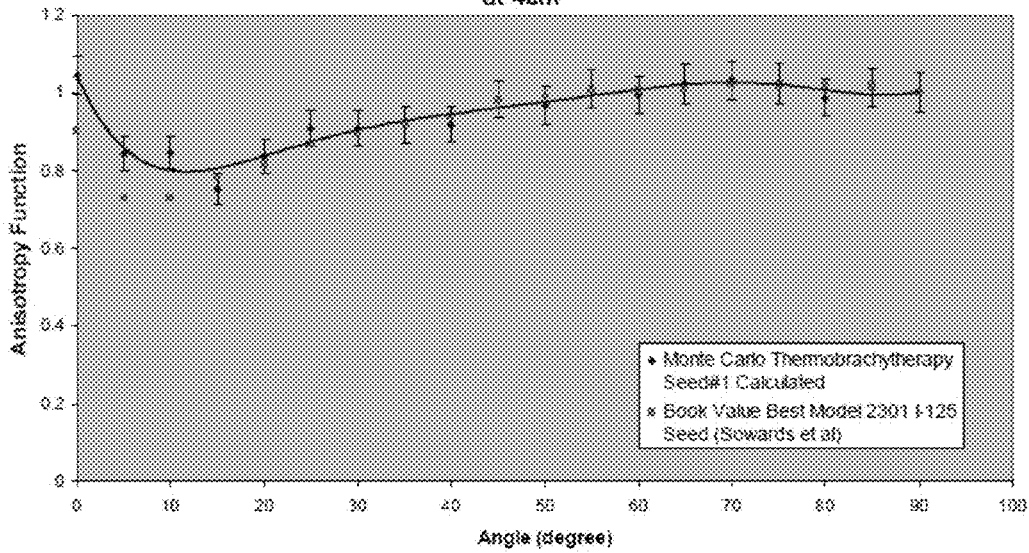
FIG. 32 illustrates the Anisotropy Function of Monte Carlo calculated value for Thermo Brachytherapy Seed#1 and the Book Value for the Best Model 2301 $^{125}$I in liquid water at 4 cm radii.

FIG. 32 illustrates the Anisotropy Function of Monte Carlo calculated value for Thermo Brachytherapy Seed#1 and the Book Value for the Best Model 2301 $^{125}$I in liquid water at 4 cm radii. The plot is fitted with a 6th order polynomial function.

Table 24e illustrates the Monte Carlo calculated Anisotropy Function of the Thermobrachytherapy Seed#1 in liquid water for Radial Distances of 5 cm. A comparison between calculated and book values of the Best Model 2301 $^{125}$I Seed is also calculated.

TABLE 24e

Monte Carlo calculated Anisotropy Function of the Thermobrachytherapy Seed#1 in liquid water for Radial Distances of 5 cm. A comparison between calculated and book values of the Best Model 2301 $^{125}$I Seed is also calculated.

| Angle | AF at 5 cm | Best Model 2301 $^{125}$I Seed | Error | Book Value (Meigooni et al) | Error |
|---|---|---|---|---|---|
| 0 | 1.01337 | 1.037909 | −0.02422 | 0.894 | 0.133524 |
| 5 | 0.808504 | 0.826259 | −0.02196 | 0.753 | 0.07371 |
| 10 | 0.765679 | 0.781112 | −0.02016 | 0.732 | 0.04601 |
| 15 | 0.762468 | 0.785625 | −0.03037 | 0.795 | −0.04092 |
| 20 | 0.805936 | 0.814253 | −0.01032 | 0.825 | −0.02311 |
| 25 | 0.785503 | 0.790151 | −0.00592 | 0.865 | −0.0919 |
| 30 | 0.931303 | 0.93407 | −0.00297 | 0.899 | 0.035932 |
| 35 | 0.874852 | 0.880933 | −0.00695 | 0.92 | −0.04907 |
| 40 | 0.899968 | 0.909002 | −0.01004 | 0.943 | −0.04563 |
| 45 | 0.950244 | 0.965222 | −0.01576 | 0.968 | −0.01834 |
| 50 | 0.929789 | 0.921762 | 0.008633 | 0.997 | −0.06741 |
| 55 | 0.988796 | 1.00322 | −0.01459 | 0.993 | −0.00423 |
| 60 | 0.954913 | 0.972524 | −0.01844 | 1.01 | −0.05454 |
| 65 | 0.99748 | 0.982562 | 0.014956 | 1.024 | −0.0259 |
| 70 | 0.970803 | 0.959269 | 0.01188 | 1.011 | −0.03976 |
| 75 | 1.029805 | 1.020911 | 0.008636 | 1.02 | 0.009613 |
| 80 | 0.997893 | 0.991336 | 0.006571 | 1.01 | −0.01199 |
| 85 | 1.019 | 1.015815 | 0.003126 | 1.011 | 0.007913 |
| 90 | 1 | 1 | 0 | 1 | 0 |

Figure 33:
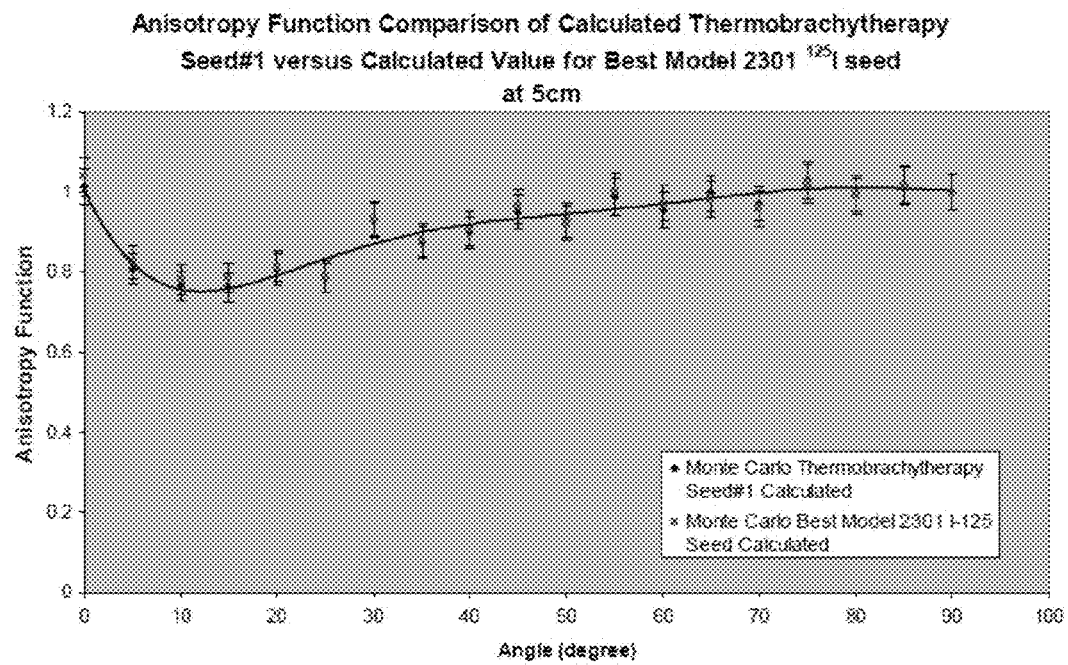
FIG. 33 illustrates the Anisotropy Function of Monte Carlo calculated value for Thermobrachytherapy Seed#1 and the Book Value for the Best Model 2301 $^{125}$I in liquid water at 5 cm radii.

FIG. 33 illustrates the Anisotropy Function of Monte Carlo calculated value for Thermobrachytherapy Seed#1 and the Book Value for the Best Model 2301 $^{125}$I in liquid water at 5 cm radii. The plot is fitted with a 6th order polynomial function.

Figure 34:
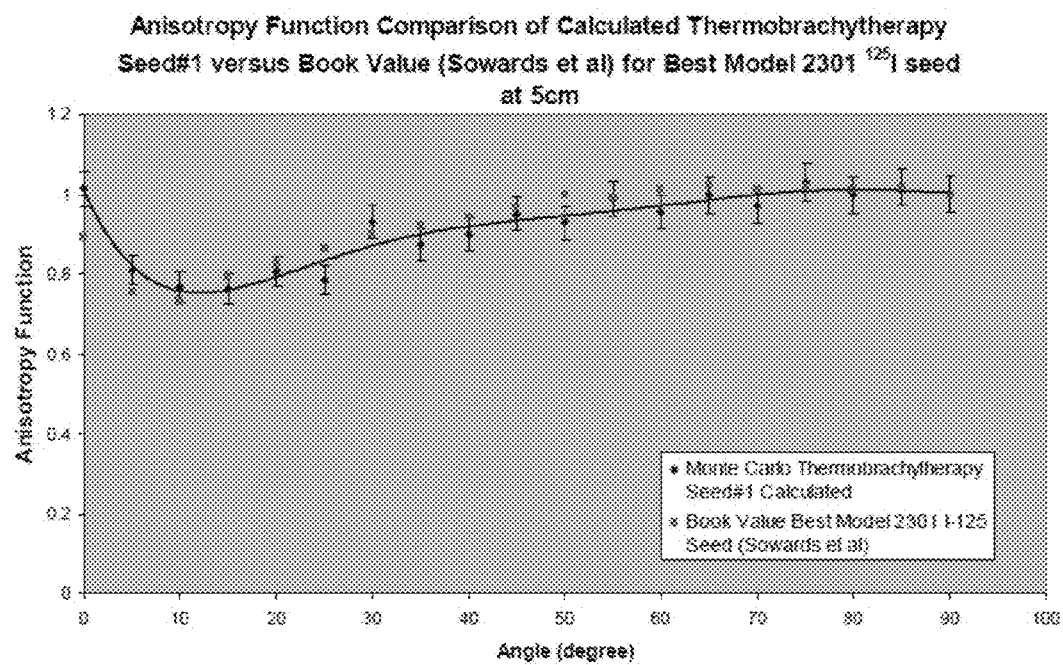
FIG. 34 illustrates the Anisotropy Function of Monte Carlo calculated value for Thermobrachytherapy Seed#1 and the Book Value for the Best Model 2301 $^{125}$I in liquid water at 5 cm radii.

FIG. 34 illustrates the Anisotropy Function of Monte Carlo calculated value for Thermobrachytherapy Seed#1 and the Book Value for the Best Model 2301 $^{125}$I in liquid water at 5 cm radii. The plot is fitted with a 6th order polynomial function.

Table 24f illustrates the Monte Carlo calculated Anisotropy Function of the Thermobrachytherapy Seed#1 in liquid water for Radial Distances of 6 cm. A comparison between calculated and book values of the Best Model 2301 $^{125}$I Seed is also calculated.

TABLE 24f

Monte Carlo calculated Anisotropy Function of the Thermobrachytherapy Seed#1 in liquid water for Radial Distances of 6 cm. A comparison between calculated and book values of the Best Model 2301 $^{125}$I Seed is also calculated.

| Angle | AF at 6 cm | Best Model 2301 $^{125}$I Seed | Error | Book Value (Meigooni et al) | Error |
|---|---|---|---|---|---|
| 0 | 0.963271 | 1.002815 | −0.04105 | 0.893 | 0.078691 |
| 5 | 0.873686 | 0.888127 | −0.01653 | 0.771 | 0.133185 |
| 10 | 0.767832 | 0.782999 | −0.01975 | 0.764 | 0.005016 |
| 15 | 0.80553 | 0.819448 | −0.01728 | 0.805 | 0.000659 |
| 20 | 0.802787 | 0.817894 | −0.01882 | 0.852 | −0.05776 |
| 25 | 0.91588 | 0.936581 | −0.0226 | 0.89 | 0.029078 |
| 30 | 0.820472 | 0.833299 | −0.01563 | 0.915 | −0.10331 |
| 35 | 0.866345 | 0.886202 | −0.02292 | 0.964 | −0.1013 |
| 40 | 0.880596 | 0.904777 | −0.02746 | 0.976 | −0.09775 |
| 45 | 0.929708 | 0.948816 | −0.02055 | 0.979 | −0.05035 |
| 50 | 0.963876 | 0.976859 | −0.01347 | 0.989 | −0.0254 |
| 55 | 0.968881 | 0.98898 | −0.02075 | 1.011 | −0.04166 |
| 60 | 0.950198 | 0.967874 | −0.0186 | 1.019 | −0.06752 |
| 65 | 0.946892 | 0.960829 | −0.01472 | 1.034 | −0.08424 |
| 70 | 0.95177 | 0.948077 | 0.00388 | 1.035 | −0.08042 |
| 75 | 0.999705 | 1.01108 | −0.01138 | 1.043 | −0.04151 |
| 80 | 0.97142 | 0.972717 | −0.00133 | 1.02 | −0.04763 |
| 85 | 1.054951 | 1.053106 | 0.001749 | 1.031 | 0.023231 |
| 90 | 1 | 1 | 0 | 1 | 0 |

Figure 35:
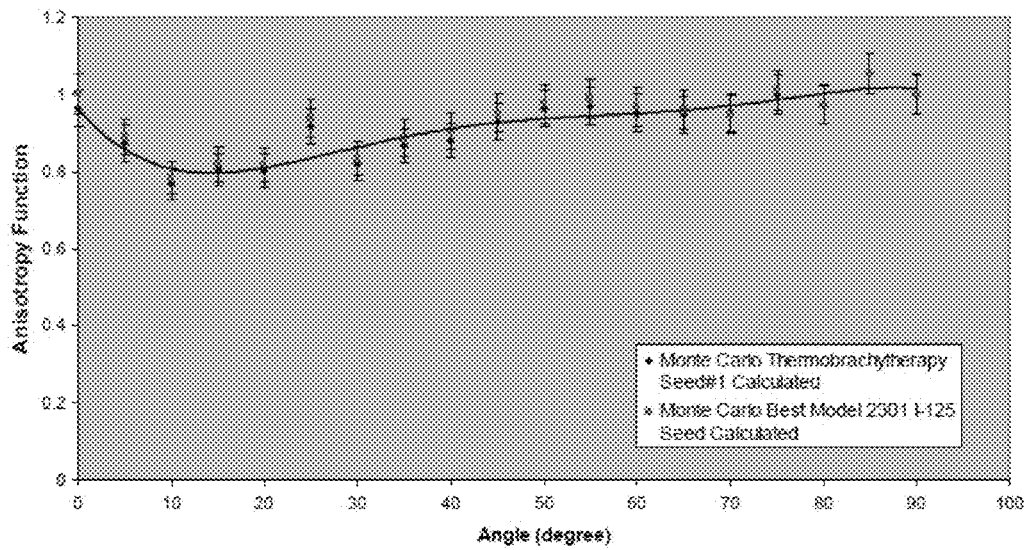
FIG. 35 illustrates the Anisotropy Function of Monte Carlo calculated value for Thermobrachytherapy Seed#1 and the Book Value for the Best Model 2301 $^{125}$I in liquid water at 6 cm radii.

FIG. 35 illustrates the Anisotropy Function of Monte Carlo calculated value for Thermobrachytherapy Seed#1 and the Book Value for the Best Model 2301 $^{125}$I in liquid water at 6 cm radii. The plot is fitted with a 6th order polynomial function.

Figure 36:
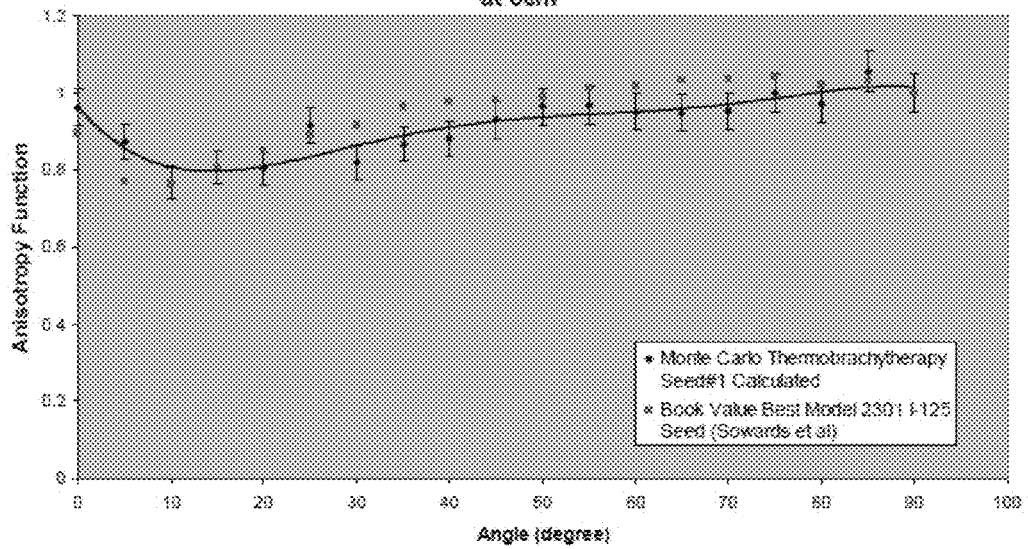
FIG. 36 illustrates the Anisotropy Function of Monte Carlo calculated value for Thermobrachytherapy Seed#1 and the Book Value for the Best Model 2301 $^{125}$I in liquid water at 6 cm radii.

FIG. 36 illustrates the Anisotropy Function of Monte Carlo calculated value for Thermobrachytherapy Seed#1 and the Book Value for the Best Model 2301 $^{125}$I in liquid water at 6 cm radii. The plot is fitted with a 6th order polynomial function.

Table 24g illustrates the Monte Carlo calculated Anisotropy Function of the Thermobrachytherapy Seed#1 in liquid water for Radial Distances of 7 cm. A comparison between calculated and book values of the Best Model 2301 $^{125}$I Seed is also calculated.

TABLE 24g

Monte Carlo calculated Anisotropy Function of the Thermobrachytherapy Seed#1 in liquid water for Radial Distances of 7 cm. A comparison between calculated and book values of the Best Model 2301 $^{125}$I Seed is also calculated.

| Angle | AF at 7 cm | Best Model 2301 $^{125}$I Seed | Error | Book Value (Meigooni et al) | Error |
|---|---|---|---|---|---|
| 0 | 1.00207 | 1.044519 | −0.04236 | 0.858 | 0.167914 |
| 5 | 0.833197 | 0.872338 | −0.04698 | 0.8 | 0.041497 |
| 10 | 0.782894 | 0.814773 | −0.04072 | 0.782 | 0.001143 |
| 15 | 0.863295 | 0.89647 | −0.03843 | 0.812 | 0.063171 |
| 20 | 0.812335 | 0.839067 | −0.03291 | 0.821 | −0.01055 |
| 25 | 0.837071 | 0.857219 | −0.02407 | 0.86 | −0.02666 |
| 30 | 0.938672 | 0.968562 | −0.03184 | 0.873 | 0.075226 |
| 35 | 0.956463 | 0.965505 | −0.00945 | 0.924 | 0.035133 |
| 40 | 0.972739 | 1.010278 | −0.03859 | 0.937 | 0.038142 |
| 45 | 0.984548 | 1.008515 | −0.02434 | 0.954 | 0.032021 |
| 50 | 0.962371 | 0.983552 | −0.02201 | 0.961 | 0.001426 |
| 55 | 0.998295 | 1.020988 | −0.02273 | 0.99 | 0.008379 |
| 60 | 0.910017 | 0.920182 | −0.01117 | 1.002 | −0.0918 |
| 65 | 1.108344 | 1.14268 | −0.03098 | 1.03 | 0.076062 |
| 70 | 1.052193 | 1.069128 | −0.01609 | 1.01 | 0.041775 |
| 75 | 1.034983 | 1.039857 | −0.00471 | 1.02 | 0.01469 |
| 80 | 0.972257 | 0.991134 | −0.01942 | 1.005 | −0.03258 |
| 85 | 1.017453 | 1.029283 | −0.01163 | 1.021 | −0.00347 |
| 90 | 0.999979 | 0.999979 | 1.11E−16 | 1 | −2.1E−05 |

Figure 37:
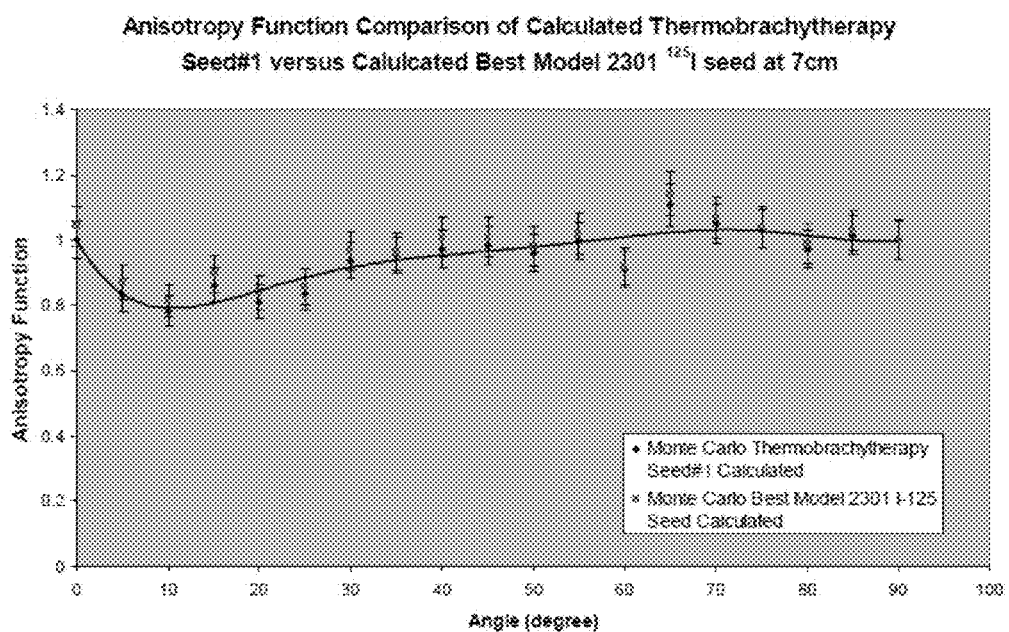
FIG. 37 illustrates the Anisotropy Function of Monte Carlo calculated value for Thermobrachytherapy Seed#1 and the Book Value for the Best Model 2301 $^{125}$I in liquid water at 7 cm radii.

FIG. 37 illustrates the Anisotropy Function of Monte Carlo calculated value for Thermobrachytherapy Seed#1 and the Book Value for the Best Model 2301 $^{125}$I in liquid water at 7 cm radii. The plot is fitted with a 6th order polynomial function.

Figure 38:
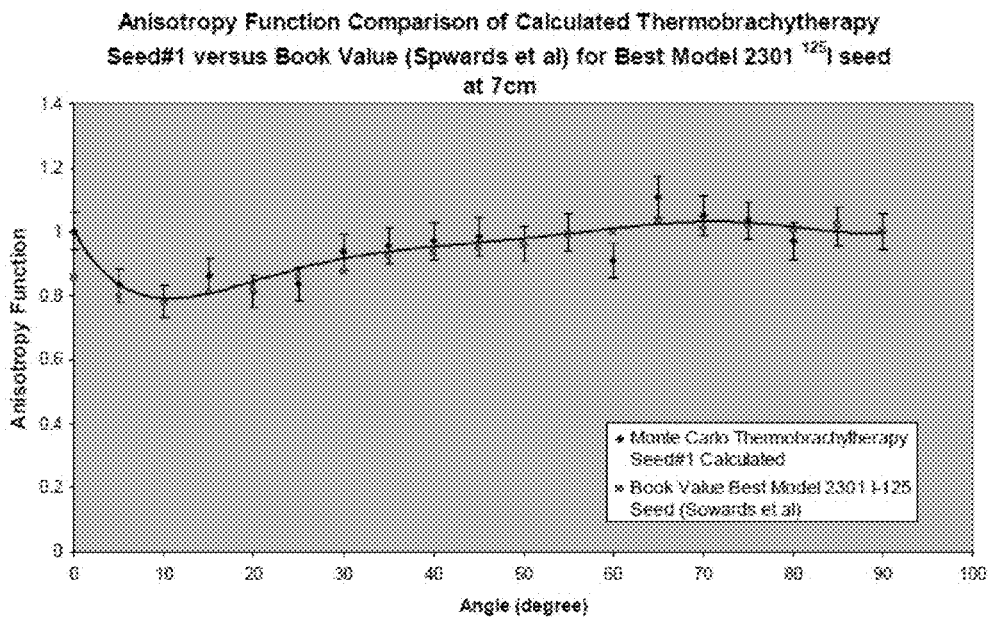
FIG. 38 illustrates the Anisotropy Function of Monte Carlo calculated value for Thermo Brachytherapy Seed#1 and the Book Value for the Best Model 2301 $^{125}$I in liquid water at 7 cm radii.

FIG. 38 illustrates the Anisotropy Function of Monte Carlo calculated value for Thermo Brachytherapy Seed#1 and the Book Value for the Best Model 2301 $^{125}$I in liquid water at 7 cm radii. The plot is fitted with a 6th order polynomial function.

Average Anisotropy Function:

The average anisotropy function is taken by taking an average of the calculated anisotropy functions for all the angles. Table 25a illustrates the Average Anisotropy Function calculated for radial distances of 1 cm in liquid water.

TABLE 25a

Average Anisotropy Function calculated for radial distances of 1 cm in liquid water

| | 1 cm | Best Model 2301 $^{125}$I Seed | Error | Book Value (Meigooni et al) | Error |
|---|---|---|---|---|---|
| Avg. Anisotropy Constant $\Phi_{an}(r)$ | 0.902 | 0.913 | −0.012 | 0.986 | −0.085 |

Table 25b illustrates the Average Anisotropy Function calculated for radial distances of 2 cm in liquid water.

TABLE 25b

Average Anisotropy Function calculated for radial distances of 2 cm in liquid water

| | 2 cm | Best Model 2301 $^{125}$I Seed | Error | Book Value (Meigooni et al) | Error |
|---|---|---|---|---|---|
| Avg. Anisotropy | 0.89 | 0.904 | −0.016 | 0.976 | −0.0881 |

TABLE 25b-continued

Average Anisotropy Function calculated for radial distances of 2 cm in liquid water

| 2 cm | Best Model 2301 $^{125}$I Seed | Error | Book Value (Meigooni et al) | Error |
|---|---|---|---|---|
| Constant $\Phi_{an}$ (r) | | | | |

Table 25c illustrates the Average Anisotropy Function calculated for radial distances of 3 cm in liquid water.

TABLE 25c

Average Anisotropy Function calculated for radial distances of 3 cm in liquid water

| 3 cm | Best Model 2301 $^{125}$I Seed | Error | Book Value (Meigooni et al) | Error |
|---|---|---|---|---|
| Avg. Anisotropy Constant $\Phi_{an}$ (r) | 0.937 | 0.946 | −0.01039 | 0.968 | −0.0325 |

Table 25d illustrates average Anisotropy Function calculated for radial distances of 4 cm in liquid water.

TABLE 25d

Average Anisotropy Function calculated for radial distances of 4 cm in liquid water

| 4 cm | Best Model 2301 $^{125}$I Seed | Error | Book Value (Meigooni et al) | Error |
|---|---|---|---|---|
| Avg. Anisotropy Constant $\Phi_{an}$ (r) | 0.947 | 0.952 | −0.00428 | 0.971 | −0.0239 |

Table 25e illustrates the Average Anisotropy Function calculated for radial distances of 5 cm in liquid water.

TABLE 25e

Average Anisotropy Function calculated for radial distances of 5 cm in liquid water

| 5 cm | Best Model 2301 $^{125}$I Seed | Error | Book Value (Meigooni et al) | Error |
|---|---|---|---|---|
| Avg. Anisotropy Constant $\Phi_{an}$ (r) | 0.920 | 0.926 | −0.006 | 0.969 | −0.05 |

Table 25f illustrates the Average Anisotropy Function calculated for radial distances of 6 cm in liquid water.

TABLE 25f

Average Anisotropy Function calculated for radial distances of 6 cm in liquid water

| 6 cm | Best Model 2301 $^{125}$I Seed | Error | Book Value (Meigooni et al) | Error |
|---|---|---|---|---|
| Avg. Anisotropy Constant $\Phi_{an}$ (r) | 0.918 | 0.932 | −0.0153 | 0.991 | −0.0741 |

Table 25g illustrates the Average Anisotropy Function calculated for radial distances of 7 cm in liquid water.

TABLE 25g

Average Anisotropy Function calculated for radial distances of 7 cm in liquid water

| 7 cm | Best Model 2301 $^{125}$I Seed | Error | Book Value (Meigooni et al) | Error |
|---|---|---|---|---|
| Avg. Anisotropy Constant $\Phi_{an}$ (r) | 0.949 | 0.972 | −0.024 | 0.969 | −0.0202 |

Source Anisotropy Constant:

The Source Anisotropy Constant is calculated by taking the average of all the Average Anisotropy Constants. Table 26 illustrates the Source Anisotropy Constant for Thermobrachytherapy Seed#1 in liquid water. The Source Anisotropy Constant is 0.923 and deviates from the Monte Carlo calculated Best Model 2301 $^{125}$I Seed by 1.28% book value by 4.6%

TABLE 26

Source Anisotropy Constant for Thermobrachytherapy Seed#1 in liquid water.

| | Calculated value | Best Model 2301 $^{125}$I Seed | Error | Book value | Error |
|---|---|---|---|---|---|
| Source Anisotropy Constant $\Phi_{an}$ (r) | 0.923 | 0.935 | −0.0128 | 0.98 | −0.0582 |

1) Thermobrachytherapy Seed#1 in Solid Water i) Dose Rate (D):

Dose Rate was calculated for seed at 1 cm on the transverse plane (θ=90°) of the source (from the center of the source) in solid water. Therefore, for this measurement the phantom was taken to be Solid Water since it is the solid water measurement. Table 27 illustrates the Dose Rate for Thermobrachytherapy Seed#1 in solid water calculated using Monte Carlo. The error is calculated by using equation #16. Therefore, the error between the calculated thermobrachytherapy value and the calculated Best Model 2301 $^{125}$I seed is 6.0%. The measured value of Dose Rate is 0.245±4.99*10$^{-3}$ cGy*sec$^{-1}$*Ci$^{-1}$.

TABLE 27

Dose Rate for Thermobrachytherapy Seed#1 in Solid Water calculated using Monte Carlo

| Calculated Dose Rate (cGy * sec$^{-1}$ * Ci$^{-1}$) | Calculated Best Model 2301 $^{125}$I Seed (cGy * sec$^{-1}$ * Ci$^{-1}$) | Error | Book Value (Meigooni et al) | Error |
|---|---|---|---|---|
| 0.244831 | 0.230994 | −0.0599 | N/A | N/A | ii) Air Kerma Strength (SK):

Air Kerma Strength was calculated for the seed again at 1 cm on the transverse plane of the source (from the center of the source) but now it was in air. Therefore, the material inside the phantom was taken as air. Also, the 0.897 WAFAC correction factor (as discussed in the Materials & Methods section) is used for SK. Table 28 illustrates the Air Kerma Strength for Thermobrachytherapy Seed#1 in solid water calculated using Monte Carlo. The error is calculated by using equation #16. Therefore, the error between the calculated thermobrachytherapy value and the calculated Best Model 2301 $^{125}$I seed is 6.0%. The measured value of Air Kerma Strength is $0.238 \pm 5.14 \times 10^{-3}$ cGy*cm$^2$*sec$^{-1}$*Ci$^{-1}$.

TABLE 28

Air Kerma Strength for Thermobrachytherapy Seed#1 in Solid Water calculated using Monte Carlo

| Calculated Air Kerma Strength (cGy * cm$^2$ * sec$^{-1}$ * Ci$^{-1}$) | Calculated Best Model 2301 $^{125}$I Seed (cGy * cm$^2$ * sec$^{-1}$ * Ci$^{-1}$) | Error | Book Value (Meigooni et al) | Error |
|---|---|---|---|---|
| 0.237773 | 0.224332 | 0.0599 | N/A | NA | iii) Dose Rate Constant (Λ):

Dose rate constant is calculated using equation #4. In order to calculate it, the ratio of the dose rate and air kerma strength is taken. Table 29a illustrates the Monte Carlo calculated Dose Rate Constant Thermobrachytherapy Seed#1 in solid water. The error is calculated by using equation #. Therefore, the error between the calculated thermobrachytherapy value and the calculated Best Model 2301 $^{125}$I seed is 0.01%. Also, the error between the calculated thermobrachytherapy value and the Book Value for Best Model 2301 $^{125}$I seed is 5.1%. The measured value of Dose Rate Constant is $1.03 \pm 0.031$ cGy*h$^{-1}$U$^{-1}$.

TABLE 29

Monte Carlo calculated Dose Rate Constant Thermobrachytherapy Seed#1 in Solid Water

| Calculated Dose Rate Constant (cGy * h$^{-1}$U$^{-1}$) | Best Model 2301 $^{125}$I Seed (cGy * h$^{-1}$U$^{-1}$) | Error | Book Value (Meigooni et al) (cGy * h$^{-1}$U$^{-1}$) | Error |
|---|---|---|---|---|
| 1.0297 | 1.02969 | 0.0001 | 0.98 | 0.051 | iv) Correction/Multiplicative Factor:

Meigooni et al calculated that a conversion factor of 1.05 was needed to convert the dose rate constant in solid water to liquid water.

The calculated Correction/Multiplicative factor obtained is 1.026.

iv) Radial Function:

Calculation of the radial function is a two fold process.

a) Geometry Function

The Geometry function is independent of the material content of the phantom. Also, the geometry (and dimension) of the source cell remains the same. Therefore, the geometry factor from Table 6 is applicable here.

b) Radial Function Using the Geometry Function

Radial Function was calculated using equation#8 incorporating the geometry function calculated in part a) above. Table 29b illustrates the Radial Function calculated at the transverse plane for the Thermobrachytherapy Seed#1 in solid water using Monte Carlo.

TABLE 29

Radial Function calculated at the transverse plane for the Thermobrachytherapy Seed#1 in Solid Water using Monte Carlo.

| Transverse distance (r) cm | Radial Function g (r, θ) | Best Model 2301 $^{125}$I Seed | Error | Book Value (Meigooni et al) | Error |
|---|---|---|---|---|---|
| 0.1 | 0.964876 | 0.9740849 | −0.00945 | | |
| 0.15 | 0.981422 | 0.9872727 | −0.00593 | | |
| 0.2 | 1.019521 | 1.0245773 | −0.00494 | | |
| 0.25 | 1.000004 | 0.997152 | 0.00286 | | |
| 0.3 | 1.000948 | 1.0106151 | −0.00957 | | |
| 0.4 | 0.994702 | 1.0024356 | −0.00771 | | |
| 0.5 | 0.992548 | 0.9962775 | −0.00374 | | |
| 0.6 | 0.951016 | 0.9601123 | −0.00947 | 1.044 | −0.08906 |
| 0.7 | 0.906666 | 0.9079231 | −0.00138 | | |
| 0.75 | 0.952771 | 0.9467391 | 0.006371 | | |
| 0.8 | 0.955798 | 0.9554107 | 0.000406 | | |
| 0.9 | 0.946121 | 0.9667486 | −0.02134 | | |
| 1 | 1.000001 | 1.0000005 | 0 | 1 | 5.07E−07 |
| 1.5 | 0.90524 | 0.9040619 | 0.001304 | 0.926 | −0.02242 |
| 2 | 0.813691 | 0.8129667 | 0.000891 | 0.842 | −0.03362 |
| 2.5 | 0.726495 | 0.728075 | −0.00217 | 0.752 | −0.03392 |
| 3 | 0.648377 | 0.6505947 | −0.00341 | 0.666 | −0.02646 |
| 3.5 | 0.563752 | 0.5635308 | 0.000392 | 0.581 | −0.02969 |
| 4 | 0.512275 | 0.5125491 | −0.00054 | 0.509 | 0.006434 |
| 4.5 | 0.434328 | 0.4328601 | 0.003391 | 0.443 | −0.01958 |
| 5 | 0.380607 | 0.3817734 | −0.00306 | 0.386 | −0.01397 |
| 5.5 | 0.318492 | 0.3178485 | 0.002026 | 0.336 | −0.05211 |
| 6 | 0.27567 | 0.2753888 | 0.001021 | 0.286 | −0.03612 |
| 6.5 | 0.234263 | 0.2309718 | 0.014249 | 0.245 | −0.04382 |
| 7 | 0.206563 | 0.2041012 | 0.012064 | 0.207 | −0.00211 |
| 7.5 | 0.178336 | 0.176629 | 0.009665 | 0.178 | 0.001888 |
| 8 | 0.158985 | 0.1571086 | 0.011944 | 0.159 | −9.3E−05 |
| 8.5 | 0.12521 | 0.1246026 | 0.004876 | 0.14 | −0.10564 |
| 9 | 0.11154 | 0.1098135 | 0.015721 | 0.116 | −0.03845 |
| 9.5 | 0.094898 | 0.093497 | 0.014987 | 0.097 | −0.02167 |
| 10 | 0.080815 | 0.079492 | 0.016645 | 0.08 | 0.010189 |

Figure 39:
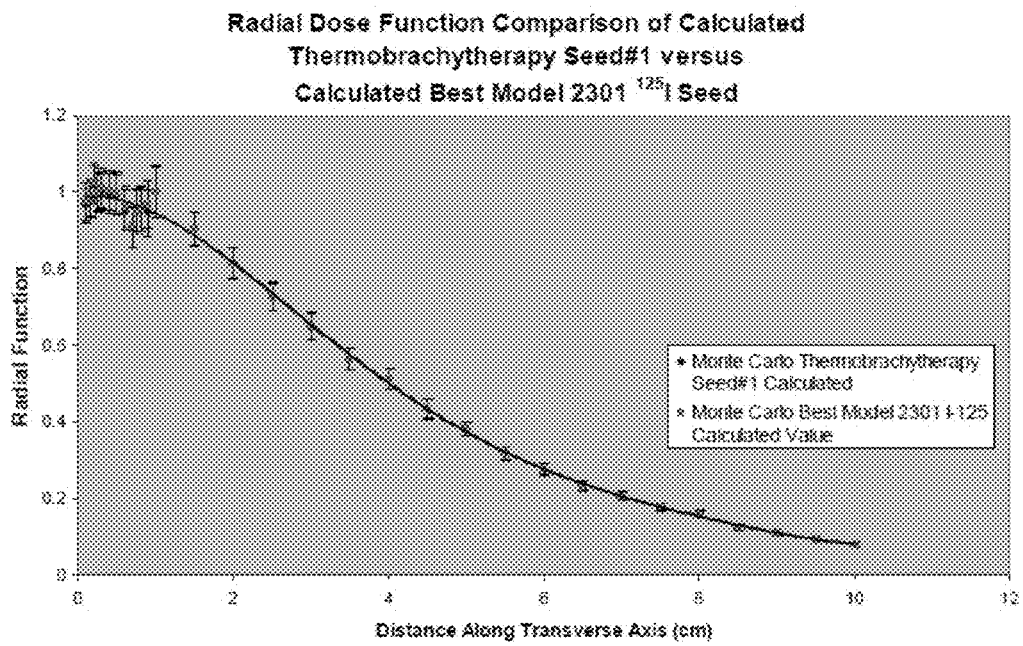
FIG. 39 illustrates the Radial Function of Monte Carlo calculated value for Thermobrachytherapy Seed#1 and the Monte Carlo calculated value for the Best Model 2301 $^{125}$I in solid water.

FIG. 39 illustrates the Radial Function of Monte Carlo calculated value for Thermobrachytherapy Seed#1 and the Monte Carlo calculated value for the Best Model 2301 $^{125}$I in solid water. The plot is fitted with a 5th order polynomial function.

Figure 40:
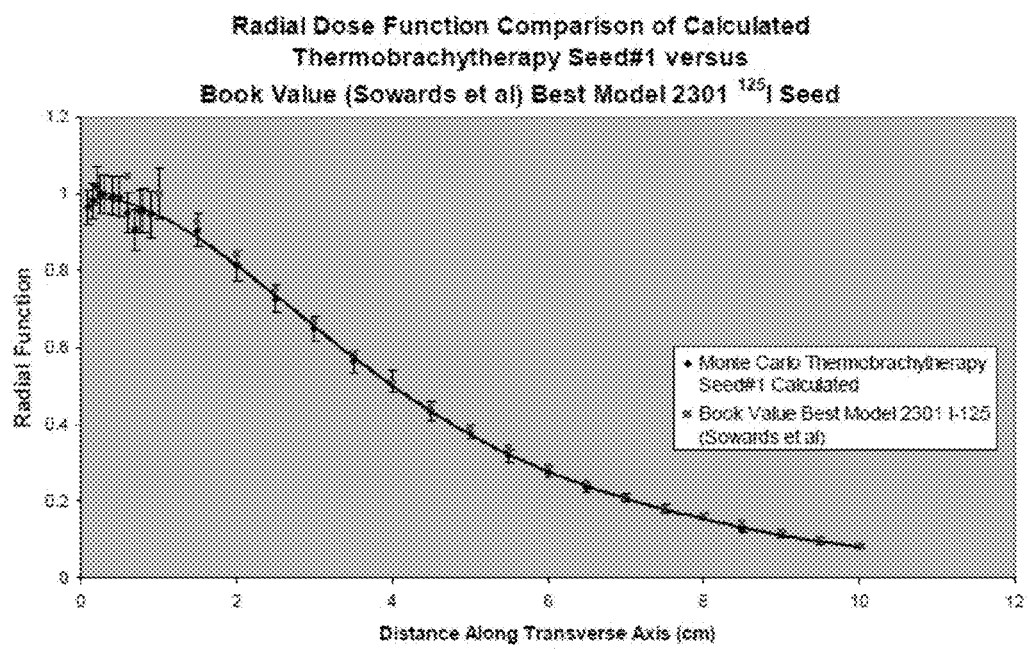
FIG. 40 illustrates the Radial Function of Monte Carlo calculated value for Thermobrachytherapy Seed#1 and the Book Value for the Best Model 2301 $^{125}$I in solid water.

FIG. 40 illustrates the Radial Function of Monte Carlo calculated value for Thermobrachytherapy Seed#1 and the Book Value for the Best Model 2301 $^{125}$I in solid water. The plot is fitted with a 5th order polynomial function.

iv) Anisotropy Function:

Calculation of the radial function is a three-fold process.

a) Calculating Geometry Function

The Geometry function is independent of the material content of the phantom and therefore, the geometry function from Table 7 is applicable here.

b) Calculating Coordinates for Detectors

The coordinates are independent of the material content of the phantom and therefore, the coordinates from Table 8 are applicable here.

c) Calculating Anisotropy Function Using the Data Accumulated in Tables 7 & 8

The Anisotropy Function was calculated using all the factors listed in equation #9. Table 7 was used to calculate the Geometry Function at various angles. Table 8 was used to find the coordinates needed to place the detectors at the various angles (and radial distances). Table 30a illustrates the Monte Carlo calculated Anisotropy Function of the Thermobrachytherapy Seed#1 in solid water for Radial Distances of 1 cm. A comparison between calculated values of the Best Model 2301 $^{125}$I Seed is also calculated.

TABLE 30a

Monte Carlo calculated Anisotropy Function of the Thermobrachytherapy Seed#1 in Solid Water for Radial Distances of 1 cm. A comparison between calculated values of the Best Model 2301 $^{125}$I Seed is also calculated.

| Angle | AF at 1 cm | Best Model 2301 $^{125}$I Seed | Error |
|---|---|---|---|
| 0 | 0.996494 | 1.026252 | −0.028996 |
| 5 | 0.847453 | 0.866304 | −0.02176 |
| 10 | 0.655995 | 0.672536 | −0.024595 |
| 15 | 0.724557 | 0.739002 | −0.019547 |
| 20 | 0.74101 | 0.75897 | −0.023664 |
| 25 | 0.777262 | 0.793086 | −0.019952 |
| 30 | 0.807494 | 0.822657 | −0.018432 |
| 35 | 0.884933 | 0.897361 | −0.013849 |
| 40 | 0.895856 | 0.906809 | −0.012078 |
| 45 | 0.946847 | 0.957336 | −0.010956 |
| 50 | 0.968148 | 0.971523 | −0.003474 |
| 55 | 0.986063 | 0.989839 | −0.003815 |
| 60 | 0.980092 | 0.987353 | −0.007354 |
| 65 | 0.990449 | 0.99135 | −0.000909 |
| 70 | 1.004312 | 0.998792 | 0.005527 |
| 75 | 1.041131 | 1.038309 | 0.002718 |
| 80 | 1.032423 | 1.032288 | 0.000131 |
| 85 | 0.994183 | 0.986828 | 0.007453 |
| 90 | 0.996037 | 0.996037 | 0 |

Figure 41:
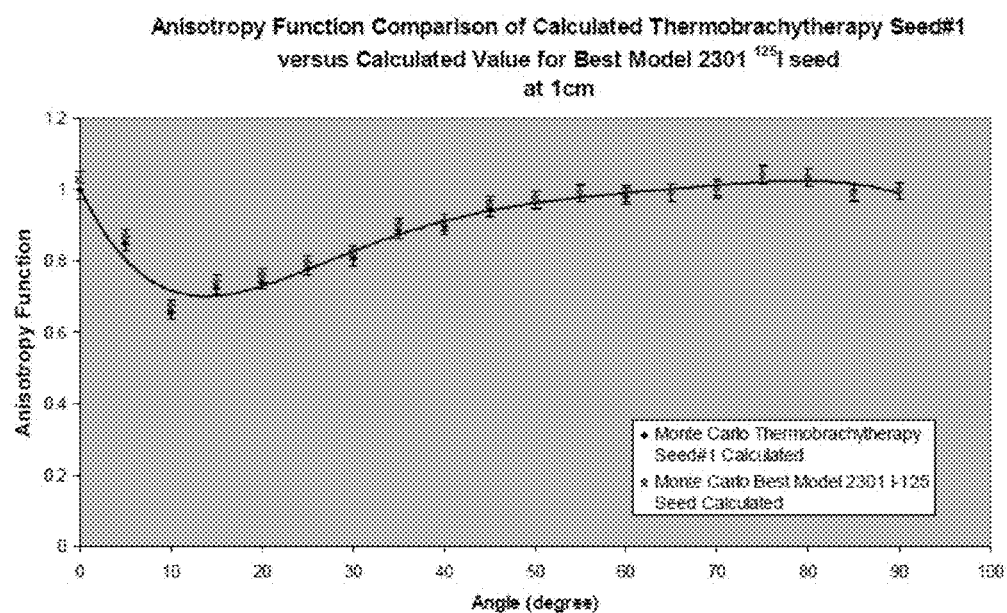
FIG. 41: Anisotropy Function of Monte Carlo calculated value for Thermobrachytherapy Seed#1 and the Monte Carlo for the Best Model 2301 $^{125}$I in solid water at 1 cm radii.

FIG. 41: Anisotropy Function of Monte Carlo calculated value for Thermobrachytherapy Seed#1 and the Monte Carlo for the Best Model 2301 $^{125}$I in solid water at 1 cm radii. The plot is fitted with a 6th order polynomial function.

Table 30b illustrates a Monte Carlo calculated Anisotropy Function of the Thermobrachytherapy Seed#1 in solid water for Radial Distances of 2 cm. A comparison between calculated and book values of the Best Model 2301 $^{125}$I Seed is also calculated.

TABLE 30b

Monte Carlo calculated Anisotropy Function of the Thermobrachytherapy Seed#1 in Solid Water for Radial Distances of 2 cm. A comparison between calculated and book values of the Best Model 2301 $^{125}$I Seed is also calculated.

| Angle | AF at 2 cm | Best Model 2301 $^{125}$I Seed | Error | Book Value (Meigooni et al) | Error |
|---|---|---|---|---|---|
| 0 | 0.98338 | 1.002986 | −0.019548 | 0.837 | 0.174887 |
| 5 | 0.807861 | 0.829332 | −0.02589 | | |
| 10 | 0.66456 | 0.677051 | −0.018449 | 0.659 | 0.008437 |
| 15 | 0.677366 | 0.689879 | −0.018139 | | |
| 20 | 0.759896 | 0.779294 | −0.024892 | 0.782 | −0.028266 |
| 25 | 0.798873 | 0.81592 | −0.020894 | | |
| 30 | 0.825427 | 0.83656 | −0.013307 | 0.882 | −0.064141 |
| 35 | 0.800079 | 0.803188 | −0.003871 | | |
| 40 | 0.867128 | 0.876871 | −0.010339 | 0.946 | −0.083374 |
| 45 | 0.894279 | 0.901717 | −0.008249 | | |
| 50 | 0.924454 | 0.924023 | 0.000466 | 0.985 | −0.061468 |
| 55 | 0.948725 | 0.948277 | 0.000524 | | |
| 60 | 0.927232 | 0.928041 | −0.000871 | 1.007 | −0.079214 |
| 65 | 0.91481 | 0.912797 | 0.002205 | | |

TABLE 30b-continued

Monte Carlo calculated Anisotropy Function of the Thermobrachytherapy Seed#1 in Solid Water for Radial Distances of 2 cm. A comparison between calculated and book values of the Best Model 2301 $^{125}$I Seed is also calculated.

| Angle | AF at 2 cm | Best Model 2301 $^{125}$I Seed | Error | Book Value (Meigooni et al) | Error |
|---|---|---|---|---|---|
| 70 | 0.960586 | 0.952063 | 0.008952 | 1.02 | −0.058249 |
| 75 | 0.991521 | 0.987641 | 0.003928 | | |
| 80 | 1.004723 | 1.004358 | 0.000363 | 1.027 | −0.021692 |
| 85 | 0.98388 | 0.984115 | −0.000239 | | |
| 90 | 1 | 1 | 0 | 1 | 0 |

Figure 42:
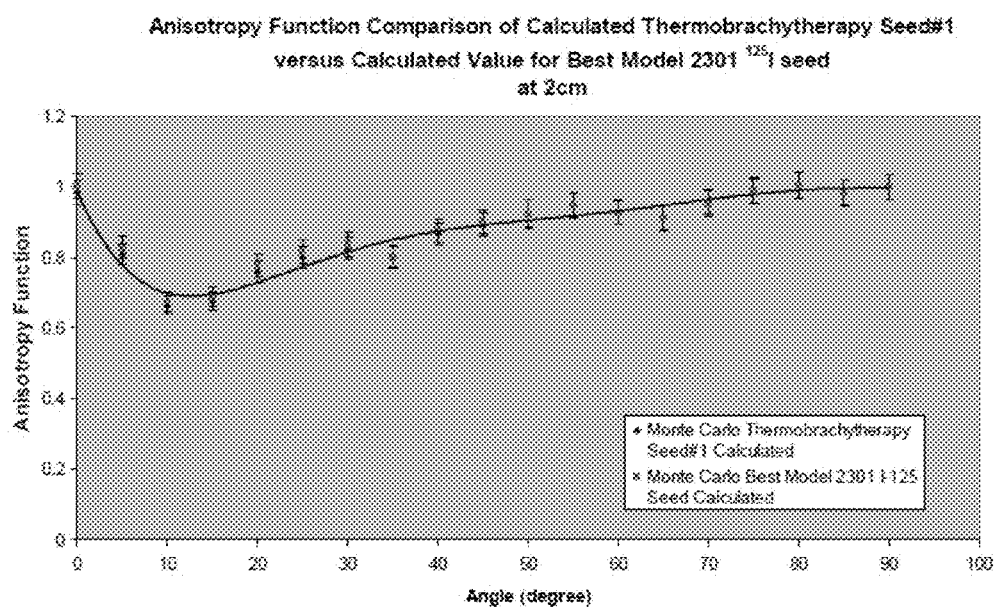
FIG. 42 illustrates the Anisotropy Function of Monte Carlo calculated value for Thermobrachytherapy Seed#1 and the Monte Carlo for the Best Model 2301 $^{125}$I in solid water at 2 cm radii.

FIG. 42 illustrates the Anisotropy Function of Monte Carlo calculated value for Thermobrachytherapy Seed#1 and the Monte Carlo for the Best Model 2301 $^{125}$I in solid water at 2 cm radii. The plot is fitted with a 6th order polynomial function.

Figure 43:
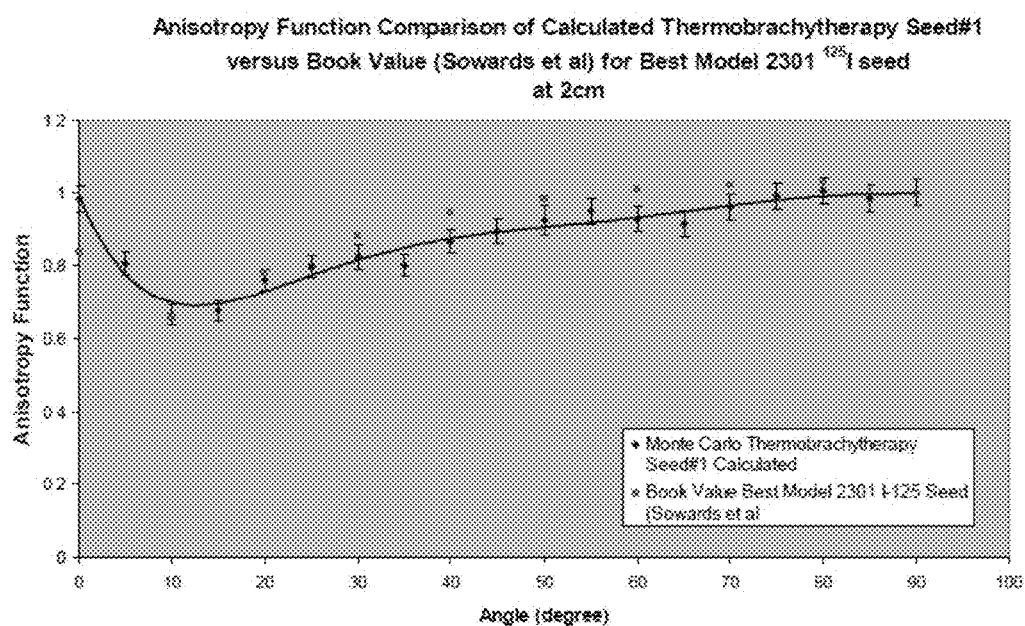
FIG. 43 illustrates the Anisotropy Function of Monte Carlo calculated value for Thermobrachytherapy Seed#1 and the Book value for the Best Model 2301 $^{125}$I in solid water at 2 cm radii.

FIG. 43 illustrates the Anisotropy Function of Monte Carlo calculated value for Thermobrachytherapy Seed#1 and the Book value for the Best Model 2301 $^{125}$I in solid water at 2 cm radii. The plot is fitted with a 6th order polynomial function.

Table 30c illustrates the Monte Carlo calculated Anisotropy Function of Thermobrachytherapy Seed#1 in solid water for Radial Distances of 3 cm. A comparison between calculated values of the Best Model 2301 $^{125}$I Seed is also calculated.

TABLE 30c

Monte Carlo calculated Anisotropy Function of Thermobrachytherapy Seed#1 in Solid Water for Radial Distances of 3 cm. A comparison between calculated values of the Best Model 2301 $^{125}$I Seed is also calculated.

| Angle | AF at 3 cm | Best Model 2301 $^{125}$I Seed | Error |
|---|---|---|---|
| 0 | 1.012225 | 1.045494 | −0.031821 |
| 5 | 0.756306 | 0.767353 | −0.014396 |
| 10 | 0.70105 | 0.706056 | −0.007091 |
| 15 | 0.736806 | 0.742168 | −0.007224 |
| 20 | 0.759654 | 0.769965 | −0.013391 |
| 25 | 0.846572 | 0.864285 | −0.020495 |
| 30 | 0.828748 | 0.835925 | −0.008586 |
| 35 | 0.875156 | 0.876294 | −0.001299 |
| 40 | 0.917407 | 0.919709 | −0.002503 |
| 45 | 0.899806 | 0.893813 | 0.006705 |
| 50 | 0.891812 | 0.89036 | 0.001631 |
| 55 | 0.911477 | 0.916484 | −0.005463 |
| 60 | 0.895706 | 0.900548 | −0.005377 |
| 65 | 0.884732 | 0.880534 | 0.004768 |
| 70 | 0.965355 | 0.97229 | −0.007132 |
| 75 | 0.958585 | 0.944857 | 0.014952 |
| 80 | 0.90757 | 0.899939 | 0.008479 |
| 85 | 0.95826 | 0.95404 | 0.004423 |
| 90 | 1 | 1 | 0 |

Figure 44:
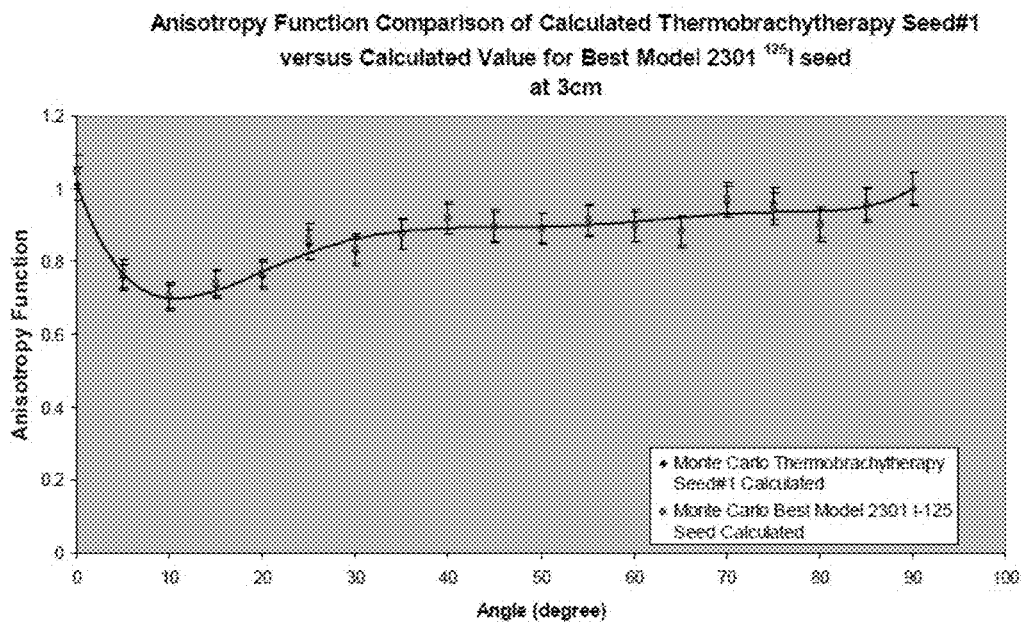
FIG. 44 illustrates the Anisotropy Function of Monte Carlo calculated value for Thermobrachytherapy Seed#1 and the Monte Carlo for the Best Model 2301 $^{125}$I in solid water at 3 cm radii.

FIG. 44 illustrates the Anisotropy Function of Monte Carlo calculated value for Thermobrachytherapy Seed#1 and the Monte Carlo for the Best Model 2301 $^{125}$I in solid water at 3 cm radii. The plot is fitted with a 6th order polynomial function.

Table 30d illustrates the Monte Carlo calculated Anisotropy Function of Thermobrachytherapy Seed#1 in solid water for Radial Distances of 4 cm. A comparison between calculated values of the Best Model 2301 $^{125}$I Seed is also calculated.

TABLE 30d

Monte Carlo calculated Anisotropy Function of Thermobrachytherapy Seed#1 in Solid Water for Radial Distances of 4 cm. A comparison between calculated values of the Best Model 2301 $^{125}$I Seed is also calculated.

| Angle | AF at 4 cm | Best Model 2301 $^{125}$I Seed | Error |
|---|---|---|---|
| 0 | 0.974327 | 0.996217 | −0.021973 |
| 5 | 0.788597 | 0.804645 | −0.019945 |
| 10 | 0.768105 | 0.786272 | −0.023105 |
| 15 | 0.751098 | 0.766287 | −0.019821 |
| 20 | 0.805114 | 0.821381 | −0.019805 |
| 25 | 0.836461 | 0.865759 | −0.03384 |
| 30 | 0.906229 | 0.928838 | −0.024341 |
| 35 | 0.9227 | 0.940615 | −0.019047 |
| 40 | 0.942636 | 0.956302 | −0.014291 |
| 45 | 0.954887 | 0.963304 | −0.008738 |
| 50 | 0.902201 | 0.909226 | −0.007726 |
| 55 | 0.999693 | 1.009165 | −0.009386 |
| 60 | 0.963996 | 0.967434 | −0.003553 |
| 65 | 0.966021 | 0.964955 | 0.001104 |
| 70 | 1.01121 | 1.007641 | 0.003542 |
| 75 | 0.978419 | 0.970099 | 0.008576 |
| 80 | 0.962388 | 0.956987 | 0.005643 |
| 85 | 1.006779 | 0.990027 | 0.016921 |
| 90 | 1 | 1 | 0 |

Figure 45:
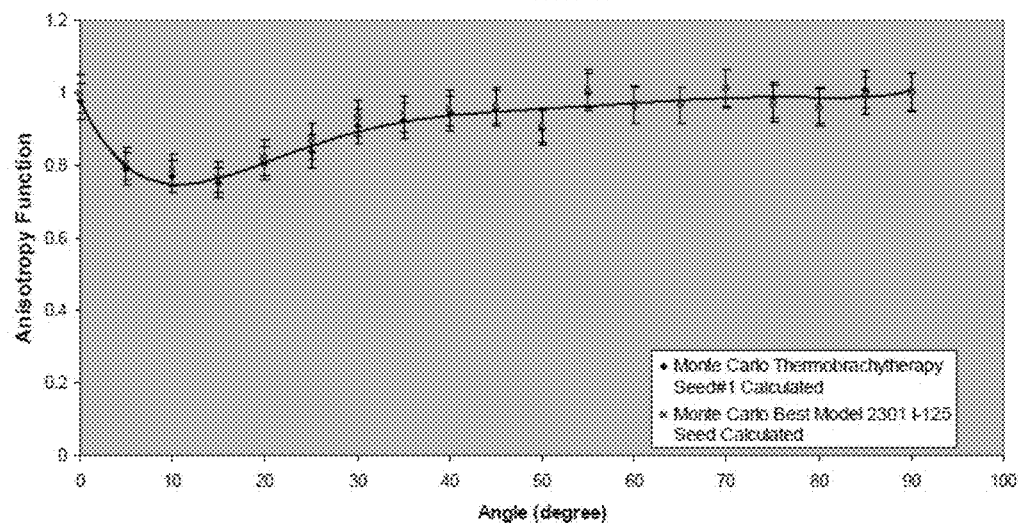
FIG. 45 illustrates the Anisotropy Function of Monte Carlo calculated value for Thermobrachytherapy Seed#1 and the Monte Carlo for the Best Model 2301 $^{125}$I in solid water at 4 cm radii.

FIG. 45 illustrates the Anisotropy Function of Monte Carlo calculated value for Thermobrachytherapy Seed#1 and the Monte Carlo for the Best Model 2301 $^{125}$I in solid water at 4 cm radii. The plot is fitted with a 6th order polynomial function.

Table 30e illustrates the Monte Carlo calculated Anisotropy Function of Thermobrachytherapy Seed#1 in solid water for Radial Distances of 5 cm. A comparison between calculated and book values of the Best Model 2301 $^{125}$I Seed is also calculated.

TABLE 30e

Monte Carlo calculated Anisotropy Function of Thermobrachytherapy Seed#1 in Solid Water for Radial Distances of 5 cm. A comparison between calculated and book values of the Best Model 2301 $^{125}$I Seed is also calculated.

| Angle | AF at 5 cm | Best Model 2301 $^{125}$I Seed | Error | Book Value (Meigooni et al) | Error |
|---|---|---|---|---|---|
| 0 | 1.01337 | 1.06538 | −0.026421 | 0.886 | 0.17069 |
| 5 | 0.808504 | 0.863781 | −0.025047 | | |
| 10 | 0.765679 | 0.788669 | −0.019244 | 0.719 | 0.075788 |
| 15 | 0.762468 | 0.773249 | −0.024994 | | |
| 20 | 0.805936 | 0.817595 | −0.007523 | 0.801 | 0.013038 |
| 25 | 0.785503 | 0.879567 | −0.012514 | | |
| 30 | 0.931303 | 0.840307 | −0.011353 | 0.873 | −0.048377 |
| 35 | 0.874852 | 0.911502 | −0.015338 | | |
| 40 | 0.899968 | 0.949538 | −0.005609 | 0.938 | 0.006622 |
| 45 | 0.950244 | 0.936324 | 0.000441 | | |
| 50 | 0.929789 | 0.99784 | 0.010052 | 0.962 | 0.047682 |
| 55 | 0.988796 | 1.018567 | −0.003368 | | |
| 60 | 0.954913 | 0.948673 | −0.004997 | 0.99 | −0.046533 |
| 65 | 0.99748 | 1.02104 | 0.018982 | | |
| 70 | 0.970803 | 1.024804 | 0.007158 | 1.001 | 0.031108 |
| 75 | 1.029805 | 1.013883 | −0.000209 | | |
| 80 | 0.997893 | 1.06825 | 0.020662 | 1.011 | 0.078459 |
| 85 | 1.019 | 1.000983 | 0.021675 | | |
| 90 | 1 | 1 | 0 | 1 | 0 |

Figure 46:
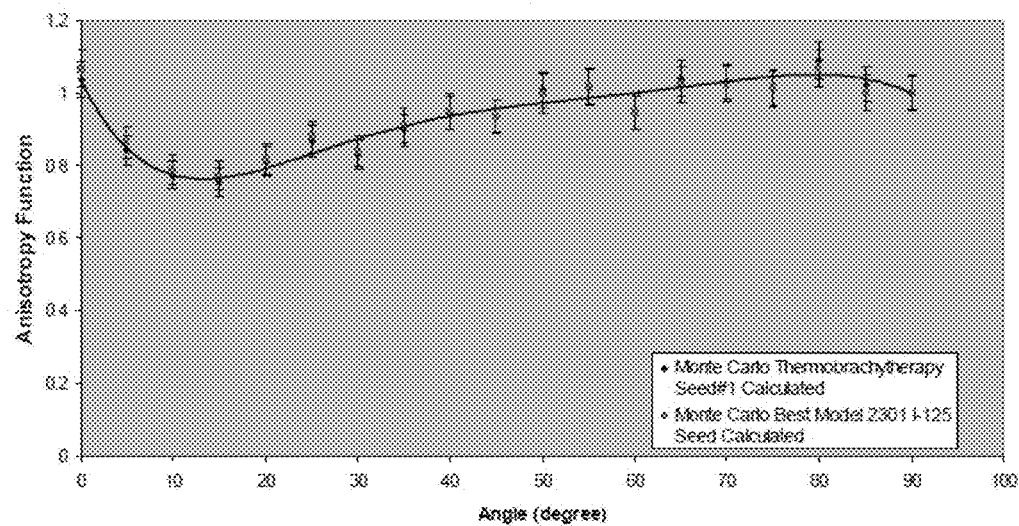
FIG. 46 illustrates the Anisotropy Function of Monte Carlo calculated value for Thermobrachytherapy Seed#1 and the Monte Carlo for the Best Model 2301 $^{125}$I in solid water at 5 cm radii.

FIG. 46 illustrates the Anisotropy Function of Monte Carlo calculated value for Thermobrachytherapy Seed#1 and the Monte Carlo for the Best Model 2301 $^{125}$I in solid water at 5 cm radii. The plot is fitted with a 6th order polynomial function.

Figure 47:
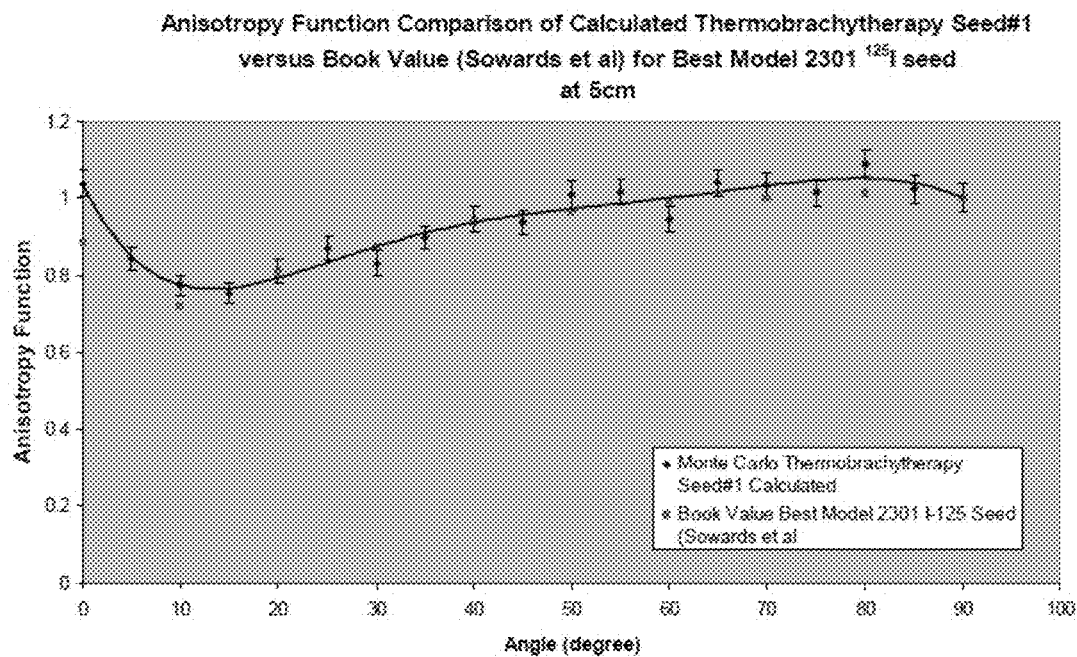
FIG. 47 illustrates the Anisotropy Function of Monte Carlo calculated value for Thermobrachytherapy Seed#1 and the Book value for the Best Model 2301 $^{125}$I in solid water at 5 cm radii.

FIG. 47 illustrates the Anisotropy Function of Monte Carlo calculated value for Thermobrachytherapy Seed#1 and the Book value for the Best Model 2301 $^{125}$I in solid water at 5 cm radii. The plot is fitted with a 6th order polynomial function.

Table 30f illustrates the Monte Carlo calculated Anisotropy Function of Thermobrachytherapy Seed#1 in solid water for Radial Distances of 6 cm. A comparison between calculated values of the Best Model 2301 $^{125}$I Seed is also calculated.

TABLE 30f

Monte Carlo calculated Anisotropy Function of Thermobrachytherapy Seed#1 in Solid Water for Radial Distances of 6 cm. A comparison between calculated values of the Best Model 2301 $^{125}$I Seed is also calculated.

| Angle | AF at 6 cm | Best Model 2301 $^{125}$I Seed | Error |
|---|---|---|---|
| 0 | 0.939123 | 0.961176 | −0.022944 |
| 5 | 0.856811 | 0.869443 | −0.014529 |
| 10 | 0.74624 | 0.754599 | −0.011077 |
| 15 | 0.770177 | 0.77439 | −0.00544 |
| 20 | 0.749627 | 0.754773 | −0.006819 |
| 25 | 0.859541 | 0.868662 | −0.0105 |
| 30 | 0.824175 | 0.82609 | −0.002317 |
| 35 | 0.868763 | 0.864491 | 0.004942 |
| 40 | 0.848343 | 0.85658 | −0.009617 |
| 45 | 0.889552 | 0.878697 | 0.012354 |
| 50 | 0.863083 | 0.853307 | 0.011458 |
| 55 | 0.939138 | 0.938518 | 0.00066 |
| 60 | 0.910432 | 0.912431 | −0.00219 |
| 65 | 1.017911 | 1.005409 | 0.012434 |
| 70 | 0.974917 | 0.962483 | 0.012918 |
| 75 | 0.977531 | 0.972179 | 0.005505 |
| 80 | 1.039824 | 1.025741 | 0.013729 |
| 85 | 0.994157 | 0.987695 | 0.006542 |
| 90 | 1 | 1 | 0 |

Figure 48:
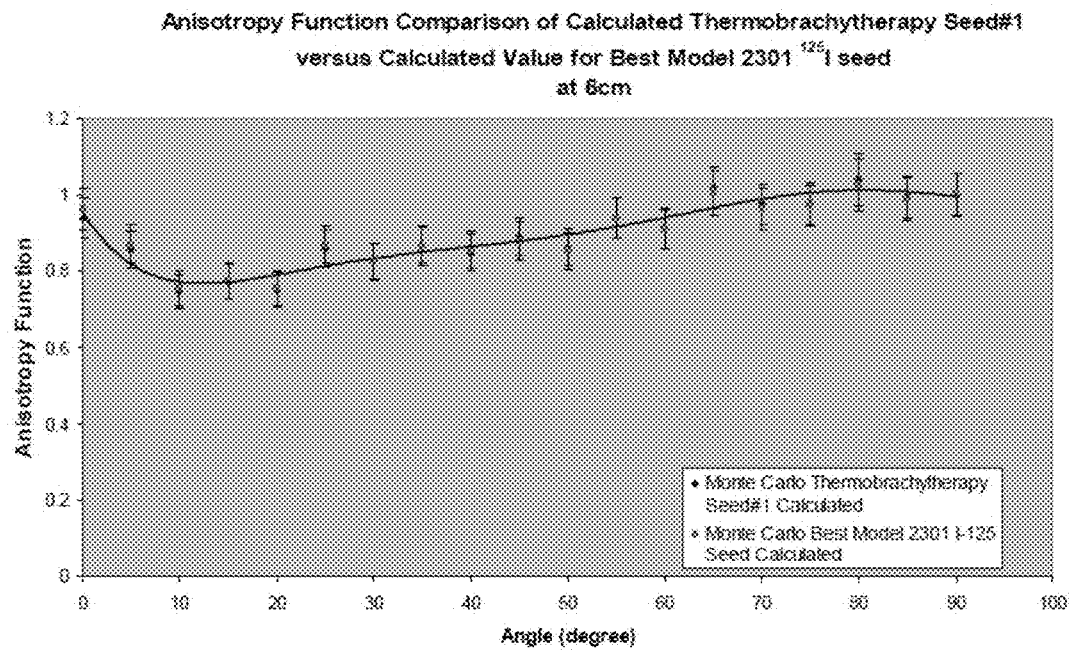
FIG. 48 illustrates the Anisotropy Function of Monte Carlo calculated value for Thermobrachytherapy Seed#1 and the Monte Carlo for the Best Model 2301 $^{125}$I in solid water at 6 cm radii.

FIG. 48 illustrates the Anisotropy Function of Monte Carlo calculated value for Thermobrachytherapy Seed#1 and the Monte Carlo for the Best Model 2301 $^{125}$I in solid water at 6 cm radii. The plot is fitted with a 6th order polynomial function.

Table 30g illustrates the Monte Carlo calculated Anisotropy Function of Thermobrachytherapy Seed#1 in solid water for Radial Distances of 7 cm. A comparison between calculated and book values of the Best Model 2301 $^{125}$I Seed is also calculated.

TABLE 30g

Monte Carlo calculated Anisotropy Function of Thermobrachytherapy Seed#1 in Solid Water for Radial Distances of 7 cm. A comparison between calculated and book values of the Best Model 2301 $^{125}$I Seed is also calculated.

| Angle | AF at 7 cm | Best Model 2301 $^{125}$I Seed | Error | Book Value (Meigooni et al) | Error |
|---|---|---|---|---|---|
| 0 | 1.00207 | 1.044519 | −0.04236 | 0.888 | 0.222344 |
| 5 | 0.833197 | 0.872338 | −0.04698 | | |
| 10 | 0.782894 | 0.814773 | −0.04072 | 0.751 | 0.255709 |
| 15 | 0.863295 | 0.89647 | −0.03843 | | |
| 20 | 0.812335 | 0.839067 | −0.03291 | 0.82 | 0.085533 |
| 25 | 0.837071 | 0.857219 | −0.02407 | | |
| 30 | 0.938672 | 0.968562 | −0.03184 | 0.905 | 0.014884 |
| 35 | 0.956463 | 0.965505 | −0.00945 | | |
| 40 | 0.972739 | 1.010278 | −0.03859 | 0.952 | 0.043336 |
| 45 | 0.984548 | 1.008515 | −0.02434 | | |
| 50 | 0.962371 | 0.983552 | −0.02201 | 0.972 | 0.025063 |
| 55 | 0.998295 | 1.020988 | −0.02273 | | |

TABLE 30g-continued

Monte Carlo calculated Anisotropy Function of Thermobrachytherapy Seed#1 in Solid Water for Radial Distances of 7 cm. A comparison between calculated and book values of the Best Model 2301 $^{125}$I Seed is also calculated.

| Angle | AF at 7 cm | Best Model 2301 $^{125}$I Seed | Error | Book Value (Meigooni et al) | Error |
|---|---|---|---|---|---|
| 60 | 0.910017 | 0.920182 | −0.01117 | 1.004 | 0.06859 |
| 65 | 1.108344 | 1.14268 | −0.03098 | | |
| 70 | 1.052193 | 1.069128 | −0.01609 | 0.999 | −0.019711 |
| 75 | 1.034983 | 1.039857 | −0.00471 | | |
| 80 | 0.972257 | 0.991134 | −0.01942 | 1.015 | 0.079653 |
| 85 | 1.017453 | 1.029283 | −0.01163 | | |
| 90 | 0.999979 | 0.999979 | 1.11E−16 | 1 | −2.1E−05 |

Figure 49:
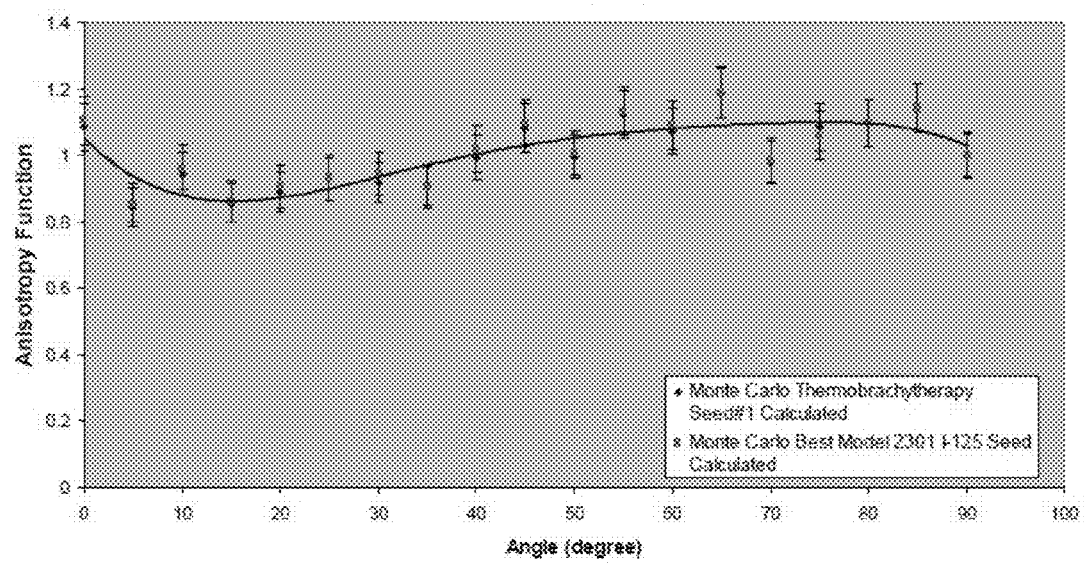
FIG. 49 illustrates the Anisotropy Function of Monte Carlo calculated value for Thermobrachytherapy Seed#1 and the Monte Carlo for the Best Model 2301 $^{125}$I in solid water at 7 cm radii.

FIG. 49 illustrates the Anisotropy Function of Monte Carlo calculated value for Thermobrachytherapy Seed#1 and the Monte Carlo for the Best Model 2301 $^{125}$I in solid water at 7 cm radii. The plot is fitted with a 6th order polynomial function.

Figure 50:
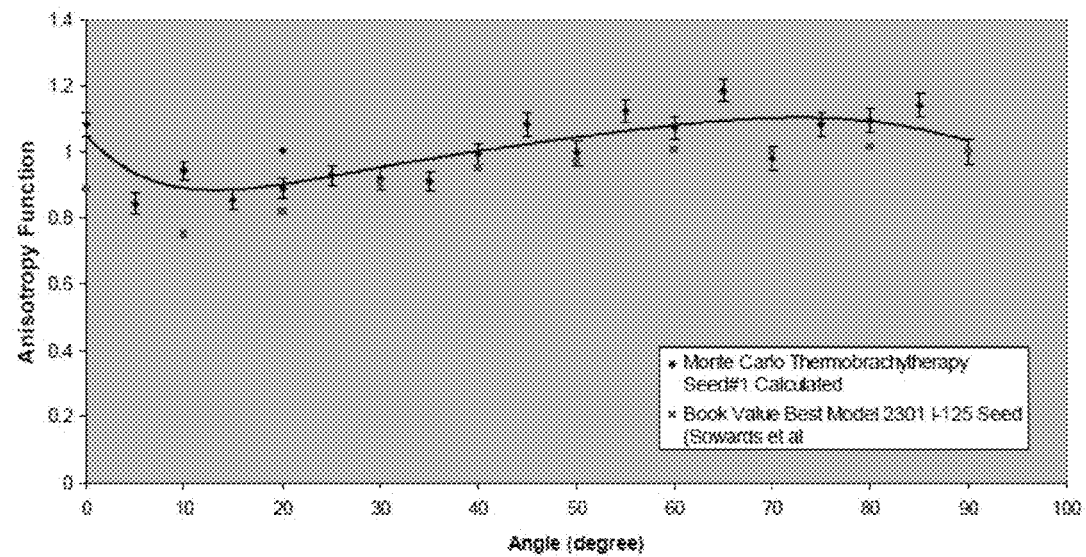
FIG. 50 illustrates the Anisotropy Function of Monte Carlo calculated value for Thermobrachytherapy Seed#1 and the Book value for the Best Model 2301 $^{125}$I in solid water at 7 cm radii.

FIG. 50 illustrates the Anisotropy Function of Monte Carlo calculated value for Thermobrachytherapy Seed#1 and the Book value for the Best Model 2301 $^{125}$I in solid water at 7 cm radii. The plot is fitted with a 6th order polynomial function.

Average Anisotropy Function:

The average anisotropy function is taken by taking an average of the calculated anisotropy functions for all the angles. Table 31a illustrates the Average Anisotropy Constant calculated for radial distances of 1 cm in solid water.

TABLE 31a

Average Anisotropy Constant calculated for radial distances of 1 cm in Solid Water

| | 1 cm | Best Model 2301 $^{125}$I Seed | Error |
|---|---|---|---|
| Average Anisotropy Constant $\Phi_{an}(r)$ | 0.909 | 0.917 | −0.009 |

Table 31b illustrates the Average Anisotropy Constant calculated for radial distances of 2 cm in solid water.

TABLE 31b

Average Anisotropy Constant calculated for radial distances of 2 cm in Solid Water

| | 2 cm | Best Model 2301 $^{125}$I Seed | Error | Book Value (Meigooni et al) | Error |
|---|---|---|---|---|---|
| Average Anisotropy Constant $\Phi_{an}(r)$ | 0.881 | 0.898 | −0.01924 | 0.975 | −0.096 |

Table 34c illustrates the Average Anisotropy Constant calculated for radial distances of 3 cm in solid water.

TABLE 34c

Average Anisotropy Constant calculated for radial distances of 3 cm in Solid Water

| | 3 cm | Best Model 2301 $^{125}$I Seed | Error |
|---|---|---|---|
| Average Anisotropy Constant $\Phi_{an}(r)$ | 0.879 | 0.883 | −0.0043 |

Table 34d illustrates the Average Anisotropy Constant calculated for radial distances of 4 cm in solid water.

TABLE 34d

Average Anisotropy Constant calculated for radial distances of 4 cm in Solid water

| | 4 cm | Best Model 2301 $^{125}$I Seed | Error |
|---|---|---|---|
| Average Anisotropy Constant $\Phi_{an}(r)$ | 0.918 | 0.928 | −0.0093 |

Table 34e illustrates the Average Anisotropy Constant calculated for radial distances of 5 cm in solid water.

TABLE 34e

Average Anisotropy Constant calculated for radial distances of 5 cm in Solid Water

| | 5 cm | Best Model 2301 $^{125}$I Seed | Error | Book Value (Meigooni et al) | Error |
|---|---|---|---|---|---|
| Average Anisotropy Constant $\Phi_{an}(r)$ | 0.940 | 0.950 | −0.0105 | 0.965 | −0.0258 |

Table 34f illustrates the Average Anisotropy Constant calculated for radial distances of 6 cm in solid water.

TABLE 34f

Average Anisotropy Constant calculated for radial distances of 6 cm in Solid Water

| | 6 cm | Best Model 2301 $^{125}$I Seed | Error |
|---|---|---|---|
| Average Anisotropy Constant $\Phi_{an}(r)$ | 0.8984 | 0.898 | −0.00015 |

Table 34g illustrates the Average Anisotropy Constant calculated for radial distances of 7 cm in solid water.

TABLE 34g

Average Anisotropy Constant calculated for
radial distances of 7 cm in Solid Water

| | 7 cm | Best Model 2301 $^{125}$I Seed | Error | Book Value (Meigooni et al) | Error |
|---|---|---|---|---|---|
| Average Anisotropy Constant $\Phi_{an}$ (r) | 1.006 | 1.01 | −0.005 | 0.977 | −0.03 |

Table 35 illustrates the Source Anisotropy Constant. The Source Anisotropy Constant is calculated by taking the average of all the Average Anisotropy Constants. The Source Anisotropy Constant is 0.918 and deviates from the Monte Carlo calculated Best Model 2301 $^{125}$I Seed by 0.08% and the Book value by 5.4%.

TABLE 35

Source Anisotropy Constant:
The Source Anisotropy Constant is calculated by taking
the average of all the Average Anisotropy Constants

| | Calculated value | Best Model 2301 $^{125}$I Seed | Error | Book value | Error |
|---|---|---|---|---|---|
| Source Anisotropy Constant $\overline{\Phi_{an}}$ (r) | 0.918 | 0.926 | −0.0008 | 0.97 | −0.0536 |

Thermobrachytherapy Seed#2 in Liquid Water
i) Dose Rate (D):
Dose Rate was calculated for seed at 1 cm on the transverse plane (θ=90°) of the source (from the center of the source) in water. Therefore, for this measurement the phantom was taken to be liquid water since it is the liquid water measurement. Table 36 illustrates the Dose Rate for Thermobrachytherapy Seed#2 in liquid water calculated using Monte Carlo. The error is calculated by using equation #16. Therefore, the error between the calculated thermobrachytherapy value and the calculated Best Model 2301 $^{125}$I seed is 4.5%. The measured value of Dose Rate is 0.248±4.95*10$^{-3}$ cGy*sec$^{-1}$*Ci$^{-1}$.

TABLE 36

Dose Rate for Thermobrachytherapy Seed#2 in
liquid water calculated using Monte Carlo

| Calculated Dose Rate (cGy * sec$^{-1}$ * Ci$^{-1}$) | Calculated Best Model 2301 $^{125}$I Seed (cGy * sec$^{-1}$ * Ci$^{-1}$) | Error | Book Value (Meigooni et al) | Error |
|---|---|---|---|---|
| 0.247556 | 0.236993 | 0.0446 | N/A | N/A | ii) Air Kerma Strength (SK):
Air Kerma Strength was calculated for the seed again at 1 cm on the transverse plane of the source (from the center of the source) but now it was in air. Therefore, the material inside the phantom was taken as air. Also, the 0.897 correction factor (as discussed in the Materials & Methods section) is used for SK.

Table 37 illustrates the Air Kerma Strength for Thermobrachytherapy Seed#2 in liquid water calculated using Monte Carlo. The error is calculated by using equation #16. Therefore, the error between the calculated thermobrachytherapy value and the calculated Best Model 2301 $^{125}$I seed is 4.3%. The measured value of Air Kerma Strength is 0.234±5.1*10$^{-3}$ cGy*cm$^2$sec$^{-1}$*Ci$^{-1}$.

TABLE 37

Air Kerma Strength for Thermobrachytherapy Seed#2 in
liquid water calculated using Monte Carlo

| Calculated Air Kerma Strength (cGy * cm$^2$ sec$^{-1}$ * Ci$^{-1}$) | Calculated Best Model 2301 $^{125}$I Seed (cGy * cm$^2$ sec$^{-1}$ * Ci$^{-1}$) | Error | Book Value (Meigooni et al) | Error |
|---|---|---|---|---|
| 0.234046 | 0.224332 | 0.0433 | N/A | N/A | iii) Dose Rate Constant (Λ):
Dose rate constant is calculated using equation #4. In order to calculate it, the ratio of the dose rate and air kerma strength is taken. Table 38 illustrates the Monte Carlo calculated Dose Rate Constant for Thermobrachytherapy Seed#2 in liquid water. The error is calculated by using equation #16. Therefore, the error between the calculated thermobrachytherapy value and the calculated Best Model 2301 $^{125}$I seed is 0.15%. Also, the error between the calculated thermobrachytherapy value and the Book Value for Best Model 2301 $^{125}$I seed is 4.75%. The measured value of Dose Rate is 1.058±0.031 cGy*h$^{-1}$U$^{-1}$.

TABLE 38

Monte Carlo calculated Dose Rate Constant for
Thermobrachytherapy Seed#2 in liquid water

| Calculated Dose Rate Constant (cGy * h$^{-1}$U$^{-1}$) | Best Model 2301 I$^{125}$ Seed Dose Rate Constant (cGy * h$^{-1}$U$^{-1}$) | Error | Book Value (Meigooni et al) | Error |
|---|---|---|---|---|
| 1.0577 | 1.05644 | 0.00148 | 1.01 | 0.0475 | iv) Radial Function:
Calculation of the radial function is a two fold process.
a) Geometry Function
The Geometry function is independent of the material content of the phantom. And also, the geometry (and dimension) of the source cell remains the same. Therefore, the geometry factor from Table 6 is applicable here.
b) Radial Function Using the Geometry Function.
Radial Function was calculated using equation# incorporating the geometry function calculated in part a) above. Table 39 illustrates the Radial Function calculated at the transverse plane for the Thermobrachytherapy Seed#2 in liquid water using Monte Carlo.

TABLE 39

Radial Function calculated at the transverse plane for the
Thermobrachytherapy Seed#2 in liquid water using Monte Carlo.

| Transverse distance (r) cm | Radial Function g(r) | Best Model 2301 $^{125}$I Seed | Error | Book Value (Meigooni et al) | Error |
|---|---|---|---|---|---|
| 0.1 | 0.891505 | 0.9456286 | −0.05724 | 1.033 | −0.09512 |
| 0.15 | 0.947105 | 0.972143 | −0.02575 | 1.029 | −0.06396 |
| 0.2 | 0.994958 | 1.0043252 | −0.00933 | 1.028 | −0.03105 |
| 0.25 | 0.979154 | 0.9786852 | 0.000479 | 1.027 | −0.05171 |
| 0.3 | 1.003378 | 0.9995776 | 0.003802 | 1.027 | −0.03944 |

TABLE 39-continued

Radial Function calculated at the transverse plane for the Thermobrachytherapy Seed#2 in liquid water using Monte Carlo.

| Transverse distance (r) cm | Radial Function g(r) | Best Model 2301 $^{125}$I Seed | Error | Book Value (Meigooni et al) | Error |
|---|---|---|---|---|---|
| 0.4 | 1.030407 | 0.9913498 | 0.039398 | 1.027 | −0.04739 |
| 0.5 | 1.013596 | 1.0205403 | −0.0068 | 1.028 | −0.01474 |
| 0.6 | 1.008642 | 0.9631128 | 0.047273 | 1.034 | −0.0779 |
| 0.7 | 0.997534 | 0.9312438 | 0.071184 | 1.036 | −0.10966 |
| 0.75 | 0.975717 | 0.9597881 | 0.016596 | 1.03 | −0.06847 |
| 0.8 | 1.007574 | 0.9358905 | 0.076594 | 1.024 | −0.09 |
| 0.9 | 1.000351 | 1.0388782 | −0.03708 | 1.013 | 0.006 |
| 1 | 1.000001 | 1.0000005 | 2.22E-16 | 1 | 5.07E-07 |
| 1.5 | 0.937707 | 0.9266222 | 0.011962 | 0.938 | −0.01535 |
| 2 | 0.857589 | 0.8476955 | 0.011672 | 0.866 | −0.02708 |
| 2.5 | 0.077099 | 0.7624361 | −0.89888 | 0.79 | −0.04164 |
| 3 | 0.701005 | 0.6881108 | 0.018739 | 0.707 | −0.03494 |
| 3.5 | 0.623307 | 0.6073126 | 0.026336 | 0.635 | −0.04997 |
| 4 | 0.52286 | 0.5365308 | −0.02548 | 0.555 | −0.03966 |
| 4.5 | 0.468085 | 0.4829325 | −0.03074 | 0.488 | −0.01996 |
| 5 | 0.414212 | 0.4070779 | 0.017526 | 0.427 | −0.05126 |
| 5.5 | 0.364463 | 0.3609578 | 0.009711 | 0.372 | −0.03365 |
| 6 | 0.318889 | 0.2993458 | 0.065285 | 0.32 | −0.06271 |
| 6.5 | 0.28487 | 0.2680607 | 0.062708 | 0.285 | −0.05771 |
| 7 | 0.230912 | 0.2394946 | −0.03583 | 0.248 | −0.03223 |
| 7.5 | 0.203728 | 0.2032859 | 0.002173 | 0.215 | −0.05844 |
| 8 | 0.181191 | 0.1818156 | −0.00343 | 0.187 | −0.03885 |
| 8.5 | 0.16731 | 0.1542993 | 0.08432 | 0.16 | −0.04464 |
| 9 | 0.141106 | 0.1326667 | 0.063616 | 0.142 | −0.06087 |
| 9.5 | 0.120217 | 0.1015704 | 0.183581 | 0.123 | −0.16272 |
| 10 | 0.089152 | 0.0994859 | −0.10388 | 0.103 | −0.01152 |

Figure 51:
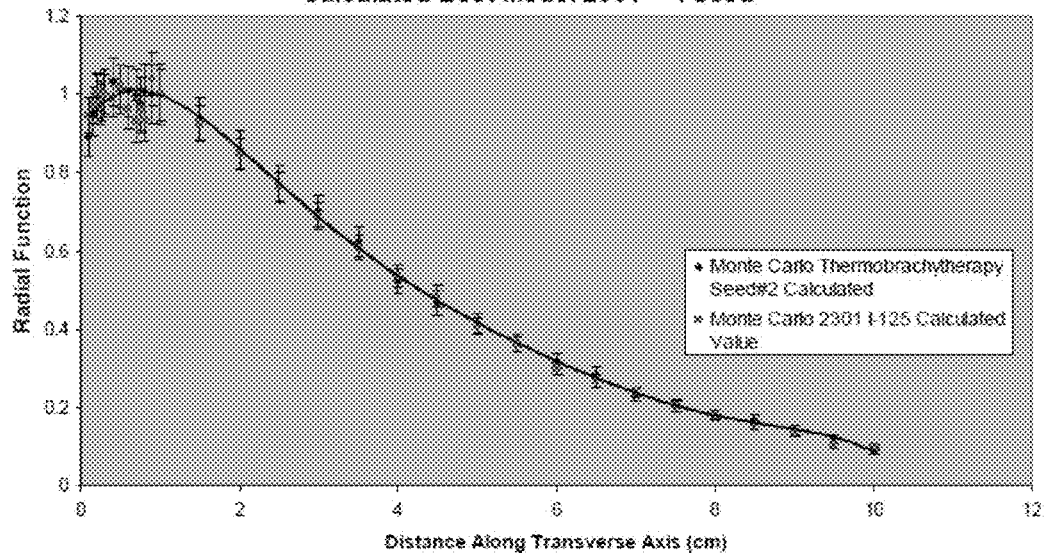
FIG. 51 illustrates the Radial Function of Monte Carlo calculated value for Thermobrachytherapy Seed#2 and the Monte Carlo calculated Value for the Best Model 2301 $^{125}$I in liquid water.

FIG. 51 illustrates the Radial Function of Monte Carlo calculated value for Thermobrachytherapy Seed#2 and the Monte Carlo calculated Value for the Best Model 2301 $^{125}$I in Liquid water. The plot is fitted with a 5th order polynomial function.

Figure 52:
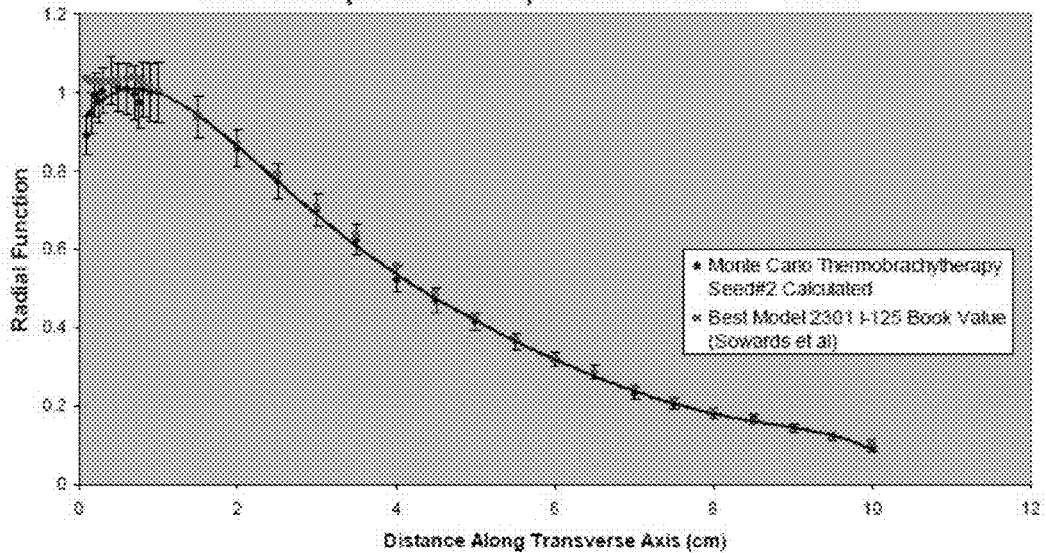
FIG. 52 illustrates the Radial Function of Monte Carlo calculated value for Thermobrachytherapy Seed#2 and the Book Value for the Best Model 2301 $^{125}$I in liquid water.

FIG. 52 illustrates the Radial Function of Monte Carlo calculated value for Thermobrachytherapy Seed#2 and the Book Value for the Best Model 2301 $^{125}$I in Liquid water. The plot is fitted with a 5th order polynomial function.

iv) Anisotropy Function:

Calculation of the radial function is a three fold process.

a) Calculating Geometry Function

The Geometry function is independent of the material content of the phantom and therefore, the geometry function from Table 8 is applicable here.

b) Calculating Coordinates for detectors

The coordinates are independent of the material content of the phantom and therefore, the coordinates from Table 9 are applicable here.

c) Calculating Anisotropy Function Using the Data Accumulated in Tables 8a, 8b & 9

The Anisotropy Function was calculated using all the factors listed in equation #9. Tables 8a & 8b were used to calculate the Geometry Function at various angles. Table 9 was used to find the coordinates needed to place the detectors at the various angles (and radial distances). Table 40a illustrates the Monte Carlo calculated Anisotropy Function of Thermobrachytherapy Seed#2 in Liquid Water for Radial Distances of 1 cm. A comparison between calculated and book values of the Best Model 2301 $^{125}$I Seed is also calculated.

TABLE 40a

Monte Carlo calculated Anisotropy Function of Thermobrachytherapy Seed#2 in Liquid Water for Radial Distances of 1 cm. A comparison between calculated and book values of the Best Model 2301 $^{125}$I Seed is also calculated.

| Angle | AF at 1 cm | Best Model 2301 $^{125}$I Seed | Error | Book Value (Meigooni et al) | Error |
|---|---|---|---|---|---|
| 0 | 1.000033 | 1.016857 | −0.01655 | 0.867 | 0.15344 |
| 5 | 0.844234 | 0.857865 | −0.01589 | 0.724 | 0.16607 |
| 10 | 0.668452 | 0.677306 | −0.01307 | 0.653 | 0.023664 |
| 15 | 0.717345 | 0.725931 | −0.01183 | 0.721 | −0.00507 |
| 20 | 0.737649 | 0.7474 | −0.01305 | 0.785 | −0.060319 |
| 25 | 0.794388 | 0.803672 | −0.01155 | 0.85 | −0.065425 |
| 30 | 0.810683 | 0.821182 | −0.01278 | 0.9 | −0.099241 |
| 35 | 0.880462 | 0.890772 | −0.01157 | 0.946 | −0.069279 |
| 40 | 0.897858 | 0.906355 | −0.00937 | 0.982 | −0.085684 |
| 45 | 0.942573 | 0.953106 | −0.01105 | 1.001 | −0.058369 |
| 50 | 0.95692 | 0.959333 | −0.00251 | 1.014 | −0.056292 |
| 55 | 0.977092 | 0.978387 | −0.00132 | 1.024 | −0.045809 |
| 60 | 0.980928 | 0.98857 | −0.00773 | 1.3 | −0.047643 |
| 65 | 0.988725 | 0.988487 | 0.000241 | 1.033 | −0.04286 |
| 70 | 0.989279 | 0.986962 | 0.002348 | 1.036 | −0.045097 |
| 75 | 1.030734 | 1.031196 | −0.00045 | 1.039 | −0.007956 |
| 80 | 1.007915 | 1.009489 | −0.00156 | 1.1 | −0.083714 |
| 85 | 1.00081 | 0.998686 | 0.002127 | 1 | 0.00081 |
| 90 | 0.996037 | 0.996037 | 0 | 1 | −0.003963 |

Figure 53:
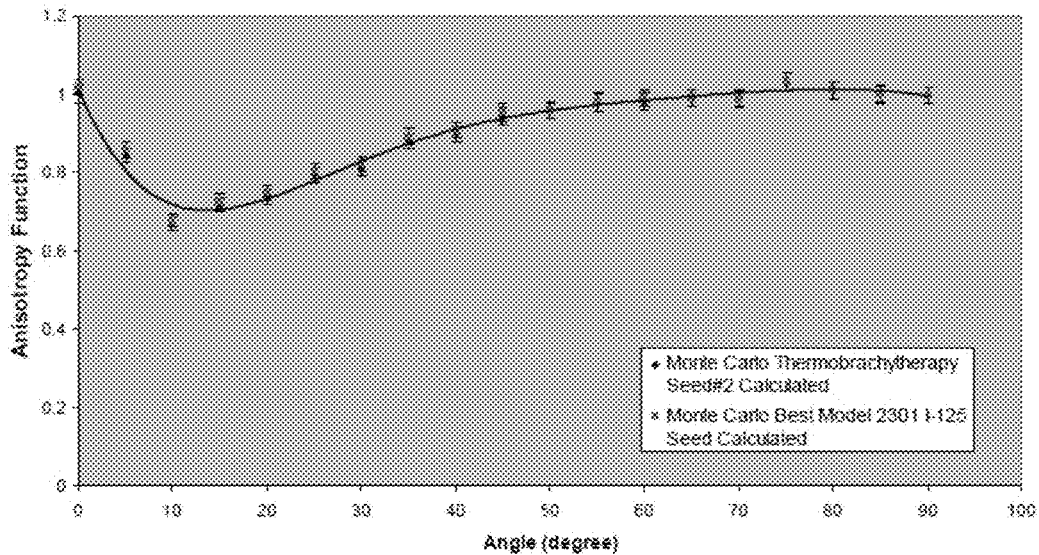
FIG. 53 illustrates the Anisotropy Function of Monte Carlo calculated value for Thermobrachytherapy Seed#2 and the Monte Carlo calculated value for the Best Model 2301 $^{125}$I in liquid water at 1 cm radii.

FIG. 53 illustrates the Anisotropy Function of Monte Carlo calculated value for Thermobrachytherapy Seed#2 and the Monte Carlo calculated value for the Best Model 2301 $^{125}$I in liquid water at 1 cm radii. The plot is fitted with a 6th order polynomial function.

Figure 54:
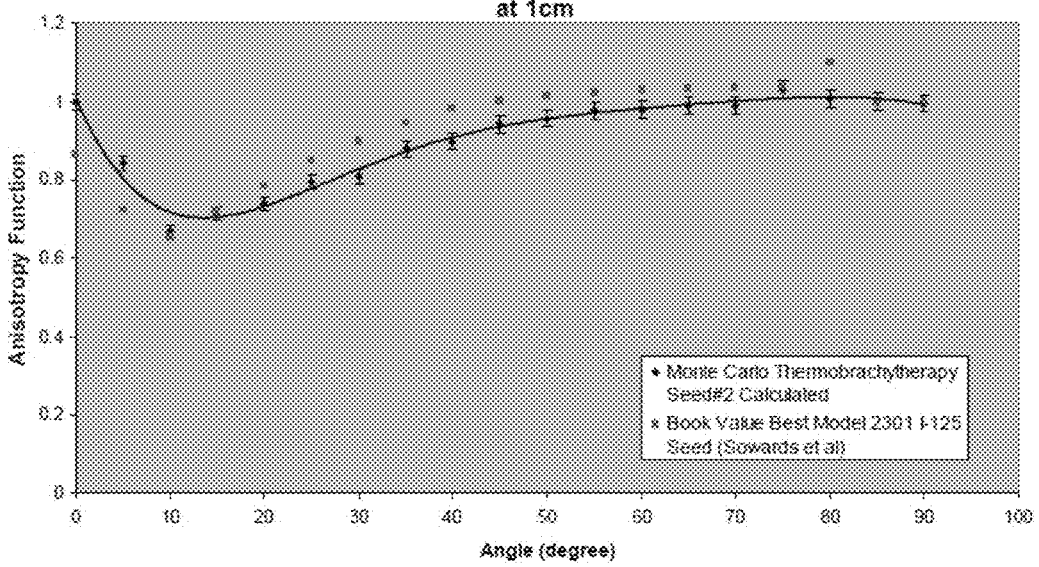
FIG. 54 illustrates the Anisotropy Function of Monte Carlo calculated value for Thermobrachytherapy Seed#2 and the Book Value for the Best Model 2301 $^{125}$I in liquid water at 1 cm radii.

FIG. 54 illustrates the Anisotropy Function of Monte Carlo calculated value for Thermobrachytherapy Seed#2 and the Book Value for the Best Model 2301 $^{125}$I in liquid water at 1 cm radii. The plot is fitted with a 6th order polynomial function.

Table 40b illustrates the Monte Carlo calculated Anisotropy Function of Thermobrachytherapy Seed#2 in liquid water for Radial Distances of 2 cm. A comparison between calculated and book values of the Best Model 2301 $^{125}$I Seed is also calculated.

TABLE 40b

Monte Carlo calculated Anisotropy Function of Thermobrachytherapy Seed#2 in liquid water for Radial Distances of 2 cm. A comparison between calculated and book values of the Best Model 2301 $^{125}$I Seed is also calculated.

| Angle | AF at 2 cm | Best Model 2301 $^{125}$I Seed | Error | Book Value (Meigooni et al) | Error |
|---|---|---|---|---|---|
| 0 | 0.972591 | 0.986817 | −0.01442 | 0.854 | 0.138866 |
| 5 | 0.797157 | 0.810992 | −0.01706 | 0.72 | 0.107163 |
| 10 | 0.711869 | 0.724824 | −0.01787 | 0.671 | 0.060908 |
| 15 | 0.704106 | 0.718106 | −0.01949 | 0.734 | −0.040727 |
| 20 | 0.804406 | 0.819861 | −0.01885 | 0.794 | 0.013105 |
| 25 | 0.835115 | 0.853352 | −0.02137 | 0.847 | −0.014032 |
| 30 | 0.853212 | 0.858304 | −0.00593 | 0.89 | −0.041335 |
| 35 | 0.814789 | 0.821552 | −0.00823 | 0.926 | −0.120098 |
| 40 | 0.922932 | 0.940464 | −0.01864 | 0.954 | −0.032566 |
| 45 | 0.873368 | 0.883125 | −0.01105 | 0.978 | −0.106985 |
| 50 | 0.895748 | 0.903854 | −0.00897 | 0.992 | −0.097028 |
| 55 | 0.936683 | 0.944112 | −0.00787 | 1.003 | −0.066119 |
| 60 | 0.953816 | 0.963059 | −0.0096 | 1.01 | −0.055627 |
| 65 | 0.960706 | 0.971319 | −0.01093 | 1.019 | −0.057207 |
| 70 | 0.982271 | 0.984718 | −0.00248 | 1.026 | −0.04262 |
| 75 | 0.996574 | 1.000409 | −0.00383 | 1.029 | −0.031512 |
| 80 | 1.016478 | 1.019994 | −0.00345 | 1.03 | −0.013128 |
| 85 | 0.971341 | 0.976201 | −0.00498 | 1.022 | −0.049568 |
| 90 | 1 | 1 | 0 | 1 | 0 |

Figure 55:
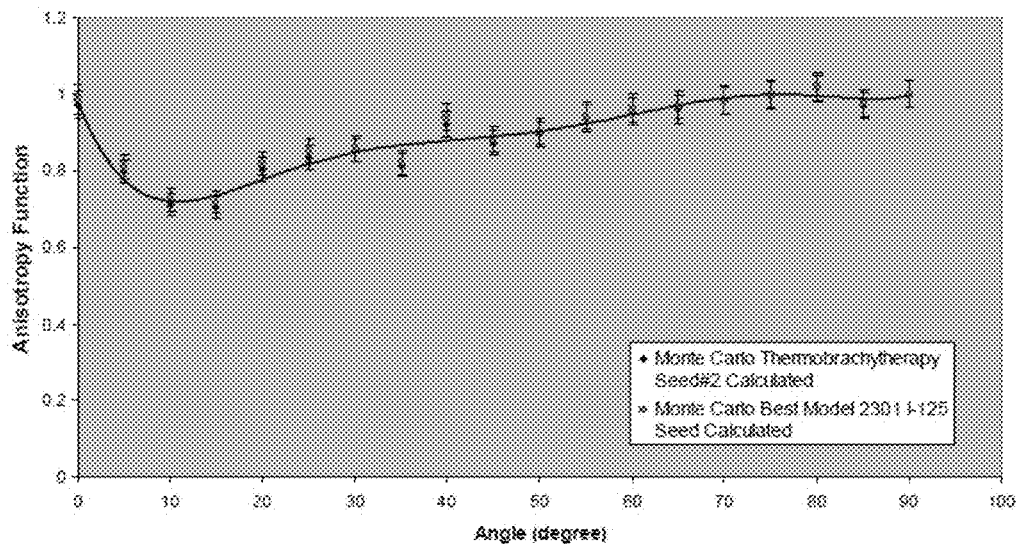
FIG. 55 illustrates the Anisotropy Function of Monte Carlo calculated value for Thermobrachytherapy Seed#2 and the Monte Carlo calculated for the Best Model 2301 $^{125}$I in liquid water at 2 cm radii.
Figure 56:
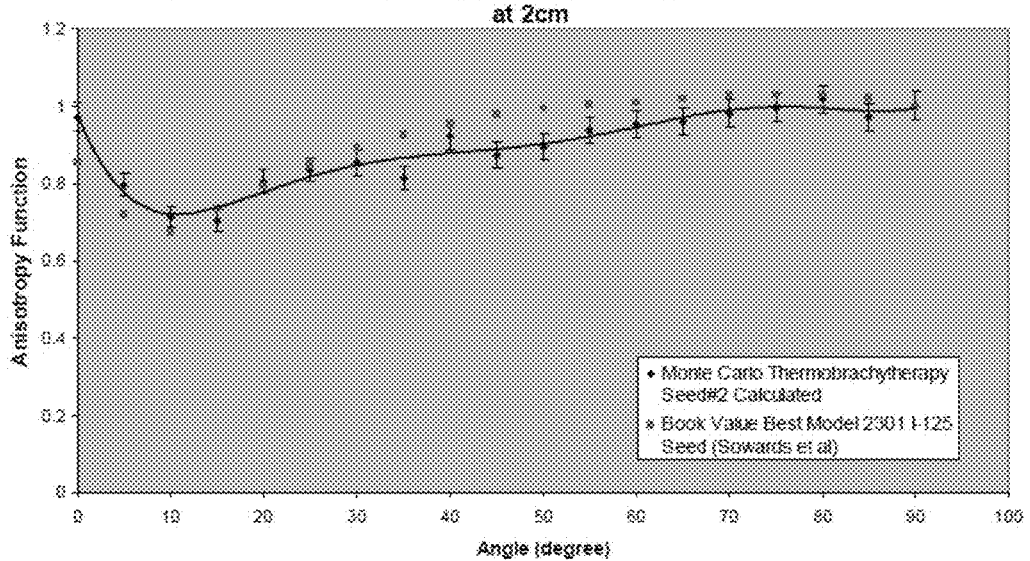
FIG. 56 illustrates the Anisotropy Function of Monte Carlo calculated value for Thermobrachytherapy Seed#2 and the Book Value for the Best Model 2301 $^{125}$I in liquid water at 2 cm radii.

FIG. 55 illustrates the Anisotropy Function of Monte Carlo calculated value for Thermobrachytherapy Seed#2 and the Monte Carlo calculated for the Best Model 2301 $^{125}$I in liquid water at 2 cm radii. The plot is fitted with a 6th order polynomial function FIG. 56 illustrates the Anisotropy Function of Monte Carlo calculated value for Thermobrachytherapy Seed#2 and the Book Value for the Best Model 2301 $^{125}$I in liquid water at 2 cm radii. The plot is fitted with a 6th order polynomial function.

Table 40c illustrates the Monte Carlo calculated Anisotropy Function of Thermobrachytherapy Seed#2 in liquid water for Radial Distances of 3 cm. A comparison between calculated and book values of the Best Model 2301 $^{125}$I Seed is also calculated.

TABLE 40c

Monte Carlo calculated Anisotropy Function of Thermobrachytherapy Seed#2 in liqiud water for Radial Distances of 3 cm. A comparison between calculated and book values of the Best Model 2301 $^{125}$I Seed is also calculated.

| Angle | AF at 3 cm | Best Model 2301 $^{125}$I Seed | Error | Book Value (Meigooni et al) | Error |
|---|---|---|---|---|---|
| 0 | 1.062729 | 1.081703 | −0.01754 | 0.922 | 0.152634 |
| 5 | 0.84505 | 0.827586 | 0.021103 | 0.726 | 0.163981 |
| 10 | 0.745824 | 0.750467 | −0.00619 | 0.699 | 0.066987 |
| 15 | 0.827248 | 0.833466 | −0.00746 | 0.756 | 0.094243 |
| 20 | 0.799849 | 0.808948 | −0.01125 | 0.809 | −0.011311 |
| 25 | 0.860543 | 0.872956 | −0.01422 | 0.852 | 0.010027 |
| 30 | 0.928153 | 0.930988 | −0.00304 | 0.885 | 0.04876 |
| 35 | 0.939299 | 0.953275 | −0.01466 | 0.919 | 0.022088 |
| 40 | 0.991368 | 0.987268 | 0.004153 | 0.947 | 0.046851 |
| 45 | 0.955833 | 0.95516 | 0.000705 | 0.968 | −0.012569 |
| 50 | 0.970277 | 0.973073 | −0.00287 | 0.985 | −0.014947 |
| 55 | 1.000539 | 1.008446 | −0.00784 | 0.997 | 0.00355 |
| 60 | 0.984424 | 0.988973 | −0.0046 | 1.009 | −0.024356 |
| 65 | 1.003341 | 1.000178 | 0.003162 | 1.012 | −0.008556 |
| 70 | 1.019852 | 1.030136 | −0.00998 | 1.016 | 0.003791 |
| 75 | 1.013856 | 1.018382 | −0.00444 | 1.018 | −0.004071 |
| 80 | 0.961765 | 0.960588 | 0.001225 | 1.019 | −0.056168 |
| 85 | 0.994766 | 0.996809 | −0.00205 | 1.019 | −0.023782 |
| 90 | 1 | 1 | 0 | 1 | 0 |

Figure 57:
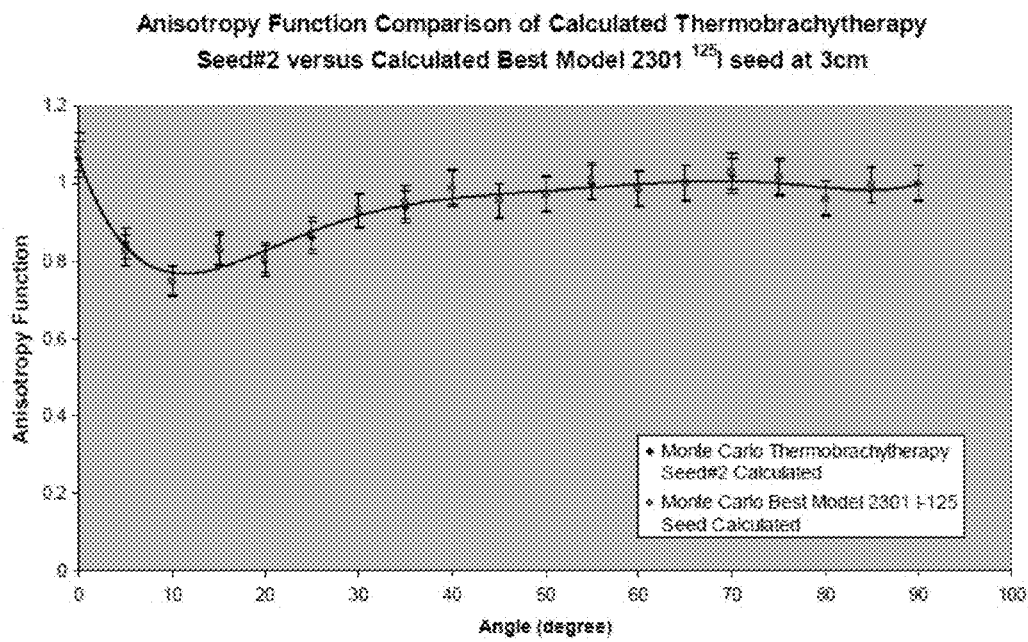
FIG. 57 illustrates the Anisotropy Function of Monte Carlo calculated value for Thermobrachytherapy Seed#2 and the Monte Carlo calculated for the Best Model 2301 $^{125}$I in liquid water at 3 cm radii.

FIG. 57 illustrates the Anisotropy Function of Monte Carlo calculated value for Thermobrachytherapy Seed#2 and the Monte Carlo calculated for the Best Model 2301 $^{125}$I in liquid water at 3 cm radii. The plot is fitted with a 6th order polynomial function.

Figure 58:
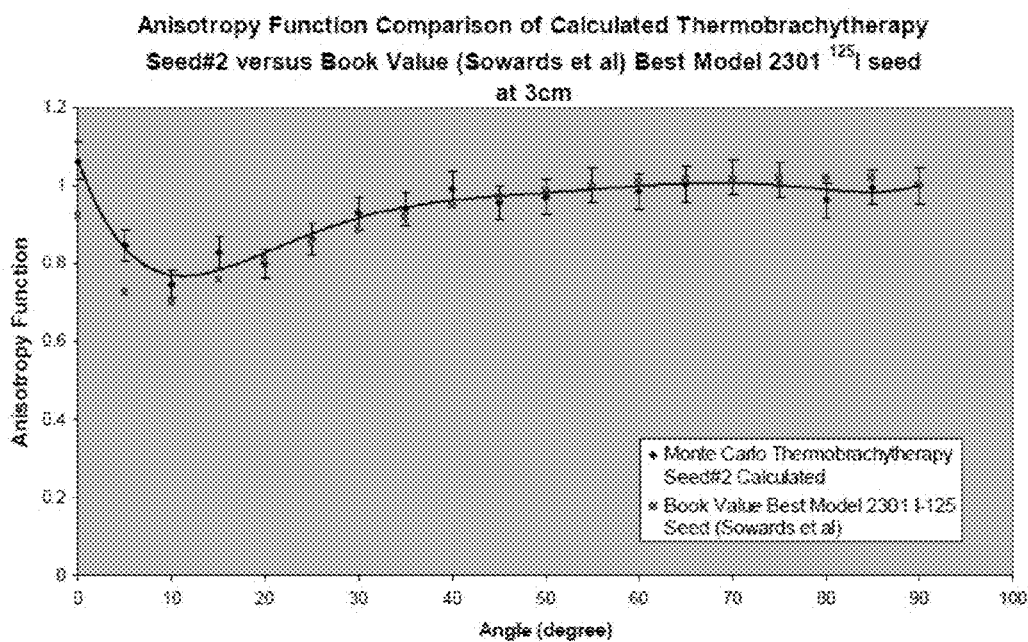
FIG. 58 illustrates the Anisotropy Function of Monte Carlo calculated value for Thermobrachytherapy Seed#2 and the Book value for the Best Model 2301 $^{125}$I in liquid water at 3 cm radii.

FIG. 58 illustrates the Anisotropy Function of Monte Carlo calculated value for Thermobrachytherapy Seed#2 and the Book value for the Best Model 2301 $^{125}$I in liquid water at 3 cm radii. The plot is fitted with a 6th order polynomial function.

Table 40d illustrates the Monte Carlo calculated Anisotropy Function of Thermobrachytherapy Seed#2 in liquid water for Radial Distances of 4 cm. A comparison between calculated and book values of the Best Model 2301 $^{125}$I Seed is also calculated.

TABLE 40d

Monte Carlo calculated Anisotropy Function of Thermobrachytherapy Seed#2 in liquid water for Radial Distances of 4 cm. A comparison between calculated and book values of the Best Model 2301 $^{125}$I Seed is also calculated.

| Angle | AF at 4 cm | Best Model 2301 $^{125}$I Seed | Error | Book Value (Meigooni et al) | Error |
|---|---|---|---|---|---|
| 0 | 1.047458 | 1.067157 | −0.01846 | 0.902 | 0.161262 |
| 5 | 0.848698 | 0.856189 | −0.00875 | 0.728 | 0.165794 |
| 10 | 0.843641 | 0.849553 | −0.00696 | 0.727 | 0.160441 |
| 15 | 0.75386 | 0.762809 | −0.01173 | 0.779 | −0.032272 |
| 20 | 0.840591 | 0.843573 | −0.00353 | 0.814 | 0.032667 |
| 25 | 0.908304 | 0.917008 | −0.00949 | 0.863 | 0.052496 |
| 30 | 0.912712 | 0.921985 | −0.01006 | 0.892 | 0.02322 |
| 35 | 0.915824 | 0.927006 | −0.01206 | 0.918 | −0.00237 |
| 40 | 0.918773 | 0.928846 | −0.01085 | 0.939 | −0.021542 |
| 45 | 0.9845 | 0.992994 | −0.00855 | 0.976 | 0.008709 |
| 50 | 0.956752 | 0.968645 | −0.01228 | 0.991 | −0.034559 |
| 55 | 1.014113 | 1.028106 | −0.01361 | 1.004 | 0.010072 |
| 60 | 0.994831 | 1.000959 | −0.00612 | 1.007 | −0.012085 |
| 65 | 1.016231 | 1.017048 | −0.0008 | 1.009 | 0.007166 |
| 70 | 1.021108 | 1.020551 | 0.000546 | 1.023 | −0.001849 |
| 75 | 1.014378 | 1.009032 | 0.005298 | 1.017 | −0.002578 |
| 80 | 0.976854 | 0.975997 | 0.000878 | 1.017 | −0.039475 |
| 85 | 0.998467 | 0.998651 | −0.00018 | 1.018 | −0.019188 |
| 90 | 1 | 0.999983 | 1.73E−05 | 1 | 0 |

Figure 59:
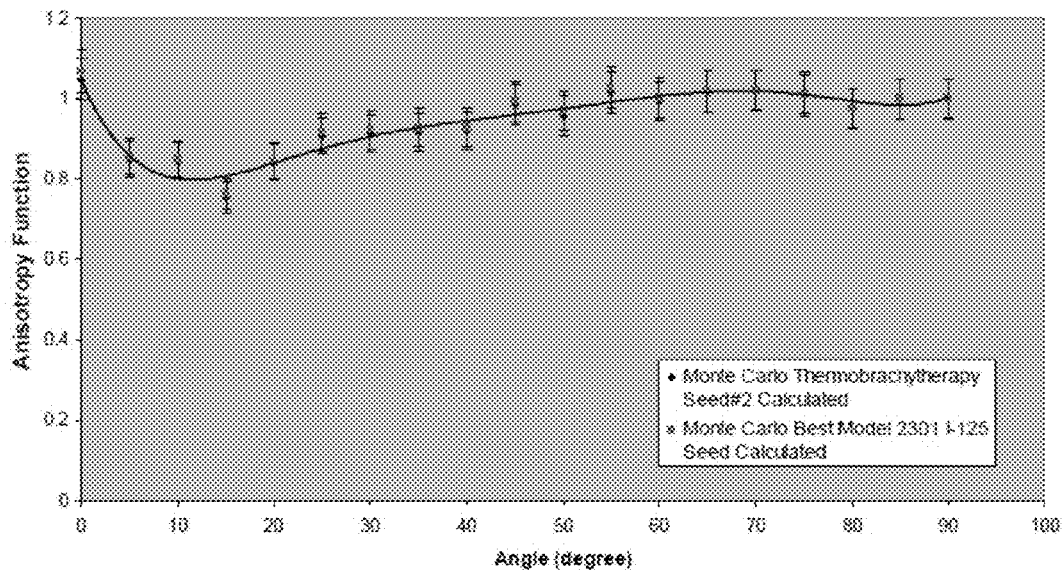
FIG. 59 illustrates the Anisotropy Function of Monte Carlo calculated value for Thermobrachytherapy Seed#2 and the Monte Carlo calculated for the Best Model 2301 $^{125}$I in liquid water at 4 cm radii.

FIG. 59 illustrates the Anisotropy Function of Monte Carlo calculated value for Thermobrachytherapy Seed#2 and the Monte Carlo calculated for the Best Model 2301 $^{125}$I in liquid water at 4 cm radii. The plot is fitted with a 6th order polynomial function.

Figure 60:
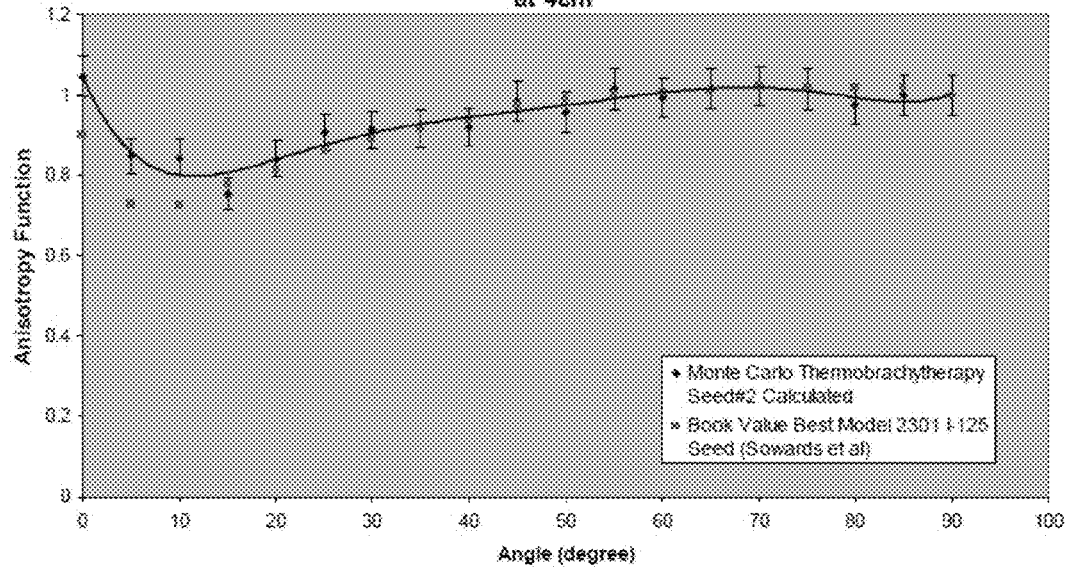
FIG. 60 illustrates the Anisotropy Function of Monte Carlo calculated value for Thermobrachytherapy Seed#2 and the Book Value calculated for the Best Model 2301 $^{125}$I in liquid water at 2 cm radii.

FIG. 60 illustrates the Anisotropy Function of Monte Carlo calculated value for Thermobrachytherapy Seed#2 and the Book Value calculated for the Best Model 2301 $^{125}$I in liquid water at 2 cm radii. The plot is fitted with a 6th order polynomial function.

Table 40e illustrates the Monte Carlo calculated Anisotropy Function of Thermobrachytherapy Seed#2 in liquid water for Radial Distances of 5 cm. A comparison between calculated and book values of the Best Model 2301 $^{125}$I Seed is also calculated.

TABLE 40e

Monte Carlo calculated Anisotropy Function of Thermobrachytherapy Seed#2 in liquid water for Radial Distances of 5 cm. A comparison between calculated and book values of the Best Model 2301 $^{125}$I Seed is also calculated.

| Angle | AF at 5 cm | Best Model 2301 $^{125}$I Seed | Error | Book Value (Meigooni et al) | Error |
|---|---|---|---|---|---|
| 0 | 1.026903 | 1.037909 | −0.0106 | 0.894 | 0.148661 |
| 5 | 0.815129 | 0.826259 | −0.01347 | 0.753 | 0.082509 |
| 10 | 0.775649 | 0.781112 | −0.00699 | 0.732 | 0.05963 |
| 15 | 0.772767 | 0.785625 | −0.01637 | 0.795 | −0.027966 |
| 20 | 0.811832 | 0.814253 | −0.00297 | 0.825 | −0.015961 |
| 25 | 0.790539 | 0.790151 | 0.00049 | 0.865 | −0.086083 |
| 30 | 0.933794 | 0.93407 | −0.0003 | 0.899 | 0.038703 |
| 35 | 0.880013 | 0.880933 | −0.00104 | 0.92 | −0.043464 |
| 40 | 0.902171 | 0.909002 | −0.00752 | 0.943 | −0.043297 |
| 45 | 0.955933 | 0.965222 | −0.00962 | 0.968 | −0.012466 |
| 50 | 0.931583 | 0.921762 | 0.010654 | 0.997 | −0.065614 |
| 55 | 0.999427 | 1.00322 | −0.00378 | 0.993 | 0.006472 |
| 60 | 0.960247 | 0.972524 | −0.01262 | 1.01 | −0.049261 |
| 65 | 1.000826 | 0.982562 | 0.018588 | 1.024 | −0.022631 |
| 70 | 0.974142 | 0.959269 | 0.015504 | 1.011 | −0.036457 |
| 75 | 1.029715 | 1.020911 | 0.008623 | 1.02 | 0.009524 |
| 80 | 0.995538 | 0.991336 | 0.004238 | 1.01 | −0.014319 |
| 85 | 1.018132 | 1.015815 | 0.002281 | 1.011 | 0.007054 |
| 90 | 1 | 1 | 0 | 1 | 0 |

Figure 61:
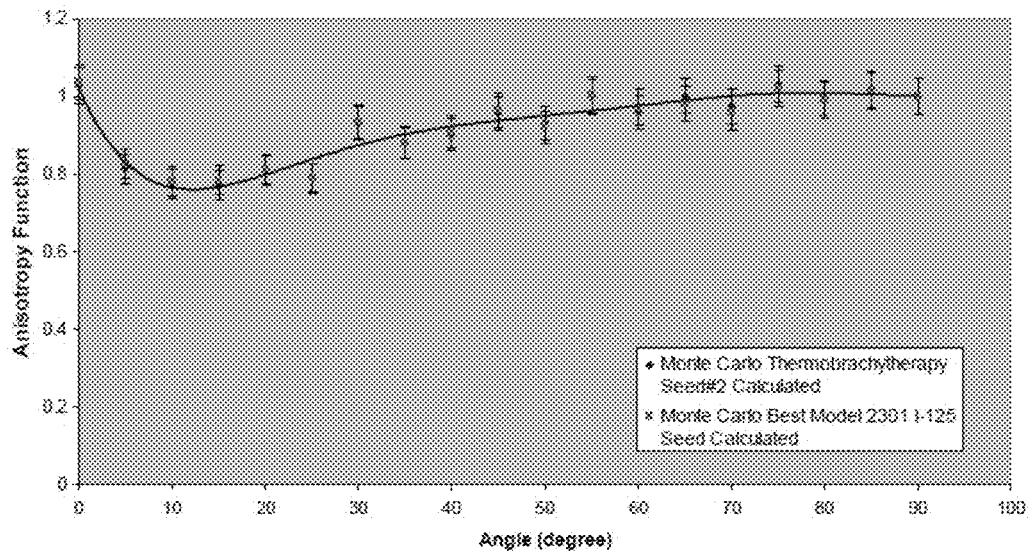
FIG. 61 illustrates the Anisotropy Function of Monte Carlo calculated value for Thermobrachytherapy Seed#2 and the Monte Carlo calculated for the Best Model 2301 $^{125}$I in liquid water at 5 cm radii.
Figure 62:
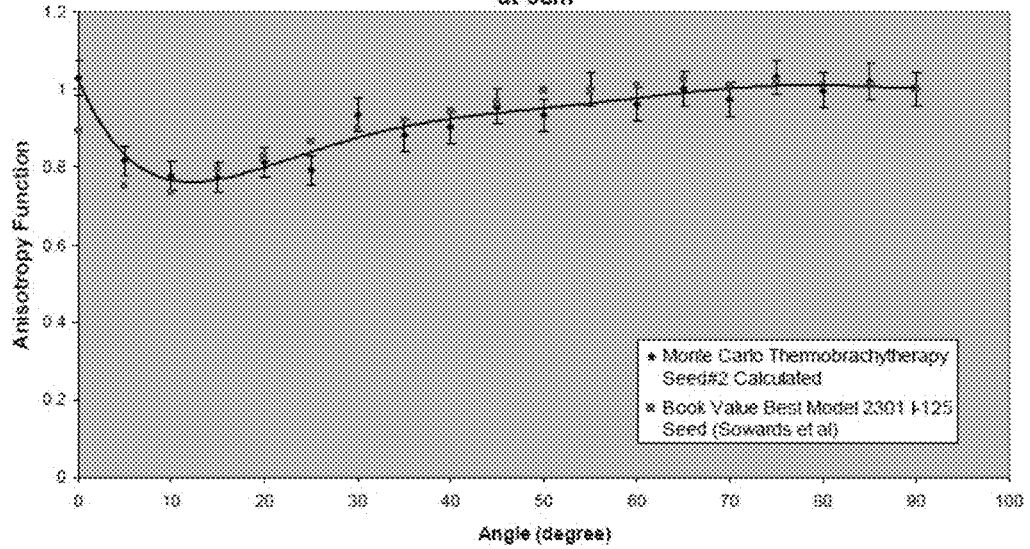
FIG. 62 illustrates the Anisotropy Function of Monte Carlo calculated value for Thermobrachytherapy Seed#2 and the Book Value for the Best Model 2301 $^{125}$I in liquid water at 5 cm radii.

FIG. 61 illustrates the Anisotropy Function of Monte Carlo calculated value for Thermobrachytherapy Seed#2 and the Monte Carlo calculated for the Best Model 2301 $^{125}$I in liquid water at 5 cm radii. The plot is fitted with a 6th order polynomial function FIG. 62 illustrates the Anisotropy Function of Monte Carlo calculated value for Thermobrachytherapy Seed#2 and the Book Value for the Best Model 2301 $^{125}$I in liquid water at 5 cm radii. The plot is fitted with a 6th order polynomial function.

Table 40f illustrates the Monte Carlo calculated Anisotropy Function of Thermobrachytherapy Seed#2 in liquid water for Radial Distances of 6 cm. A comparison between calculated and book values of the Best Model 2301 $^{125}$I Seed is also calculated.

TABLE 40f

Monte Carlo calculated Anisotropy Function of Thermobrachytherapy Seed#2 in liquid water for Radial Distances of 6 cm. A comparison between calculated and book values of the Best Model 2301 $^{125}$I Seed is also calculated.

| Angle | AF at 6 cm | Best Model 2301 $^{125}$I Seed | Error | Book Value (Meigooni et al) | Error |
|---|---|---|---|---|---|
| 0 | 0.969181 | 1.002815 | −0.03354 | 0.893 | 0.085309 |
| 5 | 0.877846 | 0.888127 | −0.01158 | 0.771 | 0.138581 |
| 10 | 0.775889 | 0.782999 | −0.00908 | 0.764 | 0.015562 |
| 15 | 0.811767 | 0.819448 | −0.00937 | 0.805 | 0.008406 |
| 20 | 0.805201 | 0.817894 | −0.01552 | 0.852 | −0.054928 |
| 25 | 0.9137 | 0.936581 | −0.02443 | 0.89 | 0.026629 |
| 30 | 0.82033 | 0.833299 | −0.01556 | 0.915 | −0.103464 |
| 35 | 0.87206 | 0.886202 | −0.01596 | 0.964 | −0.095373 |
| 40 | 0.881475 | 0.904777 | −0.02575 | 0.976 | −0.096849 |
| 45 | 0.93567 | 0.948816 | −0.01386 | 0.979 | −0.04426 |
| 50 | 0.969154 | 0.976859 | −0.00789 | 0.989 | −0.020067 |
| 55 | 0.970141 | 0.98898 | −0.01905 | 1.011 | −0.040414 |
| 60 | 0.960045 | 0.967874 | −0.00809 | 1.019 | −0.057855 |
| 65 | 0.948985 | 0.960829 | −0.01233 | 1.034 | −0.08222 |
| 70 | 0.950045 | 0.948077 | 0.002075 | 1.035 | −0.082082 |
| 75 | 1.003345 | 1.01108 | −0.00765 | 1.043 | −0.03802 |
| 80 | 0.973936 | 0.972717 | 0.001253 | 1.02 | −0.045161 |
| 85 | 1.054661 | 1.053106 | 0.001477 | 1.031 | 0.02295 |
| 90 | 1 | 1 | 0 | 1 | 0 |

Figure 63:
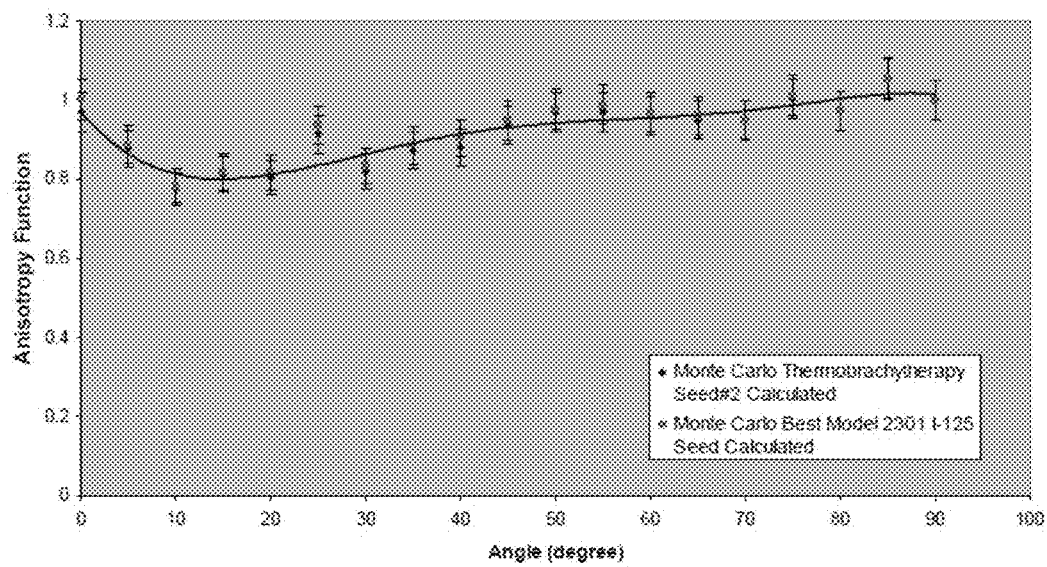
FIG. 63 illustrates the Anisotropy Function of Monte Carlo calculated value for Thermobrachytherapy Seed#2 and the Monte Carlo calculated for the Best Model 2301 $^{125}$I in liquid water at 6 cm radii.

FIG. 63 illustrates the Anisotropy Function of Monte Carlo calculated value for Thermobrachytherapy Seed#2 and the Monte Carlo calculated for the Best Model 2301 $^{125}$I in liquid water at 6 cm radii. The plot is fitted with a 6th order polynomial function.

Figure 64:
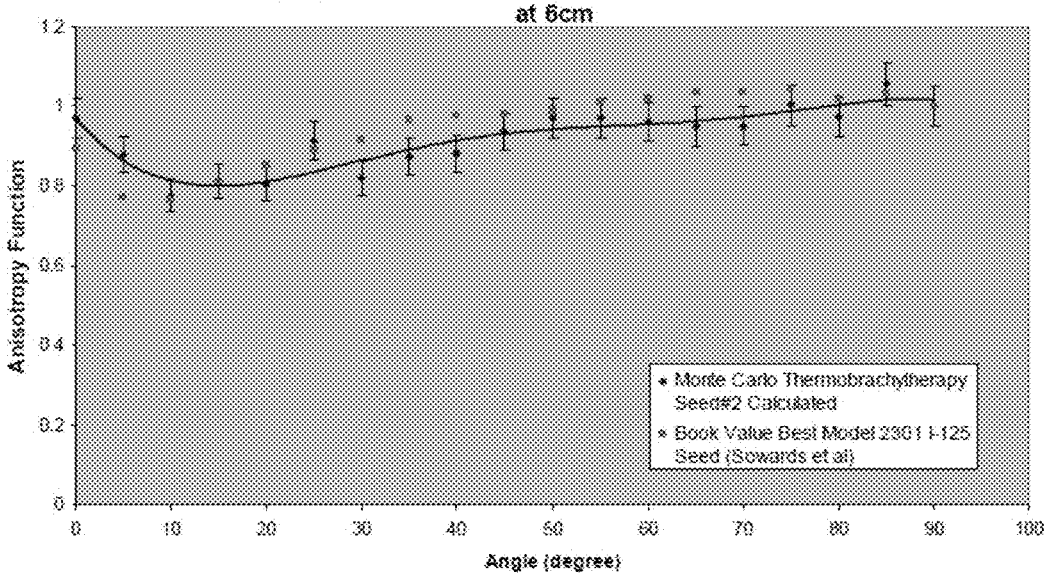
FIG. 64 illustrates the Anisotropy Function of Monte Carlo calculated value for Thermobrachytherapy Seed#2 and the Book value for the Best Model 2301 $^{125}$I in liquid water at 6 cm radii.

FIG. 64 illustrates the Anisotropy Function of Monte Carlo calculated value for Thermobrachytherapy Seed#2 and the Book value for the Best Model 2301 $^{125}$I in liquid water at 6 cm radii. The plot is fitted with a 6th order polynomial function.

Table 40g illustrates the Monte Carlo calculated Anisotropy Function of Thermobrachytherapy Seed#2 in liquid water for Radial Distances of 7 cm. A comparison between calculated and book values of the Best Model 2301 $^{125}$I Seed is also calculated.

TABLE 40g

Monte Carlo calculated Anisotropy Function of Thermobrachytherapy Seed#2 in liquid water for Radial Distances of 7 cm. A comparison between calculated and book values of the Best Model 2301 $^{125}$I Seed is also calculated.

| Angle | AF at 7 cm | Best Model 2301 $^{125}$I Seed | Error | Book Value (Meigooni et al) | Error |
|---|---|---|---|---|---|
| 0 | 1.014464 | 1.044519 | −0.02877 | 0.858 | 0.182359 |
| 5 | 0.84554 | 0.872338 | −0.03072 | 0.8 | 0.056925 |
| 10 | 0.790712 | 0.814773 | −0.02953 | 0.782 | 0.011141 |
| 15 | 0.87651 | 0.89647 | −0.02226 | 0.812 | 0.079446 |
| 20 | 0.816902 | 0.839067 | −0.02642 | 0.821 | −0.004991 |
| 25 | 0.847151 | 0.857219 | −0.01174 | 0.86 | −0.014941 |
| 30 | 0.943176 | 0.968562 | −0.02621 | 0.873 | 0.080385 |
| 35 | 0.957799 | 0.965505 | −0.00798 | 0.924 | 0.036579 |
| 40 | 0.979902 | 1.010278 | −0.03007 | 0.937 | 0.045787 |
| 45 | 0.99091 | 1.008515 | −0.01746 | 0.954 | 0.03869 |
| 50 | 0.966233 | 0.983552 | −0.01761 | 0.961 | 0.005446 |
| 55 | 1.008051 | 1.020988 | −0.01267 | 0.99 | 0.018234 |
| 60 | 0.915609 | 0.920182 | −0.00497 | 1.002 | −0.086219 |
| 65 | 1.122188 | 1.14268 | −0.01793 | 1.03 | 0.089503 |
| 70 | 1.057438 | 1.069128 | −0.01093 | 1.01 | 0.046968 |
| 75 | 1.041891 | 1.039857 | 0.001956 | 1.02 | 0.021462 |
| 80 | 0.98055 | 0.991134 | −0.01068 | 1.005 | −0.024328 |
| 85 | 1.02353 | 1.029283 | −0.00559 | 1.021 | 0.002478 |
| 90 | 0.999979 | 0.999979 | 1.11E−16 | 1 | −2.1E−05 |

Figure 65:
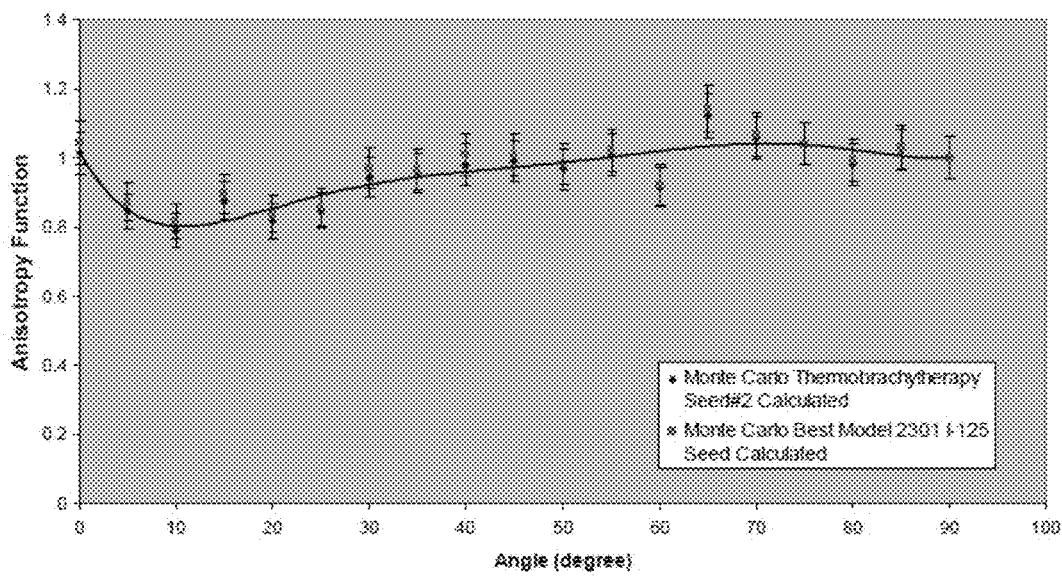
FIG. 65 illustrates the Anisotropy Function of Monte Carlo calculated value for Thermobrachytherapy Seed#2 and the Monte Carlo calculated for the Best Model 2301 $^{125}$I in liquid water at 7 cm radii.

FIG. 65 illustrates the Anisotropy Function of Monte Carlo calculated value for Thermobrachytherapy Seed#2 and the Monte Carlo calculated for the Best Model 2301 $^{125}$I in liquid water at 7 cm radii. The plot is fitted with a 6th order polynomial function.

Figure 66:
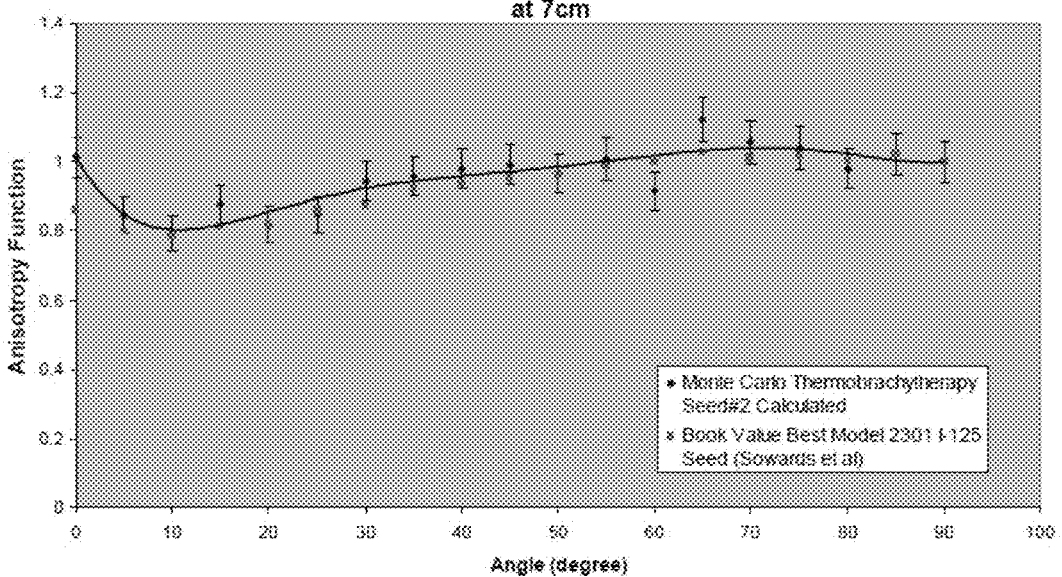
FIG. 66 illustrates the Anisotropy Function of Monte Carlo calculated value for Thermobrachytherapy Seed#2 and the Book value calculated for the Best Model 2301 $^{125}$I in liquid water at 7 cm radii.

FIG. 66 illustrates the Anisotropy Function of Monte Carlo calculated value for Thermobrachytherapy Seed#2 and the Book value calculated for the Best Model 2301 $125_I$ in liquid water at 7 cm radii. The plot is fitted with a 6th order polynomial function.

Average Anisotropy Function:

The average anisotropy function is taken by taking an average of the calculated anisotropy functions for all the angles. Table 41a illustrates the Average Anisotropy Constant calculated for radial distances of 1 cm in liquid water.

TABLE 41a

Average Anisotropy Constant calculated for radial distances of 1 cm in liquid water

| | 1 cm | Best Model 2301 $^{125}$I Seed | Error | Book Value (Meigooni et al) | Error |
|---|---|---|---|---|---|
| Average Anisotropy Constant $\Phi_{an}(r)$ | 0.906 | 0.913 | −0.00666 | 0.986 | −0.0807 |

Table 41b illustrates the Average Anisotropy Constant calculated for radial distances of 2 cm in liquid water.

TABLE 41b

Average Anisotropy Constant calculated for radial distances of 2 cm in liquid water

| | 2 cm | Best Model 2301 $^{125}$I Seed | Error | Book Value (Meigooni et al) | Error |
|---|---|---|---|---|---|
| Average Anisotropy | 0.895 | 0.904 | −0.01035 | 0.976 | −0.0831 |

TABLE 41b-continued

Average Anisotropy Constant calculated for radial distances of 2 cm in liquid water

| 2 cm | Best Model 2301 $^{125}$I Seed | Error | Book Value (Meigooni et al) | Error |
|---|---|---|---|---|
| Average Anisotropy Constant $\Phi_{an}(r)$ | | | | |

Table 41c illustrates the Average Anisotropy Constant calculated for radial distances of 3 cm in liquid water.

TABLE 41c

Average Anisotropy Constant calculated for radial distances of 3 cm in liquid water

| 3 cm | Best Model 2301 $^{125}$I Seed | Error | Book Value (Meigooni et al) | Error |
|---|---|---|---|---|
| Average Anisotropy Constant $\Phi_{an}(r)$ | 0.942 | 0.946 | −0.0041 | 0.968 | −0.0264 |

Table 41d illustrates the Average Anisotropy Constant calculated for radial distances of 4 cm in liquid water.

TABLE 41d

Average Anisotropy Constant calculated for radial distances of 4 cm in liquid water

| 4 cm | Best Model 2301 $^{125}$I Seed | Error | Book Value (Meigooni et al) | Error |
|---|---|---|---|---|
| Average Anisotropy Constant $\Phi_{an}(r)$ | 0.945 | 0.952 | −0.0066 | 0.971 | −0.0261 |

Table 41e illustrates the Average Anisotropy Constant calculated for radial distances of 5 cm in liquid water.

TABLE 41e

Average Anisotropy Constant calculated for radial distances of 5 cm in liquid water

| 5 cm | Best Model 2301 $^{125}$I Seed | Error | Book Value (Meigooni et al) | Error |
|---|---|---|---|---|
| Average Anisotropy Constant $\Phi_{an}(r)$ | 0.925 | 0.926 | −0.001 | 0.969 | −0.0454 |

Table 41f illustrates the Average Anisotropy Constant calculated for radial distances of 6 cm in liquid water.

TABLE 41f

Average Anisotropy Constant calculated for radial distances of 6 cm in liquid water

| 6 cm | Best Model 2301 $^{125}$I Seed | Error | Book Value (Meigooni et al) | Error |
|---|---|---|---|---|
| Average Anisotropy Constant $\Phi_{an}(r)$ | 0.921 | 0.932 | −0.011 | 0.991 | −0.0709 |

Table 41g illustrates the Average Anisotropy Constant calculated for radial distances of 7 cm in liquid water.

TABLE 41g

Average Anisotropy Constant calculated for radial distances of 7 cm in liquid water

| 7 cm | Best Model 2301 $^{125}$I Seed | Error | Book Value (Meigooni et al) | Error |
|---|---|---|---|---|
| Average Anisotropy Constant $\Phi_{an}(r)$ | 0.957 | 0.972 | −0.016 | 0.969 | −0.0126 |

Source Anisotropy Constant:

The Source Anisotropy Constant is calculated by taking the average of all the Average Anisotropy Constant. Table 42 illustrates the Source Anisotropy Function for Thermobrachytherapy Seed#2 liquid water.

TABLE 42

Source Anisotropy Function for Thermobrachytherapy Seed#2 liquid water

| | Calculated value | Best Model 2301 $^{125}$I Seed | Error | Book value | Error |
|---|---|---|---|---|---|
| Source Anisotropy Constant $\overline{\Phi_{an}}(r)$ | 0.927 | 0.935 | −0.008 | 0.98 | −0.054 |

The Source Anisotropy Constant is 0.927 and deviates from the Monte Carlo calculated Best Model 2301 $^{125}$I Seed by 0.8% and the Book value by 5.4%

1) Thermobrachtherapy Seed#2 in Solid Water i) Dose Rate (D):

Dose Rate was calculated for seed at 1 cm on the transverse plane (θ=90°) of the source (from the center of the source) in solid water. Therefore, for this measurement the phantom was taken to be Solid Water since it is the solid water measurement. Table 43 illustrates the Dose Rate for Thermobrachytherapy Seed#2 in solid water calculated using Monte Carlo. The error is calculated by using equation #16. Therefore, the error between the calculated thermobrachytherapy value and the calculated Best Model 2301 $^{125}$I seed is 4.23%. The measured value of Dose Rate is $0.24 \pm 4.89 \times 10^{-3}$ cGy*sec$^{-1}$*Ci$^{-1}$.

TABLE 43

Dose Rate for Thermobrachytherapy Seed#2 in Solid Water calculated using Monte Carlo

| Calculated Dose Rate (cGy * sec$^{-1}$ * Ci$^{-1}$) | Calculated Best Model 2301 $^{125}$I Seed (cGy * sec$^{-1}$ * Ci$^{-1}$) | Error | Book Value (Meigooni et al) | Error |
|---|---|---|---|---|
| 0.240788 | 0.230994 | 0.0423 | N/A | | ii) Air Kerma Strength (SK):

Air Kerma Strength was calculated for the seed again at 1 cm on the transverse plane of the source (from the center of the source) but now it was in air. Therefore, the material inside the phantom was taken as air. Also, the 0.897 WAFAC correction factor (as discussed in the Materials & Methods section) is used for SK. Table 44 illustrates the Air Kerma Strength for Thermobrachytherapy Seed#2 in Air calculated using Monte Carlo in solid water. The error is calculated by using equation #16. Therefore, the error between the calculated thermobrachytherapy value and the calculated Best Model 2301 $^{125}$I seed is 4.3%. The measured value of Air Kerma Strength is 0.234±5.1*10$^{-3}$ cGy*cm$^2$*sec$^{-1}$*Ci$^{-1}$.

TABLE 44

Air Kerma Strength for Thermobrachytherapy Seed#2 in Air calculated using Monte Carlo in Solid Water

| Calculated Air Kerma Strength (cGy * cm$^2$ * sec$^{-1}$ * Ci$^{-1}$) | Calculated Best Model 2301 $^{125}$I Seed (cGy * cm$^2$ * sec$^{-1}$ * Ci$^{-1}$) | Error | Book Value (Meigooni et al) | Error |
|---|---|---|---|---|
| 0.234046 | 0.224332 | 0.043 | N/A | N/A | iii) Dose Rate Constant (Λ):

Dose rate constant is calculated using equation #4. In order to calculate it, the ratio of the dose rate and air kerma strength is taken. Table 45 illustrates the Monte Carlo calculated Dose Rate Constant for Thermobrachytherapy Seed#2 in solid water. Therefore, the error between the calculated thermobrachytherapy value and the calculated Best Model 2301 $^{125}$I seed is 0.09%. Also, the error between the calculated thermobrachytherapy value and the Book Value for Best Model 2301 $^{125}$I seed is 4.97%. The measured value of Dose Rate is 1.029±0.031 cGy*h$^{-1}$*U$^{-1}$.

TABLE 45

Monte Carlo calculated Dose Rate Constant for Thermobrachytherapy Seed#2 in Solid Water

| Calculated Dose Rate Constant (cGy * h$^{-1}$ * U$^{-1}$) | Best Model 2301 $^{125}$I Seed (cGy * h$^{-1}$ * U$^{-1}$) | Error | Book Value (Meigooni et al) (cGy * h$^{-1}$ * U$^{-1}$) | Error |
|---|---|---|---|---|
| 1.0288 | 1.02969 | −0.0009 | 1.01 | 0.0497 | iv) Correction/Multiplicative Factor:

Meigooni et al calculated that a conversion factor of 1.05 was needed to convert the dose rate constant in solid water to liquid water. The calculated Correction/Multiplicative factor obtained is 1.028.

v) Radial Function:
Calculation of the radial function is a two fold process.
a) Geometry Function
The Geometry function is independent of the material content of the phantom. Also, the geometry (and dimension) of the source cell remains the same. Therefore, the geometry factor from Table 6 is applicable here.
b) Radial Function Using the Geometry Function
Radial Function was calculated using equation#8 incorporating the geometry function calculated in part a) above. Table 46 illustrates the Radial Function calculated at the transverse plane for the Thermobrachytherapy Seed#2 in solid water using Monte Carlo.

TABLE 46

Radial Function calculated at the transverse plane for the Thermobrachytherapy Seed#2 in Solid Water using Monte Carlo.

| Transverse distance (r) cm | Radial Function g(r) | Best Model 2301 $^{125}$I Seed | Error | Book Value (Meigooni et al) | Error |
|---|---|---|---|---|---|
| 0.1 | 0.879539 | 0.9740849 | −0.09706 | | |
| 0.15 | 0.93508 | 0.9872727 | −0.05287 | | |
| 0.2 | 0.974717 | 1.0245773 | −0.04866 | | |
| 0.25 | 0.953075 | 0.997152 | −0.0442 | | |
| 0.3 | 0.968299 | 1.0106151 | −0.04187 | | |
| 0.4 | 1.03533 | 1.0024356 | 0.032815 | | |
| 0.5 | 1.030962 | 0.9962775 | 0.034814 | | |
| 0.6 | 0.991435 | 0.9601123 | 0.032624 | 1.044 | −0.089 |
| 0.7 | 0.964844 | 0.9079231 | 0.062694 | | |
| 0.75 | 0.969485 | 0.9467391 | 0.024026 | | |
| 0.8 | 0.93192 | 0.9554107 | −0.02459 | | |
| 0.9 | 0.966224 | 0.9667486 | −0.00054 | | |
| 1 | 1.000001 | 1.0000005 | 0 | 1 | 5.0669E−07 |
| 1.5 | 0.884876 | 0.9040619 | −0.02122 | 0.926 | −0.0444108 |
| 2 | 0.79886 | 0.8129667 | −0.01735 | 0.842 | −0.05123498 |
| 2.5 | 0.705464 | 0.728075 | −0.03106 | 0.752 | −0.06188283 |
| 3 | 0.607673 | 0.6505947 | −0.06597 | 0.666 | −0.08757784 |
| 3.5 | 0.541119 | 0.5635308 | −0.03977 | 0.581 | −0.0686426 |
| 4 | 0.45677 | 0.5125491 | −0.10883 | 0.509 | −0.10261204 |
| 4.5 | 0.394066 | 0.4328601 | −0.08962 | 0.443 | −0.11046108 |
| 5 | 0.359463 | 0.3817734 | −0.05844 | 0.386 | −0.06874904 |
| 5.5 | 0.305903 | 0.3178485 | −0.03758 | 0.336 | −0.08957374 |
| 6 | 0.26603 | 0.2753888 | −0.03398 | 0.286 | −0.06982505 |
| 6.5 | 0.233636 | 0.2309718 | 0.011536 | 0.245 | −0.0463822 |
| 7 | 0.195227 | 0.2041012 | −0.04348 | 0.207 | −0.05687288 |
| 7.5 | 0.171557 | 0.176629 | −0.02871 | 0.178 | −0.03619428 |
| 8 | 0.139226 | 0.1571086 | −0.11382 | 0.159 | −0.12436229 |
| 8.5 | 0.125306 | 0.1246026 | 0.005648 | 0.14 | −0.10495467 |
| 9 | 0.107734 | 0.1098135 | −0.01893 | 0.116 | −0.07125574 |
| 9.5 | 0.104874 | 0.093497 | 0.121687 | 0.097 | 0.08117992 |
| 10 | 0.078577 | 0.079492 | −0.0115 | 0.08 | −0.01778224 |

Figure 67:
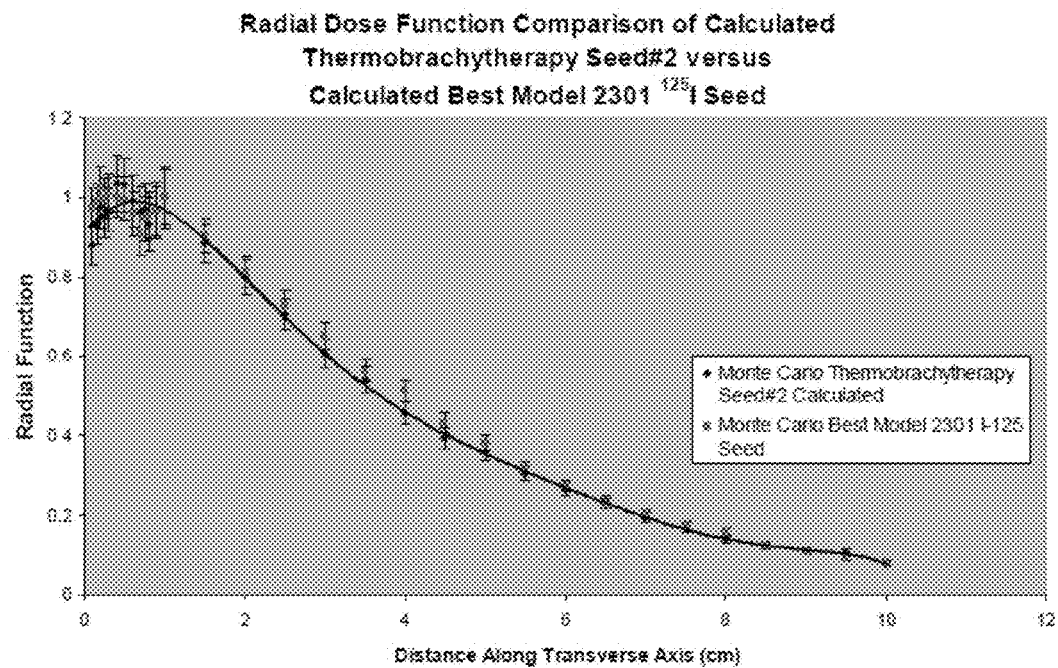
FIG. 67 illustrates the Radial Function of Monte Carlo calculated value for Thermobrachytherapy Seed#2 and the Monte Carlo calculated value for the Best Model 2301 $^{125}$I in solid water.

FIG. 67 illustrates the Radial Function of Monte Carlo calculated value for Thermobrachytherapy Seed#2 and the Monte Carlo calculated value for the Best Model 2301 $^{125}$I in solid water. The plot is fitted with a 5th order polynomial function.

Figure 68:
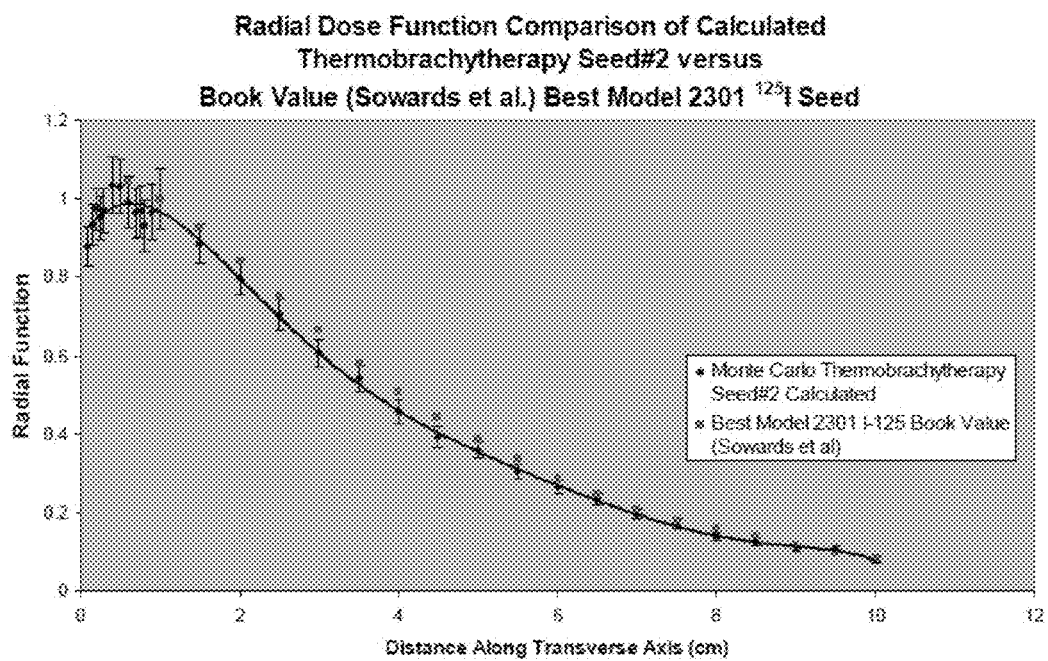
FIG. 68 illustrates the Radial Function of Monte Carlo calculated value for Thermobrachytherapy Seed#2 and the Book Value for the Best Model 2301 $^{125}$I in solid water.

FIG. 68 illustrates the Radial Function of Monte Carlo calculated value for Thermobrachytherapy Seed#2 and the Book Value for the Best Model 2301 $^{125}$I in solid water. The plot is fitted with a 5th order polynomial function.

vi) Anisotropy Function:
Calculation of the radial function is a three fold process.
a) Calculating Geometry Function
The Geometry function is independent of the material content of the phantom and therefore, the geometry function from Tables 8a and 8b are applicable here.
b) Calculating Coordinates for Detectors
The coordinates are independent of the material content of the phantom and therefore, the coordinates from Table 9 are applicable here.

c) Calculating Anisotropy Function Using the Data Accumulated in Tables 8a, 8b & 9

The Anisotropy Function was calculated using all the factors listed in equation #9. Tables 8a and 8b were used to calculate the Geometry Function at various angles. Table 9 was used to find the coordinates needed to place the detectors at the various angles (and radial distances).

Table 47a illustrates the Monte Carlo calculated Anisotropy Function of Thermobrachytherapy Seed#2 in solid water for Radial Distances of 1 cm. A comparison between calculated values of the Best Model 2301 $^{125}$I Seed is also calculated.

TABLE 47a

Monte Carlo calculated Anisotropy Function of Thermobrachytherapy Seed#2 in Solid Water for Radial Distances of 1 cm. A comparison between calculated values of the Best Model 2301 $^{125}$I Seed is also calculated.

| Angle | AF at 1 cm | Best Model 2301 $^{125}$I Seed | Error |
|---|---|---|---|
| 0 | 1.008107 | 1.026252 | −0.01768 |
| 5 | 0.856006 | 0.866304 | −0.01189 |
| 10 | 0.663249 | 0.672536 | −0.01381 |
| 15 | 0.730725 | 0.739002 | −0.0112 |
| 20 | 0.746872 | 0.75897 | −0.01594 |
| 25 | 0.783638 | 0.793086 | −0.01191 |
| 30 | 0.811896 | 0.822657 | −0.01308 |
| 35 | 0.888686 | 0.897361 | −0.00967 |
| 40 | 0.899904 | 0.906809 | −0.00761 |
| 45 | 0.949578 | 0.957336 | −0.0081 |
| 50 | 0.969195 | 0.971523 | −0.0024 |
| 55 | 0.986483 | 0.989839 | −0.00339 |
| 60 | 0.98005 | 0.987353 | −0.0074 |
| 65 | 0.989675 | 0.99135 | −0.00169 |
| 70 | 1.002335 | 0.998792 | 0.003547 |
| 75 | 1.041047 | 1.038309 | 0.002637 |
| 80 | 1.032589 | 1.032288 | 0.000291 |
| 85 | 0.991752 | 0.986828 | 0.004989 |
| 90 | 0.996037 | 0.996037 | 0 |

Figure 69:
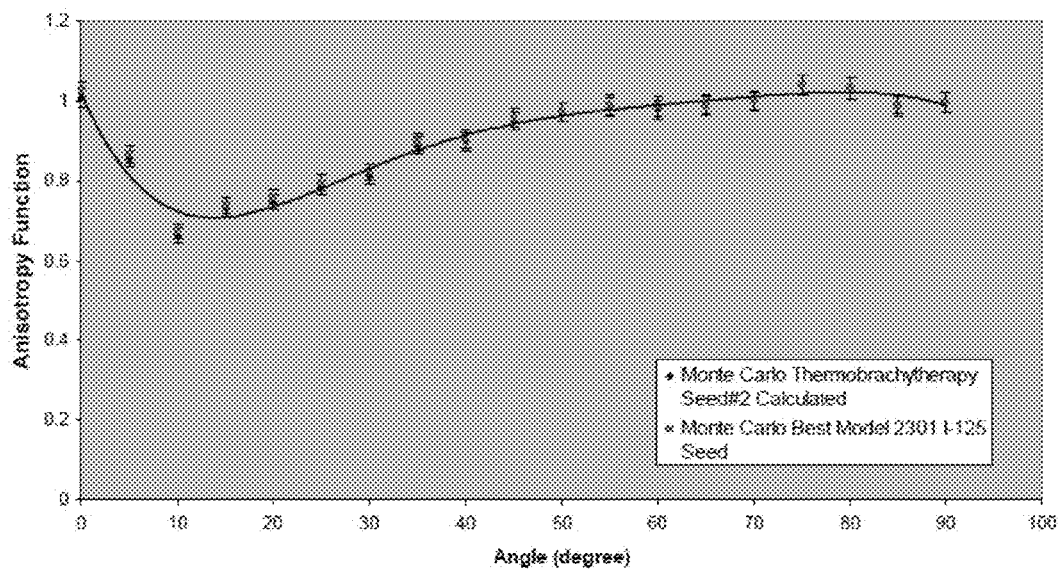
FIG. 69 illustrates the Anisotropy Function of Monte Carlo calculated value for Thermobrachytherapy Seed#2 and the Monte Carlo calculated for the Best Model 2301 $^{125}$I in solid water at 1 cm radii.

FIG. 69 illustrates the Anisotropy Function of Monte Carlo calculated value for Thermobrachytherapy Seed#2 and the Monte Carlo calculated for the Best Model 2301 $^{125}$I in solid water at 1 cm radii. The plot is fitted with a 6th order polynomial function.

Table 47b illustrates the Monte Carlo calculated Anisotropy Function of the Best Model 2301 $_I$125 Seed in solid water for Radial Distances of 2 cm. A comparison between calculated and book values of the Best Model 2301 $^{125}$I Seed is also calculated.

TABLE 47b

Monte Carlo calculated Anisotropy Function of the Best Model 2301 I$^{12}$ Seed in Solid Water for Radial Distances of 2 cm. A comparison between calculated and book values of the Best Model 2301 $^{125}$I Seed is also calculated.

| Angle | AF at 2 cm | Best Model 2301 $^{125}$I Seed | Error | Book Value (Meigooni et al) | Error |
|---|---|---|---|---|---|
| 0 | 0.994972 | 1.002986 | −0.00799 | 0.837 | 0.188736 |
| 5 | 0.815758 | 0.829332 | −0.01637 | | |
| 10 | 0.670149 | 0.677051 | −0.01019 | 0.659 | 0.016918 |
| 15 | 0.684052 | 0.689879 | −0.00845 | | |
| 20 | 0.770323 | 0.779294 | −0.01151 | 0.782 | −0.014933 |
| 25 | 0.806397 | 0.81592 | −0.01167 | | |
| 30 | 0.830939 | 0.83656 | −0.00672 | 0.882 | −0.057892 |
| 35 | 0.801532 | 0.803188 | −0.00206 | | |
| 40 | 0.866698 | 0.876187 | −0.01083 | 0.946 | −0.083829 |
| 45 | 0.900694 | 0.901717 | −0.00113 | | |
| 50 | 0.925245 | 0.924023 | 0.001322 | 0.985 | −0.060665 |
| 55 | 0.953545 | 0.948227 | 0.005607 | | |
| 60 | 0.92931 | 0.928041 | 0.001367 | 1.007 | −0.07715 |
| 65 | 0.918041 | 0.912797 | 0.005745 | | |
| 70 | 0.958556 | 0.952063 | 0.006821 | 1.02 | −0.060239 |
| 75 | 0.996088 | 0.987641 | 0.008552 | | |
| 80 | 1.007711 | 1.004358 | 0.003338 | 1.027 | −0.018782 |
| 85 | 0.987205 | 0.984115 | 0.00314 | | |
| 90 | 1 | 1 | 0 | 1 | 0 |

Figure 70:
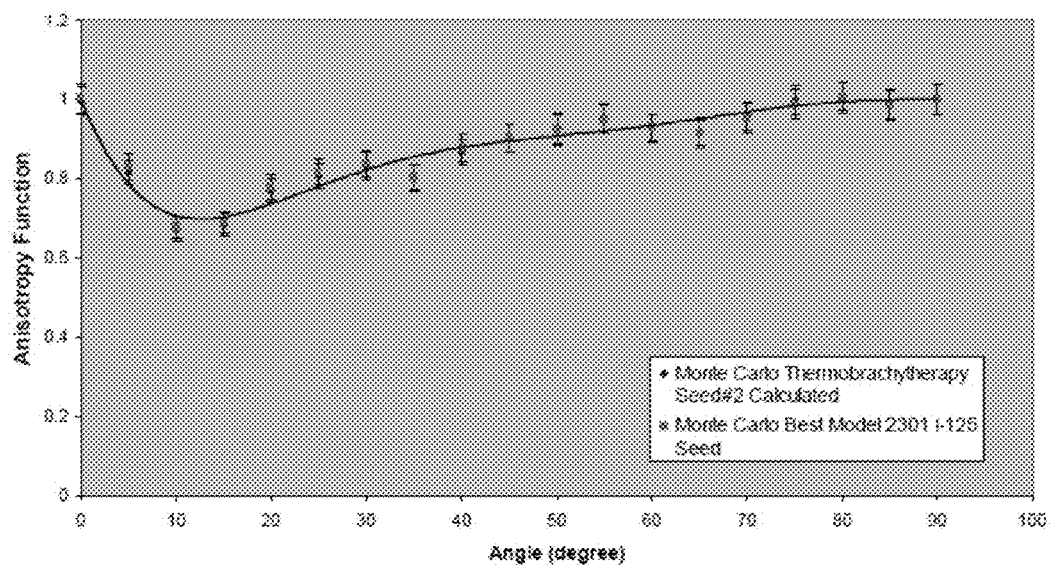
FIG. 70 illustrates the Anisotropy Function of Monte Carlo calculated value for Thermobrachytherapy Seed#2 and the Monte Carlo calculated for the Best Model 2301 $^{125}$I in solid water at 2 cm radii.

FIG. 70 illustrates the Anisotropy Function of Monte Carlo calculated value for Thermobrachytherapy Seed#2 and the Monte Carlo calculated for the Best Model 2301 $^{125}$I in solid water at 2 cm radii. The plot is fitted with a 6th order polynomial function.

Figure 71:
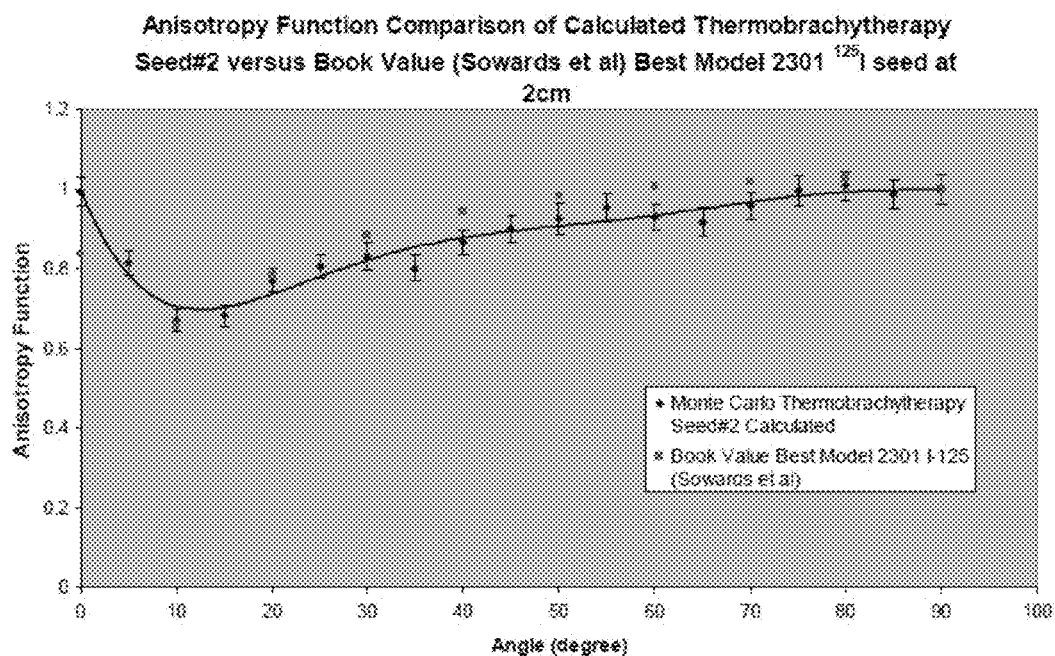
FIG. 71 illustrates the Anisotropy Function of Monte Carlo calculated value for Thermobrachytherapy Seed#2 and the Book value for the Best Model 2301 $^{125}$I in solid water at 2 cm radii.

FIG. 71 illustrates the Anisotropy Function of Monte Carlo calculated value for Thermobrachytherapy Seed#2 and the Book value for the Best Model 2301 $^{125}$I in solid water at 2 cm radii. The plot is fitted with a 6th order polynomial function.

Table 47c illustrates the Monte Carlo calculated Anisotropy Function of the Best Model 2301 $_I$125 Seed in solid water for Radial Distances of 3 cm. A comparison between calculated values of the Best Model 2301 $^{125}$I Seed is also calculated.

TABLE 47c

Monte Carlo calculated Anisotropy Function of the Best Model 2301 I$^{125}$ Seed in Solid Water for Radial Distances of 3 cm. A comparison between calculated values of the Best Model 2301 $^{125}$I Seed is also calculated.

| Angle | AF at 3 cm | Best Model 2301 $^{125}$I Seed | Error |
|---|---|---|---|
| 0 | 1.024838 | 1.045494 | −0.01976 |
| 5 | 0.765715 | 0.767353 | −0.00213 |
| 10 | 0.707137 | 0.706056 | 0.00153 |
| 15 | 0.743466 | 0.742168 | 0.001748 |
| 20 | 0.765973 | 0.769965 | −0.00518 |
| 25 | 0.84961 | 0.864285 | −0.01698 |
| 30 | 0.835195 | 0.835925 | −0.00087 |
| 35 | 0.87705 | 0.876294 | 0.000862 |
| 40 | 0.92078 | 0.919709 | 0.001164 |
| 45 | 0.904882 | 0.893813 | 0.012383 |
| 50 | 0.892654 | 0.89036 | 0.002576 |
| 55 | 0.920982 | 0.916484 | 0.004908 |
| 60 | 0.899397 | 0.900548 | −0.00128 |
| 65 | 0.88646 | 0.880534 | 0.006731 |
| 70 | 0.964466 | 0.97229 | −0.00805 |
| 75 | 0.955665 | 0.944857 | 0.011439 |
| 80 | 0.905628 | 0.899939 | 0.006321 |
| 85 | 0.950504 | 0.95404 | −0.00371 |
| 90 | 1 | 1 | 0 |

Figure 72:
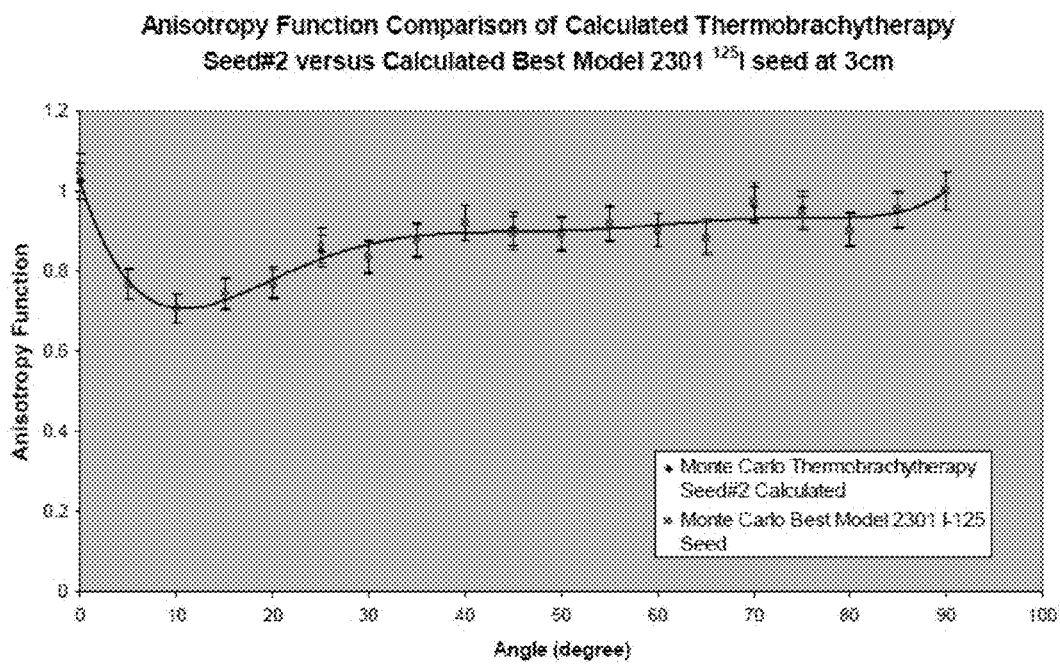
FIG. 72 illustrates the Anisotropy Function of Monte Carlo calculated value for Thermobrachytherapy Seed#2 and the Monte Carlo calculated for the Best Model 2301 $^{125}$I in solid water at 3 cm radii.

FIG. 72 illustrates the Anisotropy Function of Monte Carlo calculated value for Thermobrachytherapy Seed#2 and the Monte Carlo calculated for the Best Model 2301 $^{125}$I in solid water at 3 cm radii. The plot is fitted with a 6th order polynomial function.

Table 47d illustrates the Monte Carlo calculated Anisotropy Function of the Best Model 2301 $_I$125 Seed in solid water for Radial Distances of 4 cm. A comparison between calculated values of the Best Model 2301 $^{125}$I Seed is also calculated.

TABLE 47d

Monte Carlo calculated Anisotropy Function
of the Best Model 2301 I$^{125}$ Seed
in Solid Water for Radial Distances of 4 cm.
A comparison between calculated values of
the Best Model 2301 $^{125}$I Seed is also calculated.

| Angle | AF at 4 cm | Best Model 2301 $^{125}$I Seed | Error |
|---|---|---|---|
| 0 | 0.984572 | 0.996217 | −0.01169 |
| 5 | 0.797341 | 0.804645 | −0.00908 |
| 10 | 0.776643 | 0.786272 | −0.01225 |
| 15 | 0.761371 | 0.766287 | −0.00642 |
| 20 | 0.816284 | 0.821381 | −0.00621 |
| 25 | 0.853665 | 0.865759 | −0.01397 |
| 30 | 0.91995 | 0.928838 | −0.00957 |
| 35 | 0.931786 | 0.940615 | −0.00939 |
| 40 | 0.949714 | 0.956302 | −0.00689 |
| 45 | 0.965179 | 0.963304 | 0.001946 |
| 50 | 0.910781 | 0.909226 | 0.00171 |
| 55 | 1.008934 | 1.009165 | −0.00023 |
| 60 | 0.967338 | 0.967434 | −1E−04 |
| 65 | 0.975225 | 0.964955 | 0.010642 |
| 70 | 1.015545 | 1.007641 | 0.007844 |
| 75 | 0.976372 | 0.970099 | 0.006466 |
| 80 | 0.962731 | 0.956987 | 0.006001 |
| 85 | 1.003732 | 0.990027 | 0.013843 |
| 90 | 1 | 1 | 0 |

Figure 73:
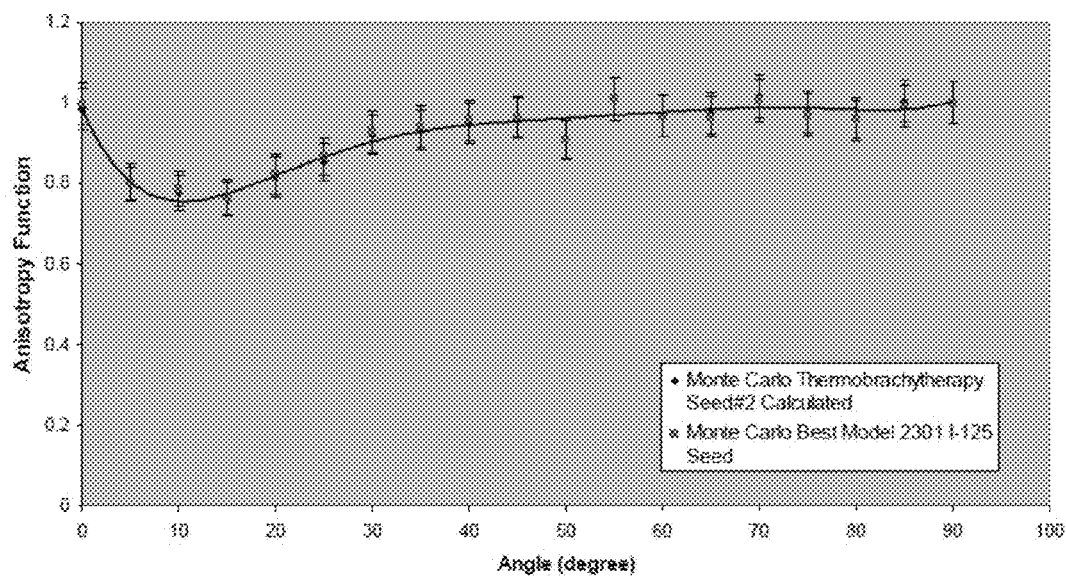
FIG. 73 illustrates the Anisotropy Function of Monte Carlo calculated value for Thermobrachytherapy Seed#2 and the Monte Carlo calculated for the Best Model 2301 $^{125}$I in solid water at 4 cm radii.

FIG. 73 illustrates the Anisotropy Function of Monte Carlo calculated value for Thermobrachytherapy Seed#2 and the Monte Carlo calculated for the Best Model 2301 $^{125}$I in solid water at 4 cm radii. The plot is fitted with a 6th order polynomial function.

Table 47e illustrates the Monte Carlo calculated Anisotropy Function of the Best Model 2301 $_I$125 Seed in solid water for Radial Distances of 5 cm. A comparison between calculated and book values of the Best Model 2301 $^{125}$I Seed is also calculated.

TABLE 47e

Monte Carlo calculated Anisotropy Function of the Best Model
2301 I$^{125}$ Seed in Solid Water for Radial Distances of 5 cm.
A comparison between calculated and book values
of the Best Model 2301 $^{125}$I Seed is also calculated.

| Angle | AF at 5 cm | Best Model 2301 $^{125}$I Seed | Error | Book Value (Meigooni et al) | Error |
|---|---|---|---|---|---|
| 0 | 1.046664 | 1.06538 | −0.01757 | 0.886 | 0.181337 |
| 5 | 0.847794 | 0.863781 | −0.01851 | | |
| 10 | 0.781505 | 0.788669 | −0.00908 | 0.719 | 0.086933 |
| 15 | 0.757011 | 0.773249 | −0.021 | | |
| 20 | 0.81059 | 0.817595 | −0.00857 | 0.801 | 0.011973 |
| 25 | 0.865762 | 0.879567 | −0.0157 | | |
| 30 | 0.826843 | 0.840307 | −0.01602 | 0.873 | −0.052872 |
| 35 | 0.898924 | 0.911502 | −0.0138 | | |
| 40 | 0.940965 | 0.949538 | −0.00903 | 0.938 | 0.003161 |
| 45 | 0.936043 | 0.936324 | −0.0003 | | |
| 50 | 1.000119 | 0.99784 | 0.002284 | 0.962 | 0.039625 |
| 55 | 1.016749 | 1.018567 | −0.00178 | | |
| 60 | 0.942986 | 0.948673 | −0.00599 | 0.99 | −0.047489 |
| 65 | 1.031563 | 1.02104 | 0.010306 | | |
| 70 | 1.031741 | 1.024804 | 0.00677 | 1.001 | 0.030711 |
| 75 | 1.014544 | 1.013883 | 0.000652 | | |
| 80 | 1.080255 | 1.06825 | 0.011239 | 1.011 | 0.068502 |
| 85 | 1.011931 | 1.000983 | 0.010936 | | |
| 90 | 1 | 1 | 0 | 1 | 0 |

Figure 74:
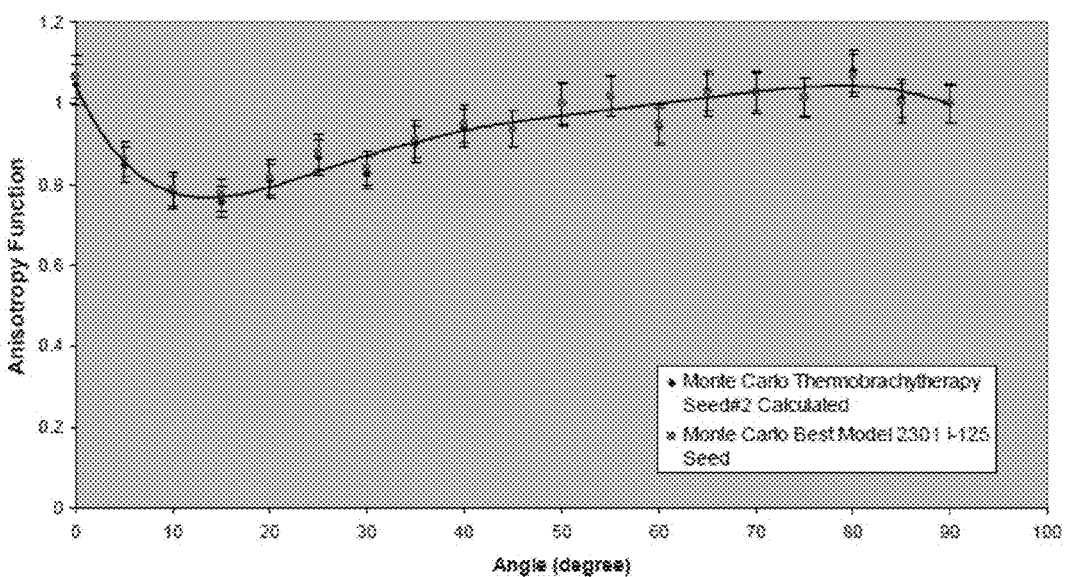
FIG. 74 illustrates the Anisotropy Function of Monte Carlo calculated value for Thermobrachytherapy Seed#2 and the Monte Carlo calculated for the Best Model 2301 $^{125}$I in solid water at 5 cm radii.

FIG. 74 illustrates the Anisotropy Function of Monte Carlo calculated value for Thermobrachytherapy Seed#2 and the Monte Carlo calculated for the Best Model 2301 $^{125}$I in solid water at 5 cm radii. The plot is fitted with a 6th order polynomial function.

Figure 75:
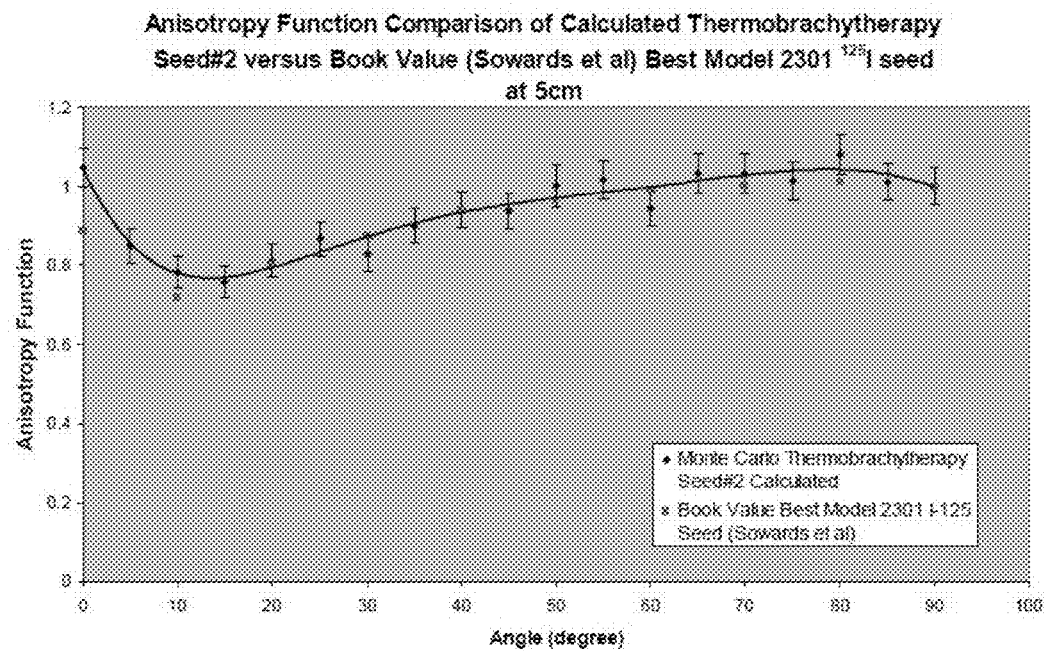
FIG. 75 illustrates the Anisotropy Function of Monte Carlo calculated value for Thermobrachytherapy Seed#2 and the Book value for the Best Model 2301 $^{125}$I in solid water at 1 cm radii.

FIG. 75 illustrates the Anisotropy Function of Monte Carlo calculated value for Thermobrachytherapy Seed#2 and the Book value for the Best Model 2301 $^{125}$I in solid water at 1 cm radii. The plot is fitted with a 6th order polynomial function.

Table 47f illustrates the Monte Carlo calculated Anisotropy Function of the Best Model 2301 I125 Seed in solid water for Radial Distances of 6 cm. A comparison between calculated values of the Best Model 2301 $^{125}$I Seed is also calculated.

TABLE 47f

Monte Carlo calculated Anisotropy Function of the
Best Model 2301 I$^{125}$ Seed in Solid Water for
Radial Distances of 6 cm. A comparison between calculated
values of the Best Model 2301 $^{125}$I Seed is also calculated.

| Angle | AF at 6 cm | Best Model 2301 $^{125}$I Seed | Error |
|---|---|---|---|
| 0 | 0.950859 | 0.961176 | −0.022944 |
| 5 | 0.867337 | 0.869443 | −0.014529 |
| 10 | 0.751525 | 0.754599 | −0.011077 |
| 15 | 0.770497 | 0.77439 | −0.00544 |
| 20 | 0.754274 | 0.754773 | −0.006819 |
| 25 | 0.866324 | 0.868662 | −0.0105 |
| 30 | 0.829422 | 0.82609 | −0.002317 |
| 35 | 0.868055 | 0.864491 | 0.004942 |
| 40 | 0.853435 | 0.85658 | −0.009617 |
| 45 | 0.892122 | 0.878697 | 0.012354 |
| 50 | 0.862775 | 0.853307 | 0.011458 |
| 55 | 0.939576 | 0.938518 | 0.00066 |
| 60 | 0.918693 | 0.912431 | −0.00219 |
| 65 | 1.016373 | 1.005409 | 0.012434 |
| 70 | 0.97542 | 0.962483 | 0.012918 |
| 75 | 0.988762 | 0.972179 | 0.005505 |
| 80 | 1.035533 | 1.025741 | 0.013729 |
| 85 | 0.997364 | 0.987695 | 0.006542 |
| 90 | 1 | 1 | 0 |

Figure 76:
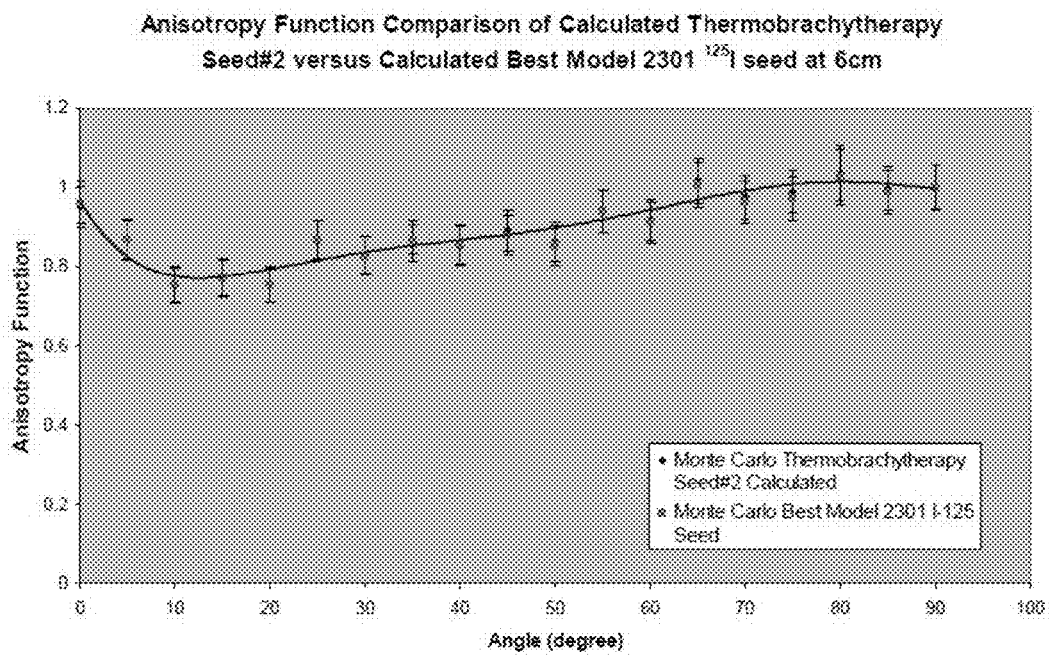
FIG. 76 illustrates the Anisotropy Function of Monte Carlo calculated value for Thermobrachytherapy Seed#2 and the Monte Carlo calculated for the Best Model 2301 $^{125}$I in solid water at 6 cm radii.

FIG. 76 illustrates the Anisotropy Function of Monte Carlo calculated value for Thermobrachytherapy Seed#2 and the Monte Carlo calculated for the Best Model 2301 $^{125}$I in solid water at 6 cm radii. The plot is fitted with a 6th order polynomial function.

Table 47g illustrates the Monte Carlo calculated Anisotropy Function of the Best Model 2301 $_I$125 Seed in solid water for Radial Distances of 7 cm. A comparison between calculated and book values of the Best Model 2301 $^{125}$I Seed is also calculated.

TABLE 47g

Monte Carlo calculated Anisotropy Function of the
Best Model 2301 I$^{125}$ Seed in Solid Water for
Radial Distances of 7 cm. A comparison between calculated and
book values of the Best Model 2301 $^{125}$I Seed is also calculated.

| Angle | AF at 7 cm | Best Model 2301 $^{125}$I Seed | Error | Book Value (Meigooni et al) | Error |
|---|---|---|---|---|---|
| 0 | 1.098314 | 1.106333 | −0.00725 | 0.888 | 0.23684 |
| 5 | 0.851477 | 0.855329 | −0.0045 | | |
| 10 | 0.955089 | 0.96212 | −0.00731 | 0.751 | 0.271757 |
| 15 | 0.862468 | 0.860677 | 0.00208 | | |
| 20 | 0.905488 | 0.907204 | −0.00189 | 0.82 | 0.104253 |

TABLE 47g-continued

Monte Carlo calculated Anisotropy Function of the
Best Model 2301 $I^{125}$ Seed in Solid Water for
Radial Distances of 7 cm. A comparison between calculated and
book values of the Best Model 2301 $^{125}I$ Seed is also calculated.

| Angle | AF at 7 cm | Best Model 2301 $^{125}I$ Seed | Error | Book Value (Meigooni et al) | Error |
|---|---|---|---|---|---|
| 25 | 0.93776 | 0.933333 | 0.004743 | | |
| 30 | 0.932488 | 0.944759 | −0.01299 | 0.905 | 0.030373 |
| 35 | 0.913629 | 0.904032 | 0.010617 | | |
| 40 | 1.010313 | 1.018978 | −0.0085 | 0.952 | 0.061253 |
| 45 | 1.093958 | 1.095808 | −0.00169 | | |
| 50 | 0.998124 | 1.006513 | −0.00833 | 0.972 | 0.026877 |
| 55 | 1.1273 | 1.133607 | −0.00556 | | |
| 60 | 1.091075 | 1.091072 | 2.4E−06 | 1.004 | 0.086728 |
| 65 | 1.191029 | 1.189276 | 0.001474 | | |
| 70 | 0.99379 | 0.984267 | 0.009675 | 0.999 | −0.005215 |
| 75 | 1.095348 | 1.061721 | 0.031671 | | |
| 80 | 1.109199 | 1.096051 | 0.011996 | 1.015 | 0.092806 |
| 85 | 1.146705 | 1.141173 | 0.004848 | | |
| 90 | 0.999979 | 0.999979 | 1.11E−16 | 1 | −2.1E−05 |

Figure 77:
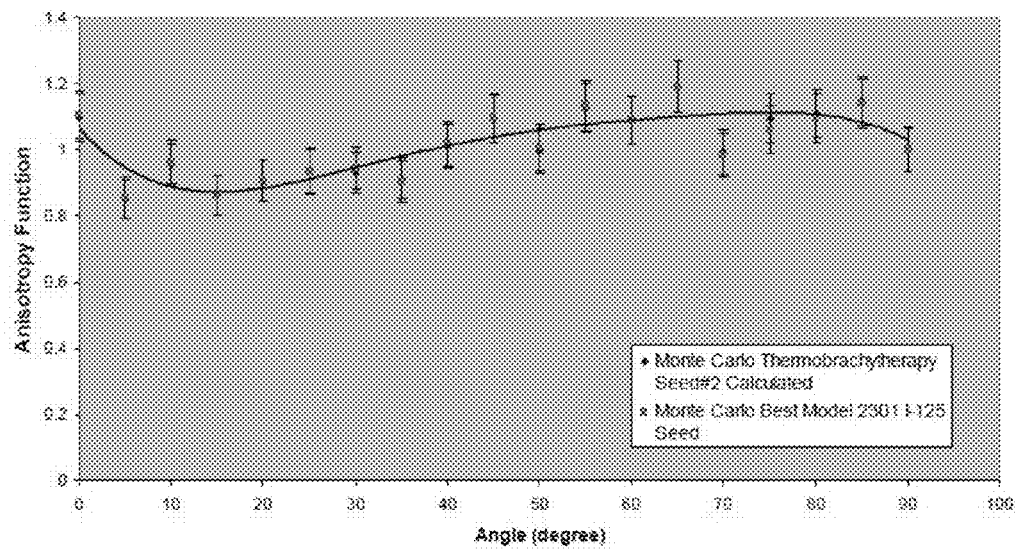
FIG. 77 illustrates the Anisotropy Function of Monte Carlo calculated value for Thermobrachytherapy Seed#2 and the Monte Carlo calculated for the Best Model 2301 $^{125}$I in solid water at 7 cm radii.
Figure 78:
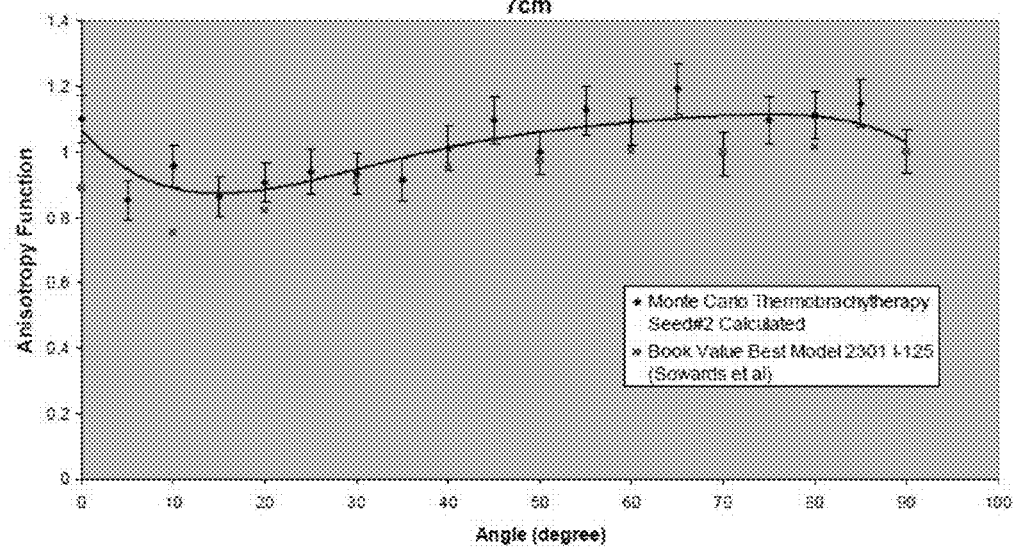
FIG. 78 illustrates the Anisotropy Function of Monte Carlo calculated value for Thermobrachytherapy Seed#2 and the Book value for the Best Model 2301 $^{125}$I in solid water at 7 cm radii.

FIG. 77 illustrates the Anisotropy Function of Monte Carlo calculated value for Thermobrachytherapy Seed#2 and the Monte Carlo calculated for the Best Model 2301 $^{125}I$ in solid water at 7 cm radii. The plot is fitted with a 6th order polynomial function FIG. 78 illustrates the Anisotropy Function of Monte Carlo calculated value for Thermobrachytherapy Seed#2 and the Book value for the Best Model 2301 $^{125}I$ in solid water at 7 cm radii. The plot is fitted with a 6th order polynomial function Average Anisotropy Function:

The average anisotropy function is taken by taking an average of the calculated anisotropy functions for all the angles. Table 48a illustrates the Average Anisotropy Constant calculated for radial distances of 1 cm in solid water.

TABLE 48a

Average Anisotropy Constant calculated
for radial distances of 1 cm in Solid Water

| | 1 cm | Best Model 2301 $^{125}I$ Seed | Error |
|---|---|---|---|
| Average Anisotropy Constant $\Phi_{an}(r)$ | 0.911 | 0.917 | −0.025 |

Table 48b illustrates the Average Anisotropy Function calculated for radial distances of 2 cm in solid water.

TABLE 48b

Average Anisotropy Function calculated for radial
distances of 2 cm in Solid Water

| | 2 cm | Best Model 2301 $^{125}I$ Seed | Error | Book Value (Meigooni et al) | Error |
|---|---|---|---|---|---|
| Average Anisotropy Constant $\Phi_{an}(r)$ | 0.885 | 0.898 | −0.014 | 0.975 | −0.092 |

Table 48c illustrates the Average Anisotropy Constant calculated for radial distances of 3 cm in solid water.

TABLE 48c

Average Anisotropy Constant calculated for radial
distances of 3 cm in Solid Water

| | 3 cm | Best Model 2301 $^{125}I$ Seed | Error |
|---|---|---|---|
| Average Anisotropy Constant $\Phi_{an}(r)$ | 0.882 | 0.883 | −0.001 |

Table 48d illustrates the Average Anisotropy Constant calculated for radial distances of 4 cm in solid water.

TABLE 48d

Average Anisotropy Constant calculated for radial
distances of 4 cm in Solid water

| | 4 cm | Best Model 2301 $^{125}I$ Seed | Error |
|---|---|---|---|
| Average Anisotropy Constant $\Phi_{an}(r)$ | 0.925 | 0.928 | −0.002 |

Table 48e illustrates the Average Anisotropy Constant calculated for radial distances of 5 cm in solid water.

TABLE 48e

Average Anisotropy Constant calculated for radial
distances of 5 cm in Solid Water

| | 5 cm | Best Model 2301 $^{125}I$ Seed | Error | Book Value (Meigooni et al) | Error |
|---|---|---|---|---|---|
| Average Anisotropy Constant $\Phi_{an}(r)$ | 0.940 | 0.950 | −0.0105 | 0.965 | −0.0259 |

Table 48f illustrates the Average Anisotropy Constant calculated for radial distances of 6 cm in solid water.

TABLE 48f

Average Anisotropy Constant calculated for radial
distances of 6 cm in Solid Water

| | 6 cm | Best Model 2301 $^{125}I$ Seed | Error |
|---|---|---|---|
| Average Anisotropy Constant $\Phi_{an}(r)$ | 0.902 | 0.898 | −0.0045 |

Table 48g illustrates the Average Anisotropy Constant calculated for radial distances of 7 cm in solid water.

TABLE 48g

Average Anisotropy Constant calculated for radial distances of 7 cm in Solid Water

| | 7 cm | Best Model 2301 $^{125}$I Seed | Error | Book Value (Meigooni et al) | Error |
|---|---|---|---|---|---|
| Average Anisotropy Constant $\Phi_{an}(r)$ | 1.017 | 1.01 | −0.004 | 0.977 | 0.04 |

The Source Anisotropy Constant was calculated where the Source Anisotropy Constant is calculated by taking the average of all the Average Anisotropy Constants.

Table 50 illustrates the Source Anisotropy Function for the Source Anisotropy Constant is 0.923 and deviates from the Monte Carlo calculated Best Model 2301 $^{125}$I Seed by 0.3% and the Book value by 4.8%.

TABLE 50

Source Anisotropy Function for Thermobrachytherapy Seed#2 in Solid Water

| | Calculated value | Best Model 2301 $^{125}$I Seed | Error | Book value | Error |
|---|---|---|---|---|---|
| Source Anisotropy Constant $\overline{\Phi_{an}}(r)$ | 0.923 | 0.926 | −0.003 | 0.97 | −0.048 |

Results

Dose Rate:

In liquid water, Best Model 2301 has a dose rate of 0.237±4.84*10$^{-3}$ cGy*sec$^{-1}$*Ci$^{-1}$, thermobrachytherapy Seed#1 has a dose rate of 0.251±4.98*10$^{-3}$ cGy*sec$^{-1}$*Ci$^{-1}$ and thermobrachytherapy Seed#2 has a value of 0.248±4.99*10$^{-3}$ cGy*sec$^{-1}$*Ci$^{-1}$.

The percentage difference between thermobrachytherapy seed #1 and Best Model seed is 6.1%. Also, the percentage difference between thermobrachytherapy seed #2 and Best Model seed is 4.5%. The difference in percentages indicates that thermobrachytherapy seed#2 is closer to the Monte Carlo calculated value for Best Model 2301.

In solid water, Best Model has a dose rate of 0.231±4.78*10$^{-3}$ cGy*sec$^{-1}$*Ci$^{-1}$, thermobrachytherapy Seed#1 has a dose rate of 0.245±4.99*10$^{-3}$ cGy*sec$^{-1}$*Ci$^{-1}$ and thermobrachytherapy Seed#2 has a value of 0.241±4.89*10$^{-3}$ cGy*cm$^2$*sec$^{-1}$*Ci$^{-1}$.

The percentage difference between thermobrachytherapy seed #1 and Best Model seed is 6.0%. Also, the percentage difference between thermobrachytherapy seed #2 and Best Model seed is 4.23%.

It is to be noted that thermobrachytherapy seed#2 is closer to the dose rate calculated through Monte Carlo calculations for Best Model 2301.

Air Kerma Strength:

In liquid water, the air kerma strength obtained for the Best Model 2301 $^{125}$I seed is 0.224±4.98*10$^{-3}$ cGy*cm$^2$sec$^{-1}$*Ci$^{-1}$, thermobrachytherapy seed #1 is 0.238±5.14*10$^{-3}$ cGy*cm$^2$sec$^{-1}$*Ci$^{-1}$, and thermobrachytherapy seed#2 is 0.234±5.1*10$^{-3}$ cGy*cm$^2$sec$^{-1}$*Ci$^{-1}$.

The percentage difference between thermobrachytherapy seed #1 and Best Model seed is 6.0%. Also, the percentage difference between thermobrachytherapy seed #2 and Best Model seed is 4.3%.

It is to be noted that the percentage differences in liquid water are in good agreement with one another. The thermobrachytherapy seed#2 is closer than thermobrachytherapy seed#1 in terms of error percentage to the Monte Carlo calculations for the Best Model Seed.

In solid water, the air kerma strength obtained for Model 2301 $^{125}$I seed is 0.22±4.98*10$^{-3}$ cGy*cm$^2$sec$^{-1}$*Ci$^{-1}$, thermobrachytherapy seed #1 is 0.24±5.14*10$^{-3}$ cGy*cm$^2$*sec$^{-1}$*Ci$^{-1}$ and thermobrachytherapy seed#2 is 0.234±5.1*10$^{-3}$ cGy*sec$^{-1}$*Ci$^{-1}$.

The percentage difference between thermobrachytherapy seed #1 and Best Model seed is 6.0%. Also, the percentage difference between thermobrachytherapy seed #2 and Best Model seed is 4.3%. Like in liquid water, the percentage differences between the different seeds are in good agreement in solid water. The percentage difference with thermobrachytherapy seed#2 is closer to the Best Model measured value as opposed to the thermobrachytherapy seed#2.

Dose Rate Constant

In Liquid Water, the dose rate constant calculated for the Best model is 1.056±0.0055 cGy*h$^{-1}$*U$^{-1}$ (Book value of 1.01: with a percentage difference of 4.6%). The value measured for thermobrachytherapy seed#1 1.057±0.031 cGy*h$^{-1}$U$^{-1}$, and thermobrachytherapy seed#2 is 1.058±0.031 cGy*h$^{-1}$U$^{-1}$.

The value obtained for thermobrachytherapy Seed#1 varies by 0.091% from the calculated Best Model value and by 4.69% from Best Model book value. Continuing the comparison, the value obtained for thermobrachytherapy Seed#2 varies by 0.15% from the measured Best Model value and by 4.75% from Best Model book value.

It is to be noted that thermobrachytherapy seed#1 has a closer value to the calculated and the Book value for the Best Model 2301 Seed. In solid water, the dose rate constant calculated for the Best model is 1.03±0.031 cGy*h$^{-1}$*U$^{-1}$ (Book value of 0.98: with a percentage difference of 5.1%). The value measured for thermobrachytherapy seed#1 1.03±0.031 cGy*h$^{-1}$U$^{-1}$ and thermobrachytherapy seeds#2 is 1.029±0.031 cGy*h$^{-1}$*U$^{-1}$.

The value obtained for thermobrachytherapy Seed#1 varies by 0.01% from the measured Best Model value and by 5.1% from Best Model book value. The value obtained for thermobrachytherapy Seed#2 varies by 0.09% from the measured Best Model value and by 4.97% from Best Model book value. In solid water, both the seeds are relatively close o both the calculated Monte Carlo value and the Book value for the Best Model 2301 Seed. Thermobrachytherapy Seed#1 is closer to the calculated Best Model Value and Thermobrachytherapy Seed#2 is closer to the Best Model Book value.

Correction/Multiplicative Factor:

The Correction/Multiplicative Factor between the Solid Water and liquid water for the calculated Best Model 2301 $^{125}$I seed is 1.026 (Book Value of 1.05). Thermobrachytherapy Seed#1 has a factor of 1.026 and Thermobrachytherapy Seed#2 is 1.028.

Radial Dose Function:

Radial dose function was taken at 0.1 cm to 10 cm at 0.1 intervals to 1 cm and then a 0.5 cm interval to 10 cm. The figures for Radial functions can be compared and it shows superposition of the data points confirming good agreement between the measured value for Best Model and the book value. The radial function from the two brachytherapy seeds is further compared to the measured values and book values of the Best Model seed and again a good agreement is seen in the results. This is true for both the liquid water and solid water measurements. The data is fitted with a 5th order polynomial function.

Anisotropy Function

Anisotropy Function was calculated for all the three seeds in both Liquid and Solid Water. The function was calculated from 1 cm to 7 cm in 1 cm increments at 0°-90° at 10° increments. Similar to comparisons in the radial function, anisotropy function data points were superimposed confirming good agreement between the measured value for Best Model and the book value. The anisotropy function from the two brachytherapy seeds is further compared to the measured values and book values of the Best Model seed and again a good agreement is seen in the results. This is true for both the liquid water and solid water measurements. The data is fitted with a 6th order polynomial function. In liquid water, the Source Anisotropy Constant for Best Model 2301 Seed is 0.935, thermobrachytherapy seed#1 is 0.923 and thermobrachytherapy seed#2 is 0.927.

For the Best Model 2301, the value deviates by 4.6% from the Book value. The values for thermobrachytherapy seed#1 deviates from the Monte Carlo calculated Best Model 2301 $^{125}$I Seed by 1.28% and the Book value by 4.6%. Thermobrachytherapy seed#2 deviates from the Monte Carlo calculated Best Model 2301 $^{125}$I Seed by 0.8% and the Book value by 5.4%.

In analyzing the above results, it is to be noted that thermobrachytherapy seed#1 is closer to the Book value but thermobrachytherapy seed#2 is closer to the Monte Carlo calculated value for the Best Model 2301 seed in liquid water. In solid water, the Source Anisotropy Constant for Monte Carlo calculated Best Model 2301 Seed is 0.926. Thermobrachytherapy seed#1 has a value of 0.918 and thermobrachytherapy seed#2 has a value of 0.923. In terms of deviation, the Monte Carlo calculated Best Model seed deviates 4.5% from the book value for the same seed. Thermobrachytherapy seed#1 deviates from the Monte Carlo calculated Best Model 2301 251 Seed by 0.08% and the Book value by 5.4%. Thermobrachytherapy seed#2 deviates from the Monte Carlo calculated Best Model 2301 $^{125}$I Seed by 0.3% and the Book value by 4.8%. It can be deciphered from the above results that, unlike the liquid water results, Thermobrachytherapy seed#1 is closer to the calculated Best Model 2301 seed values and thermobrachytherapy seed#2 is closer to the Book Values.

Conclusions

The thermobrachytherapy seeds described herein exhibit a desired synergy between radiation and heat. The thermobrachytherapy seeds provide complementary treatment modalities, with brachytherapy killing oxygenated cells and hyperthermia killing hypoxic cells.

The thermobrachytherapy seeds have a ferromagnetic component along with the radioactive source to give concurrent treatments.

Two different thermobrachytherapy seeds were modeled with a Ni (70.4%)-Cu (29.6%) ferromagnetic alloy. This alloy has a curie temperature of 48.2° C. and is appropriate around 50° C. Curie temperature (which is preferable for killing cancer cells and not overheating normal cells). The Ni—Cu alloy has a density of 8.92 g/cm$^3$ and is denser than bone. Therefore, it will be seen on films taken at kilo-voltage beams.

Thermobrachytherapy seed#1 has the radio-opaque Tungsten marker replaced by the nice alloy. Thermobrachytherapy seed#2 has the radio-opaque marker divided into three equal sections with one Tungsten marker in the middle and two outer Ni—Cu alloy sections. The results that are obtained are compared to both the Book values in the literature (Best Model 2301 $^{125}$I Seed) and measured Best Model 2301 $^{125}$I Seed, thus showing a two-fold comparison on how the thermobrachytherapy seeds can be favorably compared to Book values for radioactive seeds and also, to the measured values of the same seed.

When running the TG-43 factors in liquid water, the dose rate constant calculated for the Best model is 1.056±0.0055 Gy*h$^{-1}$*U$^{-1}$ (Book value of 1.01: with a percentage difference of 4.6%).

Furthermore, the Dose Rate constant obtained for thermobrachytherapy Seed#1 (1.057±0.031 cGy*h$^{-1}$U$^{-1}$) varies by 0.091% from the measured Best Model value and by 4.69% from Best Model book value. Continuing the comparison, the value obtained for thermobrachytherapy Seed#2 (1.058±0.031 cGy*h$^{-1}$U$^{-1}$) varies by 0.15% from the measured Best Model value and by 4.75% from Best Model book value. The Solid Water measurements mirrored good agreement like in liquid water, the dose rate constant calculated for the Best model is 1.03±0.031 cGy*h$^{-1}$*U$^{-1}$ (Book value of 0.98: with a percentage difference of 5.1%). The value measured for thermobrachytherapy seed#1 1.03±0.031 cGy*h$^{-1}$U$^{-1}$ and thermobrachytherapy seeds#2 is 1.029±0.031 cGy*h$^{-1}$*U$^{-1}$.

The value obtained for thermobrachytherapy Seed#1 varies by 0.01% from the measured Best Model value and by 5.1% from Best Model book value. The value obtained for thermobrachytherapy Seed#2 varies by 0.09% from the measured Best Model value and by 4.97% from Best Model book value.

The Correction/Multiplicative Factor (conversion of dose rate constant) between the Solid Water and liquid water measurements for the calculated Best Model 2301 $^{125}$I seed is 1.026 (Book Value of 1.05). Thermobrachytherapy Seed#1 has a factor of 1.026 and Thermobrachytherapy Seed#2 is 1.028, which are in shows close agreement for both seeds.

The Radial Dose functions from the two thermobrachytherapy seeds are further compared to the measured values and book values of the Best Model seed and again a good agreement is seen in the results. This is evident in both liquid and Solid Water. Similar to comparisons in the radial function, anisotropy function data points were superimposed confirming good agreement between the measured value for Best Model and the book value. This extends to the data points for the thermobrachytherapy seeds #1 and #2 and the comparisons with the Best Model Seed (both measured and book values).

In liquid water, the Anisotropy Source Constant for Best Model Seed is 0.935 (deviates by 4.6% from the Book value), thermobrachytherapy seed#1 is 0.923 (deviates from calculated Best Model 2301 $^{125}$I Seed by 1.28% book value by 4.6%) and thermobrachytherapy seed#2 is 0.927 (deviates from calculated Best Model 2301 $^{125}$I Seed by 0.8% book value by 5.4%).

In solid water, the Anisotropy Source Constant for Best Model Seed is 0.926 (deviates by 4.5% from the Book value), thermobrachytherapy seed#1 is 0.918 (deviates from calculated Best Model 2301 125$_I$ Seed by 0.08% book value by 5.4%) and thermobrachytherapy seed#2 is 0.923 (deviates from calculated Best Model 2301 $^{125}$I Seed by 0.3% book value by 4.8%).

The Anisotropy Source Constant is in good agreement for the two brachytherapy seeds #1 and #2 with both the Book value and measured value for the Best Model 2301 $^{125}$I Seed. This is true for both liquid and Solid Water data.

Analyzing the data, there is very little difference between thermobrachytherapy seed#1 and thermobrachytherapy seed#2 in comparison to one another. The data between the two thermobrachytherapy seeds is very comparable. Also, the results are quite similar, in terms of error percentage, between the Book values and measured value for the Best Model 2301 $^{125}$I Seed. It is also important to note that the thermobrachytherapy seed's TG-43 factors have not deviated too much from the established data on the Best Model Seed. This ensures that the radio-activity from the thermobrachytherapy seed is still established and there is no loss of activity around the thermobrachytherapy seed.

PRIOR ART FIG. 79 is a schematic top plan view of a Prior Art flat plate where a middle of the plate has a fairly larger temperature profile than the temperature profile of the peripheral areas of the plate. When such plate is used, however, the hyperthermia treatment can only be started during the last hour of brachytherapy. Referring now to FIG. 80, there is shown a schematic illustration of an embodiment where a dual-seed system 10 has an inner section 12 that is made of one or more magnetic materials. One non-limiting example of a magnetic material is Ni—Co, which is a ferromagnetic material with a curie temperature of 48.2° C. The dual-seed system 10 has at least one outer layer 14. The outer layer can be comprised on a material that is compatible with the human body. Non-limiting examples include that platinum, platinum alloys, or platinum-like materials.

Example II

A practical means of delivering both therapeutic radiation and hyperthermia to a deep-seated target has been identified as highly desirable, provided it is capable of generating sufficient temperatures over the defined planning target volume. Provided herein is a dual-modality thermo-brachytherapy (TB) seed having the capability to deliver prescribed hyperthermia to realistic deep-seated targets.

The anatomies (including the thermophysical properties of the main tissue types) and seed distributions of 6 prostate patients who had been treated with LDR brachytherapy seeds were modeled in the finite element analysis software COMSOL, using ferrite-based TB and additional hyperthermia-only (HT-only) seeds. The resulting temperature distributions were compared to those computed for patient-specific seed distributions, but in uniform anatomy with a constant blood perfusion rate. The ISA effect was quantified in the Monte Carol software package MCNP5.

Compared with temperature distributions calculated in the modeled uniform tissue, temperature distributions in the patient-specific anatomy were higher and more heterogeneous. Moreover, the maximum temperature to the rectal wall was typically 1.2° C. greater for patient-specific anatomy than for uniform anatomy. The ISA effect of the TB and HT-only seeds caused a reduction in D90 similar to that found for previously investigated NiCu-based seeds, but of a slightly smaller magnitude.

The differences between temperature distributions computed for uniform and patient-specific anatomy for ferrite-based seeds are significant enough that heterogeneous anatomy should be considered. Both types of modeling indicate that ferrite-based seeds provide sufficiently high and uniform hyperthermia to the prostate, without excessively heating surrounding tissues. The ISA effect of these seeds is slightly less than that for the NiCu-based seeds.

The TB seed in this Example is based on the ubiquitous low dose-rate (LDR) brachytherapy permanent implant. Heat is generated by incorporating a ferromagnetic core within the seed and placing the patient in an oscillating external magnetic field, producing eddy currents within the core and hence Joule heating. A strategically-selected Curie temperature results in thermal self-regulation. The magnetic and thermal properties of the TB seed were studied experimentally by means of seeds placed in a tissue-mimicking phantom and heated with an industrial induction heater, as well as computationally in the finite element analysis (FEA) solver COMSOL Multiphysics. Realistic patient-specific seed distributions derived from LDR permanent prostate implants previously conducted at our institution were simulated in COMSOL to evaluate their ability to adequately cover a defined target volume and to overcome the loss of heat due to blood perfusion within the target. The calculated temperature distributions were analyzed by generating temperature-volume histograms, which were used to quantify coverage and temperature homogeneity for varied blood perfusion rates, seed Curie temperatures and thermal power production rates. Use of additional hyperthermia-only (HT-only) seeds in unused spots within the implantation needles was investigated, as was an increase in these seeds' core size to increase their power. The impact of the interseed attenuation and scatter (ISA) effect on radiation dose distributions of this seed was also quantified by Monte Carlo studies in the software package Monte Carlo N-Particle Version 5 (MCNP5).

The results show that increasing the power production of the seeds, as well as increasing their Curie point, increase the maximum blood perfusion rate that a given seed distribution can overcome to obtain an acceptable temperature distribution. However, this also increases the maximum temperatures generated at the seed surfaces. Auxiliary HT-only seeds serve to improve the temperature uniformity within the target, as well as decrease the seed power generation requirements. Both an increase in their core size and an increase in both seed types' Curie temperatures enhance the resulting temperature coverage. The interseed and scatter effect caused by both the TB and HT-only seeds was found to reduce the dose to 90% of the target volume ($D_{90}$) by a factor of 1.10±0.02.

A systematic approach of combining LDR prostate brachytherapy with hyperthermia is described in this Example, and its ability to provide sufficient and uniform temperature distributions in realistic patient-specific implants was evaluated. TB and HT-only seeds may be used to produce a uniform temperature distribution in a defined target, and various modeled changes to their design, such as optimization of their Curie temperature, improve their ability to overcome the thermal effects of blood perfusion. The enhanced radiation interseed effect of the TB and HT-only seeds should be taken into account for dose calculations, but is manageable.

Introduction

Hyperthermia, typically defined as temporarily raising the temperature of tissues to between 41° C. and 46° C., is a well-developed modality of cancer therapy, and has been shown to be a highly attractive adjuvant to radiation therapy. This is due to its synergistic relationship with radiation therapy, in which direct killing or weakening cells during hyperthermia sessions occur along with transient enhancement of sensitivity to radiation. The latter effect, known as hyperthermia-induced radiosensitivity, is believed to be the result of a number of biochemical and physiological effects, including that of reoxygenation of tissues in a hypoxic state.

Despite technological and clinical improvements in the use of hyperthermia with radiation therapy, as well as demonstrated radiobiological advantages over radiation therapy alone and improvements in local control and patient outcome, it remains technically difficult to deliver an adequate hyperthermia treatment to targets far from a body orifice or the body surface. Consequently, technical improvements in the ability of hyperthermia to heat a defined target volume deep within the body are warranted.

Hyperthermia to deep-seated targets may be accomplished by external, intraluminal, or intracavitary sources of energy, or by interstitial hyperthermia, in which implanted sources distributed within the target deposit thermal energy. To be successful, sources used in interstitial hyperthermia should be placed closely together and cover the entire target; failure to do this has been seen to result in suboptimal treatment, and often, local failure. In one analysis of a Phase III study of interstitial hyperthermia delivery combined with external beam radiation therapy, the implants frequently did not completely cover the defined planning target volume (PTV) and were spaced too far apart to achieve sufficiently high temperatures in between implants. The analysis indicates that only one of the 86 patients randomized to the radiation plus hyperthermia arm fulfilled their criteria for an adequate hyperthermia treatment. As the drop-off of tissue temperature rise over normal body temperature from the surface of such an implant is very fast, separation distances between heat sources of 1 cm or less are recommended, but are often difficult to achieve in practice.

The ubiquitous low dose-rate (LDR) permanent prostate implant treatment is an ideal framework for depositing numerous small implants throughout the human prostate gland. By making each radiation source also an interstitial magnetic hyperthermia source, and by placing additional small hyperthermia-only (HT-only) seeds, a high hyperthermia implant density may be achieved. Moreover, concurrent delivery of both modalities offered in our approach permits maximum hyperthermia-induced radiosensitivity. This is in contrast to previously-applied methods of simultaneously combining brachytherapy with interstitial hyperthermia, which required use of separate sources for each of the two modalities. This Example describes a thermo-brachytherapy (TB) seed, aided by additional HT-only seeds, as a means of adding hyperthermia to LDR prostate implant treatments without the need for adding another implant procedure or additional implantation needles.

Computational and experimental studies of the thermal properties of the TB seed, and the effects of various modifications to it, were conducted. A combination of TB and HT-only was evaluated for the radiation interseed and scatter effect, which should be somewhat higher than that of a standard LDR seed implant. Comparisons between the results of phantom experiments with seeds and computational studies are made, and the ability of realistic patient-specific distributions of the seeds to provide sufficient temperature coverage to defined PTVs is evaluated.

Materials and Methods

Description of the Thermo-Brachytherapy Seed

Figure 81:
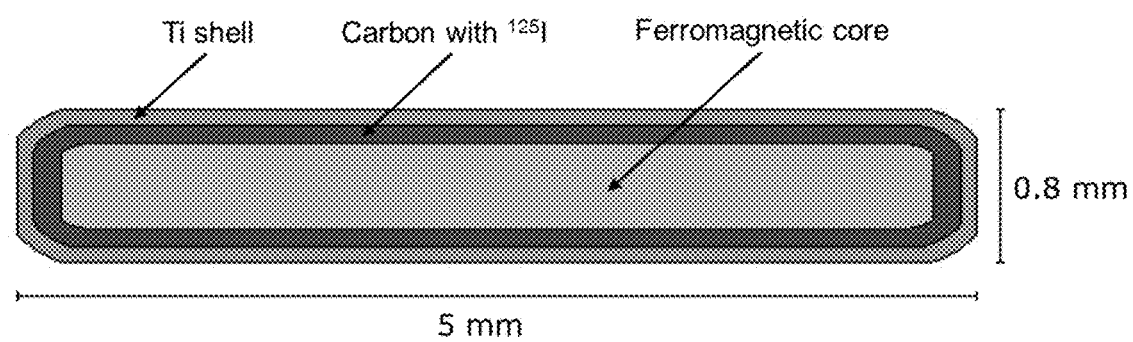
FIG. 81 is a Monte Carlo model of the TB seed described in Example II herein, which is a BEST Medical Model 2301 LDR seed modified as described in Example II.

The TB seed consisted of a LDR prostate permanent brachytherapy seed, the BEST Medical Model 2301 modified such that the tungsten radiographic marker was replaced with a ferromagnetic alloy. (FIG. 81.) This alloy, such as NiCu in the current Example, produces heat by the production of eddy currents when placed in an oscillating magnetic field; these eddy currents generate heat by resistive heating of the alloy. The NiCu core in this Example was larger than the tungsten marker in the BEST 2301 seed, both to maximize power generation and to permit good thermal contact with the titanium capsule. It has been demonstrated that there is no loss in visibility of the TB seed in kilovoltage x-ray images as a result of this change to the core. The second-order transition of the alloy from a ferromagnetic state to a paramagnetic state near a particular temperature, defined as the Curie temperature $T_C$, greatly decreases its magnetization and consequently the magnitude of the eddy currents and power generated within it. Conceptually, this transition is the result of alignment of magnetic spins in a magnetic domain being lost due to thermal motion. Mathematically, $T_C$ may be defined as the point of maximum gradient (zero second derivative) of the magnetic permeability with temperature.

Figure 82:
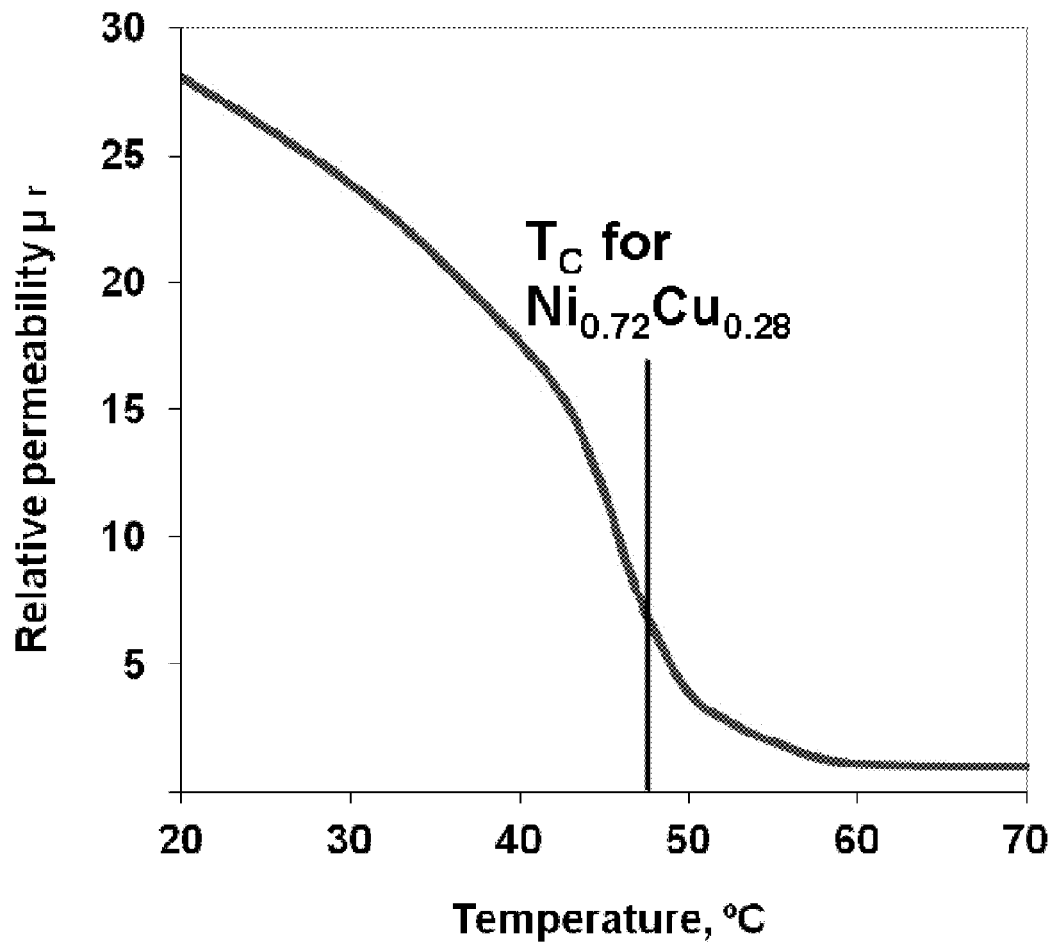
FIG. 82 illustrates magnetic relative permeability for a particular NiCu alloy as a function of temperature.

The permeability data in PRIOR ART FIG. 82 is for a NiCu alloy with a $T_C$ of ~48.8° C., determined by the second-derivative method. Strategic selection of $T_C$, which is determined primarily by the composition of the alloy, permits thermal self-regulation, in which the implants produce less and less heat as they approach and exceed this temperature. The tissue-implant system eventually reaches a point of equilibrium in which heat generated by the seeds equals heat absorbed by the surrounding tissue and the blood perfusing the heated region.

In addition to this TB seed, a variant that contains no radioactive material and produces only hyperthermia was evaluated. This hyperthermia-only (HT-only) seed differed from the TB seed in that the radioactive material was omitted. Two versions of the HT-only seed were evaluated: one that had a core of the same size as that of the TB seed and a non-radioactive carbon layer, and the other whose core size was increased to occupy the entire interior of the titanium shell.

Outline of Study

Figure 83:
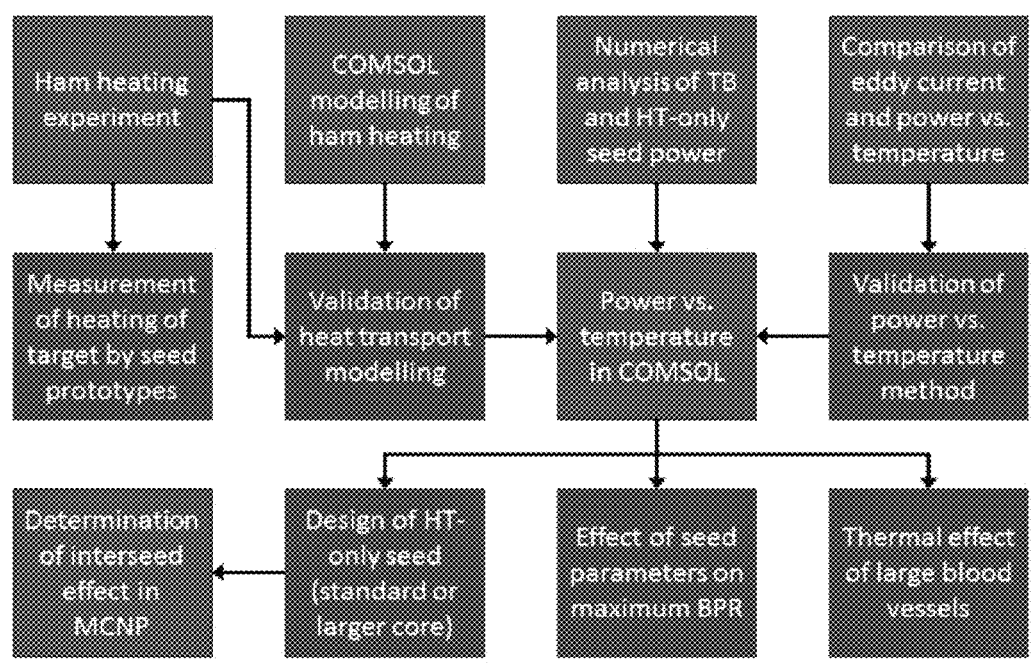
FIG. 83 is a visual representation of the frame of the evaluation described in Example II herein. Blue items indicate computational or experimental studies, and red items indicate their results, which were used to inform subsequent experiments.

This Example involved both experimental and computational parts. (FIG. 83.) First, seed-sized pieces of NiCu alloy (seeds) were experimentally studied for their performance in heating a defined area in a small ex vivo tissue-mimicking phantom, referred to as the "ham phantom" in this Example. In addition to providing a measurement of seed heating performance, the data from this experiment were used to validate thermal modeling in a finite element analysis (FEA) solver. The accuracy of the application of the so-called "temperature-dependent power modeling" approximation of ferromagnetic seed thermal properties was ensured by comparison with the previously-used method of eddy current calculation; both modeling methods were used to calculate temperature distributions surrounding a TB seed in the so-called "single-seed phantom." Next, dependencies for seed power as a function of temperature for both TB and HT-only seeds were generated numerically from first principles, and imported into the FEA solver. Patient-specific TB and HT-only seed distributions were modeled in the FEA solver, to analyze the effects of use of one or the other design of HT-only seed described above, to quantify the effects of the blood perfusion rate, to study the results of changes to the physical parameters of the TB and HT-only seeds, and to study the thermal effects of large discrete blood vessels. For all thermal modeling of patient-specific seed distributions, a generalized phantom with the thermophysical properties of tissue was used, the "patient phantom" described in this Example. Finally, the impact of the interseed effect on patient-specific distributions of TB and HT-only seeds was analyzed by modeling in a Monte Carlo software package.

Experimental Analysis of Seeds

Figure 84:
FIG. 84 is a photograph of the seed-implanted tissue-mimicking phantom within the coils of the induction heater. The coil is 6 cm in diameter. The yellow cable in the lower left of the image is the fiber optic thermometer cable.

The ability of TB seed-sized pieces of ferromagnetic material to heat a defined ex vivo tissue target was first experimentally studied. Pieces of NiCu alloy needles, 29.6% copper by mass, of length 5.5 cm, and diameter 0.9 mm, were cut into 5 mm-long pieces and implanted into 4.3 cm diameter, 1.5 cm thick cylindrical ham slices. These ham slices acted as tissue-mimicking phantoms, having approximately the thermophysical properties of human tissue. Sixteen of these implants were placed in each ham slice in a 4×4 arrangement with their axes perpendicular to the ham surface by means of a LDR prostate brachytherapy needle and obturator, such that the seed-to-seed distance along one axis was 0.9 cm. Each of these seed-implanted phantoms was placed within the 6 cm-diameter coils of a 10 kW industrial induction heater (Across International Model IHG10), which provided a 164 kHz oscillating magnetic field of amplitude 23.0 kA/m, bringing the seeds to a high temperature. (FIG. 84.) The coil was hollow to permit cooling via cold water continuously run through it. While these magnetic field parameters are too high for safe use of hyperthermia in the human pelvis, with its relatively large cross-sectional area, they were appropriate for this experiment, aiming at the validation of the numerical heat transport calculations. For the low implantation density of 16 seeds in the 22 $cm^3$ ham phantom, these parameters were required to reach hyperthermia-range temperatures throughout the phantom volume.

Data on the temperature of the seeds and ham were obtained during the experiment with a GaAs fiber optic thermometer (Omega Engineering HHTFO-101) and a microbolometer-based infrared camera (Fluke Ti100 thermal imager). The fiber optic thermometer probe was placed in the center of the phantom, at the depth of the implants. The probe contained no metal components near the point of measurement, and therefore did not generate heat when placed inside the coil.

While maximum temperatures were nearly reached after 10 minutes of heating, the phantom continued to be heated until the temperature distribution in the ham had reached equilibrium (which had occurred after approximately 30 minutes). At 40 minutes from the start of heating, a final surface temperature distribution was taken with the thermal camera, and the induction heater shut off.

Measurement of Magnetic Field Parameters of the Induction Heater

The amplitude and frequency of the magnetic field of the induction heater coil, as well as two other interchangeable coils, were measured by means of a loop probe (Beehive Electronics Model 100A magnetic field probe) used with an oscilloscope (Instek GDS-1052-U). The coils studied were of diameter 5 cm, 15 cm, and 25 cm, comprising 6 loops, 4 loops, and 2 loops, respectively. (The 5 cm-diameter coil had been used for the ham heating experiment.) The frequency was measured to be 164 kHz with the 5 cm coil, 122 kHz with the 15 cm coil, and 139 kHz with the 25 cm coil. These values did not vary with the current setting on the heater.

Figure 96:
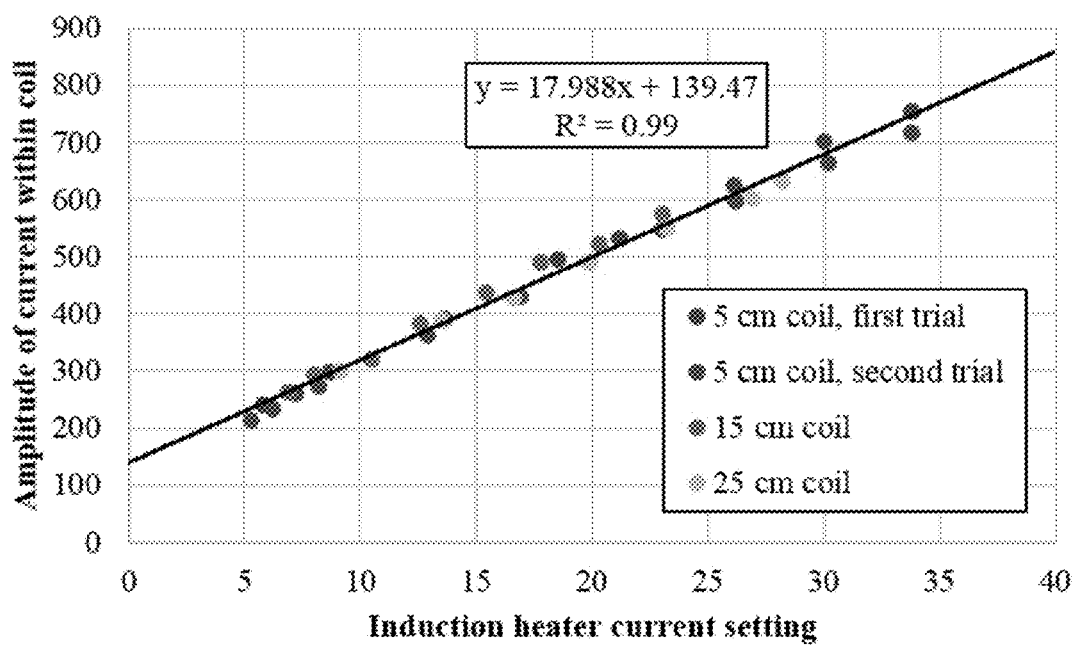
FIG. 96 shows the amplitude of calculated current in amperes within the induction heater coils as a function of current setting of the induction heater.

The radius of the loop was measured in the kV image to be 4.74 mm, and the voltage amplitude among the measurements for the three coils ranged from 7.4 mV to 135 mV at the measured locations. Application of the manufacturer's empirical equation leads to magnetic field amplitude measurements that deviates from those calculated from first principles by 8%. As shown in FIG. 96, the calculated amplitude of the current in the coils was found to have a linear relationship with the current setting of the induction heater:

$$I_{coil} = (18.0 \times I_{set}) + 140 \tag{18}$$

Here, $I_{coil}$ is the amplitude of the AC current within the loop in amperes, and $I_{set}$ is the current setting of the induction heater.

Figure 97:
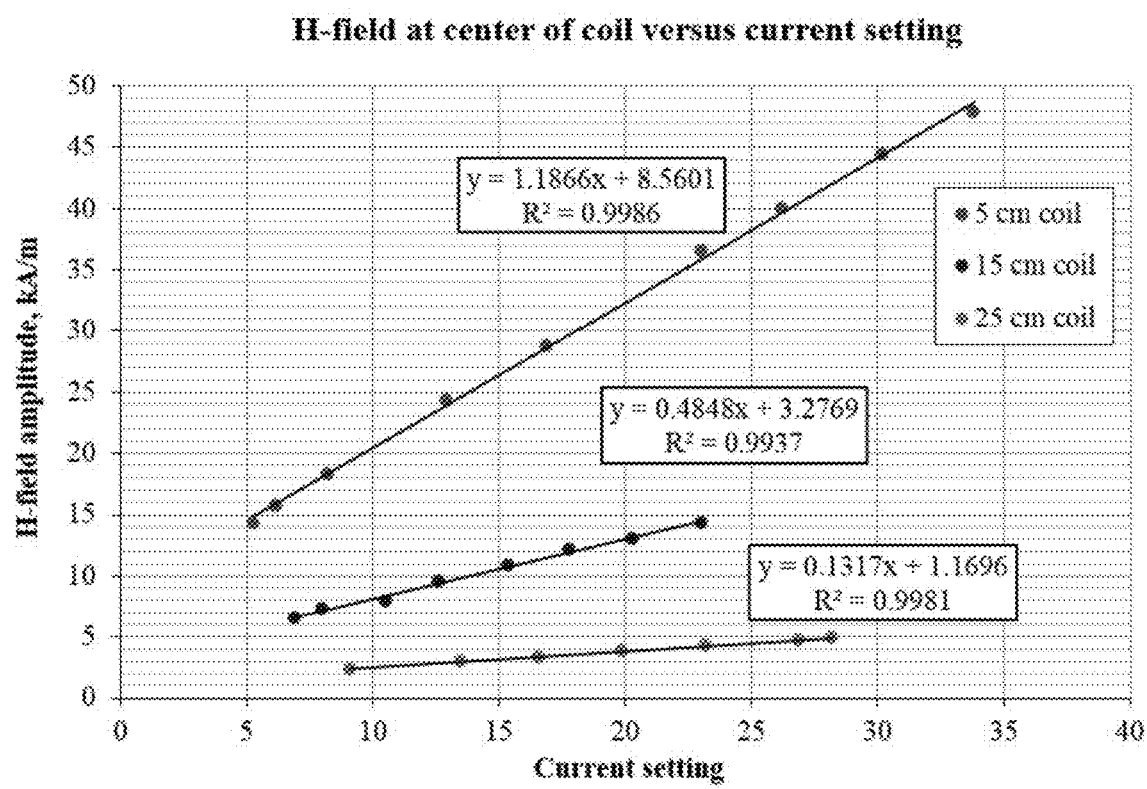
FIG. 97 shows the amplitude of the magnetic field at the center of each of the induction heater coils as a function of current setting.

FIG. 97 depicts the calculated magnetic field amplitudes for each of the three coils as a function of current setting. During the ham heating experiment, the displayed current reading of the induction heater was "12.15," indicating that the ham and implant were exposed had an approximate amplitude of 23.0 kA/m, at the aforementioned 164 kHz frequency. Note that the 25 cm-diameter coil produced magnetic fields of the appropriate parameters for magnetic hyperthermia of the pelvis.

The loop probe was placed a known distance (12.5 to 34.0 cm) above the center of each coil, oriented to be perpendicular to the direction of the magnetic field. The frequency of the magnetic field was determined directly by observing the trace of the induced EMF on the oscilloscope screen, and the amplitude of the EMF as used to determine the amplitude of the magnetic field at that point. A simple application of the Biot-Savart law on the geometry of the experimental setup, modeling each induction coil as a series of circular current-carrying loops, permitted a derivation of current within each coil, which was in turn used to obtain the magnetic field amplitude at the center of the coil.

The EMF produced across the leads of the loop probe was used to obtain the magnitude of the magnetic field by means of an empirical equation provided by the probe's manufacturer. The equation was verified from first principles by application of Faraday's Law (the magnitude of the amplitude of induced EMF by a single loop is equal to the rate of change of the magnetic flux in the loop), as a check of the magnetic field amplitude returned by the equation.

Validation of Thermal Modeling by Experimental Results

This experimental setup of the ham phantom, with the same dimensions described above, was reproduced in the finite element analysis (FEA) program COMSOL Multiphysics version 4.4, in order to validate the modeling of heat transport from TB seed-sized samples. Modeling and calculations in COMSOL were carried out on a workstation with four 3.6 GHz CPU cores, 60 gigabytes of RAM, and three 1 terabyte hard drives. The "Heat Transfer in Solids" physics modeling in COMSOL was used with a time-dependent study, containing subnodes for surface-to-ambient radiative cooling and convective cooling. Heat flux lost by thermal radiation $q_{ra}$ was included in the model, applied to the external surfaces of the ham phantom:

$$q_{ra} = \epsilon\sigma(T_{hot}^4 - T_{amb}^4) \tag{19}$$

where $\epsilon$ is the emissivity of the surface, a is the Stefan-Boltzmann constant, $T_{hot}$ is the surface temperature, and $T_{amb}$ is the ambient temperature (set to room temperature measured at the time of the experiment). Emissivity $\epsilon$ was set to 0.98, as this value has been measured for tissue. Similarly, a term for heat flux lost to convective cooling by the surrounding air $q_{cc}$ was estimated:

$$q_{cc} = h\Delta T \tag{20}$$

where $\Delta T$ is the temperature difference between the ham surface and room temperature, and the heat transfer coefficient h estimated by the simplified dimensional formula for natural convection of air over a flat surface:

$$h \approx C\left(a\frac{\Delta T}{L}\right)^n \tag{21}$$

where L is the length or diameter of the surface in question, a is a constant of 1 m/K to make the base of the exponent dimensionless, and C and n are empirical constants. Provided ΔT is given in kelvin and L is given in meters, h is in units of W/(m²K). C is approximately 1.42, 1.32, and 0.59 W/(m²K) for a vertical surface, a horizontal surface on the top side of the heated object, and a horizontal surface on the bottom of the heated object, respectively. The constant n is dimensionless, of value 0.25. $q_{cc}$ was calculated in this way for each of the surfaces of the ham phantom, averaged over the entire surface area, and entered into the COMSOL model.

Transient conductive heat transport was modeled within the ham phantom:

$$\rho C_P \frac{\partial T}{\partial t} + \nabla \cdot (-k\nabla T) = Q \quad (22)$$

Here, ρ is the density of the medium, $C_P$ is its heat capacity at constant pressure, k is its thermal conductivity, and Q is the thermal power density. Values for the thermal conductivity and heat capacity of ham within the range of published values were used (Table 51). For this initial study, a constant-temperature approximation was used for the seeds. To do this, Q was set to zero, implying no explicit modeling of thermal power generation within the seeds. Instead, one additional boundary condition added in that the surface temperature of the seeds was set to a constant value. This was determined separately by observing the rate of temperature drop-off from the surface of a single seed. (The resolution of the infrared camera was insufficient in directly measuring the temperature of the seeds.)

Figure 85:
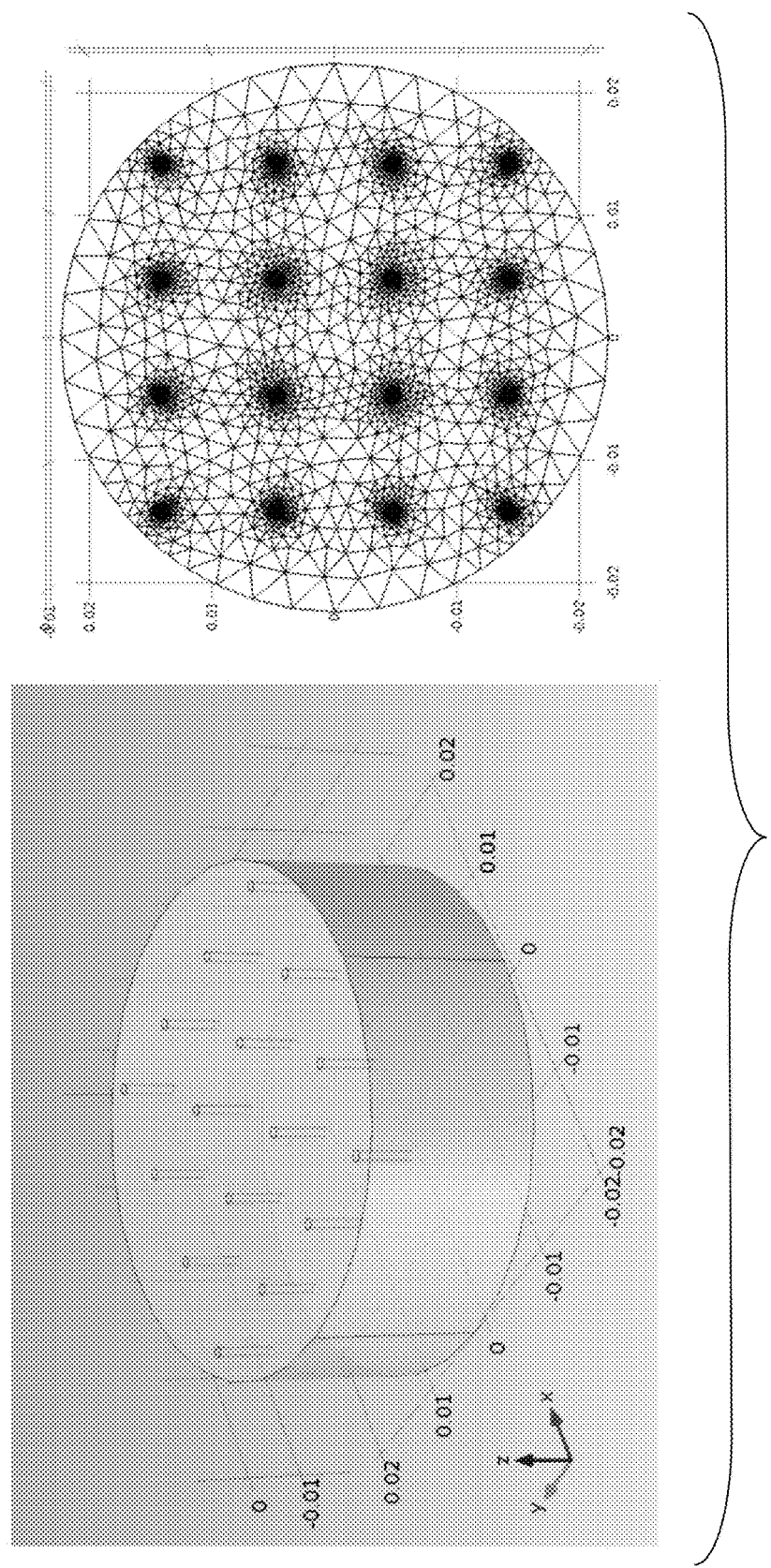
FIG. 85 illustrates the overall geometry (left) and plot of calculation mesh (right) used for FEA study of the ham slice. The unit on all the axes is meters.

In summary, transient heat conduction as per Equation 4 was modeled throughout the domain of the problem corresponding to the ham slice. The boundary conditions of the temperature-dependent heat flux terms $q_{ra}+q_{cc}$ (Equations 19 and 20) on the ham surfaces and of constant temperature on the seed surfaces were applied.

elements. (FIG. 85.) The average mesh density was $1.7\times10^{10}$ elements/m³ within the tissue-mimicking phantom, and $2.9\times 10^{12}$ elements/m³ within the seeds.

Temperature as a function of time and the surface temperature distribution after 40 minutes of heating were calculated in COMSOL. Comparisons between the calculated and experimentally-measured surface temperature distributions were made via gamma analysis, using temperature rise above room temperature rather than dose. This was done by a modified form of the frequently-used gamma analysis equation:

$$\Gamma(r_m, r_c) \equiv \sqrt{\frac{|r_c - r_m|^2}{\Delta d_m^2} + \frac{[T_c(r_c) - T_m(r_m)]^2}{\Delta T_m^2}} \quad (23)$$

Here, $r_m$ and $r_c$ are the position vectors of points within measured and calculated temperature distributions, respectively, and $T_m(r_m)$ and $T_c(r_c)$ are the temperatures measured and calculated at those positions, respectively. $\Delta d_m^2$ is the distance-to-agreement criterion, $\Delta T_m^2$ is the temperature difference criterion, and $\Gamma(r_m, r_c)$ is a function for the surface of acceptance (an ellipsoid in the space of the position vectors in two spatial dimensions and temperature in the third, non-spatial dimension) of $r_m$ and $r_c$. Provided that for a point $r_m$ in the measured temperature distribution there is also some point $r_c$ in the calculated distribution that fulfills $\Gamma(r_m, r_c) \le 1$, that point meets the acceptance criterion. Note that in the above equation, an absolute temperature comparison is made with respect to an absolute temperature criterion (in degrees Celsius). Gamma analysis was performed for comparison of corresponding halves of the experimentally-obtained and COMSOL-computed temperature distributions within the central seed-implanted region, using the experimental

TABLE 51

Physical parameters used for materials modeled in COMSOL

| Parameter | NiCu | Graphite | Titanium | Ham | Water | Prostate tissue | Adipose tissue | Blood |
|---|---|---|---|---|---|---|---|---|
| Density, g/cm³ | 8.90 | 2.667 | 4.54 | 1.016 | 1 | 1.045 | 0.911 | 1.060 |
| Heat capacity, J/kg · K | 440 | 709 | 531 | 3120 | 4200 | 3760 | 2348 | 3400 |
| Thermal conductivity, W/m · K | 26.0 | 140 | 15.12 | 0.50 | 0.6 | 0.51 | 0.21 | N/A |
| Electrical conductivity, S/m | $2.57 \times 10^6$ | $3.00 \times 10^3$ | $5.62 \times 10^5$ | N/A | 0.1 | N/A | N/A | N/A |

The algorithm for generating the time-dependent solver in COMSOL automatically selected an iterative solution algorithm, the program's embodiment of the generalized minimal residual (GMRES) method. The problem was set to terminate and report the results once the criterion of the absolute tolerance of 0.001 of the solved variable (temperature) had been met or exceeded. A maximum of $10^4$ iterations was allowed to meet or exceed this goal.

The only modeled initial condition was the starting temperature of the ham phantom, set to the initial temperature of the interior of the ham measured by the fiber optic thermometer at the start of the experiment. The geometry of the model, comprising the ham slice and implanted array of seeds, was subdivided into a mesh of $5\times10^5$ tetrahedral data from the infrared camera as the measured dataset and the COMSOL data as the calculated dataset.

Computational Evaluation of Irradiated and Heated Volumes

In order to assure the efficacy of the TB seed as a source of both radiation and heat, computational evaluations of volumetric dose coverage were conducted for both modalities. A portion of a modeled 15 cm-diameter cylindrical water phantom, with no blood perfusion or convection, was considered to be irradiated to a prescription radiation dose and heated to the temperature range of induction of radio-sensitivity for two- and three-dimensional implantation patterns of TB seeds. For the two-dimensional case, a 4×4 array of TB seeds was placed in the center of the phantom, with the axes of the seeds perpendicular to the implantation plane and a separation distance of 1 cm along an axis between centers of neighboring seeds. The three-dimensional array of TB seeds consisted of three parallel layers of 4×4 two-dimensional arrays of seeds, placed 1 cm apart. A planning target volume (PTV) was defined as a right rectangular prism 0.5 cm from the centers of seeds along the edges of the implant.

Temperature distributions reached in a cylindrical water phantom were obtained via COMSOL 3.5 using similar modeling parameters used in the ham slice model, this time also using subnodes from the "Magnetic Fields" physics modeling (AC/DC module). The modeling of magnetic fields and heat generation was coupled such that calculated eddy current density dictated heat generation within the seed cores, and the resulting temperature of the cores changed their magnetic relative permeability. A mesh of ~$10^8$ tetrahedral elements was used for each model, and the unsymmetric-pattern multifrontal method (UMFPACK) solver in COMSOL was used. The corresponding radiation dose distributions for the same seed arrangements were calculated by the Monte Carlo software package Monte Carlo N-Particle Version 5 (MCNP5). For the two-dimensional case, the computed dose values were normalized so that the average dose 0.5 cm from the edge of the implant was considered to be 100% of a "prescription" dose. The resulting radiation distribution was compared with the temperature distribution from COMSOL, the magnetic field strength at the center of the implant having been adjusted for a particular magnetic field frequency until the 42° C. isothermal line corresponded with the 100% radiation isodose line.

For the case of three parallel layers of seeds, a three-dimensional grid of tallies was defined filling the previously-described PTV, and their values normalized such that the 100% isodose line covered 90% of the volume of the PTV. The tallies were then tabulated to yield a cumulative DVH of radiation dose within the PTV. A temperature volume histogram was calculated from COMSOL data by finding the volume of isothermal lines surrounding the implant, and subtracting the volume of any part of the isothermal line that extended beyond the PTV. These histograms were compared to evaluate the correspondence between the volumes radiosensitized to hyperthermia and exposed to doses near the prescribed dose.

Figure 98:
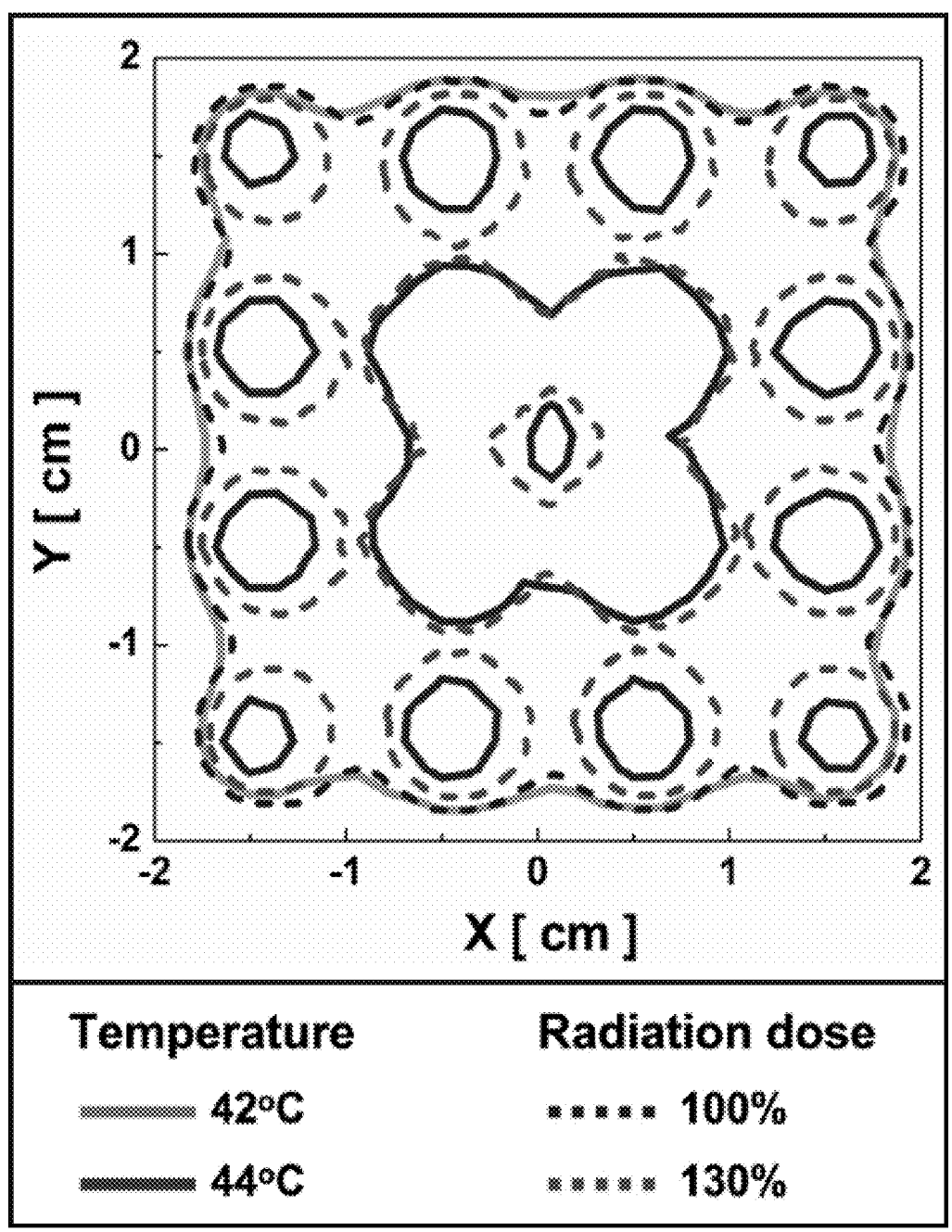
FIG. 98 shows a spatial comparison of the radiation and thermal dose distributions for a two-dimensional 4×4 array of thermo-brachytherapy seeds, spaced 1 cm between seed centers. The solid lines represent the thermal data and the dotted lines represent radiation isodose lines.

A qualitative comparison of the radiation and thermal dose distributions for the two-dimensional case reveals that when the 42° C. isothermal line is made to correspond with the 100% radiation isodose line by adjusting the magnetic field strength for a particular field frequency (125 kHz), the area heated above 44° C. receives approximately 130% or more of the prescription radiation dose (FIG. 98 with solid and dashed lines corresponding to radiation and thermal isodoses, respectively).

Figure 99:
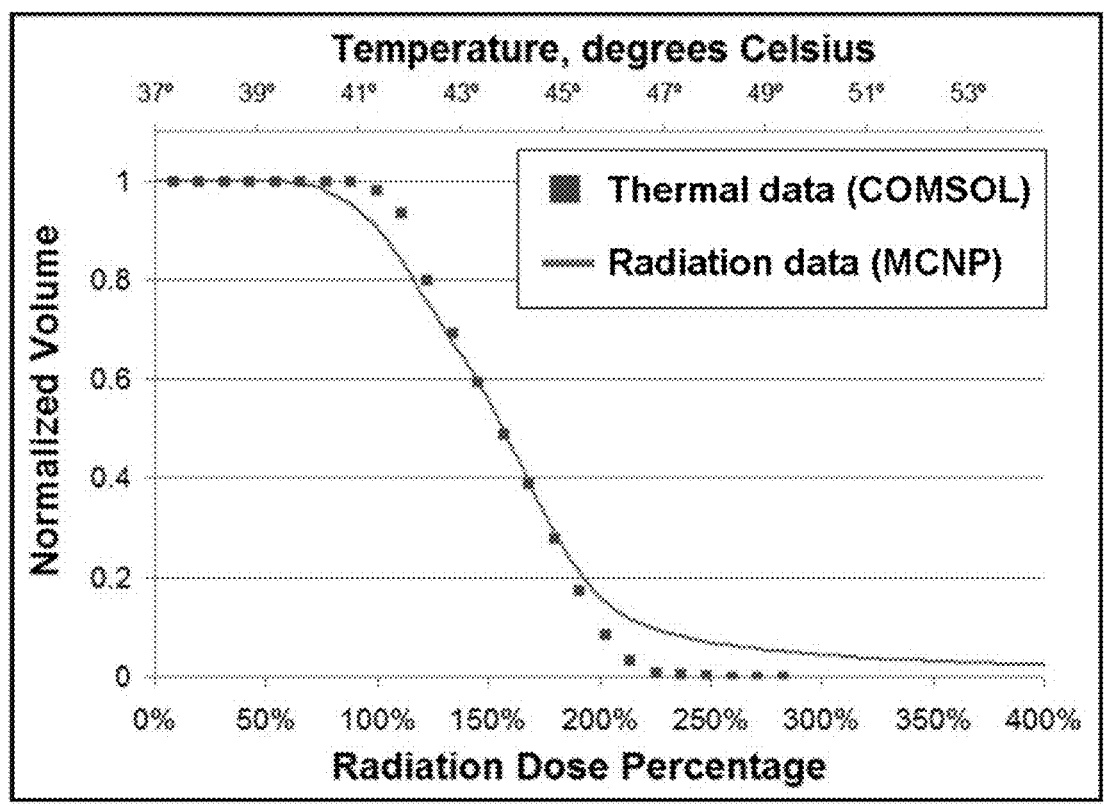
FIG. 99 shows generated cumulative dose and temperature volume histograms for radiation and temperature in the PTV defined for the three-dimensional seed distribution. Thermal data is shown by the points and the radiation dose volume histogram is given by the solid line.

A comparison of the radiation and temperature distributions of the three-dimensional case was done by relating the radiation DVH and temperature-volume histogram (TVH) obtained from MCNP5 and COMSOL 3.5, respectively. As shown in FIG. 99 for this arrangement, the "shoulder" of the TVH occurs slightly below 42° C., indicating that almost all of the volume of the PTV is exposed to at least the minimum temperature that induces radiosensitivity. About 44% of the volume of the PTV is exposed to temperatures of 44° C. or greater; the same percentage of the PTV volume receives 177% of the radiation prescription dose. Finally, 6% of the PTV volume receives 208% of the radiation prescription dose and is heated to 46° C.

Monte Carlo Modeling of Two- and Three-Dimensional Seed Arrangements

The MCNP models consisted of the seed distributions at the center of a 20 cm-radius water phantom, more than large enough to fulfill the characteristic of an effectively infinite water medium for $^{125}$I photons. The seeds were modeled with rounded ends. For each model, a lattice of cubical 1 mm-wide tally cells was made large enough to cover the area of interest. Dose was estimated in each tally cell by the MCNP tally function F6, tracking energy deposited in the cell by photons per unit mass per history, in MeV/g. The F6 tally in MCNP uses a track length estimate of energy deposition to obtain the energy deposition Ht in the tally cell. The photon-tracking version of the F6 tally, F6:P, was used since the maximum photon energy from $^{125}$I is 35 keV. Photons of this energy generate secondary electrons by both Compton scattering and the photoelectric effect, the latter of which may result in secondary electrons of energy nearly up to ~35 keV. The range of such electrons in water is very small; according to the Stopping Powers and Ranges for Electrons (ESTAR) database, 35 keV electrons have a continuous slowing down approximation (CSDA) range of 2.306×10-3 g/cm2 in liquid water, or ~0.02 mm. This justifies the use of local dose deposition (i.e., not explicitly modeling secondary electrons) in the MCNP models, as the tally cells are much larger than the range of even the highest-energy electrons that may be produced.

The recommended photon spectrum for $^{125}$I published in the AAPM Task Group 43 Report (TG-43) was used for the modeled energy distribution in the MCNP models. The interaction of these photons with the seed components and the phantom by the photoelectric effect, Compton scattering, and coherent scattering were specified. The number of simulated histories of starting particles was made large enough for the ten automatically-generated statistical robustness tests in MCNP5 to pass.

Validation of a Method to Determine Temperature-Dependent Seed Output Power

In order to improve the efficiency of calculations of temperature distributions from large numbers of TB and HT-only seeds in COMSOL, making calculation of temperature distributions from patient-specific implants possible, the "power-versus-temperature" method was developed. Rather than directly model magnetic fields and eddy current generation, this method involves generating a plot of volumetric thermal power generation within the seed as a function of temperature, and setting that as a heat source in the COMSOL model. This was done by calculating the approximate power generation as a function of temperature from first principles using published data for the magnetic behavior of NiCu alloy with temperature and magnetization.

To validate the method of a temperature-dependent seed power function, a single TB seed at the center of a 20 cm-diameter, 10 cm-height cylindrical "single-seed phantom" was modeled in COMSOL, and the calculated heat distribution in the material surrounding the seed was found with direct eddy current modeling. This was done with the "Induction Heating" modeling in COMSOL 4.4 for a "Frequency-Transient" study, which considers heat generation in electrically-conductive media as well as conductive and (if applicable) radiative heat transport. The thermophysical properties (density, thermal conductivity, and heat capacity) of water were applied to the single-seed phantom, but no convection was modeled, i.e., it was "gelled" or "solid." A segregated solver was used to solve for the temperature and the magnetic vector potential, using the GMRES iterative solver for the former and a biconjugate gradient stabilized method (BiCGStab) iterative solver for the latter. Again, an absolute tolerance of 0.001 was specified for each of the solved variables. The meshing density was $1.2 \times 10^{14}$ elements/m$^3$ for the TB seed and $3.5 \times 10^7$ elements/m$^3$ for the phantom. The outer surfaces of the phantom were set to a constant temperature of 37° C.; this was also the initial condition of temperature throughout the phantom interior. The core, graphite layer, and titanium shell of the TB seed, as well as the phantom, were each modeled, and the physical parameters of each inputted. (Table 51.) The magnetic relative permeability was set to 1 for each component, except for the NiCu core, which was a temperature-dependent function of taken from Brezovich et al. (FIG. 82.) Volumetric power density due to eddy currents $Q_{ext}$ was calculated according to external current density $J^e$ and electrical conductivity $\sigma$:

$$Q_{ext} = \frac{1}{2\sigma}|J^e|^2 \quad (24)$$

External current density was calculated:

$$J^e = (i\omega\sigma - \omega^2\epsilon)A + \nabla \times (\mu^{-1}\nabla \times A) \quad (25)$$

Here, $\omega$ and $\mu$ are angular frequency and magnetic permeability, as before, i is the unit imaginary number, $\epsilon$ is the electrical permittivity, and A is the magnetic vector potential. Flux density B is the curl of A:

$$B = \nabla \times A \quad (26)$$

B is obtained from the inputted magnetic field H, assuming a soft magnetic material:

$$H = \frac{B}{\mu} \quad (27)$$

H was defined as a sinusoidal oscillating field, of amplitude 5 kA/m and of frequency 100 kHz, magnetic field parameters similar to what would be used in actual hyperthermia treatments. Conductive heat transport was modeled by Equation 4. Loss of generated heat due to uniform, isotropic blood perfusion within the modeled region was modeled by the blood perfusion term in the Pennes' bioheat equation:

$$Q_{per} = \rho_b C_b \omega_b (T_b - T) \quad (28)$$

Here, $Q_{per}$ is the thermal power density absorbed by tissue due to blood perfusion, $\rho_b$ is the density of blood, $C_b$ is the heat capacity of blood, $\omega_b$ is the volumetric blood perfusion rate, $T_b$ is the temperature of the incoming arterial blood (set to the normal core body temperature of 37° C.), and T is the temperature at a given location within the tissue. The volumetric blood perfusion rate $\omega_b$ is the product of blood perfusion rate (BPR) as used here (in units of mL of perfusing blood per minute per 100 g of perfused tissue) and tissue density. Temperature distributions were computed for BPRs varying from 0 to 30 mL per minute per 100 g.

This done, power generation within each component of the seed versus time and average temperature of each component versus time were exported from COMSOL, to obtain a function of power versus temperature. These functions were fitted to second-order polynomials, inputted into the COMSOL model of the single-seed phantom, and modeling of eddy currents turned off. The same problem mesh and thermophysical parameters were reused. Again, temperature distributions for blood perfusion rates of 0 to 30 mL per minute per 100 g were obtained, using the GMRES iterative solver. Temperature distributions obtained from the eddy-current and temperature-dependent power modeling methods were compared.

Finally, for purposes of illustrating the rapidity of temperature drop-off with distance and blood perfusion, the single-seed phantom model was reused, this time setting the surface of the TB seed to 50° C. instead of modeling its power production. This was done to ensure the temperature immediately adjacent to the seed remained constant despite variations in the BPR, providing a more appropriate comparison among plots of temperature drop-off over a range of BPRs. Once again, the BPR was varied from 0 to 30 mL per minute per 100 g.

Modeling of Realistic Patient-Specific Seed Distributions

Figure 86A:
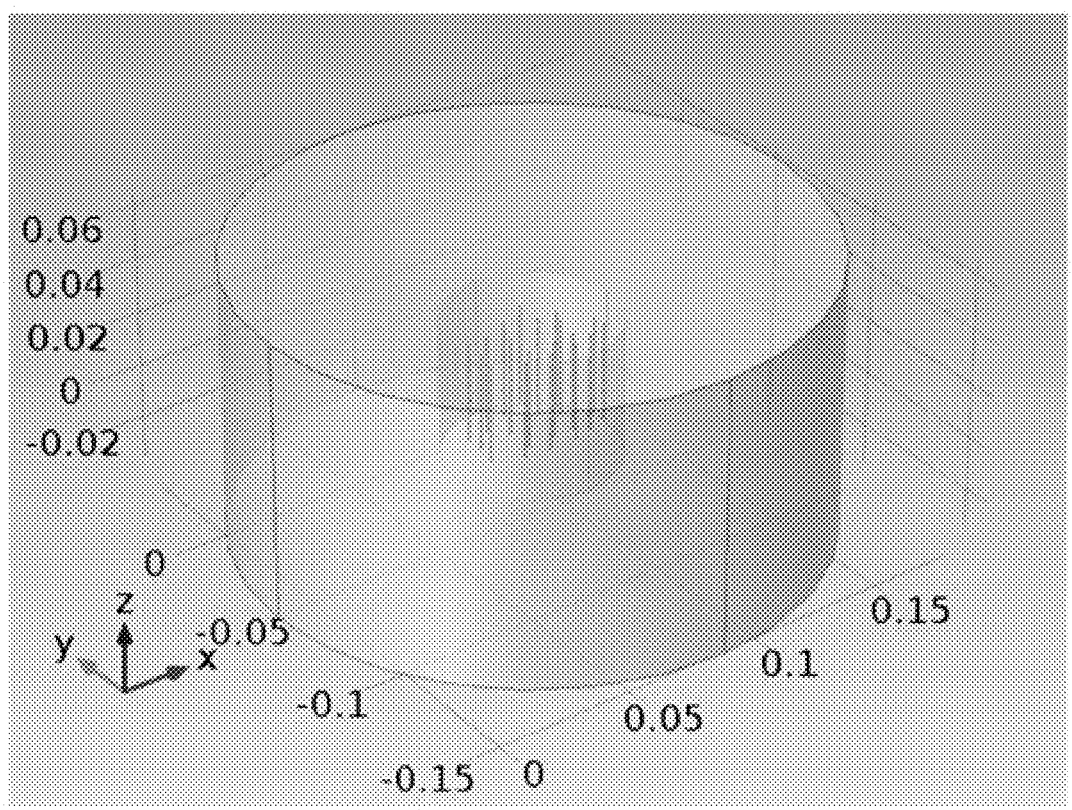
FIGS. 86A-86B illustrate the modeled geometry for one of the patient-specific seed distributions in the patient phantom (FIG. 86A) and the corresponding mesh (FIG. 86B).

The ability of distributions of TB seeds to provide an acceptable hyperthermia treatment in realistic clinical scenarios was evaluated by simulating the heat production of patient-specific distributions of TB seeds. To do this, past LDR permanent prostate brachytherapy plans that had been created in the treatment planning system Varian VariSeed version 8.0 and delivered to patients were reproduced in COMSOL, except that the ordinary LDR seeds that had actually been used for these treatments were replaced with TB seeds. Moreover, HT-only seeds were modeled as occupying locations within the implantation needles not used by TB seeds. (FIG. 86A.) The phantom in which they were embedded, referred to here as the "patient phantom," consisted of an inner cylindrical region of diameter 6 cm and height 5 cm, with thermophysical parameters set to those of prostate tissue (Table 51) and an outer cylindrical region of diameter 20 cm and height 10 cm, set to the thermophysical properties of adipose tissue. Boundary conditions were defined such that the external surfaces of the phantom were set to normal core body temperature.

For heat transport within these COMSOL models, the thermal power density (Q in Equation 24) was set to be temperature-dependent. Within the domains of the problem geometry representing the seeds, the power density was the function of power generation versus temperature, found numerically, divided by the seed volume. For the tissue domains, heat loss due to blood perfusion was modeled.

The simulated external magnetic field was of 100 kHz frequency and 5 kA/m amplitude. To account for the skin effect and consequent attenuation of the magnetic field amplitude in the electrically-conductive patient tissues and titanium seed capsules, the equation for attenuation due to the skin effect was used:

$$\frac{I(x)}{I_0} = \exp\left(-\frac{x}{\sqrt{\frac{2}{\sigma\omega\mu}}}\right) \quad (29)$$

Here, $I(x)/I_0$ is the relative intensity of an electromagnetic field of angular frequency $\omega$ after having penetrated a distance x into a conducting medium, of electrical conductivity $\sigma$ and magnetic permeability $\mu$. To obtain the attenuation of the magnetic field due to the patient, published data on the electrical conductivity of tissues at a frequency of 100 kHz were used, and the magnetic relative permeability of tissues was assumed to be to 1. Given radial thicknesses for a particularly large patient (presenting the worst-case scenario in tissue attenuation) of 3 mm of skin, 15 cm of fat, 9 cm of muscle, 1 cm of cancellous bone, and 4 mm of cortical bone, a total tissue attenuation coefficient of 0.94 was calculated. In the same way, the attenuation coefficient due to the titanium shell was calculated to be 0.96. Thus, the total magnetic field amplitude for the seed cores was set to 5.0 kA/m×0.94×0.96=4.5 kA/m.

Figure 86B:
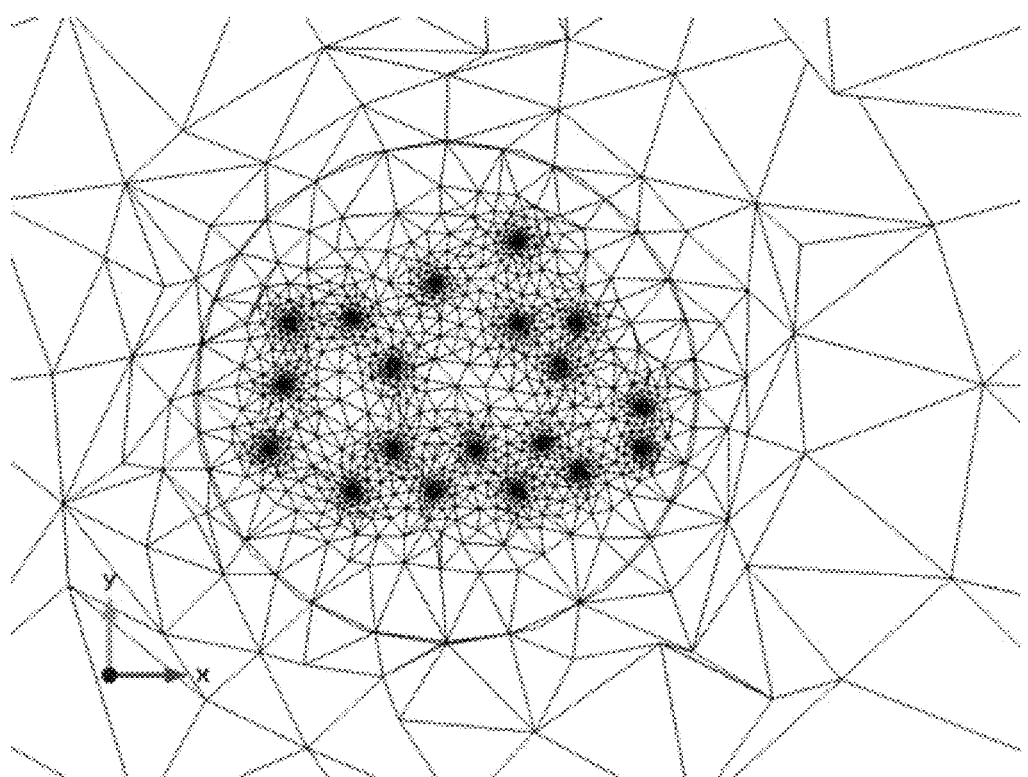

For the tissue domains, heat loss due to blood perfusion (Equation 29) was modeled. As before, the GMRES iterative solver, with a maximum absolute tolerance of 0.001 of the solved variable and a maximum of $10^4$ solver iterations was used. In accordance with the minimum meshing density identified by a meshing density study, the mesh density for the seeds was typically $4.1 \times 10^{11}$ tetrahedral elements/m$^3$, while the average of the inner cylindrical "prostate" region was $4.0 \times 10^9$ elements/m$^3$. A lower mesh density of $1.2 \times 10^6$ elements/m$^3$ was used for the outer part of the patient phantom. (FIG. 86B.)

In this way, the thermal distributions that would have resulted had these patients been treated with the TB and HT-only seeds could be obtained. The goal criterion was selected as coverage of 90% or more of the PTV by the 42° C. isotemperature line once the implant-tissue system had reached thermal equilibrium. 42° C. was chosen since this is approximately at the threshold of induction of radiosensitivity, and also permits a relatively high thermal dose delivery if maintained for the duration of treatment.

An in-house program was written in C++ to use the temperature distributions calculated by COMSOL to generate temperature volume histograms (TVHs) for the patient-specific PTVs. As the version of VariSeed used did not have a function for exporting drawn regions of interest (ROIs) as a DICOM-RTSTRUCT structure set file, the ultrasound image captures from the treatment plans, which included the original ROIs drawn by the physician operating the ultrasound unit, were recontoured in the software package MIM version 6.2.2. The resulting PTV contours were exported from MIM to a DICOM-RTSTRUCT file. The in-house program was then able to use data describing the PTV from the RT structure set with the positional temperature data calculated by COMSOL to generate differential temperature volume histograms, which it used to create cumulative TVHs.

For one of the patient seed distributions (Patient 1, with a prostatic volume of 40 cc; the same patient plan on which both types of HT-only seeds were studied), both described versions of the HT-only seed (one with a core of the same size as that of the TB seed and a non-radioactive carbon layer, and the other with a core filling the entire interior of the titanium shell) were modeled, and temperature distributions were obtained to quantify the effect of such larger HT-only seed cores. The anatomy and seed distributions were used for this as the prostatic anatomy and number of PTV slices were within the middle of the range encountered for prostate LDR patients. Moreover, the relatively low number of seeds per volume of the PTV means that the heating requirements drawn from this geometry are slightly more conservative than those drawn from a patient with an average number of seeds.

To determine the seed design requirements, three patient plans were chosen from the pool of previously-treated patients, with prostatic volumes covering the range typically encountered in the clinic. The blood perfusion rates that the combination of TB and hyperthermia-only seeds could overcome to achieve the goal of 90% of the PTV covered by the 42° C. isotemperature surface were determined. This was done for both the NiCu seed cores, and an alternative composed of a magnesium ferrite surrounded by a conductive layer of optimal thickness.

Evaluation of the Blood Perfusion Effect

An evaluation of the seed parameters needed to overcome higher rates of blood perfusion within the target was conducted for two cases: uniform over the whole target volume, and restricted to a centrally located large blood vessel. The distribution for TB and HT-only seeds defined for one of the patient plans studied for the preliminary test (prostatic volume of 40 cc; the same patient plan on which both types of HT-only seeds were studied) was again used, along with the patient phantom. Again, the power-vs.-temperature approximation was used. The modeled normalized function for power generation as a function of temperature was iteratively multiplied by a factor (ranging from 1-10), and the temperature distribution recalculated to determine the power needed to overcome a range of defined uniform blood perfusion rates. Study was also made of the decrease in power requirements through increase in the Curie temperature of the seeds, and the corresponding increase in temperature heterogeneity within the target.

As with the seeds with NiCu cores, theoretical power generation of ferrite-based cores was calculated from first principles and inputted in COMSOL as power-versus-temperature data; the same patient-specific seed distributions were used with these simulated ferrite seeds to determine power generation requirements versus Curie temperature and blood perfusion rate.

Heterogeneity of the temperature distributions was quantified according to the heterogeneity coefficient (HC) defined as follows:

$$HC \equiv \frac{T_{10} - T_{90}}{T_{90} - T_{body}} \tag{30}$$

Here, $T_{10}$ and $T_{90}$ are the temperatures covering 10% and 90% of the volume of the defined PTV, respectively, and $T_{body}$ is the normal core body temperature, taken to be 37° C. (Note that HC=0 for a hypothetical perfectly uniform temperature distribution, and increases as the temperature difference between hot spots and cold spots in the PTV increases.)

Finally, for this same patient plan, again used within the patient phantom, the thermal effect of discrete blood vessels was investigated by calculating the thermal distributions in COMSOL. Blood vessels parallel to the axis of the seeds (the z-axis) and traversing the length of the inner cylinder of the phantom were modeled such that the entire blood supply to the target region was simulated as travelling through the vessels before perfusing the target region. To do this, a heat sink condition was defined for the part of the geometry modeling the blood vessel:

$$Q_{per} = \rho_b C_b \omega_b \frac{V_{prostate}}{V_{vessels}} (T_b - T_{avg,vessels}) \tag{31}$$

$Q_{vessel}$ is the heat absorption within a modeled blood vessel, not to be confused with $Q_{per}$, the term for uniform, isotropic blood perfusion within modeled tissue. While the equation resembles that for $Q_{per}$ in Equation 28, it differs first in that the factor of $V_{prostate}/V_{vessels}$ is used to simulate the entire blood supply travelling through the blood vessels. $V_{prostate}$ is the volume of the inner cylinder of the phantom (representing the region of the prostate), and $V_{vessels}$ is the volume of the blood vessels. Also, $T_{avg,vessels}$, the volume-averaged temperature within the blood vessels, is used instead of T for a given voxel. Use of an average temperature of the interior of the blood vessels as input for the magnitude of the vessels' heat sink was taken as equivalent to thorough, convective fluid mixing within the vessels. Further, $T_{avg,vessels}$ was used instead of $T_b$ in Equation 31 for the inner part of the phantom, accounting for the small increase in temperature of the capillary blood supply due to blood having been heated within the blood vessel.

As with the validation of the temperature-dependent power modeling method, the meshing density of the large blood vessels was varied, from $4.8 \times 10^8$ elements/m³ to $6.0 \times 10^9$ elements/m³, observing the variation of calculated temperature coverage with meshing density for a blood perfusion rate of 5 mL per min per 100 g. Once a mesh of sufficient density to give stable results had been identified, various vessel configurations were studied to determine the one that had the greatest effect on the thermal coverage. The studied configurations included: (1) A single 2 millimeter-diameter blood vessel along the central axis of the inner cylinder of the patient phantom; (2) two blood vessels of combined cross-sectional area equal to the 2 millimeter-diameter vessel and separated along the x-axis (FIGS. 86A-86B) by a distance of two-thirds the diameter of the inner cylinder of the patient phantom; and (3) the same configuration of two blood vessels but separated along the y-axis. With the "worst possible scenario" of blood vessels thus selected, the blood perfusion rate was varied from 0 to 15 mL per minute per 100 g, to observe the thermal effect as a function of blood perfusion rate.

To provide a point of comparison with standard magnetic interstitial hyperthermia seeds known in the art, a modeled distribution of PdCo ferromagnetic seeds (ThermoRods, Ablation Technologies, San Diego, Calif.) was devised in COMSOL to cover the patient PTV used in the study of NiCu and ferrite seed power requirements. These seeds, 14 mm long and 1 mm wide cylinders, were arranged throughout the PTV with 1 cm spacing along both axes in the axial plane, totaling 41 seeds. This seed spacing followed an example that had used these seeds in hyperthermia, as well as a recommendation that seed-to-seed spacing be limited to 1 cm. Calorimetric data on thermal power generation of these seeds in a 5.6 kA/m amplitude, 50 kHz magnetic field versus temperature were entered into the COMSOL model. Data for seeds with $T_C$'s of both 55° C. and 60° C. were inputted. As before, the BPRs were varied to determine the thresholds at which the defined temperature criterion was fulfilled for each of the $T_C$'s.

Quantification of Interseed Effect

As use of additional radioactively-inert hyperthermia-only seeds in the target to increase the number of sources of heat would intensify the interseed attenuation and scatter (ISA) effect, it was deemed important to quantify this effect. Input files for the Monte Carlo software package Monte Carlo N-Particle Version 5 (MCNP5) were generated from the 7 aforementioned previous patient plans produced in Variseed for BEST 2301 seeds. As with the two- and three-dimensional regular seed distributions, 1 mm F6:P voxels were used, covering the regions of interest drawn by the physician in the original treatment plans.

For each of these patients, three dose distributions were modeled with MCNP. First, in order to obtain a dose distribution that does not consider ISA, a superposition dose distribution was generated by obtaining the dose distribution surrounding a single TB seed, following known methodology. This single-seed Monte Carlo dose distribution was used to obtain a superposition dose distribution for each patient by shifting the center of the former to each seed location in the original patient plan, summing the total dose in 1-millimeter increments over the entire dose calculation volume encompassing the target and OARs. TB-only dose distributions were then made by creating MCNP input files that had a TB seed at each seed location in the original treatment plans. The resulting dose distributions then included the effect of ISA due to the TB seeds only. Finally, TB and HT-only input files were obtained from the TB-only input file by placing a radioactively-inert HT-only seed at each unused seed location, in a similar way to what was done for modeling TB and HT-only seeds in COMSOL. For the HT-only seeds, the larger ferromagnetic core used to maximize power production was modeled. The dose distribution resulting from this input file then included the effect of ISA from both the TB and the HT-only seeds. In all cases, dose distributions were obtained from F6 (energy deposition per unit mass per history) tallies.

The program used to obtain TVHs from COMSOL-generated temperature distributions and inputted regions of interest was then used to obtain DVHs for each of the MCNP-generated dose distributions, as well as to determine the number of histories necessary to obtain an accurate DVH. For one of the patient-specific models, the number of histories was varied from $1 \times 10^6$ to $5 \times 10^8$ by factors of ~2 to find the minimum number of histories for which D90 and V 100 were within 0.1% of their true value.

DVHs were calculated for the original physician-defined PTVs, as well as prostatic urethra and rectum contours. The extent of the ISA effect on dose metrics in TG-137 (AAPM Task Group No. 137 Report) to the clinical target volume (CTV) and critical organs at risk (OARs) was quantified. (Table 52.)

TABLE 52

Pre-implantation planning criteria for the CTV and OARs

| Region of interest | Planning criterion | Explanation |
|---|---|---|
| CTV | $V_{100} > 95\%$ | The fraction of the CTV receiving 100% or more of the prescribed dose ($V_{100}$) must be greater than 95% |
| CTV | $V_{150} \leq 50\%$ | The fraction of the CTV receiving 150% or more of the prescribed dose ($V_{150}$) may be no more than 50% |
| Rectum | $D_{2\ cc} < Rx$ dose | The maximal dose to 2 cc of the rectum ($D_{2\ cc}$) must be less than the prescribed dose |
| Rectum | $D_{0.1\ cc} < 150\%$ Rx dose | The maximal dose to 0.1 cc of the rectum ($D_{0.1\ cc}$) must be less than 150% of the prescribed dose |
| Prostatic urethra | $D_{10} < 150\%$ | The maximal dose to 10% of the volume of the prostatic urethra ($D_{10}$) must be less than 150% of the prescribed dose |
| Prostatic urethra | $D_{30} < 130\%$ | The maximal dose to 30% of the volume of the prostatic urethra ($D_{30}$) must be less than 130% of the prescribed dose |

Estimate of the Thermal Enhancement Ratio

Finally, an estimate of the thermal enhancement ratio (TER) from use of the TB and HT-only seeds was made, following a known method of temperature dependency within the linear-quadratic cell model. Three functions have been proposed for the variation of the linear parameter α with temperature, making the simplifying assumption that the quadratic parameter β does not vary with temperature. These functions include a simple linear dependence between α and temperature, an exponential dependence, and a linear dependence with differing slopes before and after a breakpoint temperature of 42.5° C. Since the latter may be most consistent with experimental observations of an increased rate of cell killing above a breakpoint temperature, a result that led to the definition of CEM 43° C. for thermal dose, this function was used to calculate the TER in subsequent calculations.

For three patient plans among the seven that had been used to assess temperature coverage and the ISA effect, temperature distributions calculated in COMSOL for blood perfusion rates of 30 mL per minute per 100 g were used. Dose distributions generated in MCNP for combinations of TB and HT-only seeds were also used, the calculated dose multiplied by a previously-obtained factor in order to correct for ISA. Three-dimensional dose and temperature grids with points in 1-mm increments covering the regions of interest were tabulated in a spreadsheet. Peak TER at each of these points was estimated as α(T)/α(37° C.), using the approximation that the quadratic component of cell killing in the linear-quadratic model is small compared to the linear component at the low dose rate.

Since most of the radiation dose delivered by TB seeds is deposited well before or after hyperthermia treatments, the effective TER over the time period both modalities would be delivered was calculated by means of a time integral.

$$\text{Average } TER = 1 + TER_{max} \frac{\int_0^\tau 2 \times e^{-\frac{t \ln(2)}{T_{1/2}}} dt}{\tau} \qquad (32)$$

As two hyperthermia treatments were considered to be delivered per week, 84 hours=half of one week was taken as the average time between hyperthermia treatments, or τ in the above equation. TERmax is the maximum TER achieved during a hyperthermia session, T½ is the half-life of radiosensitization, taken to be 2 hours based on published data on TER vs. time between hyperthermia and radiation treatments to cells in culture, and t is time elapsed after a hyperthermia treatment. The above equation thus assumes that thermal enhancement of radiation dose delivered drops off exponentially with time before or after a hyperthermia treatment. The factor of 2 within the integral reflects that hyperthermia treatments increase the effectiveness of dose already delivered and dose yet to be delivered.

The TER for each calculated point in the dose grid for the entire regimen of hyperthermia and radiation was then calculated as the weighted average of time-averaged TER during the dual-modality phase of treatment (considered to be one month of semi-weekly hyperthermia treatments starting immediately after implantation) and a TER of 1 for the subsequent radiation-only phase of treatment. This weighted-average TER was multiplied by the aforementioned radiation dose at each point to obtain an effective dose. As had been done previously, the unmodified and effective dose distributions for the three patients were used with data on the physician-drawn PTVs and OARs to obtain DVHs for these structures.

To estimate the effective dose enhancement to the PTV and OARs for the three patients, the method of equivalent uniform dose (EUD) was used. This converts volumetric dose data from a DVH to the estimated dose which, if delivered in a perfectly uniform fashion to the entire region or organ, would result in the same effect as that of the inhomogenous dose actually delivered. The standard definition of the generalized EUD was used:

$$EUD = \left( \sum_i v_i D_i^a \right)^{1/a} \qquad (33)$$

Here, $v_i$ is a fractional sub-volume of the structure of interest, $D_i$ is the dose to that sub-volume, and the parameter α is the volume-effect exponent, describing the change in effective dose to a structure with heterogeneity of the dose distribution to which it is exposed. The following values for a were applied: −10 for the PTV, 8 for the rectum, and the value 8 for the bladder used for the prostatic urethra.

Results

Validation of Thermal Modeling by Experimental Results

Figure 87:
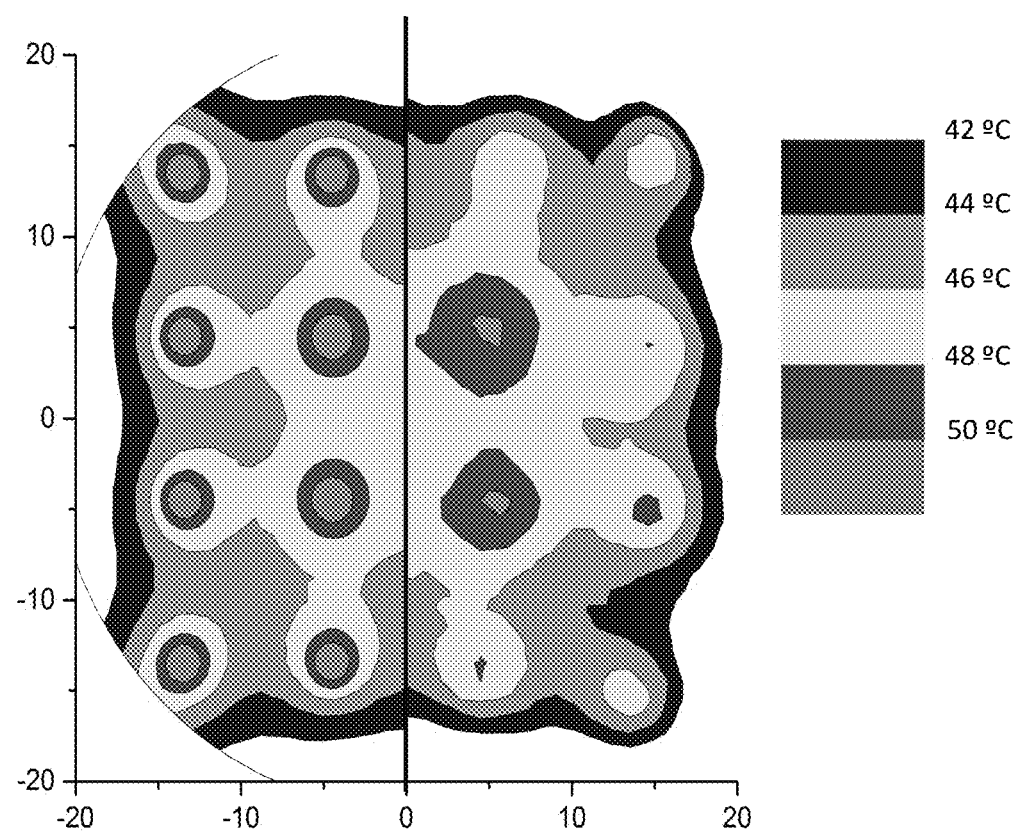
FIG. 87 shows a comparison between temperature distribution calculated by COMSOL at the surface of the tissue-mimicking ham phantom (left) and experimental data from the IR camera (right). Scale is in mm. As discussed in Example II herein, the difference between the two is largely due to physical limitations of the IR camera.

Comparisons between the measured and computed temperatures for the ham heating experiment are presented in FIG. 87. The difference between the computed and experimental temperature maps is largely due to physical limitations with the IR camera, in that a pixel length in the IR image corresponds to ~1 mm on the ham surface. As a result, small features such as the implants could not be completely resolved. Subtle differences between the upper and lower halves of the COMSOL-calculated temperature distribution arise from the slightly non-symmetric model mesh generated in COMSOL. (See FIG. 85.)

Within a 10 mm-radius of the center of the temperature distributions, a gamma analysis comparison between the two halves of FIG. 87 (one mirrored to the other side) results in a passing rate of 86.6% for a $\Delta d_m$ of 1 mm and a $\Delta T_m$ of 1° C. Increasing $\Delta d_m$ to 1.5 mm and a $\Delta T_m$ to 1.5° C. increases the passing rate to 100.0%.

Validation of a Method to Determine Temperature-Dependent Seed Output Power

It was found that the error arising from use of the temperature-dependent seed power method is small (calculated maximum 2% difference in seed temperature rise between the power-vs.-temperature and eddy current modeling method for a single seed over the range of blood perfusion rates 0-30 mL per minute per 100 g). This method thus serves as an acceptable approximation for calculating seed heating.

Figure 88A:
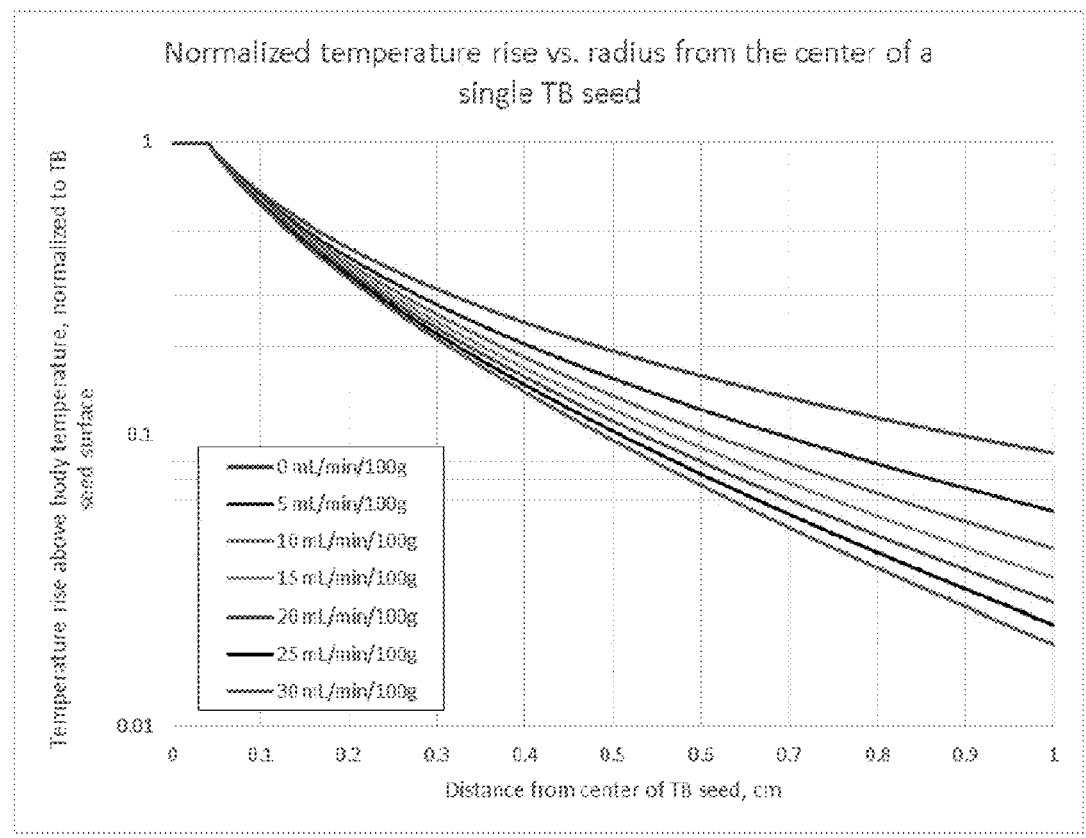
FIGS. 88A-88B illustrate normalized drop-off of temperature (above normal body temperature) vs. radial distance from the center of a modeled TB seed. The vertical axis is normalized such that 1 represents the total temperature rise above body temperature, or 13° C.

COMSOL modeling confirmed that the temperature rise above normal body temperature ΔT has a rapid drop-off with distance from the seed surface. As shown in FIG. 88A, normalization for temperature rise above normal body temperature was set to unity at the surface of the seed. Temperature rise above body temperature 1 cm from the seed center (in the transverse plane according to TG-43 formalism) is 2.9 times greater for a blood perfusion rate of 5 mL/minute/100 g than it is for a blood perfusion rate of 30 mL/minute/100 g.

Figure 88B:
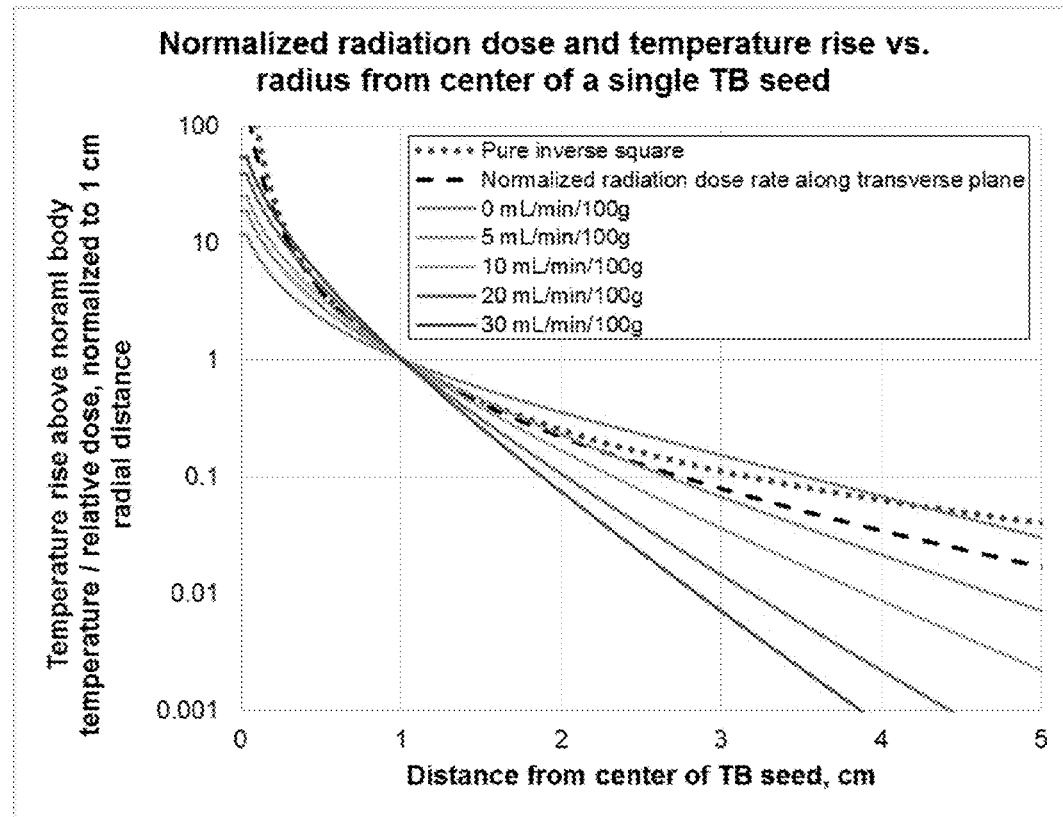

As shown in FIG. 88B, normalization for temperature rise above normal body temperature or dose was set to unity 1 cm from the center of the seed, in the transverse plane of the seed (θ=90°). For uniform blood perfusion rates of more than 5 mL of arterial blood flow per minute per 100 g of perfused tissue, the drop-off in temperature rise more than 1 cm from the center of the TB seed is much more rapid than the drop-off in radiation dose. Notably, at distances of less than 1 cm, the trend of increasingly rapid gradient of temperature rise with increasing blood perfusion rate holds.

Modeling of Realistic Patient-Specific Seed Distributions

Figure 89:
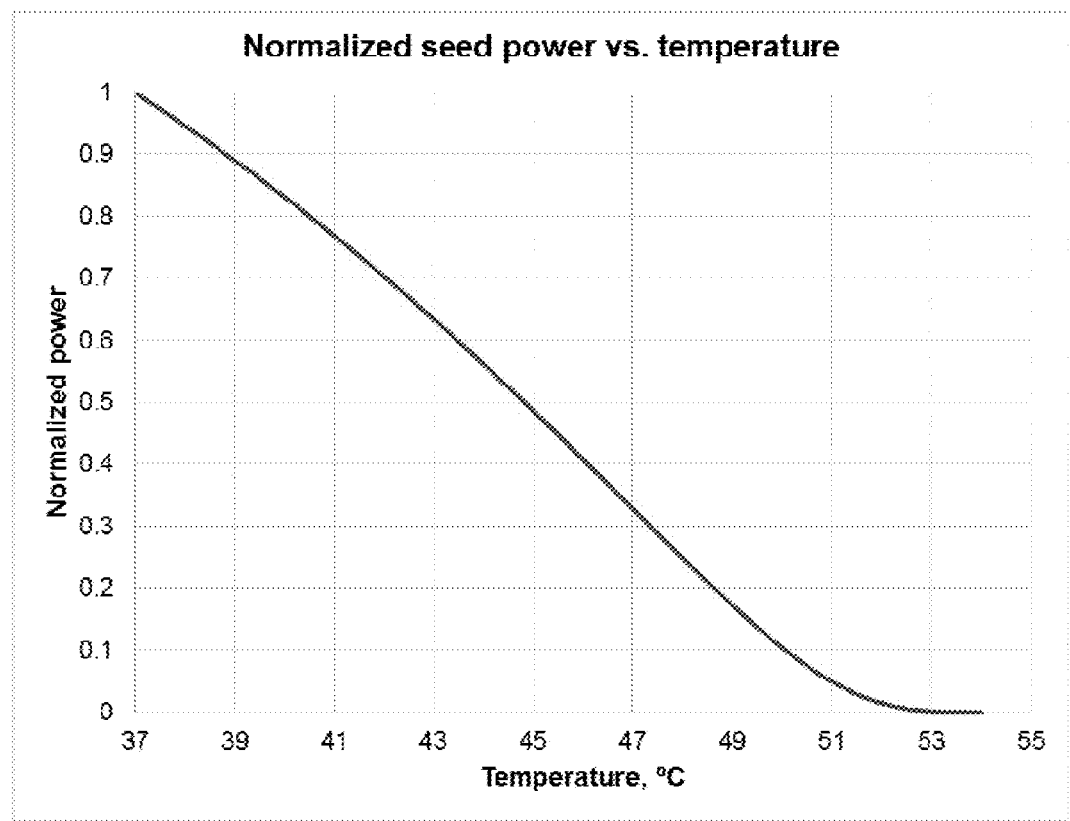
FIG. 89 illustrates normalized plot of power vs. temperature for the NiCu-based TB seed, as calculated analytically, using the plot of magnetic relative permeability for NiCu in FIG. 82. The normalization temperature is taken at 37° C., normal core body temperature.
Figure 90:
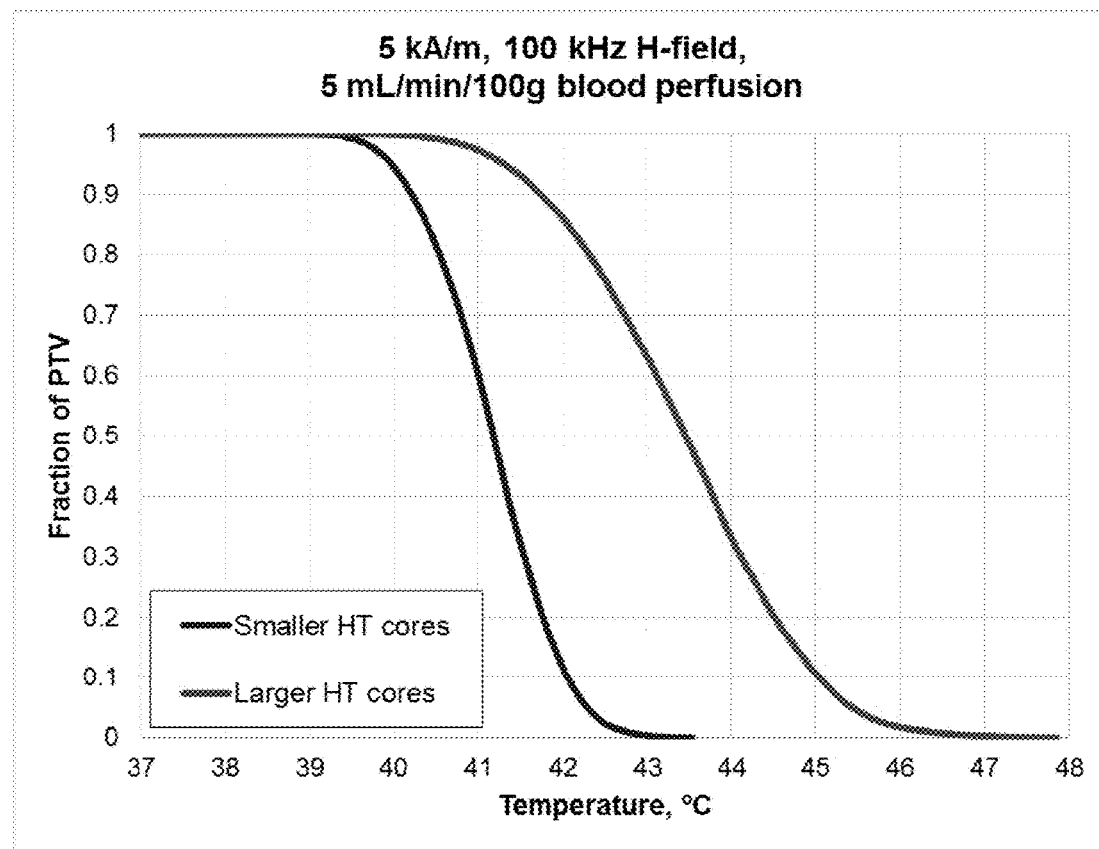
FIG. 90 illustrates cumulative temperature volume histograms for Patient 1, with the use of smaller vs. larger cores in HT-only seed cores. In both cases, HT-only seeds were used in the empty spots in the needles used to accomplish the seed implantation.

FIG. 89 depicts the analytically-calculated function of normalized power of the TB seed versus temperature. Eliminating the carbon layer, used as the $^{125}$I medium in regular LDR seeds, permitted an increase in the core size by 0.1 mm radially and 0.3 mm in length, thus increasing the core volume by a factor of 2.3. This modification was found to result in notably greater power production in the hyperthermia-only seeds. (FIG. 90.)

The estimated error reported by COMSOL due to the solver (typically $\sim 10^{-5}$ K) was negligible compared to the $\sim 2\%$ difference due to the temperature-dependent power modeling approximation. Among the three patients in the initial study of thermal coverage versus blood perfusion rate, it was found that the implant design with the as-described TB seeds and larger-core HT-only seeds was able to cover 90% of the PTV with the 42° C. isotemperature line for blood perfusion rates up to an average of 4.6 mL of blood per minute per 100 g of tissue.

Evaluation of the Blood Perfusion Effect

Figure 91A:
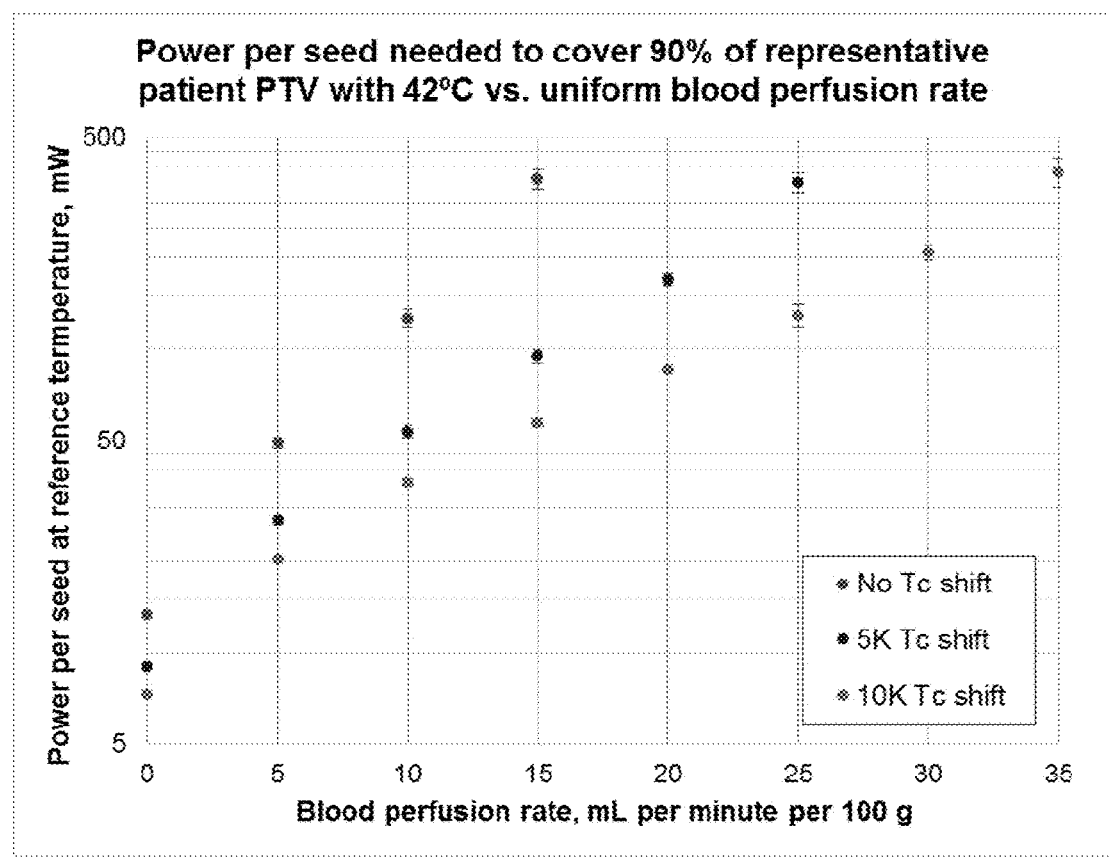
FIG. 91A shows power per seed at the reference temperature (37° C.) needed to cover the PTV of a representative patient, for various blood perfusion rates and increases in the Curie temperature.

The results of varying the normalized power generation to overcome higher rates of blood perfusion for seeds are summarized in FIG. 91A. The results of varying the normalized power generation to overcome higher rates of blood perfusion for seeds are summarized in FIG. 91B. In all cases, the previously-determined normalized function of power-vs.-temperature calculated analytically for the NiCu TB seeds in the baseline design was multiplied by an iteratively-determined factor. The temperature distribution was repeatedly computed in COMSOL, adjusting this factor until 90% of the PTV was covered by the 42° C. isothermal line at equilibrium. For the data taken with a Curie temperature shift, the power-vs.-temperature function was also shifted 5K or 10K (from the initial Curie temperature of $\sim 49°$ C.) to simulate the effect of an increase in the seeds' Curie temperature on the resultant temperature distribution. It was found from these data that for the power-vs.-temperature curve calculated for the NiCu-core seeds, power requirements increase approximately exponentially with increasing blood perfusion rates, but that an increase in the Curie temperature greatly decreases the power required. Power requirements for ferrite-core seeds are less severe. Increasing the Curie point, however, leads to a moderate increase in temperature heterogeneity. The changes in HC with blood perfusion rate and changes in the Curie temperature of the seed cores are presented in Table 53.

TABLE 53

Temperature heterogeneity coefficients in the PTV for Patient 1, the seed power iteratively adjusted in each case to exactly cover 905 of the PTV volume with the 42° C. isotemperature line.

| Curie temperature increase | Arterial blood perfusion rate, mL blood per minute per 100 g target tissue | | | | | | | |
|---|---|---|---|---|---|---|---|---|
| | 0 | 5 | 10 | 15 | 20 | 25 | 30 | 35 |
| 0 K | 0.355 | 0.569 | 0.730 | 0.869 | — | — | — | — |
| 5 K | 0.382 | 0.614 | 0.788 | 0.936 | 1.070 | 1.209 | — | — |
| 10 K | 0.395 | 0.639 | 0.824 | 0.980 | 1.126 | 1.399 | 1.538 | 1.703 |

Figure 100A:
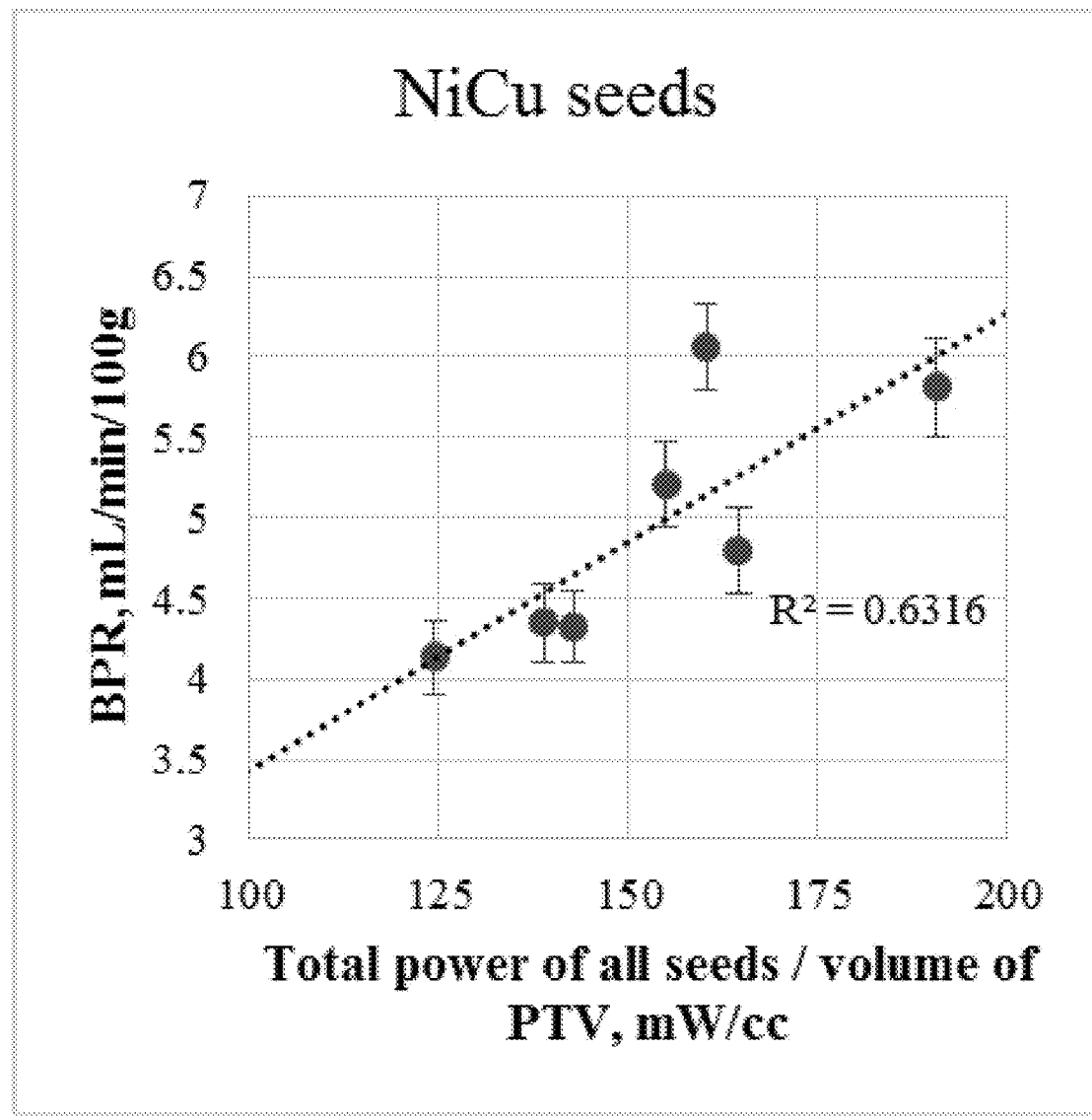
FIGS. 100A-100B show the maximum BPR still resulting in the temperature coverage criterion, for TB and HT-only seeds with NiCu cores (FIG. 100A) and ferrite/conductive layer cores (FIG. 100B).
Figure 100B:
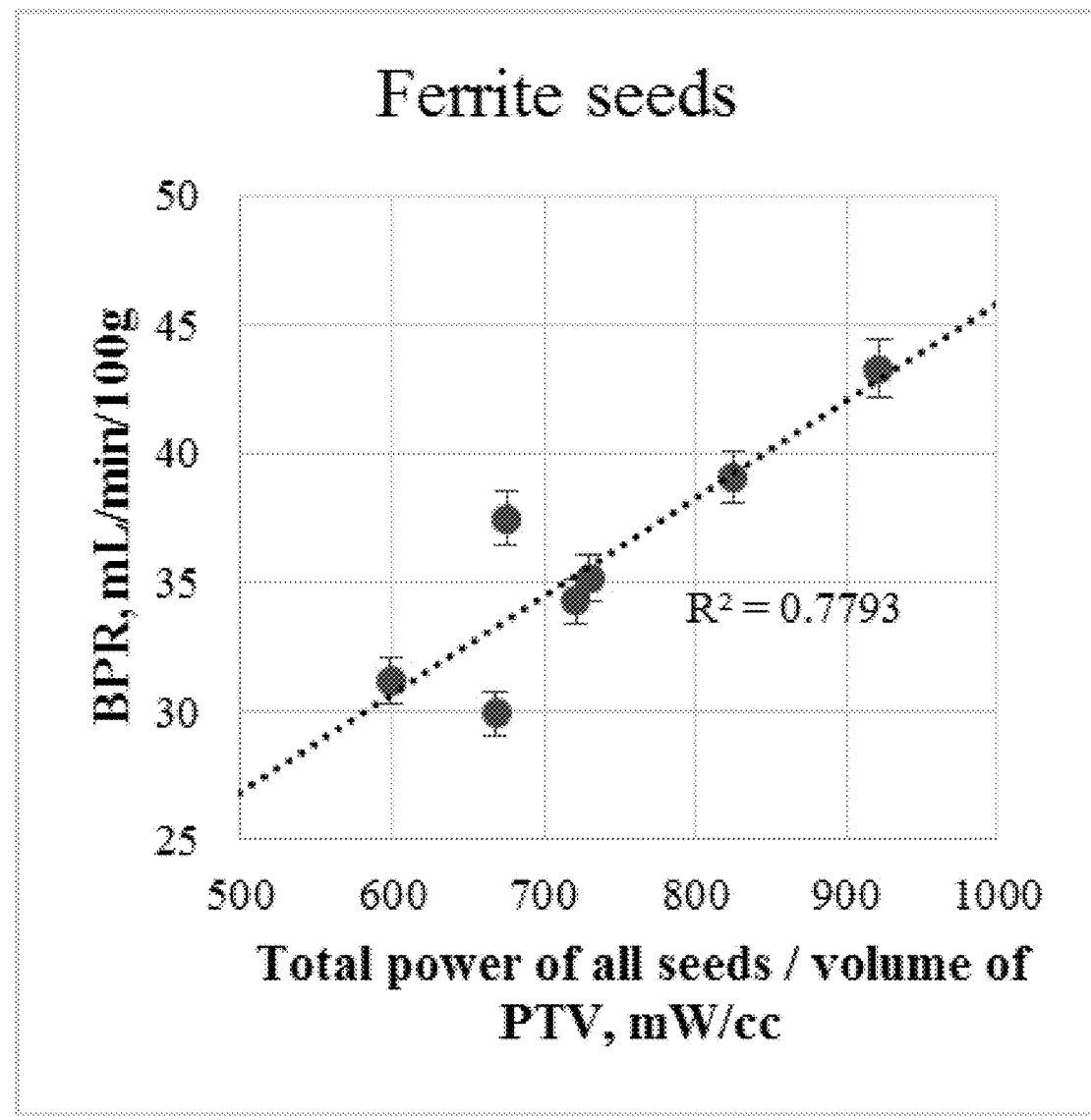

Ferrite/conductive layer seeds were calculated and modeled as generating 200 mW/seed at the reference temperature, calculated for an optimal magnetic field frequency of 10 kA/m amplitude and 50 kHz frequency. (While greater power generation was possible by decreasing the frequency and increasing the amplitude, the lower limit of the magnetic field frequency was kept at 50 kHz, noting the possibility of nerve stimulation at lower frequencies.) The inputted function of power versus temperature was shifted by 6° C. for to obtain a $T_C$ of $\sim 55°$ C. These seeds were found to reach the temperature coverage goal at BPRs ranging from 29.9±0.8 to 43.3±1.1 mL per minute per 100 g. (FIGS. 100A-100B.)

For the results from both NiCu and ferrite seeds, for the seven patient volumes analyzed, a correlation was noted between the maximum BPR that could be overcome to attain the temperature coverage criterion and the total power generation of the seeds at the reference temperature divided by the volume of the PTV. (FIGS. 100A-100B.) As the normalized seed power per unit volume within the defined PTV increases, the maximum manageable BPR also increases. Each data point corresponds to the analyzed patient-specific PTV.

Due largely to ferrite seeds' ability to maintain a higher magnetic relative permeability and therefore higher power before reaching the $T_C$ than the NiCu seeds can, the required power generation per seed at the reference temperature to achieve the temperature coverage goal is greater for the NiCu seeds than for the ferrite seeds. (FIG. 99.) Observation of the power requirements for ferrite for different $T_C$'s indicated the selection of a $T_C$ of 55° C. to bring the maximum BRR to $\sim 30$ mL/min/100 g for the patient cohort.

The arrangement of 41 PdCo seeds was found to achieve the defined temperature coverage criterion at 25.0±0.8 mL per minute per 100 g for a $T_C$ of 55° C., and 32.1±0.9 mL per minute per 100 g for a $T_C$ of 60° C.

Variation of the meshing density of a single 2 mm-diameter blood vessel going through the center of the target was found to change the computed fraction of the PTV receiving 42° C. by <0.5% over the specified range. As there was no particular trend in the coverage fraction versus meshing density, but solution times increased from $7.9 \times 10^3$ s to $1.3 \times 10^5$ s over the meshing density range, the lowest meshing density ($4.8 \times 10^8$ elements/m$^3$) was used.

A single 2 mm-diameter blood vessel was found to have the greatest impact on temperature coverage of the studied situations, and thus be the close to the worst possible scenario in reduction of temperature coverage of the target. At a BPR of 5 mL per minute per 100 g, the fraction of the PTV receiving 42° C. or greater was reduced from 42° C. with no blood vessel, to 83.6% with a single 2 mm-diameter blood vessel. Two blood vessels separated along the x-axis resulted in coverage by the 42° C. isotemperature line of 83.8%, and two vessels separated along the y-axis, 85.6%.

Figure 92:
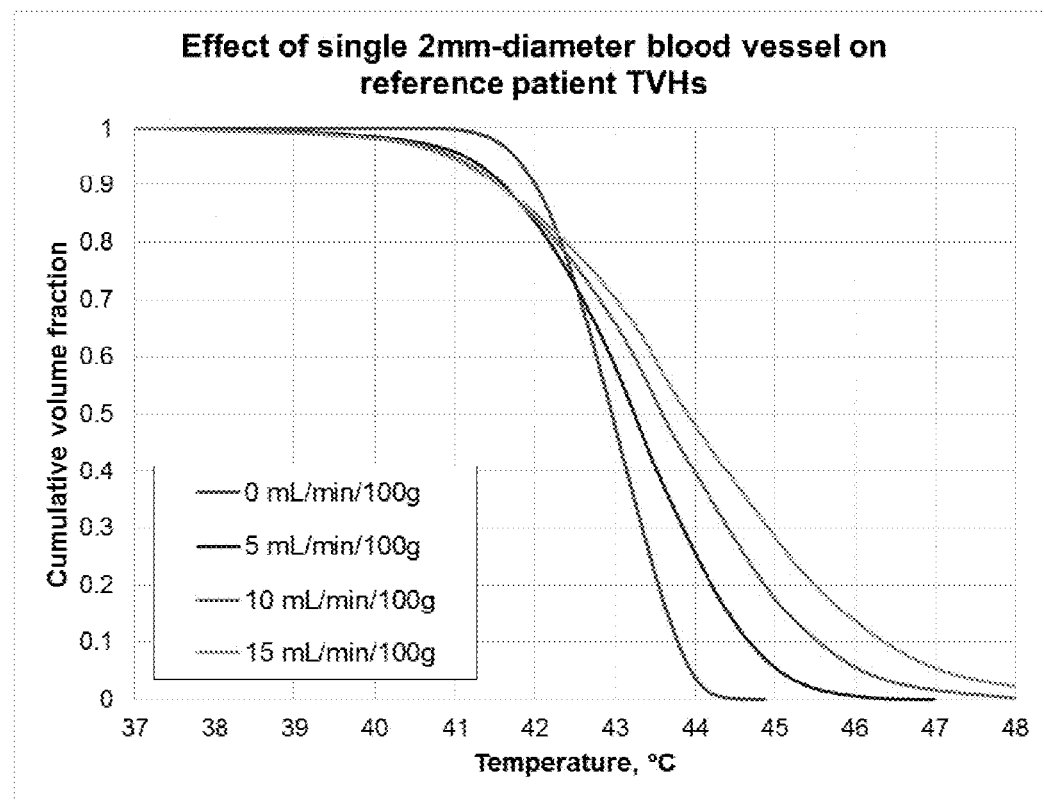
FIG. 92 illustrates the effect on TVHs of a 2 mm-diameter blood vessel travelling through the center of the implant for Patient 1, modeled such that it conveyed all arterial blood perfusing the target region. In all cases, normalized power per seed was set to the values previously empirically found to cover 90% of the PTV with 42° C. or more for the case of uniform blood perfusion.

The effect of a single 2 mm-diameter blood vessel travelling through the center of the implantation array is shown in FIG. 92. As the modeled vessel causes a substantial cold track through the center of the PTV due to its high heat absorption, the resulting TVHs have an intercept with 42° C. at a somewhat lower cumulative volume than they would for a uniform blood perfusion rate.

Quantification of Interseed Effect

Figure 101:
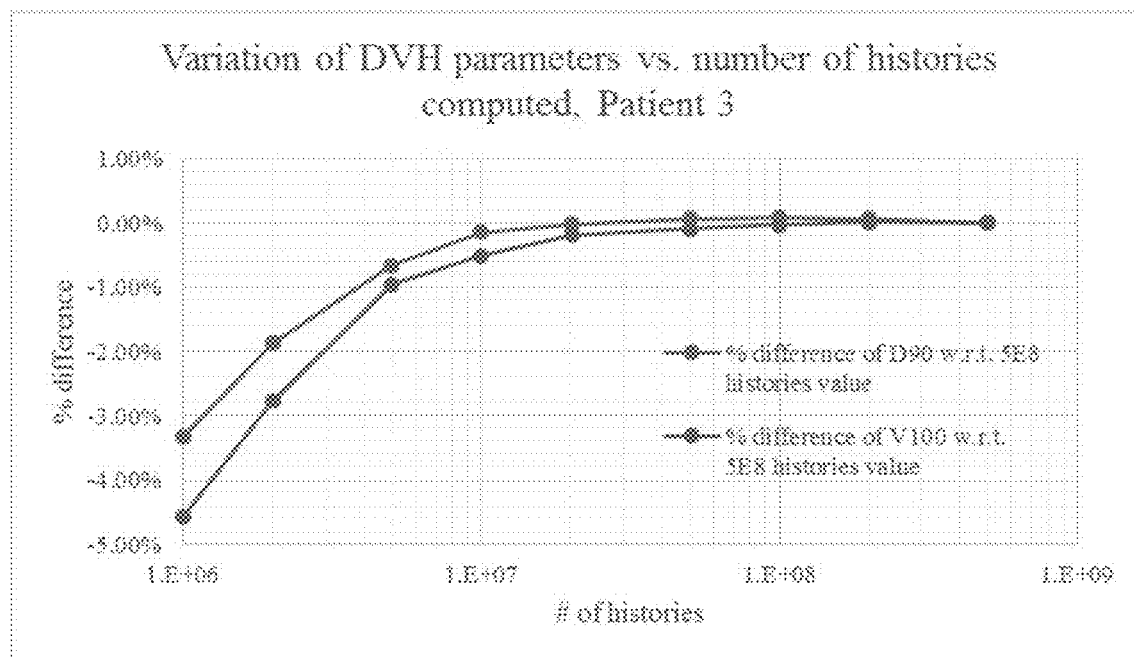
FIG. 101 illustrates the values of $D_{90}$ and $V_{100}$ for DVH computed for the Patient 3 TB+HT-only seeds model, versus number of histories simulated.

For one of the MCNP models used to assess the interseed and scatter (ISA) effect (the model containing TB and HT-only seeds for Patient 3), it was found that using $5 \times 10^6$ histories was sufficient in bringing the values of $D_{90}$ and $V_{100}$ computed for the PTV to within 1% to those found for $5 \times 10^8$ histories, and that using $5 \times 10^7$ histories brought $D_{90}$ and $V_{100}$ to within 0.1%. (FIG. 101.) There was practically no change in $D_{90}$ or $V_{100}$ when more than $5 \times 10^7$ histories were used. Consequently, $5 \times 10^7$ histories were used for the other models in calculating ISA.

Figure 93:
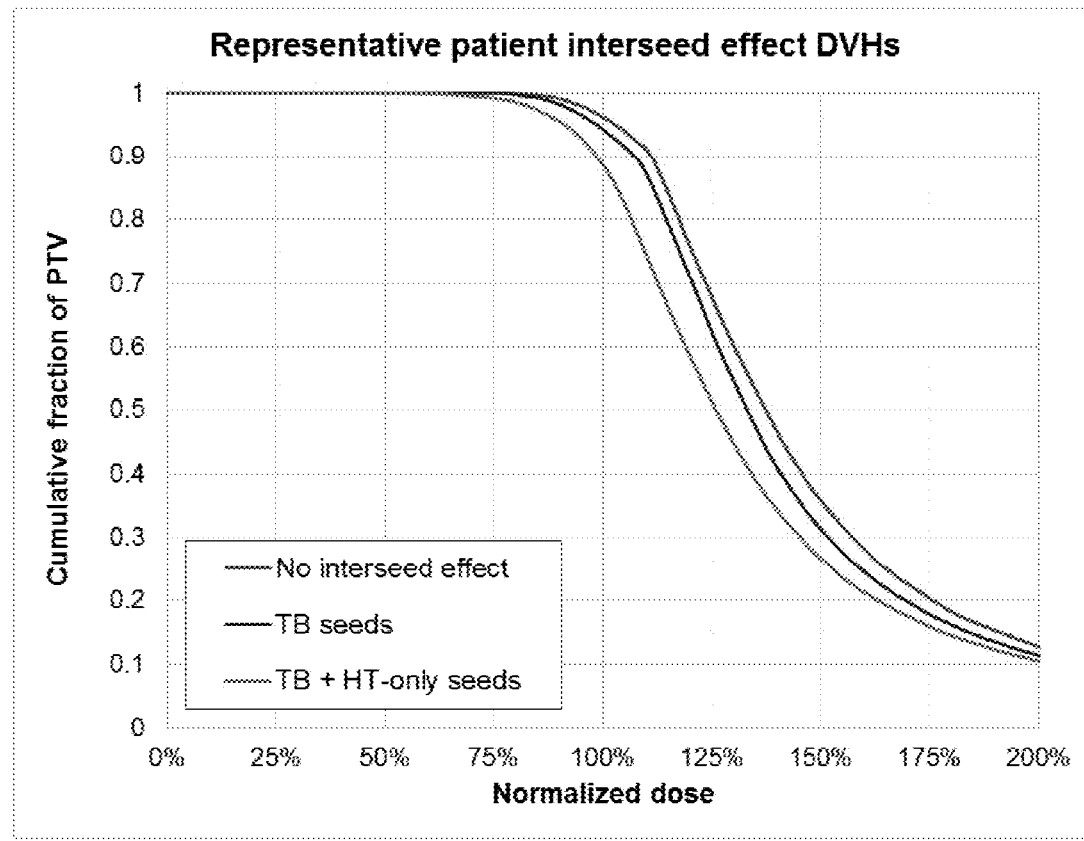
FIG. 93 shows example cumulative dose-volume histograms calculated from MCNP5 for no interseed effect (superposition of the dose distribution for a single seed), the NiCu-core TB seeds only (taking their interseed and scatter effect into account), and the combination of TB and HT-only seeds (taking into account the interseed and scatter effect of both types of seeds).

FIG. 93 depicts DVHs for the PTV of one of the representative patients (Patient 1) implanted with NiCu-core seeds, normalized to the original prescribed dose. Table 54 provides details of the effect of the interseed attenuation and scatter on various TG-137 dose parameters as well. It also tabulates their values after dose renormalization to restore the dose to 90% of the target volume ($D_{90}$) from its value for the TB+HT-only dose distribution to that of the superposition dose distribution. It is noteworthy that this renormalization factor to correct for dose attenuation and scatter by the TB and the HT-only seeds is 1.10-0.02 for the population of 7 patients. Also, it is evident that increasing the dose in the TB+HT-only seed distribution such that its $D_{90}$ matches that of the superposition dose distribution usually increases the dose parameters of the rectum and prostatic urethra by a small amount. The fraction of the PTV receiving 150% of the prescribed dose or more also increases by a small amount (by up to 4.6% of the volume).

Table 54—TG-137 parameters obtained from MCNP5-generated cumulative DVHs, for the population of 7 patients previously treated with BEST 2301 seeds. The modeled TB and HT-only seeds have NiCu cores.

TABLE 54

TG-137 parameters obtained from MCNP5-generated cumulative DVHs, for the opulation of 7 patients previously treated with BEST 2301 seeds. The modeled TB and HT-only seeds have NiCu cores.

| | | Average ± standard deviation | Range |
|---|---|---|---|
| PTV volume | | 43.6 ± 12.2 cc | 27.4-59.9 cc |
| # of TB seeds | | 77.4 ± 11.6 | 64-94 |
| # of HT-only seeds | | 78.6 ± 22.4 | 56-122 |
| Activity per seed | | 0.433 ± 0.023 U | 0.398-0.476 U |
| Renormalization factor for D90 restoration | | 1.103 ± 0.015 | 1.084-1.123 |
| PTV D90 | Superposition | 109.7% ± 6.0% | 101.7%-116.3% |
| (recommended | TB only | 106.8% ± 5.5% | 99.3%-113.2% |
| >100%) | TB + HT-only | 99.4% ± 5.2% | 92.3%-107.3% |
| | TB + HT-only after renormalization | 109.7% ± 6.0% | 101.7%-116.3% |
| PTV V150 | Superposition | 28.5% ± 8.5% | 19.3%-40.4% |
| (recommended | TB only | 25.3% ± 7.5% | 17.2%-36.4% |
| ≤50%) | TB + HT-only | 21.7% ± 6.3% | 15.1%-31.0% |
| | TB + HT-only after renormalization | 31.7% ± 9.6% | 21.7%-45.0% |
| Prostatic urethra | Superposition | 120.6% ± 10.0% | 105.0%-131.6% |
| D30 (recommended | TB only | 118.1% ± 10.0% | 100.8%-126.9% |
| <130%) | TB + HT-only | 112.5% ± 9.1% | 97.0%-122.9% |
| | TB + HT-only after renormalization | 124.0% ± 10.0% | 106.8%-133.6% |
| Prostatic urethra | Superposition | 128.0% ± 14.4% | 111.3%-151.5% |
| D10 (recommended | TB only | 125.8% ± 14.9% | 106.3%-150.8% |
| <150%) | TB + HT-only | 120.1% ± 13.7% | 101.7%-141.0% |
| | TB + HT-only after renormalization | 132.5% ± 15.5% | 112.1%-157.7% |
| Rectum D2 cc | Superposition | 52.5% ± 9.8% | 41.6%-64.8% |
| (recommended | TB only | 51.1% ± 9.6% | 40.3%-64.3% |
| <100%) | TB + HT-only | 48.7% ± 9.0% | 38.0%-62.1% |
| | TB + HT-only after renormalization | 53.8% ± 9.8% | 41.9%-67.3% |
| Rectum D0.1 cc | Superposition | 76.6% ± 13.6% | 60.3%-98.7% |
| (recommended | TB only | 74.6% ± 13.3% | 58.1%-97.2% |
| <150%) | TB + HT-only | 71.5% ± 12.4% | 55.1%-93.1% |
| | TB + HT-only after renormalization | 78.9% ± 13.4% | 60.7%-100.9% |

While the magnitude of the interseed effect was found to be somewhat higher than ~2%, accepted for a typical LDR seed implant, it is still small and can be easily managed through ~10% increase in the activity per seed.

Estimate of the Thermal Enhancement Ratio

Figure 102:
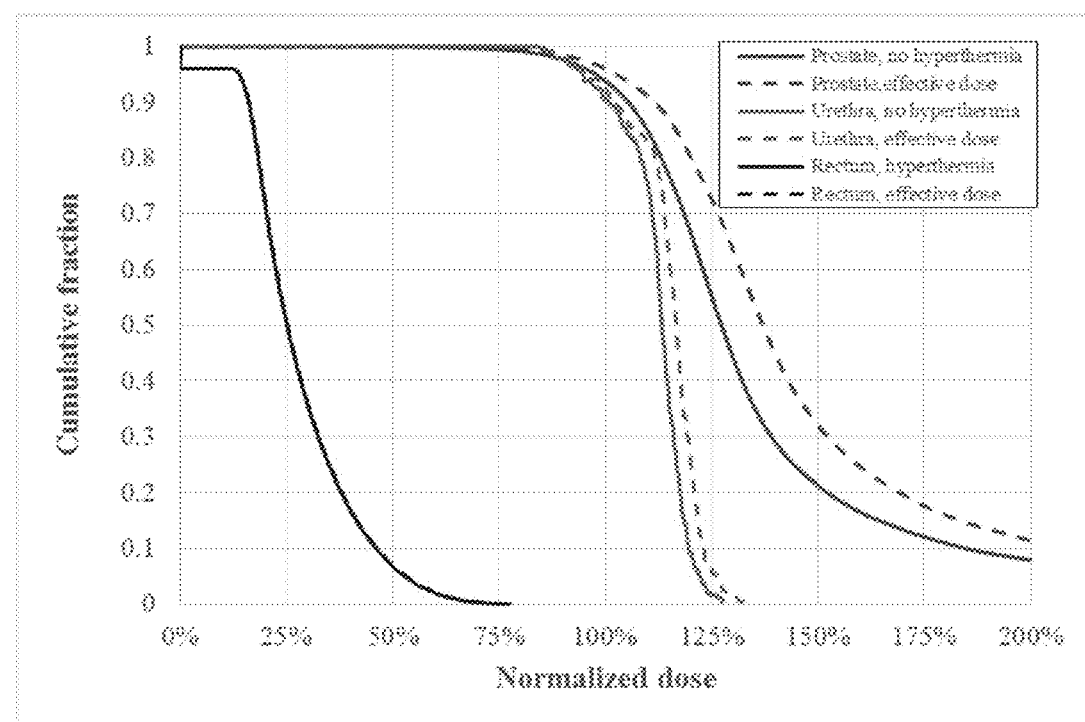
FIG. 102 shows DVHs for no hyperthermia and effective DVHs for radiation and hyperthermia for the prostate, prostatic urethra, and rectum of one of the patients.

Among the three patients for whom thermal dose was assessed, the calculated EUD to the PTV was found to increase by a factor of 1.08 to 1.16 when hyperthermia was added, the EUD of the rectum by a factor of 1.005 to 1.014, and that of the prostatic urethra by 1.02 to 1.06. Thus, hyperthermia was found to provide a higher effective dose escalation to the PTV than to the OARs. FIG. 102 plots the DVHs and effective DVHs calculated for one of the patients (Patient 2). Note that there is almost no difference in plots for the rectum.

Discussion

In this Example, a COMSOL model of ferromagnetic seed heating was successfully validated in a tissue-mimicking ham phantom. The differences between the experimental and computed two-dimensional isothermal lines on the ham surface were mainly due to limitations of the infrared camera. As discussed above, since placing the camera too close to the coil would have caused excessive interference of the magnetic field with the camera's electronics, it was placed at a distance at which each pixel in the IR image corresponds to a ~1 mm$^2$ area on the ham surface. This prevents the resolution of the finest structures in the IR image, as the seeds themselves were 0.9 mm in diameter. Moreover, use of the constant-temperature model for the seeds rather than the power-vs.-temperature model slightly overestimated the temperature of the corner seeds.

Setting the modeled seed surfaces to a constant temperature was a reasonable approximation in COMSOL modeling of the ham phantom experiment, since the condition of interest is thermal equilibrium between the tissue-mimicking phantom and the seeds. If thermal power generation by the seeds is equal to power absorption by the surrounding medium, both attain a constant temperature distribution. This constant-temperature modeling has been found useful, though it gives inaccurate results for the time dependence of temperature near the seeds.

Gamma comparison is an established means of providing a quantitative comparison between a pair of two-dimensional distributions that may not be of the same resolution.

Therefore, the results of comparison between the two halves of FIG. 87 are satisfactory, thus validating the COMSOL model.

It had been previously determined that use of only TB seeds in place of the original LDR brachytherapy seeds did not result in a uniform temperature distribution in the realistic plan-derived seed positioning pattern. This was due not only to the rapid drop-off of temperature with distance from a seed, but also because of the limitations in TB seed power production as a result of their small ferromagnetic core size and the safety limit on magnetic field parameters (field strength and frequency) used in the pelvis. Without wishing to be bound by theory, it is believed that the product of magnetic field amplitude and frequency should remain below $4\text{-}5 \times 10^8$ A/m·s for patient safety purposes. Hence, a product of amplitude and frequency no higher than $5 \times 10^8$ A/m·s was used in the evaluations of patient-specific seed distributions. However, use of HT-only seeds in unused needle positions was found to greatly improve the power production and temperature uniformity.

As the standard TB and HT-only seeds were found to overcome only a relatively low rate of blood perfusion of ~5 mL per minute per 100 g, it was considered desirable to further modify the TB and hypothermia-only seeds to permit adequate coverage compensating for higher rates of blood perfusion, of 15 mL per minute per 100 g or greater. Therefore, the power production needed per seed and reductions in power requirements of increasing the Curie temperature were analyzed. While increasing the Curie temperature over the range investigated would moderately increase the HC, the variation in HC over the range of blood perfusion rates examined is much greater than that induced by Curie temperature adjustment. For the effect of a large blood vessel on the temperature coverage, no Curie temperature shifts were used for the modeled seeds. The volume of the PTV reaching 42° C. was found to be decreased by up to 6.3% over the blood perfusion range of 0-15 mL per minute per 100 g, while the temperature covering 90% of the PTV decreased by up to 0.5° C. This loss of coverage may be overcome by a moderate increase in seed power production.

The variation of temperature coverage with meshing density of the modeled discrete blood vessel was considered to arise from expected errors in the converged solutions. The tolerance of the computed temperature, $\Delta T/T$, was set to remain under 0.001, and COMSOL's internal unit of temperature is the Kelvin; at 42° C.=315 K, the estimated error may be as high as $\Delta T = 315 \text{ K} \times 0.001 = 0.3°$ C. The calculated temperature covering 90% of the volume of the PTV varied by less than 0.03° C. over the entire range of studied mesh densities, well within the maximum error permitted by the solver for the entire problem.

A 2 mm-diameter vessel as considered in this Example is large for an artery supplying the prostate; an in vivo study previously conducted of prostate vasculature in men with benign prostate hyperplasia measured prostatic artery diameters among 75 patients as 1.6±0.3 mm. The actual thermal coverage of a given PTV due to the effects of blood flow within the target tissue is thus considered to lie between the best possible scenario of uniform, isotropic blood perfusion (no cold spots induced by large blood vessels) and the worst possible scenario of a relatively large blood vessel creating a substantial low-temperature track through the target.

Although COMSOL has the ability to directly model the eddy currents generated in the seeds by the oscillating magnetic field, and the consequent Joule heating, doing so with the number of seeds used in a patient and with a sufficiently high finite element meshing density was found to result in models that took an excessive length of time to calculate, or could not be calculated at all due to their excessive RAM requirements. For the case of a patient-specific implant of 150 seeds, it is estimated from smaller models that such direct numerical calculation would have resulted in a model requiring ~120 GB of RAM and taking more than a week to compute. This remained so even with optimizations in the model to simplify the geometry and to decrease the meshing density in non-critical areas, as well as with use of different solver algorithms. To overcome this limitation, a temperature-dependent power function was defined. This approach proved vastly more efficient: models used ~4 GB of RAM and reached converged solutions in ~1 hour.

In the NiCu-based TB and HT-only seeds, the weighted average power production at a 100 kHz frequency, 5 kA/m amplitude oscillating magnetic field was ~50 mW per seed, or ~100 mW/cm. (Both the TB and HT-only seeds were 0.5 cm long.) It has been reported that for seed spacing typically used in interstitial ferromagnetic seed hyperthermia, ~200 mW/cm is sufficient for many clinical applications; this requirement is more than met by the ferrite-based seed core, which is calculated to generate ~400 mW/cm if properly implemented. However, this assessment may not have correctly estimated the blood perfusion rate, particularly in the tendency of tissue to dramatically increase its blood perfusion rate in response to heat.

It has been found that while regional hyperthermia delivered with external phased microwave applicators raised the blood perfusion rate by a factor of ~1.5 by the end of the hyperthermia treatment, hyperthermia delivered by high-frequency interstitial electrodes raised the blood perfusion rate by a factor of ~4.5. In both cases, the achieved temperature in 50% of the prostate was calculated to be typically 41-42° C. Without wishing to be bound by theory, it is believed that the difference in increase in blood perfusion is thought to be primarily due to the "steal effect": as thermal energy is deposited in tissues surrounding the target region, the body attempts to reduce their elevated temperatures. Since cooling is done by increasing the blood perfusion in these areas, less blood is available to the target region, whose perfusion correspondingly increases by a lesser degree than it would otherwise.

Ferromagnetic seed hyperthermia is similar to regional hyperthermia in that most power deposited in the patient is delivered to tissues outside the target area, due to currents induced in the patient's tissues by the oscillating field. It can be calculated from the inductive heating of the patient's tissues, with a magnetic relative permeability of 1, an effective patient conductivity of 0.4 S/m, an average patient radius of 0.15 m, a length of the patient within the external coil of 0.65 m, and magnetic field parameters 5 kA/m amplitude and 100 kHz frequency, that a total estimated power absorption within the tissues enclosed by the external magnetic coil is ~400 W. Taking the same dimensions of the treated region, and assuming the patient has an average density equal to that of water, yields an average specific absorption rate (SAR) of ~9 W/kg. This is of the same order as SAR in regional microwave hyperthermia. By comparison, the power generated by an implantation of 100 TB and HT-only seeds of average power production 100 mW each is 10 W. (This is why no metabolic heat source was modeled as in the full form of the Pennes' bioheat equation, since it is considered insignificant compared to the other heat source and sink terms. In a 30 cc prostate with a metabolic heat production rate of 700 W/m³ for glandular tissue, the metabolic heat generation rate within the entire prostate volume is only 21 mW.) Temperatures are higher in the target region than in the surrounding tissues due to the substantially higher SAR due to the seeds. Taking a typical prostate mass of 30 g, the volume-averaged SAR within the prostate due to the seeds is ~300 W/kg. To put these figures into perspective, the FDA requires medical supervision of the patient if SAR due to RF power deposition within the patient in magnetic resonance studies is expected to exceed 2 W/kg.

Figure 94:
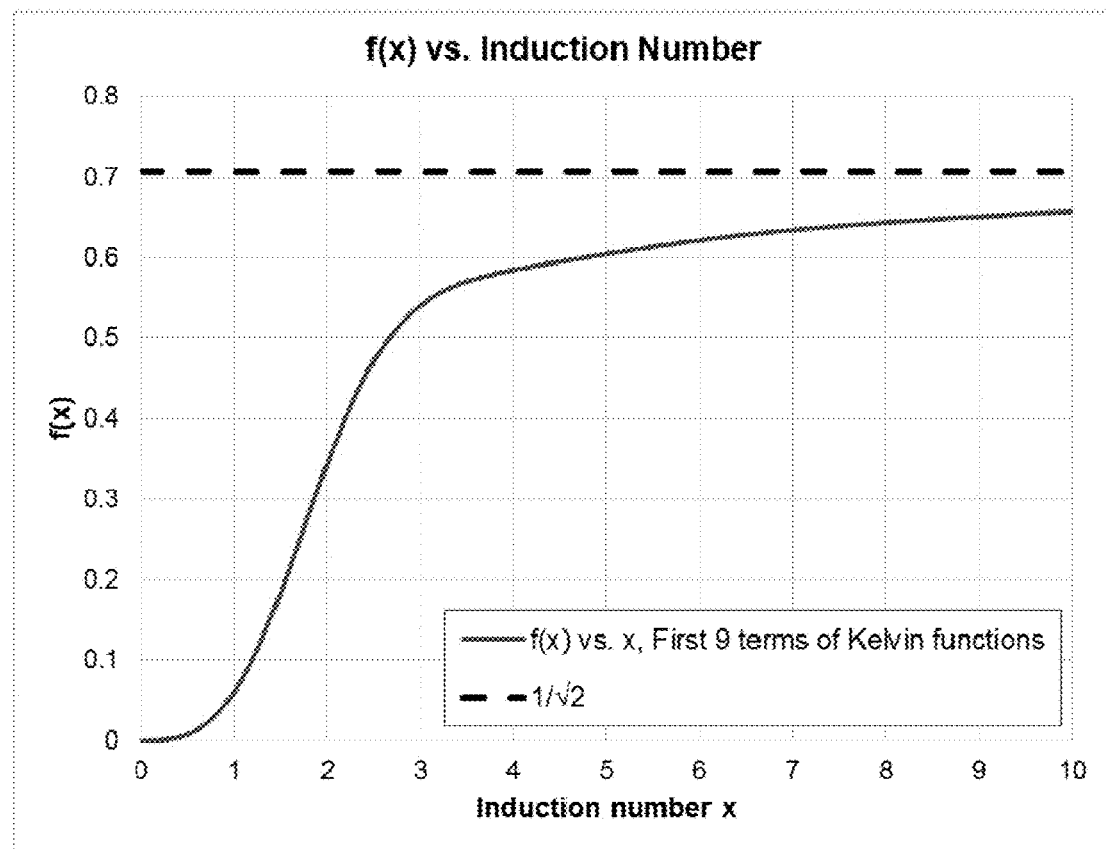
FIG. 94 illustrates f(x) versus induction number x, calculated based on first-order Kelvin functions. For very high induction numbers, $f(x) \approx 1/\sqrt{2}$, but f(x) is approximately linear for a range of small induction numbers.

For the relatively small seed cores described in this Example, the induction number x mainly occurs in the rapidly increasing region off(x), as illustrated in FIG. 94. Note that only a few terms of the Kelvin functions are necessary to calculate f(x) for all induction numbers likely to be encountered. For the TB and HT-only seeds the calculated induction number varies from ~0.3-3.0, i.e., primarily in the nearly linear portion of f(x). While one cannot use a constant to approximate f(x) in this case (for high induction numbers, f(x)≈1/√2), a nearly linear shape of f(x) in this range of induction numbers indicates that for small induction numbers:

$$P(T) \sim R^2 l \mu \omega H_0^2 \tag{34}$$

This relation gives a sense of what properties of the seed should be adjusted to increase its heating capacity. Seed core conductivity $\sigma$ cancels out in this domain of induction numbers, but magnetic relative permeability $\mu_r$ is nearly linear with power for the TB seed. This indicates that improvements in the effective magnetic permeability would have a greater effect on the heating power of the TB seed than for seeds with large induction numbers, whose power production goes approximately as $\sqrt{(\mu/\sigma)}$. Moreover, the gradient of $\mu$ with temperature (rate of decrease in magnetic permeability near the Curie point) results in a higher power gradient with temperature for the small TB seeds than for larger seeds, improving the ability of the seeds to self-regulate at a set temperature.

In the reference design for the TB and HT-only seeds presented in this Example, the weighted average power production at a 100 kHz frequency, 5 kA/m amplitude oscillating magnetic field is ~50 mW per seed, or ~100 mW/cm. (Both the TB and HT-only seeds are 0.5 cm long.) For seed spacing typically used in interstitial ferromagnetic seed hyperthermia, ~200 mW/cm is sufficient for many clinical applications. However, this assessment may not have correctly estimated the blood perfusion rate, particularly in the tendency of tissue to dramatically increase its blood perfusion rate in response to heat.

The prostatic blood perfusion in prostate cancer patients has been measured before and at the end of interstitial and regional hyperthermia treatments, and it was found from doing so that while regional hyperthermia delivered with external phased microwave applicators raised the blood perfusion rate by a factor of ~1.5 by the end of the hyperthermia treatment, hyperthermia delivered by high-frequency interstitial electrodes raised the blood perfusion rate by a factor of ~4.5. In both cases, the achieved temperature in 50% of the prostate was calculated to be typically 41-42° C. The difference in increase in blood perfusion is thought to be primarily due to the "steal effect:" as thermal energy is deposited in tissues surrounding the target region, the body attempts to reduce their elevated temperatures. Since cooling is done by increasing the blood perfusion in these areas, less blood is available to the target region, whose perfusion correspondingly increases by a lesser degree than it would otherwise. In the regional hyperthermia treatments delivered in one test, substantially more total power was delivered to surrounding tissues than to the target area; by contrast, in the application of interstitial hyperthermia, almost all of the power was delivered to the region enclosed by the interstitial electrodes.

Without wishing to be bound by theory, it is believed that ferromagnetic seed hyperthermia is similar to regional hyperthermia in that most power deposited in the patient is delivered to tissues outside the target area, due to currents induced in the patient's tissues by the oscillating field. Inductive heating of the patient's tissues with a magnetic relative permeability of 1, an effective patient conductivity of 0.4 S/m, an average patient radius of 0.15 m, a length of the patient within the external coil of 0.65 m, and magnetic field parameters 5 kA/m amplitude and 100 kHz frequency, results in a total estimated power absorption within the tissues enclosed by the external magnetic coil of ~400 W. Taking the same dimensions of the treated region and assuming the patient has an average density equal to that of water yields an average specific absorption rate (SAR) of ~9 W/kg. This is of the same order as SAR in regional microwave hyperthermia. By comparison, the power generated by an implantation of 100 TB and HT-only seeds of average power production 100 mW each is 10 W. (This is why no metabolic heat source was modeled as in the full form of the Pennes' bioheat equation, since it is considered insignificant compared to the other heat source and sink terms. In a 30 cc prostate with a metabolic heat production rate of 700 W/m³ for glandular tissue, the metabolic heat generation rate within the entire prostate volume is only 21 mW.) Temperatures are higher in the target region than in the surrounding tissues due to the substantially higher SAR due to the seeds: taking a typical prostate mass of 30 g, the volume-averaged SAR within the prostate due to the seeds is ~300 W/kg. To put these figures into perspective, the FDA requires medical supervision of the patient if SAR due to RF power deposition within the patient in magnetic resonance studies is expected to exceed 2 W/kg.

If one assumes a typical value of 15 mL/min/100 g for the resting blood perfusion rate of the prostate, and estimates a perfusion enhancement factor due to ferromagnetic seed hyperthermia and the steal effect of ~2, the average blood perfusion rate one may expect to see at equilibrium in this treatment is ~30 mL/min/100 g. Referring to FIG. 91, for NiCu cores this blood perfusion rate may be overcome to achieve the goal of temperature coverage for TB and HT-only seeds with a Curie temperature of ~59° C. and a normalized power production of ~200 mW/seed (~400 mW/cm). As a Curie temperature of 59° C. may be too high for hyperthermia, these parameters may be reduced by the use of a core material with a more rapid Curie transition, which would maintain a higher magnetic relative permeability while approaching the Curie temperature, rather than more gradually approaching 1.

For the case of a distribution of TB and HT-only seeds, the ISA effect was found to reduce $D_{90}$ by a factor of 1.10±0.02. This indicates that increasing the dose by a factor of 1.1 over that predicted by superposition-type calculations (e.g., TG-43 formalism) is a good correction for the scatter and attenuation produced by both types of seeds. In clinical practice, this correction may be done, for example, by using TG-43 dosimetry in planning to a prescription isodose line 1.1 times the actual desired prescription, knowing that the ISA effect will reduce the planned dose to the prescription dose. It should also be kept in mind that this correction for ISA has the tendency of increasing prostatic urethra and rectum doses slightly above what would be expected for the case of superposition-type dose calculation with no ISA effect. For these reasons, extra care should be taken in planning to ensure the dose metrics for the organs at risk remain below the values recommended in TG-137.

Figure 91B:
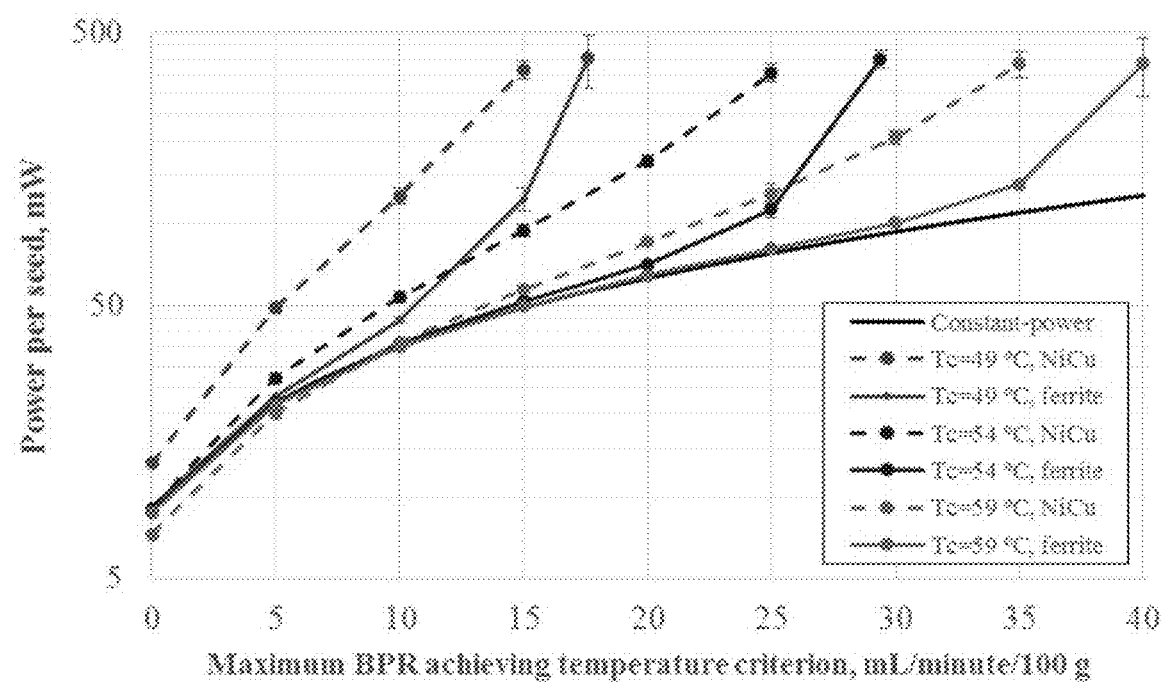
FIG. 91B shows the same for NiCu and ferrite seeds.

As discussed above, magnesium ferrite seed cores demonstrate superior magnetic relative permeability and power gradients compared to NiCu cores, a feature reflected by their decreased power requirements, as illustrated in FIG. 91B. However, since ferrites are practically non-conductive, they should be surrounded by a conductive layer of the proper resistance to support eddy currents. Applied to the TB and HT-only seeds described in this Example, this conductive layer may consist of an electroplated metal layer, for example gold or copper, of thickness ~15 m.

To obtain an estimate for seed power production as a function of temperature for the TB and HT-only seed designs, the following theoretical power production equation was used:

$$P(T) = \pi R l \sqrt{\frac{\mu_r(T, H_0, \gamma)\mu_0 \omega}{\sigma}} f(x) H_0^2 \qquad (35)$$

Here, R and l are the radius and length of the seed core, respectively, $\sigma$ is its electrical conductivity, and $\omega$ and $H_0$ are the angular frequency and amplitude of the applied magnetic field, respectively. $\mu_r$ is the effective magnetic permeability of the core as a function of temperature T, magnetic field amplitude, and aspect ratio $\gamma=l/2R$, while $\mu_0$ is the permeability of free space. The function $f(x)$ includes Kelvin functions of the induction number x, $$f(x) = \frac{ber(x)ber'(x) + bei(x)bei'(x)}{ber^2(x) + bei^2(x)} \qquad (36)$$

$$x = R\sqrt{\mu_r(T, H_0, \gamma)\mu_0 \omega \sigma} \qquad (37)$$

The functions ber(x) and bei(x) are Kelvin functions of order zero, while ber(x) and bei(x) are their first derivatives with respect to x. It should be noted that the magnetic permeability of the seed core in question depends not only on the material used and the temperature, but also on the magnetic field parameters and the geometry of the core. In particular, when an external magnetic field magnetizes a finite sample, the aligned domains themselves produce a magnetic field that opposes the applied field, an effect known as demagnetization. The total field within the core is then found as the difference between the external applied field and the demagnetizing field. A common way of accounting for this effect is to use a demagnetizing factor to calculate an effective magnetic permeability. For the TB and HT-only seeds, the aspect ratios $\gamma$ of the cores, defined as the length divided by the diameter, were 10.3 and 7.6, respectively, considered large enough to use the above approximation of infinite length in calculating the power production, provided demagnetization is taken into account.

The approximation of an arctangent fit for magnetic relative permeability $\mu_r$ of a soft ferromagnetic material as a function of effective magnetic field H was used:

$$\mu_r(H) = \left\{\left(\frac{A}{H}\right)\arctan\left(\frac{H}{C}\right)\right\} + 1 \qquad (38)$$

A and C are fitting parameters, related to saturation magnetization $M_{sat}=\pi A/2$ and to magnetic relative permeability in the limit of magnetic field approaching zero $\mu_r$, low field=(A/C)+1. A and C used in subsequent calculations were obtained from previous data.

Rather than using $\mu_r$ calculated for the amplitude or rootmean-squared value of the magnetic field as done by others, a time-averaged value was calculated in a spreadsheet. To do this, magnetic field as a function of time was modeled as a sine function, producing a time-averaged $\mu_r$ calculated over one-quarter cycle of the magnetic field function $$\mu_r(H) = 1 + \frac{\int_{s=0}^{s=\pi/2} [\mu_r(H(s)) - 1]ds}{\pi/2} \qquad (39)$$

$$H(s) = H_0 \sin(s) \qquad (40)$$

$$ds = \frac{\sec(s)}{H_0}dH \qquad (41)$$

$H_0$ is the amplitude of the magnetic field, s is the product of angular frequency and time $\omega t$, and ds is its derivative. ($\mu_r-1$ is used rather than $\mu_r$ so that magnetic susceptibility $\chi m$ may be used.) Replacing the integral with a summation, one may obtain:

$$\mu_r(T, H_0, \gamma) = 1 + \frac{2}{\pi H_0}\sum_{i=0}^{N-1}[\mu_{r,i,temp,demag}(T, H_i, \gamma) - 1] \qquad (42)$$

$$\times \sec\left(\arcsin\left(\frac{H_i}{H_0}\right)\right)\Delta H = 1 + \frac{2}{\pi}\sum_{i=0}^{N-1} \qquad (43)$$

$$\times [\mu_{r,i,temp,demag}(T, H_i, \gamma) - 1]\sqrt{\frac{1}{N^2 - i^2}} \qquad (44)$$

Here i is an index running from 0 to a large integer N, which is chosen to be large enough that $\Delta H=H_0/N$ is small enough to be nearly infinitesimal. (For the spreadsheet, 1000 was used for N.) $H_i$ is the value of magnetic field at step i, while $\mu_{r,i,\ temp,\ demag}(T,H_i,\gamma)$ is the magnetic relative permeability at step i, accounting for the effects of temperature and demagnetization on the alloy. To obtain the latter value, magnetic relative permeability at step i, $\mu_r$, i, was calculated according to Equation (44) for magnetic field $H_i$, multiplying by normalized data points for permeability as a function of temperature for NiCu, normalized to 1 at room temperature. The thus-calculated temperature-corrected magnetic relative permeability $\mu_{r,i,temp}$ was corrected for the effects of demagnetization within the alloy as a result of having been magnetized, using the method of a demagnetization factor $N_M$, $$\frac{1}{\mu_{r,i,temp,demag} - 1} = \frac{1}{\mu_{r,i,temp} - 1} + N_M(\gamma, \mu_{r,i,temp}) \quad (45)$$

Magnetometric demagnetization factors for cylinders were taken from prior work. A further explanation of the demagnetization effect is given above.

Finally, a term for eddy current generation within the titanium shell of the TB and HT-only seeds was considered. The approximate power generation due to this source was:

$$P(T) = \frac{\{X_L(T)/H_0\}^2}{2R_S\left[1 + \frac{X_L^2(T)}{R_S^2}\right]} \quad (46)$$

Here $X_L(T)$ is the inductive reactance of the core as a function of temperature and $R_S$ is the sheath resistance.

$$X_L(T) = \frac{\pi r_{core}^2 \mu_r(T, H_0, \gamma)\mu_0 \omega}{l} \quad (47)$$

$$R_S = \frac{2\pi r_{sheath}}{\sigma_{sheath} t_{sheath} l} \quad (48)$$

As before, $\mu_r(T,H_0,\gamma)$ is the magnetic relative permeability of the core material, $\omega$ is the angular frequency of the magnetic field, l is the length of the seed, and $H_0$ is the magnetic field amplitude. Also, $r_{core}$ and $r_{sheath}$ are the outer radius of the core and the average radius of the sheath (assuming a thin sheath), respectively, $\sigma_{sheath}$ is the electrical conductivity of the sheath, and $t_{sheath}$ is the sheath thickness.

With both terms of power generation computed for each type of seed, total theoretical power generation as a function of temperature was fitted to an exponential of a third-order polynomial. This function was later entered in the FEA model.

Conclusions

Experimental and computational analysis was used to quantitatively examine the ability of thermobrachytherapy seeds to deliver hyperthermia of an acceptable quality to deep-seated solid tumors, specifically carcinoma of the prostate. The baseline design and improved designs of the dual-modality and hyperthermia-only seeds, based on standard LDR permanent implant brachytherapy seeds modified accordingly, were analyzed to find expected temperature distributions from realistic patient-specific implants, as well as to quantify the radiation interseed and scatter effect. A combination of increasing the seeds' Curie temperature, improving their power production, and increasing the gradient of the Curie transition may be used to greatly increase the blood perfusion rate that may be overcome to produce a sufficient temperature distribution. Use of a combination of dual-modality seeds (for example, ferrite core seeds at the correct Curie temperature and with an optimized conductive layer sheath) in a typical modified peripheral loading design and additional hyperthermia-only seeds is capable of producing a uniform temperature distribution for blood perfusion rates greater than 30 mL of blood per minute per 100 g of tissue. Moreover, the increased interseed effect caused by radioactively-inert hyperthermia-only seeds in the target tissue results in only a small change in dose to critical organs, provided their additional radiation attenuation is properly taken into account during planning. The seeds provide a practical means of concurrent radiation and hyperthermia in a challenging target for hyperthermia.

From this Example, it is seen that TB seeds that are ferrite-core seeds of a Curie temperature of ~55° C., with a properly-optimized conducting layer, are sufficient in generating adequate and uniform temperature distributions. Lower Curie temperatures may result in insufficient heating at high blood perfusion rates. Hyperthermia treatments should be delivered, in a sample regimen, at a rate of two treatments per week for the first month after seed implantation, to take advantage of the relatively high decay rate of the radioactive material shortly after the implantation. In the same vein, $^{103}$Pd should be considered against $^{125}$I, as the former has a much lower half-life and delivers most of its dose in the first month after implantation, thereby achieving a higher thermal enhancement ratio.

A plan consisting of TB seeds should be generated in a treatment planning software, just as would be done with ordinary prostate permanent implant seeds. However, this plan should be to a prescription dose 10% higher than the actual intended dose; this properly accounts for the ISA effect from the TB and HT-only seeds. During the planning process, the ratio of the total seed power generation to the volume of the PTV should be computed as a check that the seed distribution may attain acceptable temperatures despite potentially high blood perfusion rates. HT-only seeds should be placed in as many vacant locations as possible within the needles used to implant the TB seeds to cover the entire length of the target; an extra need should not be used unless there exists a large gap in the implant design likely to result in a significant cold spot.

To avoid overheating the prostatic urethra, seeds should not be placed too close to it. As the drop-off of temperature from the seed surface is much more rapid than the radiation drop-off, following the guidelines for prostate permanent implant brachytherapy that advise against placing seeds within 0.5 cm of the urethra, applied to the TB and HT-only seeds, suffices.

Due to the overall increase in D30 and D10 of the prostatic urethra over superposition-calculated dose by ~3% after the ISA effect and dose renormalization, as well as thermal enhancement of the prostatic urethra, extra care should be taken to ensure that the dose parameters specified in TG-137 are not violated by the addition of hyperthermia.

Finally, the actual blood perfusion rate and temperatures attained within the prostate during TB seed hyperthermia sessions should be measured, in order to verify the hyperthermia treatments are safe and effective.

Example III

Figure 103:
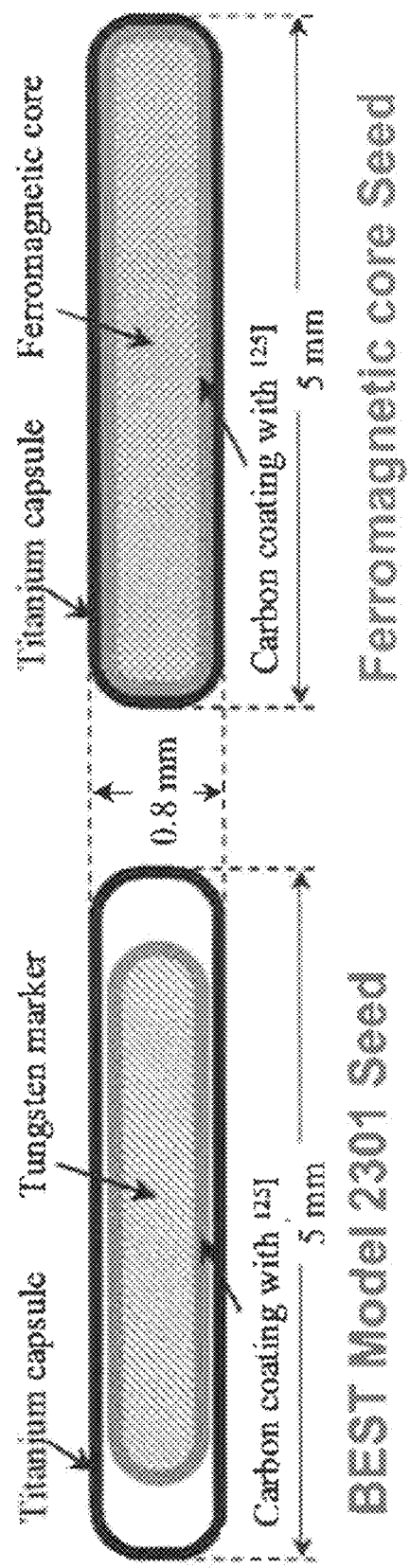
FIG. 103 shows schematics of the BEST Model 2301 seed and the TB seed described in Example III herein. The electroplated layer on the surface of the ferromagnetic core is not depicted.

TB and HT-only seeds were modified versions of the BEST Model 201 seed, which consists of a cylindrical tungsten radiographic marker surrounded by a $^{125}$I-impregnated graphite coating, sealed within a titanium shell. For the TB seed, the tungsten marker was replaced with a ferrite core electroplated with a metal (gold, for example) to support eddy current generation (FIG. 103.) The HT-only seed was of the same design, except that the ferrite core took up the entire interior space of the titanium shell to generate more power, as it does not need to contain the radioactive layer.

To assess the target coverage and temperatures reached by organs at risk during hyperthermia treatments, the seed distributions of six patients who had been treated with ordinary LDR brachytherapy seeds were reproduced in the finite element analysis program COMSOL Multiphysics version 5.2, replacing the standard seeds with TB seeds. HT-only seeds were modeled as occupying empty spots within the needles used to implant the seeds. Seed distributions thus assumed that no additional implantation needles would be used in a thermo-brachytherapy implant that would not have been used in a typical LDR implant.

Figure 104:
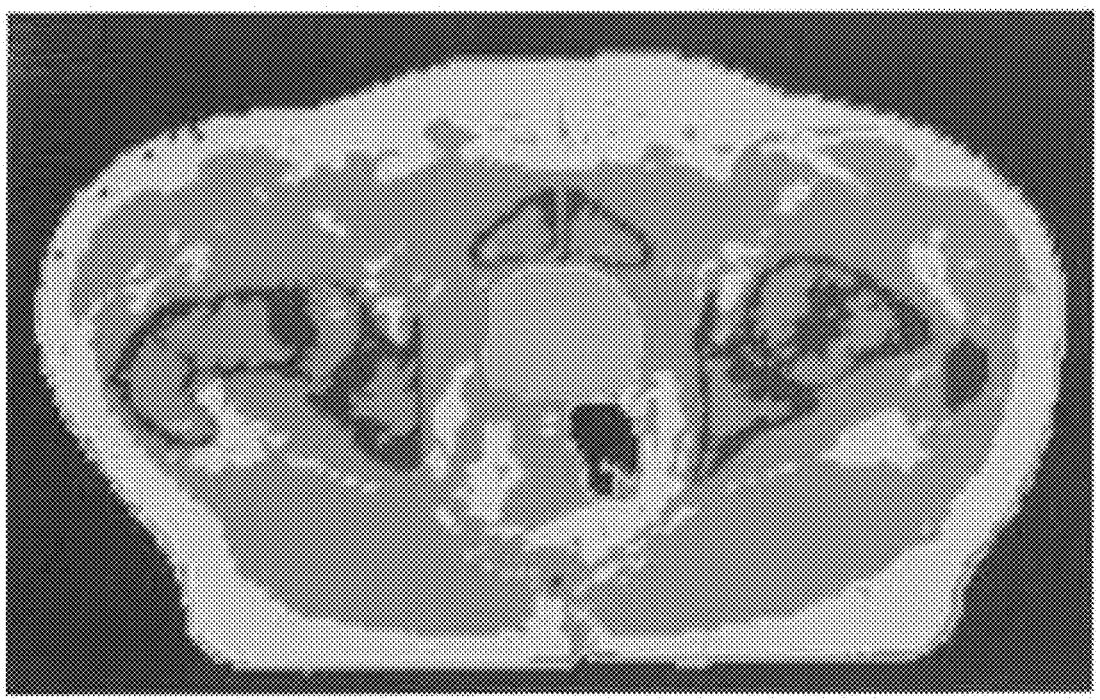
FIG. 104 is an example digitized transverse CT slice imported into COMSOL. The various colors indicate different assigned material types (Table 55). Note that various material types immediately adjacent to the prostate, perturbing the temperature distribution from that of uniform anatomy. For the case of uniform, homogeneous anatomy, the thermophysical properties of the prostate (light blue) were applied to the entire problem geometry. The seed distribution is not depicted in this image.

In addition, patient anatomy was incorporated into the model by importing the patient-specific implantation CT scans. These were used to specify regions of the anatomy as glandular, adipose, muscle, or bone tissue, as well as urine within the bladder and air (FIG. 104). These regions were set to have tissue-specific biophysical properties, including blood perfusion rate, density, thermal conductivity, and heat capacity. Values for these properties were taken from the literature (Table 55). Temperature distributions from these heterogeneous models were compared with those of uniform anatomy, and temperature-volume histograms, analogous to radiation dose-volume histograms, were computed via in-house software.

Table 55—Modeled thermophysical properties of tissues, as inputted into COMSOL. Note the high rate of blood perfusion in the prostate (glandular tissue).

TABLE 55

Modeled thermophysical properties of tissues, as inputted into COMSOL.

| Tissue/non-tissue material | Blood perfusion rate, mL/min/100 g | Density, g/cc | Thermal conductivity, W/m · K | Heat capacity, J/kg · K |
|---|---|---|---|---|
| Glandular tissue | 30 | 1.045 | 0.51 | 3760 |
| Adipose tissue | 21 | 0.911 | 0.21 | 2348 |
| Muscle tissue | 10 | 1.090 | 0.49 | 3421 |
| Bone | 7.4 | 1.908 | 0.32 | 1313 |
| Blood | N/A | 1.060 | N/A | 3400 |
| Air | N/A | $1.160 \times 10^{-3}$ | 0.027 | 1004 |
| Urine (in bladder) | N/A | 1.060 | 0.60 | 4200 |

Note the high rate of blood perfusion in the prostate (glandular tissue).

The radiation interseed and scatter (ISA) effect was evaluated by the superposition method in the Monte Carlo software package MCNP5. Dose distributions were calculated for no interseed effect, the ISA of the TB seeds alone, and the ISA for both TB and HT-only seeds for the collection of patients.

Results

Figure 105:
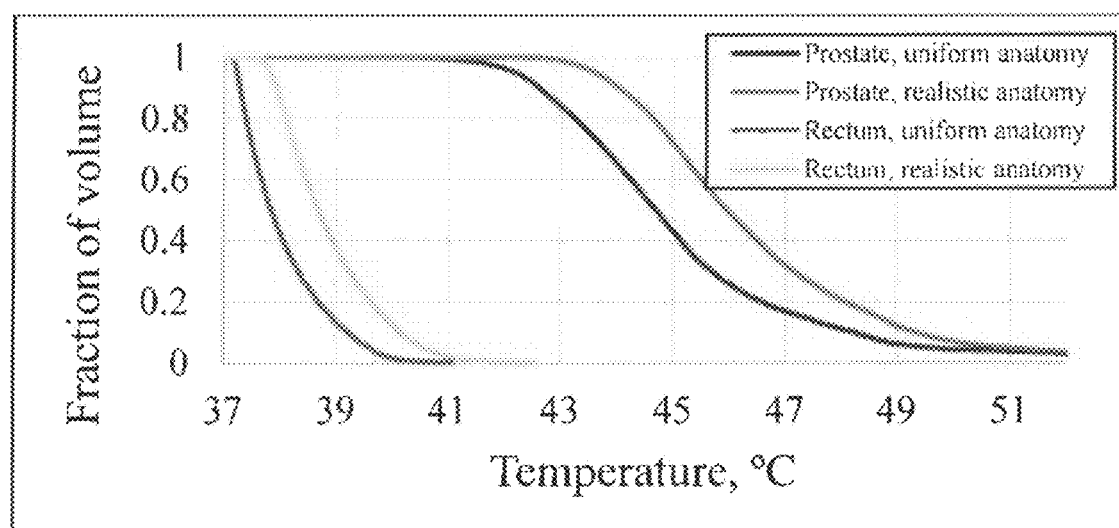
FIG. 105 shows sample temperature-volume histograms for the prostate and rectum for the same patient data, computed for uniform and patient-specific heterogeneous anatomy.

Computed temperatures were higher when patient-specific anatomy was considered than for the case of uniform anatomy, primarily due to tissues surrounding the prostate having lower rates of blood perfusion than that of the prostate (FIG. 105). Nevertheless, the maximum temperature to the rectum was low, owing to the very rapid drop-off of temperature from the surface of the hyperthermia seeds.

Compared to the data in Example II for TB and HT-only seeds with NiCu cores, the ferrite cores produced a lesser ISA effect: while seeds with NiCu cores reduced $D_{90}$ by ~9.3%, seeds with ferrite cores reduced it by ~8.7%. The ISA effect due to the TB seeds alone was slightly lower for the ferrite seeds than for the NiCu seeds.

Conclusions

For calculation of temperature distributions, patient-specific spatial information on the BPR is important. This was a major factor in temperature distribution differences between the uniform-anatomy and patient-specific anatomy cases. The temperature distributions obtained indicate that nearby organs at risk are not excessively heated. Finally, the increased interseed effect due to HT-only seeds used with the TB seeds is manageable by slightly increasing the prescribed dose.

From the above discussion and these Examples, one skilled in the art can ascertain the essential characteristics of this invention, and without departing from the spirit and scope thereof, can make various changes and modifications of the invention to adapt it to various usages and conditions. All publications, including patents and non-patent literature referred to in this specification, are expressly incorporated by reference herein.

While the invention has been described with reference to various and preferred embodiments, it should be understood by those skilled in the art that various changes may be made and equivalents may be substituted for elements thereof without departing from the essential scope of the invention. In addition, many modifications may be made to adapt a particular situation or material to the teachings of the invention without departing from the essential scope thereof.

Therefore, it is intended that the invention not be limited to the particular embodiment disclosed herein contemplated for carrying out this invention, but that the invention will include all embodiments falling within the scope of the claims.

The publication and other material used herein to illuminate the invention or provide additional details respecting the practice of the invention, are incorporated by reference herein, and for convenience are provided in the following bibliography.

Citation of any of the documents recited herein is not intended as an admission that any of the foregoing is pertinent prior art. All statements as to the date or representation as to the contents of these documents is based on the information available to the applicant and does not constitute any admission as to the correctness of the dates or contents of these documents.

What is claimed is:

1. A brachytherapy seed comprising:
   a seed having within an interior space thereof a core comprising a ferromagnetic material;
   an electroplated conductive layer sheath on the surface of the core; and
   at least one layer comprising a radiation emission material that surrounds the core, wherein the radiation emission material comprises one or more of I-125, Pd-103, or Cs-131 radionuclides; and
   a metal shell surrounding the at least one layer comprising the radiation emission material;
   wherein no void exists between the core and the radiation emission material that surrounds the core.

2. The brachytherapy seed of claim 1, wherein the ferromagnetic material comprises a ferrite.

3. The brachytherapy seed of claim 1, wherein the seed exhibits a Curie point in a therapeutic range of from about 49° C. to about 60° C.

4. The brachytherapy seed of claim 1, wherein the electroplated conductive layer sheath comprises gold or copper.

5. The brachytherapy seed of claim 1, wherein the electroplated conductive layer sheath has a thickness of about 15 microns.

6. The brachytherapy seed of claim 1, wherein the ferromagnetic material comprises magnesium ferrite and copper.

7. The brachytherapy seed of claim 1, wherein the ferromagnetic material comprises $Cu_{(0.5-x)}Mg_xZn_{0.5}Fe_2O_4$, wherein x ranges from 0 to 0.5.

8. The brachytherapy seed of claim 7, wherein x is 0.25.

9. The brachytherapy seed of claim 1, wherein the ferromagnetic material comprises $Mn_xZn_{(1-x)}Fe_2O_4$, wherein x ranges from 0 to 1.

10. The brachytherapy seed of claim 9, wherein x is about 0.32.

11. The brachytherapy seed of claim 1, wherein the ferromagnetic material comprises NiCu.

12. The brachytherapy seed of claim 1, wherein the ferromagnetic material comprises $Ni_{0.72}Cu_{0.28}$.

13. The brachytherapy seed of claim 1, wherein the electroplated conductive layer sheath is directly on the surface of the ferromagnetic material, and the at least one layer comprising a radiation emission material is directly on the electroplated conductive layer sheath.

14. The brachytherapy seed of claim 1, wherein the metal shell comprises Ti.

15. A system, comprising:
one or more implantable medical seeds, each implantable medical seed of the one or more implantable medical seeds including a body having an interior space and having at least one outer surface;
one or more ferromagnetic energy-emitting elements comprising a ferromagnetic material positioned within the interior space of each said implantable medical seed, the one or more ferromagnetic energy-emitting elements configured to at least intermittently deliver a therapeutic dose of heat to tissue proximate to the at least one outer surface of each said implantable medical seed; and
one or more radiation-emitting elements positioned within the interior space of each of the implantable medical seeds, the one or more radiation-emitting elements forming at least one layer that completely surrounds the one or more ferromagnetic energy-emitting elements positioned within the interior space of each said implantable medical seed, the one or more radiation-emitting elements configured to deliver a therapeutic dose of radiation to tissue proximate to the at least one outer surface of each said implantable medical seed;
wherein the system is adapted to include a controller configured to apply an electro-magnetic or magnetic field to the one or more implantable medical seeds; and
wherein no void exists between the ferromagnetic energy-emitting elements of each said implantable medical seed and the one or more radiation-emitting elements that surround the ferromagnetic energy-emitting elements.

16. The system of claim 15, wherein the ferromagnetic energy-emitting element is covered with an electroplated conductive layer sheath.

17. The system of claim 16, wherein the electroplated conductive layer sheath comprises gold or copper.

18. The system of claim 16, wherein the electroplated conductive layer sheath has a thickness of about 15 microns.

19. The system of claim 15, wherein the ferromagnetic material comprises magnesium ferrite and copper.

20. The system of claim 15, wherein the ferromagnetic material comprises $Cu_{(0.5-x)}Mg_xZn_{0.5}Fe_2O_4$, wherein x ranges from 0 to 0.5.

21. The system of claim 20, wherein x is 0.25.

22. The system of claim 15, wherein the ferromagnetic material comprises NiCu.

23. The system of claim 15, wherein the ferromagnetic material comprises $Ni_{0.72}Cu_{0.28}$.

24. A method of treating a subject in need thereof, the method comprising inserting at least one brachytherapy seed of claim 1 into the subject, and inducing a magnetic field applied to the brachytherapy seed to deliver a therapeutic dose of heat to tissue of the subject in proximity to the brachytherapy seed, wherein the brachytherapy seed also delivers a therapeutic dose of radiation to the tissue.

25. The method of claim 24, wherein the magnetic field strength is from about 2.5 kA/m to about 10 kA/m.

26. The method of claim 24, wherein the magnetic field oscillates at a frequency in the range of from about 50 kHz to about 200 kHz.

* * * * *